United States Patent
Osterloh et al.

(10) Patent No.: US 11,439,618 B2
(45) Date of Patent: *Sep. 13, 2022

(54) COMPOSITIONS AND METHODS FOR LOWERING TRIGLYCERIDES

(71) Applicant: Amarin Pharmaceuticals Ireland Limited, Dublin (IE)

(72) Inventors: Ian Osterloh, Kent (GB); Pierre Wicker, Mystic, CT (US); Rene Braeckman, Richboro, PA (US); Paresh Soni, Mystic, CT (US); Mehar Manku, Birmingham (GB)

(73) Assignee: Amarin Pharmaceuticals Ireland Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 17/148,449

(22) Filed: Jan. 13, 2021

(65) Prior Publication Data
US 2021/0206710 A1 Jul. 8, 2021

Related U.S. Application Data

(63) Continuation of application No. 16/795,761, filed on Feb. 20, 2020, which is a continuation of application No. 16/364,720, filed on Mar. 26, 2019, now Pat. No. 10,842,768, which is a continuation of application No. 16/273,875, filed on Feb. 12, 2019, which is a continuation of application No. 15/182,695, filed on Jun. 15, 2016, now abandoned, which is a continuation of application No. 15/095,860, filed on Apr. 11, 2016, now abandoned, which is a continuation of application No. 13/404,686, filed on Feb. 24, 2012, now abandoned, which is a continuation of application No. 12/815,569, filed on Jun. 15, 2010, now Pat. No. 8,455,472.

(60) Provisional application No. 61/187,132, filed on Jun. 15, 2009.

(51) Int. Cl.
| | | |
|---|---|---|
| A61K 31/202 | (2006.01) | |
| A61K 31/232 | (2006.01) | |
| A61P 9/10 | (2006.01) | |
| C07C 57/03 | (2006.01) | |
| A61P 3/06 | (2006.01) | |
| A61K 31/366 | (2006.01) | |
| A61K 31/40 | (2006.01) | |
| A61K 31/505 | (2006.01) | |
| A61K 9/48 | (2006.01) | |

(52) U.S. Cl.
CPC ............. *A61K 31/232* (2013.01); *A61K 9/48* (2013.01); *A61K 31/202* (2013.01); *A61K 31/366* (2013.01); *A61K 31/40* (2013.01); *A61K 31/505* (2013.01); *A61P 3/06* (2018.01); *A61P 9/10* (2018.01); *C07C 57/03* (2013.01)

(58) Field of Classification Search
CPC .................................................. A61K 31/202
See application file for complete search history.

(56) References Cited

U.S. PATENT DOCUMENTS

| | | |
|---|---|---|
| 4,377,526 A | 3/1983 | Fujita et al. |
| 4,526,902 A | 7/1985 | Rubin |
| 4,920,098 A | 4/1990 | Cotter et al. |
| 4,935,243 A | 6/1990 | Borkan et al. |
| 5,013,443 A | 5/1991 | Higashidate et al. |
| 5,116,871 A | 5/1992 | Horrobin et al. |
| 5,178,873 A | 1/1993 | Horrobin et al. |
| 5,198,468 A | 3/1993 | Horrobin |
| 5,215,630 A | 6/1993 | Hata et al. |
| 5,252,333 A | 10/1993 | Horrobin |
| 5,343,389 A | 8/1994 | Otvos |
| 5,385,929 A | 1/1995 | Bjorge et al. |
| 5,457,130 A | 10/1995 | Tisdale et al. |
| 5,502,077 A | 3/1996 | Breivik et al. |
| 5,567,730 A | 10/1996 | Miyashita et al. |
| 5,589,508 A | 12/1996 | Schlotzer et al. |
| 5,603,959 A | 2/1997 | Horrobin et al. |
| 5,604,119 A | 2/1997 | Haraldsson et al. |
| 5,618,558 A | 4/1997 | Horrobin et al. |
| 5,656,667 A | 8/1997 | Breivik et al. |
| 5,674,488 A | 10/1997 | Reich |
| 5,698,594 A | 12/1997 | Breivik et al. |
| 5,760,081 A | 6/1998 | Leaf et al. |
| 5,763,496 A | 6/1998 | Holland |
| 5,776,978 A | 7/1998 | Bruzzese |
| 5,792,795 A | 8/1998 | Buser et al. |
| 5,837,731 A | 11/1998 | Vaddadi |
| 5,840,944 A | 11/1998 | Furihata et al. |
| 5,886,037 A | 3/1999 | Klor et al. |
| 5,888,541 A | 3/1999 | Horrobin et al. |
| 5,948,818 A | 9/1999 | Buser et al. |

(Continued)

FOREIGN PATENT DOCUMENTS

| | | |
|---|---|---|
| CA | 2628305 | 5/2007 |
| CA | 2653787 | 12/2007 |

(Continued)

OTHER PUBLICATIONS

U.S. Appl. No. 17/148,409, dated Jan. 2021, Osterloh; Ian.*

(Continued)

*Primary Examiner* — Svetlana M Ivanova

(74) *Attorney, Agent, or Firm* — Perkins Coie LLP

(57) ABSTRACT

In various embodiments, the present invention provides compositions and methods for treating and/or preventing cardiovascular-related diseases in subject in need thereof.

7 Claims, No Drawings

(56) References Cited

U.S. PATENT DOCUMENTS

| | | | |
|---|---|---|---|
| 6,011,049 A | 1/2000 | Whitcomb | |
| 6,025,008 A | 2/2000 | Akahoshi | |
| 6,069,168 A | 5/2000 | Horrobin et al. | |
| 6,193,999 B1 | 2/2001 | Gennadios | |
| 6,207,699 B1 | 3/2001 | Rothman | |
| 6,284,268 B1 | 9/2001 | Mishra et al. | |
| 6,313,330 B1 | 11/2001 | Kiyohara et al. | |
| 6,326,031 B1 | 12/2001 | Hsia et al. | |
| 6,326,355 B1 | 12/2001 | Abbruzzese et al. | |
| 6,331,568 B1 | 12/2001 | Horrobin | |
| 6,362,236 B1 | 3/2002 | Aviram | |
| 6,368,621 B1 | 4/2002 | Engel et al. | |
| 6,383,482 B1 | 5/2002 | Gorsek | |
| 6,384,077 B1 | 5/2002 | Peet et al. | |
| 6,440,961 B1 | 8/2002 | Lohray et al. | |
| 6,479,544 B1 | 11/2002 | Horrobin | |
| 6,482,421 B2 | 11/2002 | Weidner | |
| 6,531,150 B2 | 3/2003 | Sunohara et al. | |
| 6,555,700 B1 | 4/2003 | Horrobin et al. | |
| 6,596,766 B1 | 7/2003 | Igarashi et al. | |
| 6,620,821 B2 | 9/2003 | Robl | |
| 6,689,812 B2 | 2/2004 | Peet | |
| 6,846,942 B2 | 1/2005 | Rubin | |
| 7,022,713 B2 | 4/2006 | Aoki et al. | |
| 7,112,609 B2 | 9/2006 | Hermelin et al. | |
| 7,119,118 B2 | 10/2006 | Peet | |
| 7,179,491 B1 | 2/2007 | Mag | |
| 7,205,329 B2 | 4/2007 | Chien et al. | |
| 7,405,302 B2 | 7/2008 | Hutchinson et al. | |
| 7,498,359 B2 | 3/2009 | Yokoyama et al. | |
| 7,511,131 B2 | 3/2009 | Crooke et al. | |
| 7,598,227 B2 | 10/2009 | Crooke et al. | |
| 7,642,287 B2 | 1/2010 | Guzman | |
| 7,776,881 B2 | 8/2010 | Aoki et al. | |
| 8,188,146 B2 | 5/2012 | Peet et al. | |
| 8,293,727 B2 | 10/2012 | Manku et al. | |
| 8,293,728 B2* | 10/2012 | Manku | G06F 19/00 514/183 |
| 8,298,554 B2 | 10/2012 | Manku | |
| 8,314,086 B2 | 11/2012 | Manku et al. | |
| 8,318,715 B2* | 11/2012 | Manku | A61K 31/202 514/183 |
| 8,324,195 B2* | 12/2012 | Manku | A61P 7/00 514/183 |
| 8,357,677 B1* | 1/2013 | Manku | A61P 7/00 514/183 |
| 8,367,652 B2* | 2/2013 | Manku | G16Z 99/00 514/183 |
| 8,377,920 B2* | 2/2013 | Manku | A61K 31/202 514/183 |
| 8,399,446 B2* | 3/2013 | Manku | A61K 45/06 514/183 |
| 8,410,086 B2* | 4/2013 | Osterloh | A61K 31/366 514/183 |
| 8,415,335 B2* | 4/2013 | Manku | A61K 45/06 514/183 |
| 8,426,399 B2* | 4/2013 | Manku | G06F 19/00 514/183 |
| 8,431,560 B1 | 4/2013 | Manku et al. | |
| 8,440,650 B1* | 5/2013 | Manku | A61K 31/232 514/183 |
| 8,445,003 B2* | 5/2013 | Manku | A61K 9/4825 424/400 |
| 8,445,013 B2* | 5/2013 | Manku | A61P 25/00 424/456 |
| 8,454,994 B2* | 6/2013 | Manku | A61P 3/10 424/451 |
| 8,455,472 B2* | 6/2013 | Osterloh | A61K 9/48 514/183 |
| 8,501,225 B2* | 8/2013 | Manku | A61P 3/00 424/456 |
| 8,518,929 B2* | 8/2013 | Manku | G06F 19/00 514/183 |
| 8,524,698 B2* | 9/2013 | Manku | G16Z 99/00 514/183 |
| 8,546,372 B2* | 10/2013 | Manku | A61K 31/202 514/183 |
| 8,551,521 B2 | 10/2013 | Manku et al. | |
| 8,563,608 B2* | 10/2013 | Manku | A61P 1/16 514/549 |
| 8,613,945 B2* | 12/2013 | Manku | A61P 7/02 424/451 |
| 8,617,593 B2* | 12/2013 | Manku | A61P 9/04 424/451 |
| 8,617,594 B2* | 12/2013 | Manku | A61P 3/00 424/456 |
| 8,618,166 B2* | 12/2013 | Osterloh | A61P 3/10 514/549 |
| 8,618,168 B2 | 12/2013 | Fujii et al. | |
| 8,623,406 B2* | 1/2014 | Manku | A61K 45/06 424/451 |
| 8,642,077 B2* | 2/2014 | Manku | A61P 9/00 424/451 |
| 8,660,662 B2 | 3/2014 | Manku et al. | |
| 8,663,662 B2* | 3/2014 | Manku | A61P 3/04 424/400 |
| 8,669,245 B2* | 3/2014 | Osterloh | A61P 3/10 514/183 |
| 8,680,144 B2* | 3/2014 | Osterloh | A61P 9/06 514/549 |
| 8,691,871 B2* | 4/2014 | Osterloh | A61K 31/222 514/549 |
| 8,703,185 B2* | 4/2014 | Manku | A61K 9/4858 424/451 |
| 8,709,475 B2* | 4/2014 | Manku | A61P 7/10 424/451 |
| 8,710,041 B2* | 4/2014 | Osterloh | A61P 9/04 514/183 |
| 8,802,718 B2 | 8/2014 | Yokoyama et al. | |
| 8,853,256 B2 | 10/2014 | Yokoyama et al. | |
| 8,906,964 B2 | 12/2014 | Bobotas et al. | |
| 9,006,285 B2 | 4/2015 | Ohnishi | |
| 9,060,981 B2 | 6/2015 | Sato et al. | |
| 9,060,982 B2* | 6/2015 | Manku | A61P 11/00 |
| 9,060,983 B2* | 6/2015 | Manku | A61P 9/06 |
| 9,138,415 B2 | 9/2015 | Manku et al. | |
| 9,452,121 B2 | 9/2016 | Manku et al. | |
| 9,452,150 B2 | 9/2016 | Ueshima et al. | |
| 9,585,859 B2* | 3/2017 | Osterloh | A61K 31/232 |
| 9,603,826 B2 | 3/2017 | Soni | |
| 9,610,272 B2 | 4/2017 | Soni | |
| 9,623,001 B2 | 4/2017 | Soni | |
| 9,693,984 B2 | 7/2017 | Soni | |
| 9,693,985 B2 | 7/2017 | Soni | |
| 9,693,986 B2 | 7/2017 | Soni | |
| 9,700,537 B2 | 7/2017 | Yokoyama et al. | |
| 9,855,237 B2* | 1/2018 | Osterloh | A61K 31/222 |
| 9,918,954 B2 | 3/2018 | Soni | |
| 10,010,517 B2* | 7/2018 | Manku | A61P 7/10 |
| 10,058,521 B2 | 8/2018 | Bobotas et al. | |
| 10,166,209 B2 | 1/2019 | Manku et al. | |
| 10,220,013 B2 | 3/2019 | Osterloh et al. | |
| 10,265,287 B2* | 4/2019 | Osterloh | A61P 9/00 |
| 10,265,290 B2 | 4/2019 | Manku et al. | |
| 10,278,935 B2 | 5/2019 | Soni | |
| 10,292,959 B2* | 5/2019 | Osterloh | G01N 33/96 |
| 10,441,593 B2* | 10/2019 | Loumaye | A61P 5/24 |
| 10,555,925 B1 | 2/2020 | Soni | |
| 10,557,856 B2 | 2/2020 | Singbartl et al. | |
| 10,568,861 B1 | 2/2020 | Soni | |
| 10,576,054 B1 | 3/2020 | Soni | |
| 10,624,870 B2* | 4/2020 | Osterloh | A61K 31/222 |
| 10,722,485 B2* | 7/2020 | Osterloh | A61K 31/232 |
| 10,792,267 B2* | 10/2020 | Osterloh | A61K 31/505 |
| 11,033,523 B2 | 6/2021 | Manku et al. | |
| 11,154,526 B2 | 10/2021 | Osterloh et al. | |
| 11,179,362 B2 | 11/2021 | Osterloh et al. | |
| 11,213,504 B2 | 1/2022 | Manku et al. | |
| 2001/0035125 A1 | 11/2001 | Talieh et al. | |
| 2002/0016312 A1 | 2/2002 | Seed et al. | |
| 2002/0025983 A1 | 2/2002 | Horrobin | |

(56) References Cited

U.S. PATENT DOCUMENTS

| | | |
|---|---|---|
| 2002/0035125 A1 | 3/2002 | Shear |
| 2002/0052394 A1 | 5/2002 | Mason |
| 2002/0054871 A1 | 5/2002 | Huang |
| 2002/0055529 A1 | 5/2002 | Bisgaier et al. |
| 2002/0055539 A1 | 5/2002 | Bockow et al. |
| 2002/0077361 A1 | 6/2002 | Peet et al. |
| 2002/0137082 A1 | 9/2002 | Lewandrowski et al. |
| 2002/0169209 A1 | 11/2002 | Horrobin |
| 2002/0177602 A1 | 11/2002 | Piper |
| 2002/0183389 A1 | 12/2002 | Peet |
| 2002/0193439 A1 | 12/2002 | Peet et al. |
| 2002/0198177 A1 | 12/2002 | Horrobin et al. |
| 2003/0100610 A1 | 5/2003 | Shibuya |
| 2003/0104048 A1 | 6/2003 | Patel et al. |
| 2003/0161918 A1 | 8/2003 | Kendrick et al. |
| 2003/0166614 A1 | 9/2003 | Harrison |
| 2003/0232385 A1 | 12/2003 | Breit et al. |
| 2004/0009208 A1 | 1/2004 | Edson |
| 2004/0018248 A1 | 1/2004 | Bendich |
| 2004/0048919 A1 | 3/2004 | Dreon et al. |
| 2004/0062847 A1 | 4/2004 | Koiki et al. |
| 2004/0077723 A1 | 4/2004 | Granata |
| 2004/0106591 A1 | 6/2004 | Pacioretty et al. |
| 2004/0121000 A1 | 6/2004 | Bowe et al. |
| 2004/0162348 A1 | 8/2004 | Peet et al. |
| 2004/0204356 A1 | 10/2004 | Guenzler-Pukall |
| 2004/0258645 A1 | 12/2004 | Trejo et al. |
| 2005/0042214 A1 | 2/2005 | Gershwin et al. |
| 2005/0137253 A1 | 6/2005 | Phinney et al. |
| 2005/0147665 A1 | 7/2005 | Horrobin et al. |
| 2005/0187292 A1 | 8/2005 | Aoki et al. |
| 2005/0215625 A9 | 9/2005 | Nesselroad |
| 2005/0244367 A1 | 11/2005 | Hui et al. |
| 2005/0272095 A1 | 12/2005 | Wang |
| 2006/0034815 A1 | 2/2006 | Guzman et al. |
| 2006/0051418 A1 | 3/2006 | Cowen et al. |
| 2006/0088502 A1 | 4/2006 | Sata et al. |
| 2006/0111437 A1 | 5/2006 | Aoki et al. |
| 2006/0134178 A1 | 6/2006 | Doisaki et al. |
| 2006/0134206 A1 | 6/2006 | Iyer et al. |
| 2006/0135607 A1 | 6/2006 | Kobayashi et al. |
| 2006/0135610 A1 | 6/2006 | Bortz et al. |
| 2006/0141022 A1 | 6/2006 | Kawamura et al. |
| 2006/0142390 A1 | 6/2006 | Manku et al. |
| 2006/0172012 A1 | 8/2006 | Finley et al. |
| 2006/0189682 A1 | 8/2006 | Payne et al. |
| 2006/0211749 A1 | 9/2006 | Bobotas et al. |
| 2006/0211761 A1 | 9/2006 | Kumar et al. |
| 2006/0211762 A1 | 9/2006 | Rongen |
| 2006/0211763 A1 | 9/2006 | Fawzy et al. |
| 2006/0217356 A1 | 9/2006 | Wright et al. |
| 2006/0223838 A1 | 10/2006 | Jiang et al. |
| 2006/0252833 A1 | 11/2006 | Peet et al. |
| 2007/0021504 A1 | 1/2007 | Yokoyama et al. |
| 2007/0060532 A1 | 3/2007 | Junien et al. |
| 2007/0098787 A1 | 5/2007 | Kakiuchi |
| 2007/0104779 A1 | 5/2007 | Rongen et al. |
| 2007/0105793 A1 | 5/2007 | Hendrix |
| 2007/0105954 A1 | 5/2007 | Puri |
| 2007/0141138 A1 | 6/2007 | Feuerstein et al. |
| 2007/0167520 A1 | 7/2007 | Bruzzese |
| 2007/0185198 A1 | 8/2007 | Yokoyama et al. |
| 2007/0191467 A1 | 8/2007 | Rongen et al. |
| 2007/0202159 A1 | 8/2007 | Mathur et al. |
| 2007/0212411 A1 | 9/2007 | Fawzy et al. |
| 2007/0219271 A1 | 9/2007 | Mittmann et al. |
| 2007/0265340 A1 | 11/2007 | Shalwitz et al. |
| 2007/0269507 A1 | 11/2007 | Sachetto et al. |
| 2007/0292501 A1 | 12/2007 | Udell |
| 2008/0020018 A1 | 1/2008 | Moodley et al. |
| 2008/0057115 A1 | 3/2008 | Okamoto |
| 2008/0085911 A1 | 4/2008 | Rongen et al. |
| 2008/0089876 A1 | 4/2008 | Cavazza |
| 2008/0113046 A1 | 5/2008 | Gardette |
| 2008/0125490 A1 | 5/2008 | Svensson et al. |
| 2008/0139604 A1 | 6/2008 | Fitzpatrick et al. |
| 2008/0185198 A1 | 8/2008 | Jones |
| 2008/0200453 A1 | 8/2008 | Cincotta |
| 2008/0200547 A1 | 8/2008 | Peet et al. |
| 2008/0200707 A1 | 8/2008 | Shimano et al. |
| 2008/0214531 A1 | 9/2008 | Saxena et al. |
| 2008/0299187 A1 | 12/2008 | Opheim et al. |
| 2008/0306154 A1 | 12/2008 | Svensson et al. |
| 2008/0319077 A1 | 12/2008 | Suzuki et al. |
| 2009/0012167 A1 | 1/2009 | Rongen et al. |
| 2009/0018125 A1 | 1/2009 | Mittmann et al. |
| 2009/0042979 A1 | 2/2009 | Guzman et al. |
| 2009/0054329 A1 | 2/2009 | Willemsen et al. |
| 2009/0105340 A1 | 4/2009 | Yokoyama |
| 2009/0148543 A1 | 6/2009 | Theoharides |
| 2009/0156675 A1 | 6/2009 | Yokoyama et al. |
| 2009/0182049 A1 | 7/2009 | Opheim |
| 2009/0227602 A1 | 9/2009 | Griffin et al. |
| 2009/0233843 A1 | 9/2009 | Marin |
| 2009/0239927 A1 | 9/2009 | Bobotas et al. |
| 2009/0304784 A1 | 12/2009 | Mane et al. |
| 2009/0311322 A1 | 12/2009 | Dlugatch et al. |
| 2010/0021555 A1 | 1/2010 | Geiringer et al. |
| 2010/0063018 A1 | 3/2010 | Pellicciari et al. |
| 2010/0069492 A1 | 3/2010 | Geiringen et al. |
| 2010/0113506 A1 | 5/2010 | Kawano et al. |
| 2010/0113811 A1 | 5/2010 | Yadav et al. |
| 2010/0119598 A1 | 5/2010 | Yoshinari et al. |
| 2010/0130608 A1 | 5/2010 | Ryan et al. |
| 2010/0160261 A1 | 6/2010 | Fortin |
| 2010/0233280 A1 | 9/2010 | Driscoll |
| 2010/0254951 A1 | 10/2010 | Shido et al. |
| 2010/0278879 A1 | 11/2010 | Manku |
| 2010/0285121 A1 | 11/2010 | Uchiyama et al. |
| 2010/0298379 A1 | 11/2010 | Jacobsen |
| 2010/0305205 A1 | 12/2010 | Yokoyama et al. |
| 2010/0311834 A1 | 12/2010 | Manku et al. |
| 2011/0034555 A1 | 2/2011 | Osterloh et al. |
| 2011/0065793 A1 | 3/2011 | Peet et al. |
| 2011/0071176 A1 | 3/2011 | Rowe |
| 2011/0082119 A1 | 4/2011 | Yano |
| 2011/0092592 A1 | 4/2011 | Yano |
| 2011/0105510 A1 | 5/2011 | Ishikawa |
| 2011/0130458 A1 | 6/2011 | Breivik et al. |
| 2011/0158932 A1 | 6/2011 | Jiang et al. |
| 2011/0178105 A1 | 7/2011 | Gillies et al. |
| 2011/0195061 A1 | 8/2011 | Minatelli |
| 2011/0218243 A1 | 9/2011 | Rowe |
| 2011/0223158 A1 | 9/2011 | Sacks et al. |
| 2011/0236476 A1 | 9/2011 | Manku |
| 2011/0268811 A1 | 11/2011 | Minatelli et al. |
| 2011/0288171 A1 | 11/2011 | Manku et al. |
| 2012/0035105 A1 | 2/2012 | Geho et al. |
| 2012/0035262 A1 | 2/2012 | Osterloh et al. |
| 2012/0039997 A1 | 2/2012 | Manku et al. |
| 2012/0046251 A1 | 2/2012 | Schaefer et al. |
| 2012/0093922 A1 | 4/2012 | Manku et al. |
| 2012/0093924 A1 | 4/2012 | Manku et al. |
| 2012/0100208 A1 | 4/2012 | Manku |
| 2012/0108659 A1 | 5/2012 | Manku et al. |
| 2012/0108660 A1 | 5/2012 | Manku et al. |
| 2012/0108663 A1 | 5/2012 | Manku et al. |
| 2012/0121698 A1 | 5/2012 | Manku et al. |
| 2012/0156285 A1 | 6/2012 | Manku et al. |
| 2012/0157530 A1 | 6/2012 | Manku et al. |
| 2012/0157531 A1 | 6/2012 | Osterloh et al. |
| 2012/0172432 A1 | 7/2012 | Manku et al. |
| 2012/0184595 A1 | 7/2012 | Macdonald et al. |
| 2012/0195963 A1 | 8/2012 | Peet et al. |
| 2012/0207800 A1 | 8/2012 | Abu-Baker |
| 2012/0214771 A1 | 8/2012 | Sampalis |
| 2012/0225120 A1 | 9/2012 | Manku et al. |
| 2012/0232145 A1 | 9/2012 | Osterloh et al. |
| 2012/0237594 A1 | 9/2012 | Manku et al. |
| 2012/0245121 A1 | 9/2012 | Lopez Pedrosa et al. |
| 2012/0264824 A1 | 10/2012 | Mizuguchi et al. |
| 2012/0295976 A1 | 11/2012 | Yokoyama |
| 2012/0302589 A1 | 11/2012 | Manku et al. |
| 2012/0329852 A1 | 12/2012 | Yokoyama |

(56) References Cited

U.S. PATENT DOCUMENTS

| | | |
|---|---|---|
| 2013/0004566 A1 | 1/2013 | Manku et al. |
| 2013/0004567 A1 | 1/2013 | Manku et al. |
| 2013/0004568 A1 | 1/2013 | Manku et al. |
| 2013/0004572 A1 | 1/2013 | Manku et al. |
| 2013/0005757 A1 | 1/2013 | Osterloh et al. |
| 2013/0005809 A1 | 1/2013 | Manku et al. |
| 2013/0011471 A1 | 1/2013 | Manku et al. |
| 2013/0011472 A1 | 1/2013 | Manku et al. |
| 2013/0012580 A1 | 1/2013 | Osterloh et al. |
| 2013/0017256 A1 | 1/2013 | Manku et al. |
| 2013/0065956 A1 | 3/2013 | Yokoyama |
| 2013/0079409 A1 | 3/2013 | Manku et al. |
| 2013/0090383 A1 | 4/2013 | Manku et al. |
| 2013/0095178 A1 | 4/2013 | Manku |
| 2013/0095179 A1 | 4/2013 | Davidson et al. |
| 2013/0096197 A1 | 4/2013 | Manku |
| 2013/0102674 A1 | 4/2013 | Manku |
| 2013/0115284 A1 | 5/2013 | Fujii et al. |
| 2013/0131170 A1 | 5/2013 | Manku |
| 2013/0156852 A1 | 6/2013 | Manku et al. |
| 2013/0158120 A1 | 6/2013 | Manku et al. |
| 2013/0164375 A1 | 6/2013 | Manku et al. |
| 2013/0165513 A1 | 6/2013 | Manku et al. |
| 2013/0171249 A1 | 7/2013 | Manku et al. |
| 2013/0171250 A1 | 7/2013 | Manku et al. |
| 2013/0171251 A1 | 7/2013 | Manku et al. |
| 2013/0172413 A1 | 7/2013 | Manku |
| 2013/0189355 A1 | 7/2013 | Manku et al. |
| 2013/0195972 A1 | 8/2013 | Manku et al. |
| 2013/0252989 A1 | 9/2013 | Manku et al. |
| 2013/0252990 A1 | 9/2013 | Manku et al. |
| 2013/0253030 A1 | 9/2013 | Osterloh et al. |
| 2013/0253031 A1 | 9/2013 | Osterloh et al. |
| 2013/0260403 A1 | 10/2013 | Button et al. |
| 2013/0261180 A1 | 10/2013 | Gillies et al. |
| 2013/0281534 A1 | 10/2013 | Osterloh et al. |
| 2013/0295173 A1 | 11/2013 | Machielse et al. |
| 2013/0303614 A1 | 11/2013 | Kanehiro et al. |
| 2013/0324607 A1 | 12/2013 | Mason |
| 2013/0331447 A1 | 12/2013 | Manku et al. |
| 2014/0004183 A1 | 1/2014 | Soni et al. |
| 2014/0005264 A1 | 1/2014 | Soni et al. |
| 2014/0005265 A1 | 1/2014 | Soni et al. |
| 2014/0017306 A1 | 1/2014 | Manku |
| 2014/0057981 A1 | 2/2014 | Fujii |
| 2014/0073692 A1 | 3/2014 | Peet |
| 2014/0080850 A1 | 3/2014 | Mason |
| 2014/0080909 A1 | 3/2014 | Manku |
| 2014/0088194 A1 | 3/2014 | Manku et al. |
| 2014/0094520 A1 | 4/2014 | Bobotas et al. |
| 2014/0107199 A1 | 4/2014 | Fawzy et al. |
| 2014/0127289 A1 | 5/2014 | Osterloh et al. |
| 2014/0128453 A1 | 5/2014 | Mullick et al. |
| 2014/0128464 A1 | 5/2014 | Rowe |
| 2014/0142127 A1 | 5/2014 | Almarsson |
| 2014/0154310 A1 | 6/2014 | Osterloh et al. |
| 2014/0155455 A1 | 6/2014 | Osterloh et al. |
| 2014/0155481 A1 | 6/2014 | Osterloh et al. |
| 2014/0186438 A1 | 7/2014 | Manku et al. |
| 2014/0187633 A1 | 7/2014 | Manku et al. |
| 2014/0213648 A1 | 7/2014 | Manku et al. |
| 2014/0221358 A1 | 8/2014 | Zakrzewski |
| 2014/0221452 A1 | 8/2014 | Zakrzewski |
| 2014/0221486 A1 | 8/2014 | Manku et al. |
| 2014/0221676 A1 | 8/2014 | Braeckman et al. |
| 2014/0234410 A1 | 8/2014 | Moodley et al. |
| 2014/0235716 A1 | 8/2014 | Manku et al. |
| 2014/0243389 A1 | 8/2014 | Zakrzewski |
| 2014/0249200 A1 | 9/2014 | Braeckman et al. |
| 2014/0249214 A1 | 9/2014 | Braeckman et al. |
| 2014/0249220 A1 | 9/2014 | Braeckman et al. |
| 2014/0249225 A1 | 9/2014 | Mason |
| 2014/0256809 A1 | 9/2014 | Zakrzewski |
| 2014/0271841 A1 | 9/2014 | Grandolfi |
| 2014/0271907 A1 | 9/2014 | Zakrzewski |
| 2014/0275252 A1 | 9/2014 | Zakrzewski |
| 2014/0275253 A1 | 9/2014 | Zakrzewski |
| 2014/0322314 A1 | 10/2014 | Fawzy et al. |
| 2014/0357717 A1 | 12/2014 | Braeckman et al. |
| 2014/0364459 A1 | 12/2014 | Zakrzewski |
| 2015/0045431 A1 | 2/2015 | Zakrzewski |
| 2015/0051143 A1 | 2/2015 | Harada et al. |
| 2015/0051282 A1 | 2/2015 | Zakrzewski |
| 2015/0065572 A1 | 3/2015 | Zakrzewski |
| 2015/0073050 A1 | 3/2015 | Zakrzewski |
| 2015/0141510 A1 | 5/2015 | Kiyohara et al. |
| 2015/0147276 A1 | 5/2015 | Ingber et al. |
| 2015/0157592 A1 | 6/2015 | Soni |
| 2015/0157593 A1 | 6/2015 | Braeckman et al. |
| 2015/0164850 A1 | 6/2015 | Osterloh et al. |
| 2015/0190361 A1 | 7/2015 | Osterloh et al. |
| 2015/0216831 A1 | 8/2015 | Manku et al. |
| 2015/0250754 A1 | 9/2015 | Ohta |
| 2015/0250756 A1 | 9/2015 | Mason |
| 2015/0250757 A1 | 9/2015 | Soni |
| 2015/0258051 A1 | 9/2015 | Manku et al. |
| 2015/0265566 A1 | 9/2015 | Osterloh et al. |
| 2015/0265574 A1 | 9/2015 | Rowe |
| 2015/0272917 A1 | 10/2015 | Manku et al. |
| 2015/0283074 A1 | 10/2015 | Fujii |
| 2015/0290154 A1 | 10/2015 | Roberts et al. |
| 2015/0335607 A1 | 11/2015 | Rowe |
| 2015/0359775 A1 | 12/2015 | Osterloh et al. |
| 2016/0045444 A1 | 2/2016 | Kim et al. |
| 2016/0058729 A1 | 3/2016 | Manku et al. |
| 2016/0120837 A1 | 5/2016 | Manku et al. |
| 2016/0143875 A1 | 5/2016 | Zakrzewski |
| 2016/0151319 A1 | 6/2016 | Kimura |
| 2016/0158184 A1 | 6/2016 | Ito |
| 2016/0213636 A1 | 7/2016 | Manku et al. |
| 2016/0213639 A1 | 7/2016 | Suzuki et al. |
| 2016/0220522 A1 | 8/2016 | Osterloh et al. |
| 2016/0287546 A1 | 10/2016 | Osterloh et al. |
| 2017/0014366 A1 | 1/2017 | Osterloh et al. |
| 2017/0035722 A1 | 2/2017 | Soni |
| 2017/0056361 A1 | 3/2017 | Soni |
| 2017/0079946 A1 | 3/2017 | Ohta |
| 2017/0087111 A1 | 3/2017 | Mason |
| 2017/0100363 A9 | 4/2017 | Zakrzewski |
| 2017/0119721 A1 | 5/2017 | Zakrzewski |
| 2017/0119722 A1 | 5/2017 | Manku et al. |
| 2017/0119723 A1 | 5/2017 | Soni |
| 2017/0119724 A1 | 5/2017 | Fujii |
| 2017/0128402 A1 | 5/2017 | Manku et al. |
| 2017/0128405 A1 | 5/2017 | Osterloh et al. |
| 2017/0128406 A1 | 5/2017 | Rowe |
| 2017/0136055 A1 | 5/2017 | Zakrzewski |
| 2017/0143656 A1 | 5/2017 | Soni |
| 2017/0143657 A1 | 5/2017 | Braeckman et al. |
| 2017/0143658 A1 | 5/2017 | Soni |
| 2017/0151202 A1 | 6/2017 | Mason |
| 2017/0151206 A1 | 6/2017 | Yokoyama |
| 2017/0217943 A1 | 8/2017 | Lairson et al. |
| 2017/0258753 A1 | 9/2017 | Soni |
| 2017/0258754 A1 | 9/2017 | Soni |
| 2017/0258755 A1 | 9/2017 | Soni |
| 2017/0273928 A1 | 9/2017 | Yokoyama |
| 2017/0304249 A1 | 10/2017 | Abu-Baker |
| 2017/0333377 A1 | 11/2017 | Mason |
| 2017/0348268 A1 | 12/2017 | Kimura |
| 2017/0348273 A1 | 12/2017 | Ito |
| 2017/0368184 A1 | 12/2017 | Ito |
| 2018/0015038 A1 | 1/2018 | Ito |
| 2018/0015071 A1 | 1/2018 | Braeckman et al. |
| 2018/0028480 A1 | 2/2018 | Mason |
| 2018/0028505 A1 | 2/2018 | Oshima |
| 2018/0042880 A1 | 2/2018 | Osterloh et al. |
| 2018/0042883 A1 | 2/2018 | Manku et al. |
| 2018/0064676 A1 | 3/2018 | Zakrzewski |
| 2018/0085334 A1 | 3/2018 | Soni |
| 2018/0125862 A1 | 5/2018 | Hayardeny-Nissimov et al. |
| 2018/0153846 A1 | 6/2018 | Soni |
| 2018/0185320 A1 | 7/2018 | Manku et al. |
| 2018/0280334 A1 | 10/2018 | Manku |

(56) References Cited

U.S. PATENT DOCUMENTS

| | | |
|---|---|---|
| 2018/0289657 A1 | 10/2018 | Soni |
| 2018/0289658 A1 | 10/2018 | Soni |
| 2018/0289659 A1 | 10/2018 | Soni |
| 2018/0333383 A1 | 11/2018 | Philip |
| 2019/0038590 A1 | 2/2019 | Manku |
| 2019/0054054 A1 | 2/2019 | Mason |
| 2019/0054058 A1 | 2/2019 | Thero |
| 2019/0060308 A1 | 2/2019 | Mason |
| 2019/0070141 A1 | 3/2019 | Osterloh |
| 2019/0076388 A1 | 3/2019 | Soni |
| 2019/0076389 A1 | 3/2019 | Soni |
| 2019/0076390 A1 | 3/2019 | Manku |
| 2019/0083444 A1 | 3/2019 | Manku |
| 2019/0083445 A1 | 3/2019 | Soni |
| 2019/0099422 A1 | 4/2019 | Grandolfi |
| 2019/0175535 A1 | 6/2019 | Mason |
| 2019/0175537 A1 | 6/2019 | Osterloh |
| 2019/0175538 A1 | 6/2019 | Osterloh |
| 2019/0183829 A1 | 6/2019 | Osterloh |
| 2019/0183831 A1 | 6/2019 | Osterloh |
| 2019/0183840 A1 | 6/2019 | Braeckman |
| 2019/0192472 A1 | 6/2019 | Soni |
| 2019/0201364 A1 | 7/2019 | Manku |
| 2019/0209506 A1 | 7/2019 | Mason |
| 2019/0240182 A1 | 8/2019 | Osterloh |
| 2019/0240183 A1 | 8/2019 | Manku |
| 2019/0269642 A1 | 9/2019 | Philip |
| 2019/0274991 A1 | 9/2019 | Osterloh |
| 2019/0275057 A1 | 9/2019 | Philip |
| 2019/0282533 A1 | 9/2019 | Osterloh |
| 2019/0316122 A1 | 10/2019 | Zakrzewski |
| 2019/0321323 A1 | 10/2019 | Soni |
| 2019/0343788 A1 | 11/2019 | Soni |
| 2019/0358185 A1 | 11/2019 | Mason |
| 2020/0000759 A1 | 1/2020 | Manku |
| 2020/0061011 A1 | 2/2020 | Mason |
| 2020/0061012 A1 | 2/2020 | Manku et al. |
| 2020/0069632 A1 | 3/2020 | Soni |
| 2020/0078329 A1 | 3/2020 | Soni |
| 2020/0093777 A1 | 3/2020 | Soni |
| 2020/0093778 A1 | 3/2020 | Soni |
| 2020/0093790 A1 | 3/2020 | Rowe |
| 2020/0108041 A1 | 4/2020 | Braeckman et al. |
| 2020/0113862 A1 | 4/2020 | Manku et al. |
| 2020/0113864 A1 | 4/2020 | Soni |
| 2020/0121628 A1 | 4/2020 | Osterloh et al. |
| 2020/0121630 A1 | 4/2020 | Osterloh et al. |
| 2020/0138768 A1 | 5/2020 | Soni |
| 2020/0163925 A1 | 5/2020 | Soni |
| 2020/0188343 A1 | 6/2020 | Osterloh |
| 2020/0188344 A1 | 6/2020 | Osterloh |
| 2020/0197350 A1 | 6/2020 | Manku |
| 2020/0215017 A1 | 7/2020 | Manku |
| 2020/0237699 A1 | 7/2020 | Mason |
| 2020/0237700 A1 | 7/2020 | Mason |
| 2020/0246300 A1 | 8/2020 | Manku et al. |
| 2020/0261391 A1 | 8/2020 | Soni |
| 2020/0268702 A1 | 8/2020 | Braeckman et al. |
| 2020/0289450 A1 | 9/2020 | Mason |
| 2020/0297681 A1 | 9/2020 | Rowe |
| 2020/0297682 A1 | 9/2020 | Osterloh |
| 2020/0297683 A1 | 9/2020 | Manku |
| 2020/0316006 A1 | 10/2020 | Manku |
| 2020/0338035 A1 | 10/2020 | Soni |
| 2020/0360330 A1 | 11/2020 | Rowe |
| 2020/0397735 A1 | 12/2020 | Osterloh et al. |
| 2020/0405675 A1 | 12/2020 | Manku et al. |
| 2020/0405677 A1 | 12/2020 | Osterloh et al. |
| 2021/0000779 A1 | 1/2021 | Osterloh et al. |
| 2021/0046036 A1 | 2/2021 | Manku |
| 2021/0046037 A1 | 2/2021 | Osterloh et al. |
| 2021/0069142 A1 | 3/2021 | Manku et al. |
| 2021/0069145 A1 | 3/2021 | Braeckman et al. |
| 2021/0085629 A1 | 3/2021 | Mason |
| 2021/0011351 A1 | 4/2021 | Manku et al. |
| 2021/0100764 A1 | 4/2021 | Osterloh et al. |
| 2021/0100765 A1 | 4/2021 | Osterloh et al. |
| 2021/0100768 A1 | 4/2021 | Soni |
| 2021/0108202 A1 | 4/2021 | Zakrzewski |
| 2021/0113509 A1 | 4/2021 | Osterloh et al. |
| 2021/0113513 A1 | 4/2021 | Osterloh et al. |
| 2021/0128582 A1 | 5/2021 | Manku et al. |
| 2021/0137872 A1 | 5/2021 | Philip |
| 2021/0137873 A1 | 5/2021 | Soni |
| 2021/0137879 A1 | 5/2021 | Soni |
| 2021/0145786 A1 | 5/2021 | Zakrzewski |
| 2021/0145787 A1 | 5/2021 | Manku et al. |
| 2021/0154164 A1 | 5/2021 | Soni |
| 2021/0205255 A1 | 7/2021 | Osterloh et al. |
| 2021/0206710 A1 | 7/2021 | Osterloh et al. |
| 2021/0212974 A1 | 7/2021 | Osterloh et al. |
| 2021/0212975 A1 | 7/2021 | Manku et al. |
| 2021/0251941 A1 | 8/2021 | Manku et al. |
| 2021/0260016 A1 | 8/2021 | Rowe |
| 2021/0330624 A1 | 10/2021 | Granowitz |
| 2021/0379002 A1 | 12/2021 | Osterloh |
| 2022/0000829 A1 | 1/2022 | Soni |

FOREIGN PATENT DOCUMENTS

| | | |
|---|---|---|
| CA | 2675836 | 7/2008 |
| CA | 2724983 | 11/2009 |
| CA | 2772378 | 12/2010 |
| CN | 101252837 | 8/2008 |
| EP | 0273708 | 7/1988 |
| EP | 0277747 | 8/1988 |
| EP | 0302482 | 2/1989 |
| EP | 0347509 | 12/1989 |
| EP | 0460917 | 12/1991 |
| EP | 0606012 | 7/1994 |
| EP | 0610506 | 8/1994 |
| EP | 0641562 A1 | 3/1995 |
| EP | 0843972 | 5/1998 |
| EP | 1125914 | 8/2001 |
| EP | 1157692 | 11/2001 |
| EP | 1296670 | 4/2003 |
| EP | 1549299 | 12/2003 |
| EP | 1743644 | 1/2007 |
| EP | 1782801 | 5/2007 |
| EP | 1790339 A1 | 5/2007 |
| EP | 1834639 A1 | 9/2007 |
| EP | 1946755 | 7/2008 |
| EP | 1982710 A1 | 10/2008 |
| EP | 2022495 | 2/2009 |
| EP | 2395991 | 8/2010 |
| EP | 2308493 A1 | 4/2011 |
| EP | 2343066 A1 | 7/2011 |
| EP | 2433630 | 3/2012 |
| EP | 2719382 A1 | 4/2014 |
| EP | 2792746 | 10/2014 |
| FR | 2635263 | 2/1990 |
| GB | 2148713 | 6/1985 |
| GB | 2221843 | 2/1990 |
| GB | 2229363 | 9/1990 |
| GB | 9901809.5 | 1/1999 |
| GB | 2480146 | 11/2011 |
| IL | 55227 | 12/1982 |
| JP | 61035356 | 2/1986 |
| JP | 04182426 | 6/1992 |
| JP | H0692847 | 4/1994 |
| JP | 08040981 | 2/1996 |
| JP | 09059206 | 3/1997 |
| JP | H10139662 | 5/1998 |
| JP | H1180083 A | 3/1999 |
| JP | 2001139981 | 5/2001 |
| JP | 2003306690 | 10/2003 |
| JP | 2007238598 | 9/2007 |
| JP | 2008050367 | 3/2008 |
| KR | 10-2006-0109988 | 10/2006 |
| KR | 10-2007-0058460 | 6/2007 |
| RU | 2281764 C2 | 8/2006 |
| RU | 2290185 | 12/2006 |
| RU | 2302248 C2 | 7/2007 |
| RU | 2402326 C1 | 10/2010 |

(56) References Cited

FOREIGN PATENT DOCUMENTS

| | | |
|---|---|---|
| WO | WO1990/004391 | 5/1990 |
| WO | WO1992/021335 | 12/1992 |
| WO | WO1994/010125 | 5/1994 |
| WO | WO1994/028891 | 12/1994 |
| WO | WO1995/024459 | 9/1995 |
| WO | WO1996/036329 | 11/1996 |
| WO | WO1997/039759 | 10/1997 |
| WO | WO1998/016216 | 4/1998 |
| WO | WO1999/026583 | 6/1999 |
| WO | WO1999/029316 | 6/1999 |
| WO | WO2000/044361 | 8/2000 |
| WO | WO2000/051573 | 9/2000 |
| WO | WO2001/015552 | 3/2001 |
| WO | WO2002/002105 | 1/2002 |
| WO | WO2002/058793 | 8/2002 |
| WO | WO2002/089787 | 11/2002 |
| WO | WO2002/096408 | 12/2002 |
| WO | WO2003/068216 | 8/2003 |
| WO | WO2003/092673 | 11/2003 |
| WO | WO2004/050913 | 6/2004 |
| WO | WO2004/064716 | 8/2004 |
| WO | WO2004/078166 | 9/2004 |
| WO | WO2004/082402 | 9/2004 |
| WO | WO2005/060954 | 7/2005 |
| WO | WO2005/065652 | 7/2005 |
| WO | WO2005/079797 | 9/2005 |
| WO | WO2005/079853 | 9/2005 |
| WO | WO2005/102301 | 11/2005 |
| WO | WO2005/123060 | 12/2005 |
| WO | WO2005/123061 | 12/2005 |
| WO | WO2006/017627 | 2/2006 |
| WO | WO2006/029577 | 3/2006 |
| WO | WO2006/062748 | 6/2006 |
| WO | WO2006/096806 | 9/2006 |
| WO | WO2007/011886 | 1/2007 |
| WO | WO2007/016256 | 2/2007 |
| WO | WO2007/017240 | 2/2007 |
| WO | WO2007/073176 | 6/2007 |
| WO | WO2007/075841 | 7/2007 |
| WO | WO2007/091338 | 8/2007 |
| WO | WO2007/103557 | 9/2007 |
| WO | WO2007/128801 | 11/2007 |
| WO | WO2007/142118 | 12/2007 |
| WO | WO2008/004900 | 1/2008 |
| WO | WO2008/045465 | 4/2008 |
| WO | WO2008/088415 | 7/2008 |
| WO | WO2008/106787 | 9/2008 |
| WO | WO2008/115529 | 9/2008 |
| WO | WO2008/145170 | 12/2008 |
| WO | WO2009/004999 | 1/2009 |
| WO | WO2006117668 | 2/2009 |
| WO | WO2009/085386 | 7/2009 |
| WO | WO2009/085388 | 7/2009 |
| WO | WO2010/028067 | 3/2010 |
| WO | WO2010/093634 | 8/2010 |
| WO | WO2010/103402 | 9/2010 |
| WO | WO2010/119319 | 10/2010 |
| WO | WO2010/127099 | 11/2010 |
| WO | WO2010/127103 | 11/2010 |
| WO | WO2010/134614 | 11/2010 |
| WO | WO2010/147994 | 12/2010 |
| WO | WO2011/028689 | 3/2011 |
| WO | WO2011/038122 | 3/2011 |
| WO | WO2011/047259 | 4/2011 |
| WO | WO2011/085211 | 7/2011 |
| WO | WO2011/109724 | 9/2011 |
| WO | WO2012/032414 | 3/2012 |
| WO | WO2012/074930 | 6/2012 |
| WO | WO2012/128587 | 9/2012 |
| WO | WO2013/070735 | 5/2013 |
| WO | WO2013/103958 | 7/2013 |
| WO | WO2013/136277 | 9/2013 |
| WO | WO2013/148136 | 10/2013 |
| WO | WO2014/004861 | 1/2014 |
| WO | WO2014/004993 | 1/2014 |
| WO | WO2014/005013 | 1/2014 |
| WO | WO2014/057522 | 4/2014 |
| WO | WO2014/074552 | 5/2014 |
| WO | WO2014/130200 | 8/2014 |
| WO | WO2014/134466 | 9/2014 |
| WO | WO2014/142364 | 9/2014 |
| WO | WO2014/143469 | 9/2014 |
| WO | WO2014/143523 | 9/2014 |
| WO | WO2014/205310 | 12/2014 |
| WO | WO2015/021141 | 2/2015 |
| WO | WO2015/066512 | 5/2015 |
| WO | WO2015/195662 | 12/2015 |
| WO | WO2016/140949 | 9/2016 |
| WO | WO2018/213663 | 11/2018 |
| WO | WO2020/037153 | 2/2020 |
| WO | WO2020/065402 | 4/2020 |
| WO | WO2020/068163 | 4/2020 |
| WO | WO2020/168251 | 8/2020 |
| WO | WO2021/097120 | 5/2021 |

OTHER PUBLICATIONS

U.S. Appl. No. 17/011,888, dated Sep, 2020, Osterloh; Ian.*
U.S. Appl. No. 17/016,577, dated Sep. 2020, Osterloh; Ian.*
U.S. Appl. No. 17/000,567, dated Aug. 2020, Braeckman.*
Ginsberg et al., Regulation of Plasma Triglycerides in Insulin Resistance and Diabetes, Archives of Medical Research, vol. 36, Issue 3, May-Jun. 2005, pp. 232-240.*
A study of AMR101 to evaluate its ability to reduce cardiovascular events in high risk patients with hypertriglyceridemia and on statin (REDUCE-IT). Available at: http://clinicaltrials.gov/show/NCT01492361, First Posted Dec. 15, 2011; Last Update Posted Jun. 6, 2019 (3 pages).
Aarsetoey H, Gurndt H, Nygaard O. The Role of Long-Chained Marine N-3 Polyunsaturated Fatty Acids in Cardiovascular Disease. Cardiol Res Pract. 2012. Epub Dec. 13, 2012.
Aarsland, et al., "On the Effect of Peroximsomal beta-Oxidation and Carnitine Palmitoyltransferase Activity by Eicosapentaenoic Aid in Live and Heart of Rats." Lipids, 25:546-548, (Sep. 1990); https://link.springer.com/article/10.1007/BF02537162, Accepted Jun. 6, 1990, Issue Date Sep. 1990.
Aas, V., et al., "Eicosapentaenoic acid (20:5 n-3) increases fatty acid and glucose uptake in cultured human skeletal muscle cells." Journal of Lipid Research, 47:366-374 (Feb. 2006); https://www.jlr.org/content/47/2/366.abstract, First published JLR Papers in Press, Nov. 21, 2005.
Abbey, M., et al., "Effect of fish oil on lipoproteins, lecithin:cholesterol acyltransferase, and lipidtransfer protein activity in humans." Arterioscler. Thromb. Vasc. Biol. 10:85-94 (Jan./Feb. 1990); https://www.ahajournals.org/doi/10.1161/01.ATV.10.1.85 Originally published Jan. 1, 1990.
Abela GS, Aziz K. "Cholesterol crystals cause mechanical damage to biological membranes: a proposed mechanism of plaque rupture and erosion leading to arterial thrombosis." Clin. Cardiol. (Sep. 2005);28(9):413-420; https://onlinelibrary.wiley.com/doi/abs/10.1002/clc.4960280906, First published Dec. 5, 2006.
Abelo A, Andersson TB, Antonsson M, et al. "Stereoselective metabolism of omeprazole by human cytochrome P450 enzymes." Drug Metab. Dispos. Aug. 28, 2000 (8): 966-72.
Ackman et al., "The 'Basic' Fatty Acid Composition of Atlantic Fish Oils: Potential Similarities Useful for Enrichment of Polyunsaturated Fatty Acids by Urea Complexation," JAOCS, vol. 65, 1:136-138 (Jan. 1988); https://aocs.onlinelibrary.wiley.com/doi/abs/10.1007/BF02542565, First published Jan. 1, 1988.
Adan, Y, et al., "Effects of docosahexaenoic and eicosapentaenoic acid on lipid metabolism, eicosanoid production, platelet aggregation and atherosclerosis." Biosci. Biotechnol. Biochem. 63(1), 111-119 (Jan. 1999); https://www.jstage.jst.go.jp/article/bbb/63/1/63_1_111/_article/-char/ja/.
Adan, Y., et al., "Concentration of serum lipids and aortic lesion size in female and male apo E-deficient mice fed docosahexaenoic acid." Biosci. Biotechnol. Biochem. 63(2):309-313 (Feb. 1999); https://www.tandfonline.com/doi/abs/10.1271/bbb.63.309 , Accepted Oct. 22, 1998, published online May 22, 2014.

(56) References Cited

OTHER PUBLICATIONS

Adorini et al., "Farnesoid X receptor targeting to treat nonalcoholic steatohepatitis," Drug Discover Today, 14(17-18):988-997 (Sep. 2012)(available online May 28, 2012).

Agren JJ, Vaisanen S, Hanninen O, et al. "Hemostatic factors and platelet aggregation after a fish-enriched diet or fish oil or docosahexaenoic acid supplementation." Prostaglandins Leukot Essent Fatty Acids (Oct. 1997) 57 (4-5): 419-21; https://www.sciencedirect.com/science/article/abs/pii/S095232789790421X, Available online Jun. 18, 2004.

Agren, J.J., et al., "Fatty acid composition of erythrocyte, platelet, and serum lipids in strict vegans." Lipids 30:365-369 (Apr. 1995); https://aocs.onlinelibrary.wiley.com/doi/abs/10.1007/BF02536047, First published—Apr. 1, 1995.

Agren, J.J., et al., "Fish diet, fish oil and docosahexaenoic acid rich oil lower fasting and postprandial plasma lipid levels." Eur J Clin Nutr., 50:765-771. (Nov. 1996); https://europepmc.org/article/med/8933125, Oct. 31, 1996.

Aguilar-Salinas et al., "High Prevalence of Low HDL Cholesterol Concentrations and Mixed Hyperlipidemia in a Mexican Nationwide Survey," J Lipid Res., (Aug. 2001), 42:1298-1307; https://www.jlr.org/content/42/8/1298.short, Revision received Mar. 20, 2001.

Ai M, Otokozawa S, et al., "Small dense LDL cholesterol and coronary heart disease: results from the Framingham Offspring Study." Clin. Chem. (Jun. 2010);56(6):967-976; https://academic.oup.com/clinchem/article/56/6/967/5622464 , Published Jun. 1, 2010.

Ait-Said, et al., "Inhibition by eicosapentaenoic acid of IL-1β-induced PGHS-2 expression in human microvascular endothelial cells: involvement of lipoxygenase-derived metabolites and p38 MAPK pathway." Biohimicia et Biophysica Acta, 1631:66-85 (Feb. 2003); https://www.sciencedirect.com/science/article/abs/pii/S138819810200358X, Accepted Nov. 14, 2002, Available online Dec. 4, 2002.

Albert CM, et al., Blood Levels of Long-Chain n-3 Fatty Acids and the Risk of Sudden Death. N Engl J Med 346(15):1113-1138, Apr. 2002; https://www.nejm.org/doi/full/10.1056/NEJMoa012918, Apr. 11, 2002.

Alberti K, et. al. Harmonizing the Metabolic Syndrome: A Joint Interim Statement of the International Diabetes Federation Task Force on Epidemiology and Prevention; National Heart, Lung, and Blood Institute; American Heart Association; World Heart Federation; International Atherosclerosis Society; and International Association for the Study of Obesity. Circulation. 120:1640-1645; Oct. 20, 2009.

Alderman, J.D., et al., "Effect of a modified, well-tolerated niacin regimen on serum total cholesterol, high density lipoprotein cholesterol and the cholesterol to high density lipoprotein ratio," Am. J. Cardio, 64: 725-729.A (Oct. 1989); https://www.ajconline.org/article/0002-9149(89)90754-6/fulltext, Oct. 1, 1989.

Alessandri, J-M., et al., "Estradiol favors the formation of eicosapentaenoic acid (20:5n-3) and n-3 docosapentaenoic acid (22:5n-3) from alpha-linolenic acid (18:3n-3) in SH-SY5Y neuroblastoma cells." Lipids 43:19-28 (Jan. 2008); https://link.springer.com/article/10.1007/s11745-007-3117-6, Published Oct. 3, 2007.

Allard et al. "Nutritional assessment and hepatic fatty acid composition in non-alcoholic fatty liver disease (NAFLD): a cross-sectional study." J Hepatol. Feb. 2008;48(2):300-7; https://www.sciencedirect.com/science/article/abs/pii/S0168827807005855, Available online Nov. 20, 2007.

Allred, C., et al., "PPARγ1 as a molecular target of eicosapentaenoic acid in human colon cancer (HT-29) cells." J. Nutr. 138:250-256 (Feb. 2008); https://academic.oup.com/jn/article/138/2/250/4664979, Published Feb. 1, 2008.

Almeida et al., "Effect of nebicapone on the pharmacokinetics and pharmacodynamics of warfarin in healthy subjects." Eur J Clin Pharmacol. (Oct. 2008);64(10):961-6; https://link.springer.com/article/10.1007/s00228-008-0534-2, Published Aug. 6, 2008.

Amarin Appoints Medpace as CRO for Two Phase 3 Cardiovascular Trials, published Oct. 19, 2009 (2 pages).

Amarin Corporation Announces First Patients Enrolled in Two Phase 3 Clinical Trials Assessing AMR101 for the Treatment of Cardiovascular Disease [online], Amarin Corporation, Jan. 11, 2010 [retrieved Apr. 27, 2011], Retrieved from Internet: <http://inestor.amarincorp.com/releasedetail.cfm?ReleaseID=504380> (2 pages).

Amarin Corporation, Annual Report, Jun. 24, 2010,submitted in 3 parts: Part I: Cover and pp. 1-39 (81 pages); Part II: pp. 40 through F-10 (81 pages); Part III: pp. F11-F51 (83 pages)) (245 pages total).

Amarin Corporation, Executive Informational Overview, "Neurological Disease-Focused Biopharmaceutical Opportunity," SEC filing dated Oct. 11, 2005 (99 pages).

Amarin Corporation, Globe Newswire press release, "Reduce-It™ Cardiovascular Outcomes Study of Vascepa® (icosapent ethyl) Capsules Met Primary Endpoint," Sep. 24, 2018 (4 pages).

Amarin Corporation, press release (Jan. 18, 2008)(1 page).

Amarin Presentation "Next Generation Lipid Modification in Cardiovascular Disease," (Aug. 2011)(27 pages).

Amarin Presentation "Next Generation Lipid Modification in Cardiovascular Disease," (Mar. 2010)(25 pages).

Amarin Proceeding to Phase 3 with AMR101 for Hypertriglyceridemia, published Jul. 23, 2008 (1 page).

Amarin, Next Generation Lipid Modification in Cardiovascular Disease, Investor Meetings, Nov. 2010, (http://files.shareholder.com/downloads/AMRN/0x0x417754/AA72705F-1D67-4E1D-A989-5805E5CF0244/Investor_Presentation_2010_Nov_10.pdf, accessed Jan. 6, 2015; (http://files.shareholder.com/downloads/AMRN/0x0x417754/AA72705F-1D67-4E1D-A989-5805E5CF0244/Investor_Presentation_2010_Nov_10.pdf.

Amarin's Vascepa® Briefing Document for the Endocrinologic and Metabolic Drugs Advisory Committee Meeting dated Oct. 16, 2013, (117 pages).

American Heart Association. Heart Disease and Stroke Statistics—2010 Update. Dallas, Texas: American Heart Association; 2010; Lloyd-Jones, D., Adams, R. J., Brown, T. M., Carnethon, M., Dai, S., De Simone, G., Go, A. (2010), American Heart Association Statistics Committee and Stroke Statistics Subcommittee. Executive summary: heart disease and stroke statistics—2010 update: a report from the American Heart Association. Circulation, 121(7), 948-954, https://www.ncbi.nlm.nih.gov/pubmed/20019324 , Feb. 23, 2010; Epub Dec. 17, 2009.

Anand RG, Alkadri M, Lavie CJ, Milani RV. The Role of Fish Oil in Arrhythmia Prevention. J Cardioplin Rehabil Preven., Mar./Apr. 2008; 28:92-98; https://journals.lww.com/jcrjournal/Abstract/2008/03000/The_Role_of_Fish_Oil_in_Arrhythmia_Prevention.3.aspx , Originally published Mar. 1, 2008.

Anber V, Griffin BA, McConnell M, Packard CJ, Shepherd J. Influence of plasma lipid and LDL-subfraction profile on the interaction between low density lipoprotein with human arterial wall proteoglycans. *Atherosclerosis*. Aug. 1996;124(2):261-271; https://www.sciencedirect.com/science/article/abs/pii/002191509605842X, Aug. 2, 1996.

Anderson JL, et al., ACC/AHA 2007 guidelines for the management of patients with unstable angina/non-ST-elevation myocardial infarction—executive summary. A report of the American College of Cardiology/American Heart Association Task Force on Practice Guidelines (Writing Committee to Revise the 2002 Guidelines for the Management of Patients With Unstable Angina/Non-ST-Elevation Myocardial Infarction) developed in Collaboration with the American College of Emergency Physicians, the Society for Cardiovascular Angiography and Interventions, and the Society of Thoracic Surgeons Endorsed by the American Association of Cardiovascular and Pulmonary Rehabilitation and the Society for Academic Emergency Medicine. J Am Coll Cardiol 50:652-726, Aug. 14, 2007.

Anderson TJ, et al., 2012 update of the Canadian Cardiovascular Society guidelines for the diagnosis and treatment of dyslipidemia for the prevention of cardiovascular disease in the adult. Can. J. Cardiol. Feb. 2013;29:151-167; https://www.sciencedirect.com/science/article/abs/pii/S0828282X12015103 Feb. 2013, Available online Jan. 23, 2013.

(56) References Cited

OTHER PUBLICATIONS

Anderson TJ, et al., The effect of cholesterol-lowering and antioxidant therapy on endothelium-dependent coronary vasomotion. N. Engl. J. Med. Feb. 1995;332:488-493; https://www.nejm.org/doi/full/10.1056/NEJM199502233320802, Feb. 23, 1995.
Anderson, "Lipoprotein-Associated Phospholipase A2: An Independent Predictor of Coronary Artery Disease Events in Primary and Secondary Prevention," 101 Am. J. Cardiology 23F-33F, Jun. 2008; https://www.sciencedirect.com/science/article/abs/pii/S0002914908006863, Jun. 16, 2008; Available online Jun. 10, 2008.
Ando, M., et al., "Eicosapentanoic acid reduces plasma levels of remnant lipoproteins and prevents in vivo peroxidation of LDL in dialysis patients." J. Am. Soc. Nephrol., 10:2177-2184, Oct. 1999; https://jasn.asnjournals.org/content/10/10/2177.short, Published online Oct. 1, 1999.
Ando, Y., et al., "Positional distribution of highly unsaturated fatty acids in triacyl-sn-glycerols of Artemia Nauplii enriched with docosahexaenoic acid ethyl ester." Lipids 36:733-740, Jul. 2001; https://aocs.onlinelibrary.wiley.com/doi/abs/10.1007/s11745-001-0779-4, First published Jul. 1, 2001.
Andrade, SE. et al., "Discontinuation of antihyperlipidaemic drugs, do rates reported in clinical trials reflect rates in primary care settings?" New Eng. J. Med. 332: 1125-1131. (Apr. 1995); https://www.nejm.org/doi/full/10.1056/nejm199504273321703, Apr. 27, 1995.
Andrews HE, et al., Low-density lipoproteins inhibit endotheliumdependent relaxation in rabbit aorta. Nature. May 1987;327:237-239; https://www.nature.com/articles/327237a0, Published May 21, 1987.
Angerer et al., "n-3 Polyunsaturated Fatty Acids and the Cardiovascular System", Current Opinion in Lipidology, 11(1):57-63 (Feb. 2000); https://journals.lww.com/co-lipidology/Abstract/2000/02000/n_3_Polyunsaturated_fatty_acids_and_the.9.aspx.
Anil, Eliz, "The Impact of EPA and DHA on Blood Lipids and Lipoprotein Metabolism: Influence of ApoE Genotype", Proceedings of the Nutrition Society, 66:60-68, (Feb. 2007); https://www.cambridge.org/core/journals/proceedings-of-the-nutrition-society/article/impact-of-epa-and-dha-on-blood-lipids-and-lipoprotein-metabolism-influence-of-apoe-genotype/D0D744A2217FED07F04ABB43AC5F8FA0, Published online Feb. 28, 2007.
Annex to Rule 161 Response dated Apr. 16, 2012 (4 pages).
Antman E, Anbe D, Armstrong P, et al. ACC/AHA guidelines for the management of patients with ST-elevation myocardial infarction—executive summary. A report of the American College of Cardiology/American Heart Association Task Force on Practice Guidelines (Writing Committee to revise the 1999 guidelines for the management of patients with acute myocardial infarction). J Am Coll Cardiol 44:671-719, Aug. 4, 2004.
Aoki T et al. "Experience of the use of ethyl eicosapentaenoic acid preparation (Epadel) in patients with arteriosclerosis obliterans complicated with diabetes mellitus. A study of the long-term effects on glycemic control and blood lipids," Rinsho to Kenkyu; 70:625-631. (1993) (with English translation).
Appendix A to Defendants' Invalidity Contentions, 3:14-CV-02550-MLC-DEA (D.N.J.), 478 pages (Dec. 5, 2014).
Appleton, Katherine M., et al., "Effects of n-3 long-chain polyunsaturated fatty acids on depressed mood: systematic review of published trials", Am. J. Clin. Nutr., 84(6):1308-1316, (Dec. 2006); https://academic.oup.com/ajcn/article/84/6/1308/4649114, Published Dec. 1, 2006.
Arca et al., "Treating statin-intolerant patients," Diabetes, Metabolic Syndrome and Obesity: Targets and Therapy, 4:155-156 (Apr. 28, 2011).
Armaganijan L, et al., Do Omega-3 fatty acids prevent atrial fibrillation after open heart surgery? A meta-analysis of randomized controlled trials. Clinics. 2011 (accepted for publication Jul. 19, 2011); 66(11):1923-1928.
Arrol, S. et al., "The effects of fatty acids on apolipoprotein B secretion by human hepatoma cells (HEP G2)," Atherosclerosis 150:255-264. (Jun. 2000); https://www.sciencedirect.com/science/article/abs/pii/S0021915099003743, Available online Jun. 8, 2000.
Arshad, A., et al., "Sudden cardiac death and the role of medical therapy." Progress in Cardiovascular Diseases, vol. 50, No. 6, 420-438, (May/Jun. 2008); https://www.sciencedirect.com/science/article/abs/pii/S0033062007001314, Available online May 9, 2008.
Arterburn, L., et al., "Distribution, interconversion, and dose response of n-3 fatty acids in humans." Am J Clin Nutr., 83:1467S-76S (Jun. 2006); https://academic.oup.com/ajcn/article/83/6/1467S/4633217, Published: Jun. 1, 2006.
Asahara, EPA Products What is the Clinical Significance of Epadel? Obesity and Diabetes 10(6):903-905 (2011) (with English translation).
Asano, M., et al., "Eicosapentaenoic acid inhibits vasopressin-activated Ca2q influx and cell proliferation in rat aortic smooth muscle cell lines." European Journal of Pharmacology 379:199-209 (Aug. 1999); https://www.sciencedirect.com/science/article/abs/pii/S0014299999004768, Available online Jan. 10, 2000.
Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (Apr. 1997); https://bpspubs.onlinelibrary.wiley.com/doi/full/10.1038/sj.bjp.0701047, First published:Feb. 17, 2009.
ASCEND Study Collaborative Group. Effects of n-3 fatty acid supplements in diabetes mellitus. N Engl J Med, 379(16):1540-1550 (publication date Oct. 18, 2018; epublication date Aug. 26, 2018).
Ascenta Health "Fish Oil as Triglycerides vs. Ethyl Esters: Why this Matters." (2015)(14 pages); Not found.
Astarita et al., "Targeted lipidomics strategies for oxygenated metabolites of polyunsaturated fatty acids," Biochim Biophys Acta, 1851(4):456-468 (Apr. 2015); https://www.sciencedirect.com/science/article/abs/pii/S1388198114002510, Available online Dec. 5, 2014.
Atorvastatin Package Leaflet, Reg. No. LSR-005205/08, Sep. 30, 2016 [retrieved Sep. 30, 2016] retrieved from Internet: academ-clinic.ru/drugs/atorvastatin (6 pages).
ATP III guidelines, NIH publication No. 01-3305 (2001).(6 pages).
Attie AD, et al., "Relationship between stearoyl-CoA desaturase activity and plasma triglycerides in human and mouse hypertriglyceridemia," J. Lipid Res. 2002;43:1899-907; https://www.jlr.org/content/43/11/1899.short, First Published on Aug. 16, 2002.
Ault, "Prescription omega-3 fatty acid formulation approved," OB.GYN.NEWS, (Jan. 15, 2005).
Aung T, et al., Associations of omega-3 fatty acid supplement use with cardiovascular disease risks: Meta-analysis of 10 trials involving 77917 individuals. JAMA Cardiol 3:225-34 (publication date Mar. 1, 2018; epublication date Jan. 31, 2018).
Avandia [package insert]. Research Triangle Park, NC: GlaxoSmithKline; 2011.(45 pages).
Avery et al., "Upper Gastrointestinal System," Integrating Therapeutic and Complementary Nutrition, Edited by Mary Marian, CRC Press (2006)(14 pages); https://www.routledge.com/Integrating-Therapeutic-and-Complementary-Nutrition-1st-Edition/Marian-Williams-Mullen-Bowers/p/book/9780849316128, This is a book chapter.
Aviram M, et al., Atorvastatin and gemfibrozil metabolites, but not the parent drugs, are potent antioxidants against lipoprotein oxidation. Atherosclerosis. Jun. 1998; 138(2):271-280; https://www.sciencedirect.com/science/article/abs/pii/S002191509800032X, Available online Jun. 24, 1998.
Ayton, et al., "A pilot open case series of Ethyl-EPA supplementation in the treatment of anorexia nervosa," Prostaglandins, Leukotrienes and Essential Fatty Acids 71, pp. 205-209. (Oct. 2004); https://www.sciencedirect.com/science/article/abs/pii/S0952327804000584, Available online May 18, 2004.
Ayton, et al., "Rapid improvement of severe anorexia nervosa during treatment with ethyl-eicosapentaenoate and micronutrients," European Psychiatry 19, pp. 317-319. (Aug. 2004); https://s3.amazonaws.com/academia.edu.documents/45835056/ayton_case.pdf?response-content-disposition=inline%3B%20filename%3DRapid_improvement_of_severe_anorexia_ner.pdf&X-Amz-Algorithm=AWS4-HMAC-SHA256&X-Amz-Credential=AKIAIWOWYYGZ2Y53UL3A%2F20200317%2Fus-east-1%2Fs3%2Faws4_request&X-Amz-Date=20200317T203439Z&X-Amz-

(56) References Cited

OTHER PUBLICATIONS

Expires=3600&X-Amz-SignedHeaders=host&X-Amz-Signature= 03e3af4b62a77d3e420dcefd567640b3b3549fd24910ce283bbde2b4 1fc5edd0, No publication date available, other versions available here: https://scholar.google.com/scholar?cluster=4862195463092004751 &hl=en&as_sdt=1, 14.

Baigent, C., et al., "Efficacy and safety of cholesterol-lowering treatment: prospective meta-analysis of data from 90,056 participants in 14 randomised trials of statins." Lancet; 366:1267-1278. (Oct. 2005); https://www.thelancet.com/journals/lancet/article/ PIIS0140673605673941/fulltext, Published: Sep. 27, 2005.

Baldwin RM, et al., Increased omeprazole metabolism in carriers of the CYP2C19*17 allele; a pharmacokinetic study in healthy volunteers. Br. J. Clin. Pharmacol. May 2008 65 (5): 767-74; https:// bpspubs.onlinelibrary.wiley.com/doi/full/10.1111/j.1365-2125.2008. 03104.x, First published:Feb. 20, 2008.

Baldwin SJ, Clarke SE, Chenery RJ. Characterization of the cytochrome P450 enzymes involved in the in vitro metabolism of rosiglitazone. Br. J. Clin. Pharmacol. Sep. 1999;48:424-432; https://www.ncbi. nlm.nih.gov/pmc/articles/PMC2014317/.

Balfour et al., "Rosiglitazone," Drugs, 57(6):921-930 (Jun. 1999); https://link.springer.com/article/10.2165/00003495-199957060- 00007, published Oct. 10, 2012.

Balk, E.M., et al., "Effects of omega-3 fatty acids on serum markers of cardiovascular disease risk: a systematic review. Atherosclerosis." 189:19-30. (Nov. 2006); https://www.sciencedirect.com/science/ article/abs/pii/S0021915006000694, Available online Mar. 10, 2006.

Ballantyne CM, et al., Efficacy and safety of eicosapentaenoic acid ethyl ester (AMR 101) therapy in statin-treated patients with persistent high triglycerides (from the ANCHOR study). Am J Cardiol Oct. 2012 110 (7): 984-92; https://www.sciencedirect.com/ science/article/abs/pii/S0002914912014324, Available online Jul. 20, 2012.

Ballantyne et al., "Abstract 15071: AMR101 Lowers Triglycerides, Atherogenic Lipoprotein, Phospholipase $A_2$, and High-sensitivity C-reactive Protein Levels in Patients with High Triglycerides and on Background Statin Therapy (the ANCHOR Study)," Circulation, Lippincott Williams and Wilkins, vol. 124, No. 21, Suppl., Nov. 22, 2011.

Ballantyne et al., Effects of icosapent ethyl on lipoprotein particle concentration and the fatty acid desaturation index in statiotreated patients with persistent high triglycerides (the ANCHOR study), Journ. Clin. Lipidology, 2013, 7(3):270-271; https://www.sciencedirect. com/science/article/pii/S1933287414004085, Available online Nov. 29, 2014.

Ballantyne et al., Influence of low-high density lipoprotein cholesterol and elevated triglyceride on coronary heart disease events and response to simvastatin therapy in 4S, Circulation, 104:3046-3051 (Dec. 2001); https://www.ahajournals.org/doi/full/10.1161/hc5001. 100624, Originally published Dec. 18, 2001.

Bang HO, Dyerberg J. "Plasma lipids and Lipoproteins in Greenlandic west coast Eskimos" Acta Med Scand, 192:85-94. (Jul./Aug. 1972); https://onlinelibrary.wiley.com/doi/abs/10.1111/j.0954-6820.1972. tb04782.x, First published: Jan./Dec. 1972.

Banga, A., et al., "Adiponectin translation is increased by the PPARγ agonists pioglitazone and ω-3 fatty acids." Am J Physiol Endocrinol Metab 296:480-489 (Mar. 2009); https://journals. physiology.org/doi/full/10.1152/ajpendo.90892.2008, Mar. 1, 2009.

Bangham et al., "Diffusion of univalent ions across the lamellae of swolloen phospholipids." J. Mol. Biol. (Aug. 1965) 13(1):238-252; https://www.sciencedirect.com/science/article/pii/ S0022283665800936, Available online May 7, 2009.

Bansal S, et al., "Fasting Compared With Nonfasting Triglycerides and Risk of Cardiovascular Events in Women," JAMA, 298:309- 316 (Jul. 2007); https://jamanetwork.com/journals/jama/article- abstract/208018, Jul. 18, 2007.

Barter et al., "Effectiveness of Combined Statin Plus Omega-3 Fatty Acid Therapy for Mixed Dyslipidemia." Am. J. Cardiol. 102(8):1040- 1045 (Oct. 15, 2008).

Basu, A., et al., "Dietary Factors That Promote or Retard Inflammation." Arterioscler. Thromb. Vasc. Biol. 26:995-1001 (May 2006); https:// www.ahajournals.org/doi/full/10.1161/01.atv.0000214295.86079. d1, Originally publishedFeb. 16, 2006.

Baynes JW, Role of oxidative stress in development of complications in diabetes. Diabetes. Apr. 1991;40(4):405-412; https://diabetes. diabetesjournals.org/content/40/4/405.short, Published in print Apr. 1, 1991.

Bays HE et al., "Prescription omega 3 fatty acids and their lipid effects: physiologic mechanisms of action and clinical implications," Expert Rev Cardiovasc Ther., 6:391-409. (Mar. 2008); https://www.tandfonline.com/doi/full/10.1586/14779072.6.3.391, Published online: Jan. 10, 2014.

Bays HE et al., "AMR101, a Pure Ethyl Eicosapentaenoic Acid Omega-3 Fatty Acid: Effects on Inflammation-Associated End POInts from the Marine and Anchor Studies," Journ. Clin. Lipid., vol. 6 No. 3, p. 279 (May 30, 2012), abstract #150.

Bays HE et al., Effects of prescription omega-3-acid ethyl esters on non-high-density lipoprotein cholesterol when coadministered with escalating doses of atorvastatin; Mayo Clinic Proc. 85(2):122-128 (Feb. 2010).

Bays HE, Ballantyne CM, Braeckman RA, Stirtan WG, Soni PN. Icosapent ethyl, a pure ethyl ester of eicosapentaenoic acid: effects on circulating markers of inflammation from the MARINE and ANCHOR studies. Am. J. Cardiovasc. Drugs. Feb. 2013;13(1):37- 46; https://link.springer.com/article/10.1007/s40256-012-0002-3, Published Jan. 17, 2013.

Bays HE, Braeckman RA, Ballantyne CM, et al. Icosapent ethyl, a pure EPA omega-3 fatty acid: Effects on lipoprotein particle concentration and size in patients with very high triglyceride levels (the MARINE study). J. Clin. Lipidol. Nov./Dec. 2012;6:565-572; https:// www.sciencedirect.com/science/article/abs/pii/ S1933287412002735, Available online Jul. 24, 2012.

Bays HE, Safety considerations with omega-3 fatty acid therapy. Am. J. Cardiol. Mar. 2007 99 (6A): 35C-43C; https://www. sciencedirect.com/science/article/abs/pii/S0002914906022387, Available online Nov. 28, 2006.

Bays, H., Clinical Overview of Omacor: A Concentrated Formulation of Omega-3 Polyunsaturated Fatty Acids, Am J Cardiol.; 98[suppl]:71i-76i (Aug. 2006); https://www.sciencedirect.com/ science/article/abs/pii/S0002914905021922, Available online May 30, 2006.

Bays, H., "Rationale for Prescription Omega-3-Acid Ethyl Ester Therapy for Hypertriglyceridemia: A Primer for Clinicians," Drugs of Today, 44(3); 205-246. (Mar. 2008); https://journals.prous.com/ journals/servlet/xmlxsl/pk_journals.xml_summary_pr?p_JournalId= 4&p_RefId=1166387&p_IsPs=N.

Bays, H.E., Eicosapentaenoic Acid Ethyl Ester (AMR101) Therapy in Patients With Very High Triglyceride Levels (from the Multicenter, plAcebo-controlled, Randomized, double-blINd, 12-week study with an open-label Extension [MARINE] Trial) Am J Cardiol;108:682-690. (Sep. 2011); https://www.sciencedirect.com/ science/article/abs/pii/S0002914911015992, Available online Jun. 16, 2011.

Bays, H.E., et al., "Long-term up to 24-month efficacy and safety of concomitant prescription omega-3-acid ethyl esters and simvastatin in hypertriglyceridemic patients." Curr Med Res Opin.; 26:907-915. (Apr. 2010); https://www.tandfonline.com/doi/abs/10.1185/ 03007991003645318, Published online: Feb. 15, 2010.

Beal, M.F., Annals of Neurology, vol. 38, No. 3, "Aging, Energy, and Oxidative Stress in Neurodegenerative Diseases", pp. 357-366, (Sep. 1995); https://onlinelibrary.wiley.com/doi/abs/10.1002/ana. 410380304, First published: Sep. 1995.

Beaumont et al., Design of Ester Prodrugs to Enhance Oral Absorption of Poorly Permeable Compounds: Challenges to the Discovery Scientist, Current Drug and Metabolism. (Dec. 2003) 4:461-485; https://www.ingentaconnect.com/content/ben/cdm/2003/00000004/ 00000006/art00001, Publication date: Dec. 1, 2003.

Becker LB, et al., AHA Consensus Statement: Primary Outcomes for Resuscitation Science Studies: A Consensus Statement From the American Heart Association. Circulation 2011; CIR. 0b013e3182340239 published online before print Oct. 3, 2011, doi:10.1161/CIR. 0b013e3182340239.

(56) References Cited

OTHER PUBLICATIONS

Belarbi et al., "A process for high yield and scaleable recovery of high purity eicosapentaenoic acid esters from microalgae and fish oil," Enzyme and Microbail Technology 26:516-529 (Apr. 2000); https://www.sciencedirect.com/science/article/pii/S0032959200001266, Available online Jun. 23, 2000, website says article is retracted.

Belger et al., "Assessment of prefrontal activation by infrequent visual targets and non-target noval stimuli in schisophrenia: a function MRI study," Presented at the 9th Biennial winter workshop on schizophrenia, Davos, Switzerland, Feb. 7-13, 1998, Abstract in Schizophrenia Research. vol. 29. No. 1/02, Jan. 1998.

Belikov, Pharmaceutical Chemistry in Two Parts, 1/General Pharmaceutical Chemistry 43-47 (1993) (with English translation)(9 pages); Book: https://www.biblio.com/book/belikov-vg-pharmaceutical-chemistry-volume-1/d/1262927120, Published in 1993.

Belmaker et al., "Addition of Omega-3 Fatty Acid to Maintenance Medication Treatment for Recurrent Unipolar Depressive Disorder," Am. J. Psychiatry, 159:477-479 (Mar. 2002); https://ajp.psychiatryonline.org/doi/full/10.1176/appi.ajp.159.3.477, Published Online:Mar. 1, 2002.

Belmaker, et al., "Omega-3 Eicosapentaenoic Acid in Bipolar Depression: Report of a Small Open-Label Study," J Clin Psychiatry; 66:726-729. (Jun. 2005); https://europepmc.org/article/med/15960565, May 31, 2005.

Bender NK, et al., Effects of marine fish oils on the anticoagulation status of patients receiving chronic warfarin therapy. J. Thromb. Thrombolysis Jul. 5, 1998 (3): 257-61.

Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (Oct. 1996); https://www.sciencedirect.com/science/article/abs/pii/S0952327896900101, Accepted Oct. 3, 1996. Available online Jun. 21, 2004.

Benn et al., Improving Prediction of Ischemic Cardiovascular Disease in the General Population Using Apolipoprotein B: The Copenhagen City Heart Study, 27 Arteriosclerosis, Thrombosis, & Ascular Biology 661 (Mar. 2007); https://www.ahajournals.org/doi/full/10.1161/01.ATV.0000255580.73689.8e, Originally published Dec. 14, 2006.

Bennett et al., "Treatment of IgA nephropathy with eicosapentanoic acid (EPA): a two-year prospective trial [Abstract Only]." Clin. Nephrol. 31 (3):128-131 (Mar. 1989); https://www.ahajournals.org/doi/full/10.1161/01.ATV.0000255580.73689.8e, Originally published Dec. 14, 2006.

Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J.; 343(Pt 1):191-197. (Oct. 1999); https://www.ncbi.nlm.nih.gov/pubmed/10493929, Oct. 1, 1999.

Berglund L, Brunzell JD, Goldberg AC, et al. Evaluation and treatment of hypertriglyceridemia: an endocrine society clinical practice guideline. J. Clin. Endocrinol. Metab. Sep. 2012 97 (9): 2969-89; https://academic.oup.com/jcem/article/97/9/2969/2536709, Published: Sep. 1, 2012.

Berliner JA, Watson AD. A role for oxidized phospholipids in atherosclerosis. N. Engl. J. Med. Jul. 2005;353(1):9-11; https://www.nejm.org/doi/pdf/10.1056/nejmp058118, Jul. 7, 2005.

Bertelsen M, Anggard EE, Carrier MJ. Oxidative stress impairs insulin internalization in endothelial cells in vitro. Diabetologia. May 2001;44(5):605-613; https://link.springer.com/article/10.1007/s001250051667, Published: Apr. 2001.

Betteridge, D.J., "Diabetic dyslipidaemia: past, present and future." Practical Diabetes Int, 21(2): 78-85. (Mar. 2004); https://onlinelibrary.wiley.com/doi/full/10.1002/pdi.593, First published:Mar. 26, 2004.

Bhatt DL, Eagle KA, Ohman EM, et al. Comparative determinants of 4-year cardiovascular event rates in stable outpatients at risk of or with atherothrombosis. JAMA 304(12):1350-7 (publication date Sep. 22, 2010; epublication date Aug. 30, 2010).

Bhatt DL, et al. Rationale and design of REDUCE-IT: Reduction of Cardiovascular Events with Icosapent Ethyl-Intervention Trial. Clin Cardiol 40:138-48 (publication date Mar. 2017; epublication date Mar. 15, 2017).

Bhatt DL, et al., Antiplatelet and anticoagulation therapy for acute coronary syndromes. Circ Res 114(12):1929-43 (publication date Jun. 6, 2014).

Bhatt DL, et al., CHARISMA Investigators. Clopidogrel and aspirin versus aspirin alone for the prevention of atherothrombotic events. N Engl J Med. 354(16):1706-1717 (publication date Apr. 20, 2006; epublication date Mar. 12, 2006).

Bhatt DL, et al.; REACH Registry Investigators. International prevalence, recognition and treatment of cardiovascular risk factors in outpatients with atherothrombosis. JAMA. 295(2):180-189 (publication date Jan. 11, 2006).

Bhatt et al., "Cardiovascular Risk Reduction with Icosapent Ethyl for Hypertriglyceridemia," N. Eng. J. Med., Nov. 10, 2018 (epub ahead of print)(12 pages)(downloaded from nejm.org on Nov. 13, 2018 at https://www.nejm.org/doi/full/10.1056/NEJMoa1812792).

Bild et at., "Multi-Ethnic Study of Atherosclerosis: objectives and design," Am J Epidemiol 156(9):871-81 (Nov. 1, 2002).

Billman et al., "Effects of dietary omega-3 fatty acids on ventricular function in dogs with healed myocardial infarctions: in vivo and in vitro studies." Am. J. Physiol Heart Circ. Physiol., 298:H1219-H1228 (Jan. 22, 2010).

Black et al., "Effect of intravenous eicosapentaenoic acid on cerebral blood flow, edema, and brain prostaglandins in ischemic gerbils", Prostaglandins, 28(4), pp. 545-546. (Oct. 1984); https://www.sciencedirect.com/science/article/pii/0090698084902430, Accepted Sep. 4, 1984, Available online Dec. 1, 2003.

Blankenhorn D.H. et al., "Beneficial effects of combined colestipol-niacin therapy on coronary atherosclerosis and coronary venous bypass grafts." JAMA 257: 3233-3240. (Jun. 1987); https://jamanetwork.com/journals/jama/article-abstract/366621 , Jun. 19, 1987.

Block, R.C., et al., "EPA and DHA in blood cell membranes from acute coronary syndrome patients and controls." Atherosclerosis, 197(2):821-828 (Apr. 2008); https://www.sciencedirect.com/science/article/abs/pii/S0021915007004765, Available online Sep. 17, 2007.

Blumenthal, RS, Overview of the Adult Treatment Panel (ATP III) Guidelines, Advanced Studies in Medicine, 2:148-157 (Mar. 2002); https://pdfs.semanticscholar.org/0c7c/7efd16d0297283b5d6a083616dc76c3af837.pdf.

Boden WE, et al., "Niacin in patients with low hdl cholesterol levels receiving intensive statin therapy," N. Engl. J. Med. Dec. 2011;365:2255-2267; https://www.nejm.org/doi/pdf/10.1056/NEJMoa1107579, Dec. 15, 2011 (PDF of print article).

Bonaa, KH et al., Docosahexaenoic and Eicosapentaenoic acids in plasma phospholipids are divergently associated with high density lipoprotein in humans, Arterioscler. Thromb. Vasc. Biol.;12;675-681 (Jun. 1992); https://www.ahajournals.org/doi/abs/10.1161/01.ATV.12.6.675, Originally published Jun. 1, 1992.

Bonnet et al., "Comparative Effects of 10-mg Versus 80-mg Atorvastatin on High-Sensitivity C-Reactive Protein in Patients with Stable Coronary Artery Disease: Results of the CAP (Comparative Atorvastatin Pleiotropic Effects) Study," Clinical Therapeutics. 30(12):2298-2313 (Dec. 2008); https://www.sciencedirect.com/science/article/abs/pii/S014929180800458X, Available online Jan. 22, 2009.

Borchman D, et al., The dual effect of oxidation on lipid bilayer structure. Lipids. Apr. 1992;27(4):261-265; https://link.springer.com/article/10.1007/BF02536472, Published Apr. 1992.

Bordin et al., "Effects of fish oil supplementation on apolipoprotein B100 production and lipoprotein metabolism in normolipidaemic males," Eur. J. Clin. Nutr. 52: 104-9 (Feb. 1998); https://www.nature.com/articles/1600522, Published Mar. 23, 1998.

Borow et al., "Biologic plausibility, cellular effects, and molecular mechanisms of eicosapentaenoic acid (EPA) in atherosclerosis," Atherosclerosis, 242(1):357-66 (Sep. 2015); https://www.sciencedirect.com/science/article/pii/S0021915015300551, Available online Jul. 22, 2015.

Borthwick et al., "The effects of an omega-3 ethyl ester concentrate on blood lipid concentrations in pateitns with hyperlipidemia," Clin.

(56) References Cited

OTHER PUBLICATIONS

Drug Investig. (1998) 15(5): 397-404; https://link.springer.com/article/10.2165/00044011-199815050-00004, Published: Aug. 28, 2012.

Bossaller C, et al., Impaired muscarinic endothelium-dependent relaxation and cyclic guanosine 5'-monophosphate formation in atherosclerotic human coronary artery and rabbit aorta. J. Clin. Invest. Jan. 1987;79:170-174; https://www.jci.org/articles/view/112779, First published Jan. 1, 1987.

Bousserouel, S., et al., "Different effects of n-6 and n-3 polyunsaturated fatty acids on the activation of rat smooth muscle cells by interleukin-1beta." J. Lipid Res. 44:601-611 (Mar. 2003); https://www.jlr.org/content/44/3/601.short, First published on Jan. 1, 2003.

Bousserouel, S., et al., "Modulation of cyclin D1 and early growth response factor-1 gene expression in interleukin-1 beta-treated rat smooth muscle cells by n-6 and n-3 polyunsaturated fatty acids." Eur. J. Biochem. 271:4462-4473 (Nov. 2004); https://febs.onlinelibrary.wiley.com/doi/full/10.1111/j.1432-1033.2004.04385.x, First published:Nov. 19, 2004.

Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91 (Jun. 2004); https://academic.oup.com/ajcn/article/79/6/983/4690259, Published: Jun. 1, 2004.

Braeckman et al., "Abstract 18549: Effects of AMR101, a Pure Eicosapentaenoic Omega-3 Fatty Acid, on the Fatty Acid Profile in Plasma and Red Blood Cells in Statin-Treated Patients with Persistent High Triglycerides—Results from the ANCHOR study," Circulation 126(21S):A15071 (Nov. 20, 2012)(2 pages).

Braeckman et al., "Effect of Concomitant Icosapent Ethyl (Eicosapentaenoic Acid Ethyl Ester) on Pharmacokinetics of Atorvastatin," Clinical Drug Investigation. (Jan. 2015) (3)45-51; https://link.springer.com/article/10.1007/s40261-014-0252-8, Published: Dec. 4, 2014.

Braeckman RA, et al., Icosapent ethyl, a pure EPA omega-3 fatty acid: effects on plasma and red blood cell fatty acids in patients with very high triglyceride levels (results from the MARINE study). Prostaglandins Leukot Essent Fatty Acids. Sep. 2013;89(4): 195-201; https://www.sciencedirect.com/science/article/abs/pii/S0952327813001555, Available online Jul. 31, 2013.

Braeckman RA, Stirtan WG, Soni PN. Pharmacokinetics of eicosapentaenoic acid in plasma and red blood cells after multiple oral dosing with AMR101 (ethyleicosapentaenoic acid) in healthy subjects [abstract]. Presented at: Congress of the International Society for the Study of Fatty Acids and Lipids, Vancouver, Canada, May 26-30, 2012.

Braeckman RA, Stirtan WG, Soni PN. Pharmacokinetics of eicosapentaenoic acid in plasma and red blood cells after multiple oral dosing with icosapent ethyl in healthy subjects. Clin. Pharmacol. Drug Dev. Mar. 2014 (epub Oct. 22, 2013); 3:101-108.

Braunersreuther V, et al., A novel rantes antagonist prevents progression of established atherosclerotic lesions in mice. Arterioscler. Thromb. Vasc. Biol. Jun. 2008;28:1090-1096; https://www.ahajournals.org/doi/full/10.1161/ATVBAHA.108.165423, Originally publishedApr. 3, 2008.

Breslow, J., "n-3 Fatty acids and cardiovascular disease." Am J Clin Nutr., 83:1477S-82S (Jun. 2006); https://academic.oup.com/ajcn/article/83/6/1477S/4633237, Published: Jun. 1, 2006.

Brinton EA, et al., Effects of AMR101 on lipid and inflammatory parameters in patients with diabetes mellitus-2 and residual elevated triglycerides (200-500 mg/dl) on statin therapy at LDL-C goal: the ANCHOR study.[abstract 629-P] Diabetes. 2012;61 (suppl 1):A159-A160; see also European Heart Journal (vol. 33, pp. 280-280). Great Clarendon St, Oxford OX2 6DP, England: Oxford Univ Press.

Brinton et al., "Effects of icosapent ethyl on lipid and inflammatory parameters in patients with diabetes mellitus-2, residual elevated triglycerides (200-500 mg/dL), and on statin therapy at LDL-C goal: the ANCHOR study," Cardiovasc. Diabetol. Jul. 9, 2013;12:100. doi: 10.1186/1475-2840-12-100.

Brossard, N., et al., "Retroconversion and metabolism of [13C]22:6n-3 in humans and rats after intake of a single dose of [13C]22:6n-3-3-triacyylglycerols." Am. J. Clin. Nutr. 64:577-86 (Oct. 1996).

Brouwer, I.A., et al., "Effect of fish oil on ventricular tachyarrhythmia and death in patients with implantable cardioverter defibrillators." JAMA. 295(22):2613-2619 (Jun. 2006); https://jamanetwork.com/journals/jama/article-abstract/202999, Jun. 14, 2006.

Brovkovych V, et al., Nitric oxide release from normal and dysfunctional endothelium. J. Physiol. Pharmacol. Dec. 1999;50:575-586; https://europepmc.org/article/med/10639008, Nov. 30, 1999.

Brown et al., Simvastatin and Niacin, Antioxidant Vitamins, or the Combination for the Prevention of Coronary Disease, N Engl J Med, vol. 345, No. 22, 1583-1592 (Nov. 29, 2001).

Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (Jan. 1999); https://www.ahajournals.org/doi/full/10.1161/01.ATV.19.1.106, Originally published Jan. 1, 1999.

Brown, A. J., et al., "Persistent changes in the fatty acid composition of erythrocyte membranes after moderate intake of n-3 polyunsaturated fatty acids: study design and implications." Am.J. Clin. Nutri. 54:668-73(Oct. 1991); https://academic.oup.com/ajcn/article-abstract/54/4/668/4694264, Published: Oct. 1, 1991.

Brown, G., et al., "Regression of coronary artery-disease as a result of intensive lipid-lowering therapy in men with high levels of apolipoprotein," B., N. Engl. J. Med. 323: 1289-1298. (Nov. 1990); https://www.nejm.org/doi/full/10.1056/nejm199011083231901, Nov. 8, 1990 (PDF of print article).

Brownlee M. Biochemistry and molecular cell biology of diabetic complications. Nature. Dec. 2001; 414(6865):813-820; https://www.nature.com/articles/414813a, Published: Dec. 13, 2001.

Bryhn, M., et al., "The bioavailability and pharmacodynamics of different concentrations of omega-3 acid ethyl esters." Prostaglandins, Leukotrienes and Essential Fatty Acids 75:19-24 (Jul. 2006); https://www.sciencedirect.com/science/article/abs/pii/S0952327806000536, Available online Jun. 27, 2006.

Budavari, S., Editor, "The Merck Index", Merck & Co., Inc., p. 725 item 4511 and p. 279 and item 2417 (1989); https://www.amazon.com/Merck-Index-Eleventh-Susan-Budavari/dp/B0036FBD2K, no specific date.

Budoff, "Triglycerides and Triglyceride-Rich Lipoproteins in the Causal Pathway of Cardiovascular Disease," Am. J. Cardiol., 118(1):138-45 (Jul. 1, 2016).

Bunting et al. "Depression in Parkinson's Disease". J Neurosci Nurs.; 23(3):158-164. (Abstract Only) (Jun. 1991); https://europepmc.org/article/med/1831480 , May 31, 1991.

Burdge, G.C., et al., "Eicosapentaenoic and docosapentaenoic acids are the principal products of a-linolenic acid metabolism in young men." British Journal of Nutrition 88:355-363 (Oct. 2002); https://www.cambridge.org/core/journals/british-journal-of-nutrition/article/eicosapentaenoic-and-docosapentaenoic-acids-are-the-principal-products-of-linolenic-acid-metabolism-in-young-men/602A731B990E9FE14F22F0ADD63E77D4 , Oct. 2002, Published online Mar. 9, 2007.

Burdge, G.C., et al., "Lack of effect of meal fatty acid composition on postprandial lipid, glucose and insulin responses in men and women aged 50-65 years consuming their habitual diets." British Journal of Nutrition, 96:489-500 (Sep. 2006); https://www.cambridge.org/core/journals/british-journal-of-nutrition/article/lack-of-effect-of-meal-fatty-acid-composition-on-postprandial-lipid-glucose-and-insulin-responses-in-men-and-women-aged-5065-years-consuming-their-habitual-diets/1031BE7402ED8256F1E355907E2AE159, Sep. 2006, Published online Feb. 19, 2008.

Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (Jul. 2007); https://www.cambridge.org/core/journals/british-journal-of-nutrition/article/lack-of-effect-of-meal-fatty-acid-composition-on-postprandial-lipid-glucose-and-insulin-

(56) References Cited

OTHER PUBLICATIONS responses-in-men-and-women-aged-5065-years-consuming-their-habitual-diets/1031BE7402ED8256F1E355907E2AE159, Sep. 2006. Published online Feb. 19, 2008.

Burr ML, Sweetham PM, Fehily AM. Diet and reinfarction. Eur Heart J 15:1152-1153, Aug. 1994; https://www.ncbi.nlm.nih.gov/pubmed/7988613.

Burr, M. L., et al., "Effects of changes in fat, fish and fibre intakes on death and myocardial reinfarction: Diet and reinfarction trial." The Lancet, 2(8666):757-61 (Sep. 1989); https://www.sciencedirect.com/science/article/pii/S0140673689908283 , Sep. 30, 1989. Available online Sep. 24, 2003.

Buse JB, et al. Primary prevention of cardiovascular diseases in people with diabetes mellitus: a scientific statement from the American Heart Association and the American Diabetes Association. Diabetes Care. 2007;30: 162-172; https://www.ahajournals.org/doi/full/10.1161/circulationaha.106.179294, Originally published Dec. 27, 2006.

Calabresi, L., et al., "Omacor in familial combined hyperlipidemia: effects on lipids and low density lipoprotein subclasses." Atherosclerosis 148:387-396 (Feb. 2000); https://www.sciencedirect.com/science/article/abs/pii/S0021915099002671, Available online Feb. 2, 2000.

Calder PC, Omega-3 Fatty Acids and Inflammatory Processes. Nutrients 2(3):355-374, Mar. 2010 (epub Mar. 18, 2010); https://onlinelibrary.wiley.com/doi/full/10.1002/mnfr.201100710, First published:Jul. 4, 2012.

Calder PC, The role of marine omega-3 (n-3) fatty acids in inflammatory processes, atherosclerosis and plaque stability. Mol. Nutr. Food Res. Jul. 2012;56(7):1073-1080.

Campos, H. et al., "Lowdensity lipoprotein size, pravastatin treatment, and coronary events." JAMA, 286:1468-1474 (Sep. 2001); https://jamanetwork.com/journals/jama/article-abstract/194223, Sep. 26, 2001.

Canner P.L. et al., "Fifteen year mortality in Coronary Drug Project patients: long-term benefit with niacin," J. Am. Coll. Cardiol. 8. 1245-1255. (Dec. 1986); http://www.onlinejacc.org/content/8/6/1245.abstract, Accepted Jun. 6, 1986.

Cannon CP, et al. Intensive versus moderate lipid lowering with statins after acute coronary syndromes. N Engl J Med 350(15):1495-1504 (publication date Apr. 8, 2004; epublication date Mar. 8, 2004).

Cannon CP, et al.; IMPROVE-IT Investigators. "Ezetimibe added to statin therapy after acute coronary syndromes." *N Engl J Med.* 372:2387-2397. (Jun. 18, 2015/epub Jun. 3, 2015).

Cao H, et al., Omega-3 Fatty Acids in the Prevention of Atrial Fibrillation Recurrences after Cardioversion: A Meta-analysis of Randomized Controlled Trials. Intern. Med. 2012 (epub Sep. 15, 2012); 51:2503-2508.

Cao, et al., "Cloning, Expression, and Chromosomal Locatlization . . . ", Genomics, 49:327-331, (Apr. 15, 1998).

Cao, J., et al., "Incorporation and Clearance of Omega-3 Fatty Acids in Erythrocyte Membranes and Plasma Phospholipids." Clinical Chemistry 52(12):2265-2272 (Dec. 2006); https://academic.oup.com/clinchem/article/52/12/2265/5626765, Published: Dec. 1, 2006.

Capuzzi, DM et al., "Efficacy and safety of an extended-release niacin (Niaspan): a long-term study." Am. J. Cardiol. 82: 74U-81U. (Dec. 17, 1998).

Carlson, L.A. & Rosenhamer G., "Reduction of mortaility in the Stockholm Ischaemic Heart Disease Secondary Prevention Study by combined treatment with clofibrate and nicotinic acid." Acta Med. Scand. 223, 405-418 (1988); https://pubmed.ncbi.nlm.nih.gov/3287837/.

Carlson, L.A., "Nicotinic acid: the broad spectrum lipid drug. A 50th Anniversary review", J. Int. Med., 258:94-114, (Aug. 2005); https://onlinelibrary.wiley.com/doi/full/10.1111/j.1365-2796.2005.01528.x, First published:Jul. 14, 2005.

Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390 (Feb. 2007); https://academic.oup.com/jn/article/137/2/384/4664551, Published: Feb. 1, 2007.

Carrero, J.J et al. "Efectos cardiovasculares de los acidos grasos omega-3 y alternativas para incrementar su ingesta," Nutricion Hospitalaria. (2005) (1) 63-69 [with English abstract]; http://scielo.isciii.es/pdf/nh/v20n1/alimentos1.pdf (PDF of print article), Acceptado: 7-VI-2004.

Carroll, D.N., et al., "Evidence for the Cardioprotective Effects of Omega-3 Fatty Acids." Ann Pharmacother., 36:1950-6 (Dec. 2002); https://journals.sagepub.com/doi/abs/10.1345/aph.1A314, First Published Dec. 1, 2002.

Carulli et al., "Chenodeoxycholic acid and ursodeoxycholic acid effects in endogenous hypertriglyceridemias. A controlled double-blind trial." J. Clin. Pharmacol., 21(10):436-42 (Oct. 1981); https://accp1.onlinelibrary.wiley.com/doi/abs/10.1002/j.1552-4604.1981.tb01746.x, First published: Oct. 1981.

Caughey GE, et al., The effect on human tumor necrosis factor $\alpha$ and interleukin $1\beta$ production of diets enriched in n-3 fatty acids from vegetable oil or fish oil. Am J Clin Nutr. Jan. 1996;63:116-122.

Cavender MA, et al; REACH Registry Investigators. Impact of diabetes mellitus on hospitalization for heart failure, cardiovascular events, and death: outcomes at 4 years from the reduction of atherothrombosis for continued health (REACH) registry. *Circulation.* 132(10):923-931 (publication date Sep. 8, 2015; epublication date Jul. 7, 2015).

Cawood AL, Ding R, Napper FL, et al. Eicosapentaenoic acid (EPA) from highly concentrated n-3 fatty acid ethyl esters is incorporated into advanced atherosclerotic plaques and higher plaque EPA is associated with decreased plaque inflammation and increased stability. Atherosclerosis. Sep. 2010 (epub May 20, 2010); 212:252-259.

Cazzola, R., et al., "Age- and dose-dependent effects of an eicosapentaenoic acid-rich oil on cardiovascular risk factors in healthy male subjects." Atherosclerosis 193:159-167 (Jul. 2007); https://www.sciencedirect.com/science/article/abs/pii/S0021915006003455, Available online Aug. 1, 2006.

Ceci et al., "The effects of oral 5-hydroxytryptophan administration on feeding behavior in obese adult female subjects," J Neural. Transm (1989) 76(2):109-117; https://link.springer.com/article/10.1007/BF01578751, Published: Jun. 1989.

Cefali, E.A., et al., "Aspirin reduces cutaneous flushing after administration of an optimised extended-release niacin formulation", Int. J. Clin. Pharmacol. & Ther., 45(2):78-88, (Feb. 2007); https://europepmc.org/article/med/17323787, Jan. 31, 2007.

Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/021853s000;%20021654s016_StatR.pdf. (Accessed Jan. 26, 2012) (156 pages).

Center for Drug Evaluation and Research. Approval Package for Application No. 202057Orig1s000. Review—Vascepa (formerly AMR101), 373 pages (Jul. 26, 2012)(in two parts).

Center for Drug Evaluation and Research. Approval Package for: 21-654 (Omacor/Lovaza). Statistical Review; 2004. Available at: http://www.accessdata.fda.gov/drugsatfda_docs/nda/2004/21-654_Omacor_AdminCorres_P1.pdf. Accessed Jan. 26, 2012. (54 pages).

Ceriello A, Motz E. Is oxidative stress the pathogenic mechanism underlying insulin resistance, diabetes, and cardiovascular disease? The common soil hypothesis revisited. Arterioscler. Thromb. Vasc. Biol. (May 2004);24(5):816-823; https://www.ahajournals.org/doi/full/10.1161/01.atv.0000122852.22604.78, Originally published Feb. 19, 2004.

Chait A, et al., Susceptibility of small, dense, low-density lipoproteins to oxidative modification in subjects with the atherogenic lipoprotein phenotype, pattern B. Am. J. Med. (Apr. 1993);94(4):350-356; https://www.sciencedirect.com/science/article/abs/pii/000293439390144E, Accepted Jul. 21, 1992, Available online Mar. 21, 2004.

Chan et al., "Effect of Atorvastatin and Fish Oil on Plasma High-Sensitivity C-Reactive Protein Concentrations in Individuals with

(56) References Cited

OTHER PUBLICATIONS

Visceral Obesity", Clin. Chem., vol. 48, pp. 877-883 (2002); https://academic.oup.com/clinchem/article/48/6/877/5641698, Published: Jun. 1, 2002.
Chan et al., Factorial Study of the Effects of Atorvastatin and Fish Oil on Dyslipidaemia in Visceral Obesity, 32 Euro. J. Clinical Investigation. 32(6):429-36 (Jun. 2002); https://onlinelibrary.wiley.com/doi/abs/10.1046/j.1365-2362.2002.01001.x, First published Jun. 13, 2002.
Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003); https://academic.oup.com/ajcn/article/77/2/300/4689666, Published: Feb. 1, 2003.
Chang CL, et al.,. n-3 Fatty Acids Decrease Arterial Low-Density Lipoprotein Cholesterol Delivery and Lipoprotein Lipase Levels in Insulin-Resistant Mice. Arterioscler Thromb Vasc Biol. Dec. 2010 (epub Oct. 7, 2010); 30(12):2510-2517.
Chapman, M.J., et al., "Cholesteryl ester transfer protein: at the heart of the action of lipid-modulating therapy with statins, fibrates, niacin, and cholesteryl ester transfer protein inhibitors." Eur Heart J., 31(2):149-164 (Jan. 2010); https://academic.oup.com/eurheartj/article/31/2/149/718394, Published: Oct. 12, 2009.
Chatterjee SN, Agarwal S. Liposomes as membrane model for study of lipid peroxidation. Free Radic. Biol. Med. 1988;4(1):51-72; https://www.sciencedirect.com/science/article/abs/pii/0891584988900111, Accepted May 5, 1987, Available online Jan. 10, 2003.
Chemical Book, Eicosapentaenoic acid ethyl ester, copyright 2010, printed Jun. 16, 2011 from www.chemicalbook.com. (2010).
Chen, H., et al., "Eicosapentanoic acid inhibits hypoxia-reoxygenation-induced injury by attenuating upregulation of MMP-1 in adult rat myocytes." Cardiovascular Research 59:7-13 (Jul. 2003); https://academic.oup.com/cardiovascres/article/59/1/7/283704, Published: Jul. 1, 2003.
Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (Jul. 2003); https://www.sciencedirect.com/science/article/pii/S0022282803001202, Available online Apr. 17, 2003.
Chen, I.S., et al., "In vitro clearance of chylomicron triglycerides containing (ω-3) eicosapentaenoate." Atherosclerosis, 65:193-198 (1987); https://www.sciencedirect.com/science/article/abs/pii/0021915087900347, Date: Jun. 1987.
Cheng et al., "Antagonism of the prostaglandin D2 receptor 1 suppresses nicotinic acid—induces vasodilation in mice and humans," PNAS 103(17):6682-7 (Apr. 25, 2006).
Childs, M.T., et al., "Divergent lipoprotein Responses to Fish Oils With Various Ratios of Eicosapentaenoic Acid and Docasahexaenoic Acid", American Society for Clinical Nutrition, 52:632-9, (Oct. 1990); https://academic.oup.com/ajcn/article-abstract/52/4/632/4650895, Published: Oct. 1, 1990.
Christensen, J. H., et al., "Effect of fish oil on heart rate variability in survivors of myocardial infarction: a double blind randomised controlled trial." BMJ, 312:677-678 (Mar. 16, 1996).
Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (Jan. 1995); https://academic.oup.com/ajcn/article-abstract/61/1/56/4651581, Published: Jan. 1, 1995.
Citizen Petition, Pronova BioPharma Norge AS, Docket No. FDA-2009-P-0398-0001 (Aug. 4, 2009), at ii (Appendix), available at www.regulations.gov.
Classification of Hyperlipidaemias and Hyperlipoproteinaemias, Bulletin of the World Health Organization, 43(6): 891-915 (1970).
Cleland, L.G., et al., "A Biomarker of n-3 compliance in patients taking fish oil for rheumatoid arthritis." Lipids 38:419-424 (Apr. 2003); https://link.springer.com/article/10.1007/s11745-003-1078-9, Published: Apr. 2003.
Clinical Trial NCT01047501, Effect of AMR101 (Ethyl Icosapentate) on Triglyceride (Tg) Levels in Patients on Statins With High Tg Levels (>200 and <500 mg/dL) (ANCHOR), ClinicalTrials.gov [database online], U.S. National Institute of Health, Jan. 2010 [retrieved Apr. 27, 2011], Retrieved from Internet: <http://clinicaltrials.gov/ct2/show/NCT01047501> (3 pages).
Cohen AW, et al., Role of caveolin and caveolae in insulin signaling and diabetes. American journal of physiology. Endocrinology and metabolism. (Dec. 2003);285(6):E1151-1160; https://journals.physiology.org/doi/full/10.1152/ajpendo.00324.2003, Dec. 1, 2003.
Cohen, J.D., et al., "30-year trends in serum lipids among United States adults: results from the National Health and Nutrition Examination Surveys II, III, and 1999-2006." Am J Cardiol., 106:969-975, (Dec. 15, 2010).
Cole et al., "Challenges and opportunities in the encapsulation of liquid and semi-solid formulations into capsules for oral administration," Advanced Drug Delivery Reviews, vol. 60, No. 6, pp. 747-756. (Mar. 17, 2007).
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (Aug. 21-24, 2004).
Collins, N., et al., "Differences between Dietary Supplement and Prescription Drug Omega-3 Fatty Acid Formulations: A Legislative and Regulatory Perspective." Journal of the American College of Nutrition, 27 (6):659-666 (Dec. 2008); https://www.tandfonline.com/doi/abs/10.1080/07315724.2008.10719743, Accepted Dec. 18, 2007, Published online: Jun. 14, 2013.
Committee Roster for the Oct. 16, 2013 Meeting of the Endocrinologic and Metabolic Drugs Advisory Committee, 2 pages. (2013); not online.
Conklin, S. M., et al., "Serum ω-3 fatty acids are associated with variation in mood, personality and behavior in hypercholesterolemic community volunteers." Psychiatry Research 152: 1-10 (Jul. 30, 2007).
Connor et al., "Are Fish Oils Beneficial in the Prevention and Treatment of Coronary Artery Disease?", Am J Clin Nutr vol. 66, No. 4, Jan. 1, 1997, pp. 1020S-1031S, XP002502041.
Connor et al., "Seminars in thrombosis and hemostasis," 14:271-284. (1988).
Connor, W.E., "Importance of n-3 Fatty Acids in Health and Disease", Am. J. Clin. Nutr., 71(1(S)):171S-175S, (Jan. 2000); https://academic.oup.com/ajcn/article/71/1/171S/4729333, Published: Jan. 1, 2000.
Conquer, J.A., et al., "Effect of supplementation with different doses of DHA on the levels of circulating DHA as non-esterified fatty acid in subjects of Asian Indian background. J Lipid Res." 39:286-292. (Feb. 1998); https://www.jlr.org/content/39/2/286.short. Revision received Oct. 9, 1997.
Conquer, J.A., et al., "Supplementation with an algae source of docosahexaenoic acid increases (n-3) fatty acid status and alters selected risk factors for heart disease in vegetarian subjects." J Nutr., 126: 3032-3039. (Dec. 1996); https://academic.oup.com/jn/article/126/12/3032/4724655, Published: Dec. 1, 1996.
Contacos et al. Effect of pravastatin and omega-3 fatty acids on plasma lipids and lipoproteins in patients with combined hyperlipidemia, pp. 1755-1762 (Dec. 1993); https://www.ahajournals.org/doi/abs/10.1161/01.ATV.13.12.1755, Originally published Dec. 1, 1993.
Coronary Artery Bypass Grafting, NIH, published online Feb. 23, 2012 (12 pages).
Costanzo S, di Niro V, Castelnuovo AD, et al. Prevention of postoperative atrial fibrillation in open heart surgery patients by preoperative supplementation of n-3 polyunsaturated fatty acids: An updated meta-analysis. Periop Manga. Apr. 12, 2013; epub; https://www.sciencedirect.com/science/article/pii/S0022522313003176, Oct. 2013.
Coumadin [package insert], Princeton, NJ: Bristol-Myers Squibb; 2011. (10 pages).
Cox PJ, Ryan DA, Hollis FJ, et al. Absorption, disposition, and metabolism of rosiglitazone, a potent thiazolidinedione insulin sensitizer, in humans. Drug Metab. Dispos. Jul. 2000;28:772-780; http://dmd.aspetjournals.org/content/28/7/772.short, Accepted Apr. 10, 2000, Published online Jul. 1, 2000.

(56) References Cited

OTHER PUBLICATIONS

Creager MA, Gallagher SJ, Girerd XJ, Coleman SM, Dzau VJ, Cooke JP. L-arginine improves endothelium-dependent vasodilation in hypercholesterolemic humans. J. Clin. Invest. Oct. 1992;90:1248-1253; https://www.jci.org/articles/view/115987, First published Oct. 1, 1992.
Crevel et al., "Allergenicity of Refined Vegetable Oils," Food and Chemical Toxicology, 38, pp. 385-393 (Apr. 2000); https://www.sciencedirect.com/science/article/pii/S0278691599001581, Accepted Sep. 20, 1999, Available online Sep. 13, 2000.
Criqui, M., "Triglycerides and Coronary Heart Disease Revisited (Again)," vol. 147 No. 6, pp. 425-427 (Sep. 18, 2007).
Cromwell et al., "LDL particle number and risk of future cardiovascular disease in the Framingham Offspring Study—Implications for LDL Management," Journal of Lipidololgy (Dec. 2007) 1, 583-592; https://www.sciencedirect.com/science/article/abs/pii/S1933287407002838, Accepted Oct. 11, 2007, Available online Oct. 18, 2007.
Crowe, F.L., et al., "Serum phospholipid n-3 long-chain polyunsaturated fatty acids and physical and mental health in a population-based survey of New Zealand adolescents and adults." Am J Clin Nutr 86:1278-85 (Nov. 2007); https://academic.oup.com/ajcn/article/86/5/1278/4650617, Published: Nov. 1, 2007, Accepted Jun. 11, 2007.
Cruz et al., "The metabolic syndrome in children and adolescents," Curr. Diab. Rep., vol. 4(1):53-62 (Feb. 2004); https://link.springer.com/article/10.1007%2Fs11892-004-0012-x, Published: Feb. 2004.
Culhane et al., "Rosuvastatin for the treatment of hypercholesterolemia," Pharmacotherapy, 25(7):990-1000 (Jul. 2005); https://accpjournals.onlinelibrary.wiley.com/doi/abs/10.1592/phco.2005.25.7.990, First published: Jan. 16, 2012.
Daggy, B., et al., Dietary fish oil decreases VLDL production rates. Biochimica et Biophysics Acta 920: 293-300 (Aug. 15, 1987).
Dall et al., "Clinical utility of low-density lipoprotein particle measurement in management of cardiovascular disease: a case report," Research Reports in Clin. Cardiol., vol. 2, pp. 57-62 (2011); http://www.taradall.com/resources/LowDensityParticleMeasurement.pdf, Published Apr. 26, 2011.
Daniel et al., "The Effect of Elevated Triglycerides on the Onset and Progression of Coronary Artery Disease: A Retrospective Chart Review," Cholesterol, vol. 2015, Article ID 292935, 5 pages (epub Nov. 4, 2015).
Das, U.N., Essential fatty acids as possible mediators of the actions of statins. Prostaglandins, Leukotrienes and Essential Fatty Acids 65(1):37-40, (Jul. 2001); https://www.sciencedirect.com/science/article/abs/pii/S0952327801902856, Accepted Feb. 7, 2001, Available online May 25, 2002.
Davidson MH, Ballantyne CM, Jacobson TA, et al. Clinical utility of inflammatory markers and advanced lipoprotein testing: advice from an expert panel of lipid specialists. J. Clin. Lipidol. Sep./Oct. 2011;5:338-367; https://www.sciencedirect.com/science/article/abs/pii/S1933287411006726 Accepted Jul. 29, 2011, Available online Oct. 5, 2011.
Davidson MH, et al., Effects of prescription omega-3-acid ethyl esters on lipo protein particle concentrations, apolipoproteins AI and CIII, and lipoprotein-associated phospholipase $A_2$ mass in statin-treated subjects with hypertrigylceridemia, J.Clin. Lipid., vol. 3(5), pp. 332-340 (Oct. 2009); https://www.sciencedirect.com/science/article/abs/pii/S1933287409003249 Accepted Aug. 27, 2009, Available online Aug. 31, 2009.
Davidson MH, Rosenson RS, Maki KC, Nicholls SJ, Ballantyne CM, Mazzone T, Carlson DM, Williams LA, Kelly MT, Camp HS, Lele A, Stolzenbach JC. Effects of fenofibric acid on carotid intima-media thickness in patients with mixed dyslipidemia on atorvastatin therapy: Randomized, placebo-controlled study (first). Arterioscler. Thromb. Vasc. Biol. Jun. 2014;34:1298-1306; https://www.ahajournals.org/doi/full/10.1161/atvbaha.113.302926, Originally published Apr. 17, 2014.
Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther., 29:1354-1367. (Jul. 26, 2007).
Davidson MH., "Mechanisms for the hypotriglyceridemic effect of marine omega 3 fatty acids." Am J Cardiol 98(4A):27i-33i. (Aug. 21, 2006).
Davidson, M.H., et al., "Effects of docosahexaenoic acid on serum lipoproteins in patients with combined hyperlipidemia: a randomized, doubleblind, placebo-controlled trial." J Am Coll Nutr., 16:236-243. (Jun. 1997); https://www.tandfonline.com/doi/abs/10.1080/07315724.1997.10718680, Published online Sep. 4, 2013.
Davies et al., "Rapid separation of LDL subclasses by iodixanol gradient ultracentrifugation," Clin. Chem., 49(11):1865-72. (Nov. 2003); https://academic.oup.com/clinchem/article/49/11/1865/5642057, Published: Nov. 1, 2003.
Davies-Tuck et al., "Total cholesterol and triglycerides are associated with development of new bone marrow lesions in asymptomatic middle-aged women—a prospective cohort study," Arthritis Research & Therapy, (published online Dec. 4, 2009) pp. 1-7.
De Caterina, R, et al., "Control of Endothelial Leukocyte Adhesion Molecules by Fatty Acids." Lipids, vol. 31:S57-S63 (1996); https://aocs.onlinelibrary.wiley.com/doi/abs/10.1007/BF02637052, First published: Jan. 1996.
De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994); https://www.ahajournals.org/doi/abs/10.1161/01.ATV.14.11.1829, Originally published Nov. 1, 1994.
De Graaf J, Hak-Lemmers HL, Hectors MP, Demacker PN, Hendriks JC, Stalenhoef AF. Enhanced V susceptibility to in vitro oxidation of the dense low density lipoprotein subfraction in healthy subjects. Arterioscler. Thromb. 1991;11(2):298-306; https://www.ahajournals.org/doi/abs/10.1161/01.ATV.11.2.298, Originally published Mar. 1, 1991.
De Morais et al., "Evaluation of lipid extraction and fatty acid composition of human plasma," Rev. Bras. Hematol. Hemoter. 32(6):439-443 (2010); https://www.scielo.br/scielo.php?pid=S1516-84842010000600006&script=sci_arttext, Accepted: Feb. 8, 2010.
Deckelbaum,, R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008); https://academic.oup.com/ajcn/article/87/6/2010S/4633491, Published Jun. 1, 2008.
Defendants' Invalidity Contentions, 3:14-CV-02550-MLC-DEA (D.N.J.), 520 pages (Dec. 5, 2014).
Defendants' Joint Invalidity Contentions, 3:14-CV-02550-MLC-TJB (D.N.J.), 901 pages (Dec. 5, 2014).
DeMets DL, Lan KK. Interim Analysis: the Alpha Spending Function Approach. Stat Med., Jul. 15-30, 1994; 13(13-14):1341-52.
Dewailly, E., et al., "n-3 Fatty acids and cardiovascular disease risk factors among the Inuit of Nunavik." Am J Clin Nutr 74:464-73 (2001); https://academic.oup.com/ajcn/article/74/4/464/4737394, Accepted: Apr. 16, 2001. Published: Oct. 1, 2001.
Dewey FE, Gusarova V, O'Dushlaine C, et al. Supplement to: Inactivating variants in ANGPTL4 and risk of coronary artery disease. N Engl J Med. DOI: 10.1056/NEJMoa1510926; Mar. 24, 2016 (epub Mar. 2, 2016).
Di Spirito, M., Morelli, G., Doyle, R.T., Johnson, J. & McKenney, J. Effect of omega-3-acid ethyl esters on steady-state plasma pharmacokinetics of atorvastatin in healthy adults. Expert Opin. Pharmacother. 9, 2939-2945 (2008); https://www.tandfonline.com/doi/abs/10.1517/14656560802233827, Published online Nov. 12, 2008.
Diagnostic and Statistical Manual of Mental Disorders, 4.Ed. Text revision, published by the American Psychiatric Assoc., pp. 154-163 and 369-381 (2000).
Diagnostic and Statistical Manual of Mental Disorders, 4.sup.th Ed., published by the American Psychiatric Assoc., pp. 285-286, (1994).
Dijan, P., et al., Proc. Natl. Acad. Sci., vol. 93, "Codon repeats in genes associated with human diseases: Fewer repeats in the genes of nonhuman primates and nucleotide substitutions concentrated at the sites of reiteration," pp. 417-421, (Jan. 9, 1996).

(56) References Cited

OTHER PUBLICATIONS

Dijk, J. M., et al., "Carotid intima-media thickness and the risk of new vascular events in patients with manifest atherosclerotic disease: the SMART study." European Heart Journal 27:1971-1978 (2006); https://academic.oup.com/eurheartj/article/27/16/1971/2887202, Revision received May 22, 2006, Accepted Jun. 15, 2006, Published Jul. 11, 2006.

Din et al., "Omega 3 fatty acids and cardiovascular disease—fishing for a natural treatment," BMJ, vol. 327, No. 7430, pp. 30-35 (Jan. 3, 2004).

Djousse L, Akinkuolie AO, Wu JHY, Ding EL, Gaziano JM. Fish consumption, omega-3 fatty acids and risk of heart failure: A meta-analysis. Clin Nutr. Dec. 2012 (epub Jun. 6, 2012); 31:846-853.

Do R, Stitziel NO Won HH, et al. Exome sequencing identifies rare LDLR and APOA5 alleles conferring risk for myocardial infarction. Nature. Feb. 5, 2015 (epub Dec. 10, 2014); 518(7537):102-106.

Do R, Willer CJ, Schmidt EM, et al. Common variants associated with plasma triglycerides and risk for coronary artery disease. Nat Genet Nov. 2013 (Oct. 6, 2013); 45(11):1345-52.

Dodin, S., et al., "Flaxseed on cardiovascular disease markers in healthy menopausal women: a randomized, double-blind, placebo-controlled trial." Nutrition 24:23-30 (2008); https://www.sciencedirect.com/science/article/abs/pii/S0899900707003024, Revised Sep. 26, 2007, Available online Nov. 5, 2007.

Doi M, Nosaka K, Miyoshi T, et al. Early eicosapentaenoic acid treatment after percutaneous coronary intervention reduced acute inflammatory responses and ventricular arrhythmias in patients with acute myocardial infarction: A randomized controlled study. Int J Cardiol., 176(3):577-82 (publication date Oct. 20, 2014; epublication date Aug. 19, 2014).

Dolecek, "Epidemiological Evidence of Relationships Between Dietary Polyunsaturated Farry Acids and Morality in the Multiple Risk Factor Intervention Trial", Society of Experimental Biology and Medicine, 200(2):177-182, (1991); https://journals.sagepub.com/doi/abs/10.3181/00379727-200-43413, First Published Jun. 1, 1992.

Draft Agenda for the Oct. 16, 2013 Meeting of the Endocrinologic and Metabolic Drugs Advisory Committee, 2 pages.

Draft Meeting Roster for the Oct. 16, 2013 Meeting of the Endocrinologic and Metabolic Drugs Advisory Committee, 2 pages.

Draft Questions for the Oct. 16, 2013 Meeting of the Endocrinologic and Metabolic Drugs Advisory Committee, 1 page.

Drexler H, Zeiher AM, Meinzer K, Just H. Correction of endothelial dysfunction in coronary microcirculation of hypercholesterolaemic patients by l-arginine. Lancet. 1991;338:1546-1550; https://www.sciencedirect.com/science/article/abs/pii/0140673691923729, Available online Nov. 10, 2003.

Dullenmeijer, C., et al., "n-3 Fatty acid proportions in plasma and cognitive performance in older adults." Am J Clin Nutr 86:1479-85 (2007); https://academic.oup.com/ajcn/article/86/5/1479/4650849, Accepted Jun. 1, 2007, Published Nov. 1, 2007.

Duncan, R. E., et al., "Regulation of HMG-CoA reductase in MCF-7 cells by genistein, EPA, and DHA, alone and in combination with mevastatin." Cancer Letters 224:221-228 (2005); https://www.sciencedirect.com/science/article/abs/pii/S0304383504008900, Revised Oct. 11, 2004, Accepted Nov. 1, 2004, Available online Dec. 16, 2004.

Durrington PN et al. "An omega 3 poly unsaturated fatty acid concentrate administered for one year decreased triglycerides in simvastatin treated patients with coronary heart disease and persistent Hypertriglyceridemia," Heart, 85:544-48 (2001); https://heart.bmj.com/content/85/5/544.short, May 1, 2001.

Dwyer, J. H., et al., "Arachidonate 5-Lipoxygenase Promoter Genotype, Dietary Arachidonic Acid, and Atherosclerosis." N. Engl. J. Med., 350:1 (2004); https://www.nejm.org/doi/full/10.1056/nejmoa025079, Jan. 1, 2004.

Dyerberg, J., et al., "Marine Oils and Thrombogenesis." Prog. Lipid Res. 21:255-269 (1982); https://www.sciencedirect.com/science/article/abs/pii/016378278290011X, Available online Jan. 16, 2003.

Egert, S., et al., "Dietary alpha-linolenic acid, EPA, and DHA have differential effects on LDL fatty acid composition but similar effects on serum lipid profiles in normolipidemic humans." J Nutr., 139:861-868 (2009); https://academic.oup.com/jn/article/139/5/861/4670359, Revision received Jan. 19, 2009, Accepted Feb. 4, 2009. Published Mar. 4, 2009.

Ehara S, et al., Elevated levels of oxidized low density lipoprotein show a positive relationship with the severity of acute coronary syndromes. Circulation. 2001;103(15):1955-1960; https://www.ahajournals.org/doi/full/10.1161/01.CIR.103.15.1955, Originally published Apr. 17, 2001.

Eilat-Adar et al. "Association of Intentional Changes in Body Weight with Coronary Heart Disease Event Rates in Overweight Subjects who have an Additional Coronary Risk Factor," Amer. Journ. Epidemiol.161 (4)pp. 352-358 (Sep. 9, 2004).

Eisenberg S, Bilheimer DW, Levy RI, Lindgren FT. "On the metabolic conversion of human plasma very low density lipoprotein to low density lipoprotein," Biochim Biophys Acta, 326:361-77 (1973); https://www.sciencedirect.com/science/article/abs/pii/0005276073901380, Dec. 20, 1973, Available online Dec. 13, 2002.

Eisenberg S, Rachmilewitz D. "Metabolism of rat plasma very low density lipoprotein. I. Fate in circulation of the whole lipoprotein," Biochim Biophys Acta, 326:378-90 (1973); https://www.sciencedirect.com/science/article/abs/pii/0005276073901392, Revised Aug. 7, 1973, Available online Dec. 13, 2002.

El-Serag HB, Graham DY, Satia JA, et al. Obesity is an independent risk factor for GERD symptoms and erosive esophagitis. Am. J. Gastroenterol. Jun. 2005 100 (6): 1243-50; https://journals.lww.com/ajg/Abstract/2005/06000/Obesity_Is_an_Independent_Risk_Factor_for_GERD.7.aspx, Jun. 2005.

Elam, M.B., et al., "Effect of niacin on lipid and lipoprotein levels and glycemic control in patients with diabetes and peripheral arterial disease study: a randomized trial", The ADMIT [Arterial Disease Multiple Intervention Trial] JAMA, 284:1263-1270, (2000); https://jamanetwork.com/journals/jama/article-abstract/193064, Sep. 13, 2000.

El-Saadani M, et al., A spectrophotometric assay for lipid peroxides in serum lipoproteins using commercially available reagent. J. Lipid Res. 1989;30:627-630; https://www.jlr.org/content/30/4/627.short, Apr. 1989.

El-Sohemy, A., et al., "Regulation of Mevalonate Synthesis in Low Density Lipoprotein Receptor Knockout Mice Fed n-3 or n-6 Polyunsaturated Fatty Acids." Lipids, 34 (10): 1037-43 (1999); https://link.springer.com/article/10.1007/s11745-999-0455-8, Published Oct. 1999, Revised Jun. 9, 1999, Accepted Jun. 22, 1999.

Emsley et al., "Randomized, Placebo-Controlled Study of Ethyl-Eicosapentaenoic Acid as Supplemental Treatment in Schizophrenia," Am. J. Psychiatry, 159:1596-1598 (2002); https://ajp.psychiatryonline.org/doi/full/10.1176/appi.ajp.159.9.1596, Published Online:Sep. 1, 2002.

Endo et al., "The Effects of Dietary Fatty Acids on Serum Lipids and Plasma Prostaglandin Levels in the Treatment of Obesity," Japanese Journal of Pediatric Gastroenterology and Nutrition 7(1):67-72 (Apr. 15, 1993) (with English translation)(22 pages).

ENews—JAX, "Cholesterol Crystals Induce Atherosclerosis-Associated Inflammation in Mice," 1-4 (Jun. 14, 2010)(4 pages).

Engler, et al., "Docosahexaenoic acid restores endothelial function in children with hyperlipidemia: results from the EARLY Study." International Journal of Clinical Pharmacology and Therapeutics, vol. 42—No. 12-2004 (672-679). (2004); https://www.researchgate.net/profile/Marguerite_Engler/publication/8107212_Docosahexaenoic_acid_restores_endothelial_function_in_children_with_hyperlipidemia_Results_from_the_EARLY_Study/links/0046351743e39201a8000000/Docosahexaenoic-acid-restores-endothelial-function-in-children-with-hyperlipidemia-Results-from-the-EARLY-Study.pdf, Dec. 2004, Accepted Jul. 24, 2004.

Engler, M.B., et al., "Mechanisms of vasorelaxation induced by eicosapentaenoic acid (20:5n-3) in WKY rat aorta." British Journal of Pharmacology 131:1793-1799 (2000); https://www.ncbi.nlm.nih.gov/pmc/articles/PMC1572512/, Dec. 2000, Accepted Oct. 2, 2000.

Engler, M.M., et al., "The effects of a diet rich in docosahexaenoic acid on organ and vascular fatty acid composition in spontaneously hypertensive rats." Prostaglandins, Leukotrienes and Essential Fatty

(56) References Cited

OTHER PUBLICATIONS

Acids 61(5):289-295 (1999); https://www.sciencedirect.com/science/article/abs/pii/S0952327899901023, Accepted Aug. 16, 1999, Available online May 25, 2002.

Ennis JL, Cromwell WC, Clinical utility of low-density lipoprotein particles and apolipoprotein B in patients with cardiovascular risk. J. Fam. Pract. 2013;62:1-8; https://europepmc.org/article/med/23957035, Jun. 30, 2013.

Epadel—PubChem CID 9831415, Retrieved on Apr. 9, 2014 [Retrieved from Internet] <URL:http://pubchem.ncbi.nlm.nih.gov/compound/9831415> (19 pages).

Epadel 1990 and JELIS Study (4 pages).

Epadel Capsules 300, Japan Pharmaceutical Reference 369-371 (2nd ed.) (1991). (5 pages).

Epadel drug information brochure (2000), certified English translation (36 pages).

Epadel Package Insert 2007 (with Translation)(6 pages).

Epadel Summary of Product Characteristics (SPC), Mochida Pharmaceutical Co., Ltd. Tokyo, Japan, Oct. 2013.

Epadel® [Complete prescribing information]. Update (Version 5). Tokyo, Japan: Mochida Pharmaceutical; Jan. 2007 (9 pages).

EPANOVA® (omega-3-carboxylic acids) capsules, for oral use, Prescribing information, 5 pgs., AstraZeneca Pharmaceuticals LP, (Revised: Mar. 2017)(5 pages).

Eritsland J, Arnesen H, Gronseth K, et al. Effect of dietary supplementation with n-3 fatty acids on coronary artery bypass graft patency. Am. J. Cardiol. Jan. 1996 77 (1): 31-6; https://www.sciencedirect.com/science/article/abs/pii/S0002914997891308, Accepted Sep. 18, 1995, Available online Nov. 30, 1999.

Eritsland J, Arnesen H, Seljeflot I, et al. Long-term effects of n-3 polyunsaturated fatty acids on haemostatic variables and bleeding episodes in patients with coronary artery disease. Blood Coagul. Fibrinolysis Feb. 1995 6 (1): 17-22; https://journals.lww.com/bloodcoagulation/Abstract/1995/02000/Long_term_effects_of_n_3_polyunsaturated_fatty.3.aspx, https://europepmc.org/article/med/7795149, Jan. 31, 1995.

Errata to the FDA Briefing Document Endocrinologic and Metabolic Drug Advisory Committee Meeting Oct. 16, 2013, 1 page.

Esposito, "Effect of a Mediterranean-Style Diet on Endothelial Dysfunction and Markers of Vascular Inflammation in the Metabolic Syndrome: A Randomized Trial," Journal of the American Medical Association, 2004, 292(12), 1440-1446; https://jamanetwork.com/journals/jama/article-abstract/199488, Sep. 22/29, 2004.

Essentialis Inc. press release, "Essentialis Meets Primary Endpoint in Phase 2b Trial of DCCR for Treatement of Hypertriglyceridemia and is Granted Extensive Patent Coverage in the US," PR Newswire (May 17, 2009)( 2 pages).

Exhibit A to Defendants' Joint Invalidity Contentions, 3:14-CV-02550-MLC-TJB (D.N.J.), 48 pages (Dec. 5, 2014).

Exhibit B to Defendants' Joint Invalidity Contentions, 3:14-CV-02550-MLC-TJB (D.N.J.), 6 pages (Dec. 5, 2014).

Exhibit C to Defendants' Joint Invalidity Contentions, 3:14-CV-02550-MLC-TJB (D.N.J.), 14 pages (Dec. 5, 2014).

Exhibit D to Defendants' Joint Invalidity Contentions, 3:14-CV-02550-MLC-TJB (D.N.J.), 19 pages (Dec. 5, 2014).

Exhibit E to Defendants' Joint Invalidity Contentions, 3:14-CV-02550-MLC-TJB (D.N.J.), 6 pages (Dec. 5, 2014).

Exhibit F to Defendants' Joint Invalidity Contentions, 3:14-CV-02550-MLC-TJB (D.N.J.), 10 pages (Dec. 5, 2014).

Exhibit G to Defendants' Joint Invalidity Contentions, 3:14-CV-02550-MLC-TJB (D.N.J.), 21 pages (Dec. 5, 2014).

Exhibit H to Defendants' Joint Invalidity Contentions, 3:14-CV-02550-MLC-TJB (D.N.J.), 10 pages (Dec. 5, 2014).

Exhibit I to Defendants' Joint Invalidity Contentions, 3:14-CV-02550-MLC-TJB (D.N.J.), 14 pages (Dec. 5, 2014).

Exhibit J to Defendants' Joint Invalidity Contentions, 3:14-CV-02550-MLC-TJB (D.N.J.), 13 pages (Dec. 5, 2014).

Exhibit K to Defendants' Joint Invalidity Contentions, 3:14-CV-02550-MLC-TJB (D.N.J.), 5 pages (Dec. 5, 2014).

Exhibit L to Defendants' Joint Invalidity Contentions, 3:14-CV-02550-MLC-TJB (D.N.J.), 5 pages (Dec. 5, 2014).

Exhibit M to Defendants' Joint Invalidity Contentions, 3:14-CV-02550-MLC-TJB (D.N.J.), 7 pages (Dec. 5, 2014).

Exhibit N to Defendants' Joint Invalidity Contentions, 3:14-CV-02550-MLC-TJB (D.N.J.), 15 pages (Dec. 5, 2014).

Exhibit O to Defendants' Joint Invalidity Contentions, 3:14-CV-02550-MLC-TJB (D.N.J.), 6 pages (Dec. 5, 2014).

Exhibit P to Defendants' Joint Invalidity Contentions, 3:14-CV-02550-MLC-TJB (D.N.J.), 17 pages (Dec. 5, 2014).

Exhibit Q to Defendants' Joint Invalidity Contentions, 3:14-CV-02550-MLC-TJB (D.N.J.), 64 pages (Dec. 5, 2014).

Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000); https://www.ahajournals.org/doi/full/10.1161/01.ATV.20.1.152, Originally published Jan. 1, 2000.

FDA Briefing Document, Endocrinologic and Metaboloic Drugs Advisory Committee Meeting, dated Oct. 16, 2013, available publicly at least as of Oct. 16, 2013, 115 pages.

FDA News Release, "FDA approves new orphan drug Kynamro to treat inherited cholesterol disorder," U.S. Food and Drug Administration, Protecting and Promoting Your Health (Jan. 29, 2013)(2 pages).

Fer, M., et al., "Metabolism of eicosapentaenoic and docosahexaenoic acids by recombinant human cytochromes P450." Archives of Biochemistry and Biophysics 471:116-125 (2008); https://www.sciencedirect.com/science/article/abs/pii/S0003986108000040 , Mar. 15, 2008, Revised Dec. 26, 2007, Available online Jan. 11, 2008.

Ferns, G., et al., "Investigation and management of hypertriglyceridaemia." J. Clin. Pathol. 61:1174-1183 (2008); https://jcp.bmj.com/content/61/11/1174.short Oct. 2008.

Feron O, et al., Hydroxy-methylgluataryl-coenzyme a reductase inhibition promotes endothelial nitric oxide synthase activation through a decrease in caveolin abundance. Circulation. 2001;103:113-118; https://www.ahajournals.org/doi/full/10.1161/01.cir.103.1.113, Originally published Jan. 2, 2001.

Final Agenda for the Oct. 16, 2013 Meeting of the Endocrinologic and Metabolic Drugs Advisory Committee, 2 pages.

Final Meeting Roster for the Oct. 16, 2013 Meeting of the Endocrinologic and Metabolic Drugs Advisory Committee, 2 pages.

Final Questions for the Oct. 16, 2013 Meeting of the Endocrinologic and Metabolic Drugs Advisory Committee, 1 page.

Finnen et al., "Purification and characterisation of phospholipase A2 from human epidermis,", Biochemical Society Trans,19(2):91S, 1991; https://europepmc.org/article/med/1889683, Mar. 31, 1991, https://pubmed.ncbi.nlm.nih.gov/1889683/, Apr. 1991.

Fischer, R., et al., "Dietary n-3 polyunsaturated fatty acids and direct renin inhibition improve electrical remodeling in a model of high human renin hypertension." Hypertension 51:540-546 (2008); https://www.ahajournals.org/doi/full/10.1161/hypertensionaha.107.103143, Originally published Dec. 24, 2007.

Fisher et al., Journal of Biological Chemistry (2001) 276(3) 27855-27863; https://www.jbc.org/content/276/30/27855.short, First Published on Apr. 2, 2001.

Flaten, H., et al., "Fish-oil concentrate: effects on variables related to cardiovascular disease." Am. J. Clin. Nutr. 52:300-306 (1990); https://academic.oup.com/ajcn/article-abstract/52/2/300/4651469 Published: Aug. 1, 1990.

Food and Drug Administration (FDA), (2005) *NIASPAN niacin extended release tablets*.

Food and Drug Administration (FDA), (2005) *Tablets Zocor® (Simvastatin)*.

Ford, ES et al., "Hypertriglyceridemia and Its Pharmacologic Treatment Among US Adults." Arch, Intern. Med., 169(6): 572-78 (2009); https://jamanetwork.com/journals/jamainternalmedicine/article-abstract/414870 , Mar. 23, 2009, Accepted for Publication: Oct. 12, 2008.

Fraker TD, Fihn SD. Writing on behalf of the 2002 Chronic Stable Angina Writing Committee. 2007 chronic angina focused update of the ACC/AHA guidelines for the management of patients with

(56) References Cited

OTHER PUBLICATIONS chronic stable angina. A Report of the ACC/AHA Task Force on Practice Guidelines. Circulation 50:2264-2274, Dec. 4, 2007.
Frangou et al., "Efficacy of ethyl-eicosapentaenoic acid in bipolar depression: randomised double-blind placebo-controlled study," British Journ. Psychiatry, 188, 46-50 (2006); https://www.cambridge.org/core/journals/the-british-journal-of-psychiatry/article/efficacy-of-ethyleicosapentaenoic-acid-in-bipolar-depression-randomised-doubleblind-placebocontrolled-study/28477138E1C9F99F07EE1C99F5C73E64, Jan. 2006, presented at the 3rd European Stanley Foundation Conference on Bipolar Disorder, Freiburg, Germany, Sep. 12-14, 2002, Published online by Cambridge University Press: Jan. 2, 2018.
Frey R, et al., Riociguat (BAY 63-2521) and warfarin: a pharmacodynamic and pharmacokinetic interaction study. J. Clin. Pharmacol. Jul. 2011 51 (7): 1051-60; https://accp1.onlinelibrary.wiley.com/doi/abs/10.1177/0091270010378119, First published:Mar. 7, 2013.
Frick, MH, et al., "Helsinki Heart Study. Primary prevention trial with gemfibrozil in middle-aged men with dyslipidaemia. Safety of treatment, changes in risk factors and incidence of coronary heart disease," N. Eng. J. Med., 317:1237-1245, (1987); https://www.nejm.org/doi/full/10.1056/NEJM198711123172001 Nov. 12, 1987.
Friedewald, WT et al., "Estimation of the concentration of low-density lipoprotein cholesterol in plasma, without use of the preparative ultracentrifuge." Clin Chem.,18:499-502 (1972); https://academic.oup.com/clinchem/article-abstract/18/6/499/5676160, Accepted: Mar. 13, 1972. Published: Jun. 1, 1972.
Friedman, A.N., et al., "Fish Consumption and Omega-3 Fatty Acid Status and Determinants in Long-Term Hemodialysis." Amer. J. Kidney Diseases, 47(6):1064-1071 (2006); https://www.sciencedirect.com/science/article/abs/pii/S0272638606005282 , Accepted Mar. 8, 2006, Available online Feb. 21, 2008.
Frøyland et al., "Chronic administration of eicosapentaenoic acid and docosahexaenoic acid as ethyl esters reduced plasma cholesterol and changed the fatty acid composition in rat blood and organs." Lipids 31(2):169-78 (Feb. 1996); https://link.springer.com/article/10.1007/BF02522617, Published: Feb. 1996.
Frøyland, L., et al., "Hypotriacylglycerolemic component of fish oil." Prostaglandins, Leukotrienes and Essential Fatty Acids 57 (4 & 5):387-388 (1997); https://pascal-francis.inist.fr/vibad/index.php?action=getRecordDetail&idt=2121851, Conference: ETRO/ISSFAL symposium on Lipids, Membranes and Thrombosis (Maastricht Jul. 10, 1996).
Furuta T, et al. Influence of CYP2C19 pharmacogenetic polymorphism on proton pump inhibitor-based therapies. Drug Metab. Pharmacokinet Jun. 2005 20 (3): 153-67; https://www.jstage.jst.go.jp/article/dmpk/20/3/20_3_153/_article/-char/ja/.
Futata et al., "Effect of Eicosapentaenoic Acid (EPA) Formulation on Glucose Metabolism in Non-Insulin Dependent Diabetic Patients," Journal of Clinical and Experimental Medicine 169(8):889-890 (May 21, 1994)(English translation, 4 pages).
Galan P, Kesse-Guyot E, Czernichow S, et al. Effects of B vitamins and omega 3 fatty acids on cardiovascular diseases: a randomised placebo controlled trial. Br Med J. Nov. 29, 2010;341:c6273.
Galeano NF, et al., Small dense low density lipoprotein has increased affinity for LDL receptor-independent cell surface binding sites: a potential mechanism for increased atherogenicity. J. Lipid Res. 1998;39(6):1263-1273; https://www.jlr.org/content/39/6/1263.short, Jun. 1998. Preliminary reports of this study were presented in abstract form at the Annual Meetings of the American Heart Association, Nov. 1993.
Gallagher et al., "Germline BRCA Mutations Denote a Clinicopathalogic Subset of Prostate Cancer," Amer. Assoc. Cancer Res. Clin Cancer Res., 16(7):2115-21 (Apr. 1, 2010).
Ganda OP, Bhatt DL, Mason RP, Miller M, Boden WE. Unmet need for adjunctive dyslipidemia therapy in hypertriglyceridemia management. J Am Coll Cardiol 72(3):330-43 (publication date Jul. 17, 2018).
Garber AJ, Abrahamson MJ, Barzilay JI, et al. American Association of Clinical Endocrinologists' comprehensive diabetes management algorithm 2013 consensus statement. Endocr. Pract. 2013;19(suppl 2):1-48; https://journals.aace.com/doi/pdf/10.4158/EP13176.CSUPPL, May/Jun. 2013.
Gardner CD, Fortmann SP, Krauss RM. Association of small low-density lipoprotein particles with the incidence of coronary artery disease in men and women. JAMA. 1996;276(11):875-881; https://jamanetwork.com/journals/jama/article-abstract/407945 , Sep. 18, 1996.
Garg, R., et al., "Niacin treatment increases plasma homocyst(e)ine levels", Am. Heart. J., 138:1082-1087, (1999); https://www.sciencedirect.com/science/article/abs/pii/S0002870399700736, Accepted Dec. 16, 1998, Available online Nov. 4, 2005.
Garnett, "Interactions with Hydroxymethylglutaryl-coenzyme A reductase inhibitors," Am J Health-Sys Pharm vol. 52, 1639-1645, (Aug. 1, 1995).
Geleijnse JM, et al., Blood pressure response to fish oil supplementation: metaregression analysis of randomized trials. J Hypertens. Aug. 2002;20(8):1493-1499; https://journals.lww.eom/jhypertension/Abstract/2002/08000/Blood_pressure_response_to_fish_oil.10.aspx.
Genest, JJ, et al., "Familial lipoprotein disorders in patients with premature coronary artery disease", 85:2025-2033, (1992); https://www.ahajournals.org/doi/abs/10.1161/01.cir.85.6.2025, Originally published Jun. 1, 1992.
Geppert, et al. "Microalgal docosahexaenoic acid decreases plasma triacylglycerol in normolipidaemic vegetarians: a randomized trial." British Journal of Nutrition, 95, 779-786. (2006); https://www.cambridge.org/core/journals/british-journal-of-nutrition/article/microalgal-docosahexaenoic-acid-decreases-plasma-triacylglycerol-in-normolipidaemic-vegetarians-a-randomised-trial/95911131A8FB8584F7566A0CD3BDBEB7 , Apr. 2006, Published online by Cambridge University Press: Mar. 8, 2007.
Gillet L, Roger S, Bougnoux P, Le Guennec JY, Besson P. Beneficial effects of omega-3 long-chain fatty acids in breast cancer and cardiovascular diseases: voltage-gated sodium channels as a common feature? Biochimi. Jan. 2011 (epub Feb. 16, 2010); 93:4-6.
Gillies, et al. "Effect of a Novel Eicosapentaenoic Acid-Rich Oil on Serum Cholesterol in Man," DuPont 2010.
Ginsberg HN, et al., Effects of combination lipid therapy in type 2 diabetes mellitus. N. Engl. J. Med. Apr. 29, 2010;362:1563-1574; https://pubmed.ncbi.nlm.nih.gov/20228404/, Epub Mar. 14, 2010.
Ginsberg HN. "Hypertriglyceridemia: new insights and new approaches to pharmacologic therapy," Am J Cardiol, 87:1174-1180 (2001); https://www.ajconline.org/article/S0002-9149(01)01489-8/fulltext, May 15, 2001, Accepted: Dec. 21, 2000. Received in revised form: Dec. 21, 2000.
Girotti A W. Lipid hydroperoxide generation, turnover, and effector action in biological systems. J. Lipid Res. 1998;39(8):1529-1542; https://www.jlr.org/content/39/8/1529.short, Aug. 1998. Revision received Apr. 16, 1998.
GISSI-HF Investigators. Effect of n-3 polyunsaturated fatty acids in patients with chronic heart failure (the GISSI-HF trial): a randomised, double-blind, placebo-controlled trial. Lancet. Oct. 4, 2008 (epub Aug. 29, 2008); 372(9645):1223-1230.
GISSI-Prevenzione Investigators, "Dietary Supplementation with n-3 Polyunsaturated Fatty Acids and Vitamin E after Myocardial Infarction: Results of the GISSI-Prevenzione Trial," The Lancet, 354:447-455, (Aug. 7, 1999).
Glod, "Recent Advances in the Pharmacotherapy of Major Depression", Arch. Psychiatr. Nurs., 10(6):355-364 (Dec. 1996); https://www.sciencedirect.com/science/article/abs/pii/S0883941796800495, Available online Dec. 10, 2004.
Goff DC, et al., ACC/AHA Prevention Guideline: 2013 ACC/AHA Guideline on the Assessment of Cardiovascular Risk: A Report of the American College of Cardiology/American Heart Association Task Force on Practice Guidelines. Circulation. Jun. 24, 2014 (epub Nov. 12, 2013); 129:S74-S75.
Goldberg, AC, "Combination therapy of dyslipidemia," Current Treatment Options in Cardiovascular Medicine 200708 GB, vol. 9, No. 4, pp. 249-258 (2007); https://link.springer.com/article/10.1007%2Fs11936-007-0020-7, Published: Jul. 9, 2007.

(56) References Cited

OTHER PUBLICATIONS

Goodman & Gilman (Robert W. Mahley & Thomas P. Bersot) Drug Therapy for Hypercholesterolemia and Dyslipidemia, in Goodman & Gilman's The Pharmacological Basis fo Therapeutics 971 (Hardman et al., eds 10th ed. 2001)(32 pages).

Gordon, DJ. et al., High density lipoprotein cholesterol and cardiovascular disease: four prospective American studies. Circulation. 79: 8-15. (1989); https://www.ahajournals.org/doi/abs/10.1161/01.cir.79.1.8, Originally published Jan. 1, 1989.

Gorriz JL et al., "Rhabdomyolysis and Acute Renal Failure Associated with Gemfibrozil Therapy," Nephron 74(2): 437-438 (1996); https://www.karger.com/article/Abstract/189355, Published online: Dec. 24, 2008, Issue release date: 1996.

Gorriz, JL, "Rhabdomyolysis and Acute Renal Failure Associated with Bezafibrate Treatment," Nephrol Dial Transplant 10(12):2371-2372 (1995); https://academic.oup.com/ndt/article-abstract/10/12/2371/1804883?redirectedFrom=fulltext, Published: Dec. 1, 1995.

Gosai, P, et al. Effect of omega-3-acid ethyl esters on the steady-state plasma pharmacokinetics of rosuvastatin in healthy adults. Expert Opin. Pharmacother. 9, 2947-2953 (2008); https://www.tandfonline.com/doi/abs/10.1517/14656560802532640, Published online: Nov. 12, 2008.

Goto, Y, et al., "Clinical Pharmacological Trial of Ethyl Icosapentate (MND-21)—Dose Finding Study." Journal of Clinical Therapeutic & Medicines 8:1293-309 (1992).

Gould, AL, et al., "Cholesterol reduction yields clinical benefit: impact of statin trials." Circulation, 97:946-952 (1998); https://www.ahajournals.org/doi/full/10.1161/01.CIR.97.10.946, Manuscript received Aug. 15, 1997. Manuscript accepted Nov. 18, 1997, Originally published Mar. 17, 1998.

Greenblatt DJ, et al., Interaction of warfarin with drugs, natural substances, and foods. J. Clin. Pharmacol. Feb. 2005 45 (2): 127-32; https://accp1.onlinelibrary.wiley.com/doi/abs/10.1177/0091270004271404, First published: Mar. 7, 2013. Version of Record online: Mar. 7, 2013, Submitted for publication Aug. 5, 2004; revised version accepted Sep. 23, 2004.

Grenyer, Brin, et al., "Fish Oil Supplementation in the Treatment of Major Depression: A Randomised Double-Blind Placebo-Controlled Trial", Progress in Neuro-Psychopharmacology & Biological Psychiatry, 31:1393-1396, (2007); https://www.sciencedirect.com/science/article/abs/pii/S0278584607001960, Revised Apr. 25, 2007, Accepted Jun. 12, 2007, Available online Jun. 19, 2007.

Griffin, M.D., et al., "Effects of altering the ratio of dietary n-6 to n-3 fatty acids on insulin sensitivity, lipoprotein size, and postprandial lipemia in men and postmenopausal women aged 45-70 y: the OPTILIP Study." Am J Clin Nutr 84:1290-8 (2006); https://academic.oup.com/ajcn/article/84/6/1290/4649077, Accepted Jul. 17, 2006, Published: Dec. 1, 2006.

Grimsgaard et al., "Effects of Highly Purified Eicosapentaenoic Acid and Docosahexaenoic Acid on Hemodynamics in Humans" American Society for Clinical Nutrition, 68:52-9, (1998); https://academic.oup.com/ajcn/article/68/1/52/4666036, Published: Jul. 1, 1998.

Grimsgaard S, et al., "Highly purified eicosapentaenoic acid and docosahexaenoic acid in humans have similar triacylglycerol-lowering effects but divergent effects on serum fatty acids" Am J Clin Nutr, 66:649-659, (1997); https://academic.oup.com/ajcn/article/66/3/649/4655798, Published: Sep. 1, 1997.

Gromova, O.A et al, published Jan. 2009, [found online Dec. 11, 2019] (found from Internet: t-patient.ru/articles/6417/) with English Machine Translation, и др. анализ биохимических эффектов эйкозапентаеновой и докозагексаеновой омега 3 ПНЖК : на физиологию беременности и развитие плода . Трудный пациент . Трудный пациент 2009.

Grundy SM, et al. Implications of Recent Clinical Trials for the National Cholesterol Education Prgram Adult Treatment Panel III Guidelines, Circulation. 2004; 110:227-39; https://www.onlinejacc.org/content/44/3/720.abstract, Aug. 2004. Published online Aug. 4, 2004.

Grundy SM, et al., Efficacy, safety, and tolerability of once-daily niacin for the treatment of dyslipidemia associated with type 2 diabetes: results of the Assessment of Diabetes Control and Evaluation of the Efficacy of Niaspan Trial. Arch. Intern. Med. 162: 1568-1576 (2002); https://jamanetwork.com/journals/jamainternalmedicine/article-abstract/212257, Jul. 22, 2002, Accepted for publication Dec. 3, 2001.

Grundy, Scott M, "Low-Density Lipoprotein, Non-High-Density Lipoprotein, and Apolipoprotein B as Targets of Lipid-Lowering Therapy" Circulation. 106:2526-2529 (2002); https://www.ahajournals.org/doi/full/10.1161/01.cir.0000038419.53000.d6, Originally published Nov. 12, 2002.

Guallar, E, et al., "Omega-3 fatty acids in adipose tissue and risk of myocardial infarction—The EURAMIC study." Arterioscler. Thromb. Vasc. Biol., 19:1111-1118 (1999); https://www.ahajournals.org/doi/full/10.1161/01.atv.19.4.1111, Manuscript received Feb. 9, 1998. Manuscript accepted Oct. 28, 1998, Originally published Apr. 1, 1999.

Guillot et al., "Increasing intakes of the long-chain omega-3 docosahexaenoic acid: effects on platelet functions and redox status in healthy men," The FASEV Journal, vol. 23, pp. 2909-2916 (2009); https://faseb.onlinelibrary.wiley.com/doi/abs/10.1096/fj.09-133421, First published May 14, 2009. Version of Record online May 14, 2009, Manuscript accepted: Apr. 30, 2009. Manuscript received Mar. 24, 2009.

Guizy, M, et al., "ω-3 and ω-6 Polyunsaturated fatty acids block HERG channels." Am J Physiol Cell Physiol 289:C1251-C1260 (2005); https://journals.physiology.org/doi/full/10.1152/ajpcell.00036.2005, Accepted Jun. 28, 2005, Published online Nov. 1, 2005. Published in print Nov. 1, 2005.

Gyarmathy, M., "Selection from the industrial manufacturing. 5th part: Gelatine capsules. 5/2 part: Soft gelatine capsules," Gyogyszereszet, vol. 38, No. 2, 1994, pp. 105-109, (w/English summary).

Hakonarson, H., et al., "Effects of a 5-lipoxygenase-activating protein inhibitor on biomarkers associated with risk of myocardial infarction—a randomized trial." JAMA, 293(8):2245-56 (May 11, 2005).

Hall, WL, et al., "A high-fat meal enriched with eicosapentaenoic acid reduces postprandial arterial stiffness measured by digital volume pulse analysis in healthy men." J. Nutr. 138: 287-291 (Feb. 2008); https://academic.oup.com/jn/article/138/2/287/4664997, Revision received: Sep. 26, 2007, Accepted: Nov. 14, 2007. Published: Feb. 1, 2008.

Hamazaki et al., "Docosahexaenoic Acid-Rich Fish Oil Does Not Affect Serum Lipid Concentrations of Normolipidemic Young Adults," American Institute of Nutrition, 126(11):2784-2789, Nov. 1996; https://academic.oup.com/jn/article/126/11/2784/4724665, Accepted Jul. 9, 1996. Published Nov. 1, 1996.

Hamazaki et al., "Effects of fish oil rich in eicosapentaenoic acid on serum lipid in hyperlipidemic hemodialysis patients," Kidney Int'l., 26:81-84 (Jul. 1984); https://www.sciencedirect.com/science/article/pii/S0085253815332464, Revised Jan. 27, 1984, Available online Dec. 18, 2015.

Hamazaki et al., "Effects of Orally Administered Ethyl Ester of Eicosapentaenoic Acid (EPA: C20:5, omega-3) On PG12-Like Substance Production by Rat Aorta" Prostaglandins, vol. 23 No. 4, pp. 557-567 (Apr. 1982); https://www.sciencedirect.com/science/article/abs/pii/0090698082901162, Accepted Jan. 3, 1982, Available online Dec. 1, 2003.

Hamazaki T, et al., "Reduction of microalbuminuria in diabetics by Eicosapentaenoic acid ethyl ester" Lipids. 25 (9):542-5 (Sep. 1990); https://link.springer.com/article/10.1007/BF02537161, Published: Sep. 1990, Accepted May 29, 1990.

Hampel H, et al., Meta-analysis: obesity and the risk for gastroesophageal reflux disease and its complications. Ann. Intern. Med. Aug. 2005 143 (3): 199-211; https://www.acpjournals.org/doi/full/10.7326/0003-4819-143-3-200508020-00006, ePublished Aug. 2, 2005, Issue Published Aug. 2, 2005.

(56) References Cited

OTHER PUBLICATIONS

Han, JJ, et al., "Enhancement of both reaction yield and rate of synthesis of structured triacylglycerol containing eicosapentaenoic acid under vacuum with water activity control." Lipids 34:989-995 (Sep. 1999); https://link.springer.com/article/10.1007/s11745-999-0449-6, Revised Aug. 11, 1999. Accepted Aug. 20, 1999, Issue date Sep. 1999.
Hanasaki, K., et al., "Potent modification of low density lipoprotein by group X secretory phospholipase A2 is linked to macrophage foam cell formation." J. Biol. Chem. 277(32):29116-24 (Aug. 9, 2002).
Haney, EM, et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce.org/uspstf07/chlipid/chlipidsyn.pdf. (Accessed Mar. 23, 2011)(573 pages).
Hannah, J, et al., "Effect of dietary fatty acids on LDL binding." Ann N Y Acad Sci., 683:178-182 (Jun. 14, 1993).
Hansen et al., "Comparative effects of prolonged intake of highly purified fish oils as ethyl ester or triglyceride on lipids, haemostasis and platelet function in normolipaemic men." Eur. J. Clin. Nutr. 47(7):497-507 (Jul. 1993); https://europepmc.org/article/med/8404785 , Jun. 30, 1993.
Hansen, JB, et al., "Effects of highly purified eicosapentaenoic acid and docosahexaenoic acid on fatty acid absorption, incorporation into serum phospholipids and postprandial triglyeridemia." Lipids 33:131-38 (Feb. 1998); https://aocs.onlinelibrary.wiley.com/doi/abs/10.1007/s11745-998-0188-8, Version of Record online Feb. 1, 1998, Manuscript accepted Dec. 15, 1997, Manuscript revised Dec. 15, 1997, Manuscript received Mar. 31, 1997.
Harada-Shiba et al., Journal of Clinical and Experimental Medicine, Jun. 30, 2007, vol. 221, No. 13, pp. 1068-1073 (with English translation).
Harris WS, "n-3 Fatty acids and lipoproteins: a comparison of results from human and animal studies," Lipids 31, 243-252 (Mar. 1996); https://aocs.onlinelibrary.wiley.com/doi/abs/10.1007/BF02529870 , Issue Online: Mar. 1, 1996. Version of Record online: Mar. 1, 1996, Manuscript accepted: Feb. 9, 1996. Manuscript revised: Feb. 6, 1996, Manuscript received: Sep. 19, 1995.
Harris WS, International recommendations for consumption of long-chain omega-3 fatty acids. J Cardiovasc Med (Hagerstown) 8(suppl 1):S50-S52, Sep. 2007; https://journals.lww.com/jcardiovascularmedicine/Abstract/2007/09001/International_recommendations_for_consumption_of.13.aspx.
Harris, W.S., et al., "Stearidonic acid increases the red blood cell and heart eicosapentaenoic acid content in dogs." Lipids 42:325-333 (Apr. 2007)(epub Mar. 9, 2007).
Harris, W.S., et al., "Tissue n-3 and n-6 fatty acids and risk for coronary heart disease events." Atherosclerosis 193:1-10 (Jul. 2007)(epub May 15, 2007).
Harris, WS, "Expert opinion: omega-3 fatty acids and bleeding-cause for concern?" The American Journal of Cardiology 99(6A): 45C-46C (Mar. 19, 2007).
Harris, WS, "Fish oils and plasma lipid and lipoprotein metabolism in humans: a critical review." J Lipid Res. 30:785-807 (Jun. 1989); https://www.jlr.org/content/30/6/785.short.
Harris, WS, "n-3 Fatty acids and human lipoprotein metabolism: an update." Lipids 34:S257-S258 (1999); https://search.proquest.com/openview/c23a45284d9ebd10947fb9974f83fdc3/1?pq-origsite=gscholar&cbl=35263 Jan. 1999.
Harris, WS, "n-3 Fatty acids and serum lipoproteins: human studies." Am J Clin Nutr 65:1645S-54S (1997); https://academic.oup.com/ajcn/article/65/5/1645S/4655609, Published: May 1, 1997.
Harris, WS, "Omega-3 fatty acids in cardiac biopsies from heart transplantation patients." Circulation 110;1645-1649 (Sep. 21, 2004).
Harris, WS, "The omega-3 index as a risk factor for coronary heart disease." Am J Clin Nutr 87:1997S-2002S (Jun. 2008); https://academic.oup.com/ajcn/article/87/6/1997S/4633363, Published: Jun. 1, 2008.
Harris, WS, et al. "Safety and efficacy of Omacor in severe hypertriglyceridemia," Journal of Cardiovascular Risk, 4:385-391 (Oct.-Dec. 1997); https://journals.sagepub.com/doi/abs/10.1177/174182679700400511 , First Published Jan. 1, 1997.
Harris, WS, et al., "Comparison of the effects of fish and fish-oil capsules on the n-3 fatty acid content of blood cells and plasma phospholipids." Am J Clin Nutr 86:1621-5 (Dec. 2007); https://academic.oup.com/ajcn/article/86/6/1621/4649678, Accepted Aug. 7, 2007, Published Dec. 1, 2007.
Harris, WS, et al., "n-3 Fatty acids and urinary excretion of nitric oxide metabolites in humans." Am. J. Clin. Nutr., 65:459-64 (Feb. 1997); https://academic.oup.com/ajcn/article/65/2/459/4655355, Published: Feb. 1, 1997.
Harris, WS, et al., "Omega-3 fatty acids and coronary heart disease risk: Clinical and mechanistic perspectives." Atherosclerosis 197:12-24 (Mar. 2008)(epub Dec. 26, 2007).
Harris, WS, et al., "Influence of n-3 fatty acid supplementation on the endogenous activities of plasma lipases." Am. J. Clin. Nutr. 66:254-60 (Aug. 1997); https://academic.oup.com/ajcn/article/66/2/254/4655660, Published: Aug. 1, 1997.
Hartweg, J, et al., "Potential impact of omega-3 treatment on cardiovascular disease in type 2 diabetes." Curr Opin Lipidol., 20:30-38 (Feb. 2009); https://journals.lww.com/co-lipidology/Abstract/2009/02000/Potential_impact_of_omega_3_treatment_on.7.aspx, Feb. 2009.
Hata et al., Geriatric Medicine, 30 (5), 799-852, 1992 (with English introduction).
Hawthorne, et al., "High dose eicosapentaenoic acid ethyl ester: effects on lipids and neutrophil leukotriene production in normal volunteers." Br. J. Clin. Pharmac., vol. 30, 187-194 (Aug. 1990); https://bpspubs.onlinelibrary.wiley.com/doi/abs/10.1111/j.1365-2125.1990.tb03764.x First published Aug. 1990, Issue Online Jul. 26, 2012, Version of Record online Jul. 26, 2012.
Hayashi et al., Decreases in Plasma Lipid Content and Thrombotic Activity by Ethyl Icosapentate Purified from Fish Oiles, Current Therapeutic Research, vol. 56, No. 1, pp. 24-31 (1995); https://www.sciencedirect.com/science/article/pii/0011393X95850163, Jan. 1995. Available online Oct. 10, 2001.
Herbette L, et al., A direct analysis of lamellar x-ray diffraction from hydrated oriented multilayers of fully functional sarcoplasmic reticulum. Biophys. J. Nov. 1977;20(2):245-272; https://www.sciencedirect.com/science/article/pii/S0006349577855471 , Available online Jan. 6, 2009.
Hibbeln, JR, et al., "Healthy intakes of n-3 and n-6 fatty acids: estimations considering worldwide diversity." Am J Clin Nutr. 83:1483S-93S (Jun. 2006); https://academic.oup.com/ajcn/article/83/6/1483S/4633242, Published: Jun. 1, 2006.
Higashihara et al. "Effects of Eicosapentaenoic Acid on Biochemical Failure after Radical Prostatectomy for Prostate Cancer," in vivo 24:561-566 (Jul./Aug. 2010); http://iv.iiarjournals.org/content/24/4/561.short.
Hilpert, KF, et al., "Postprandial effect of n-3 polyunsaturated fatty acids on apolipoprotein B-containing lipoproteins and vascular reactivity in type 2 diabetes." Am J Clin Nutr 85:369-76 (Feb. 2007); https://academic.oup.com/ajcn/article/85/2/369/4649471, Accepted Sep. 12, 2006, Published Feb. 1, 2007.
Hirafuji, M., et al., "Docosahexaenoic acid potentiates interleukin-1beta induction of nitric oxide synthase through mechanism involving p44/42 MAPK activation in rat vascular smooth muscle cells." British Journal of Pharmacology 136:613-619 (Jun. 2002).
Hirai, A., et al., "The effects of the oral administration of fish oil concentrate on the release and the metabolism of [14C] arachidonic acid and [14C] eicosapentaenoic acid by human platelets", Thromb. Res., 28:285-298, (Nov. 1, 1982).
Hirano T, et al., Clinical significance of small dense low-density lipoprotein cholesterol levels determined by the simple precipitation method. Arterioscler. Thromb. Vase. Biol. Mar. 2004;24(3):558-563.(epub Jan. 15, 2004).

(56) References Cited

OTHER PUBLICATIONS

Hirano, R, et al., "Regulation by long-chain fatty acids of the expression of cholesteryl ester transfer protein in HepG2 cells." Lipids, 36:401-406 (Apr. 2001); https://link.springer.eom/article/10.1007/s11745-001-0735-3, Revised Mar. 9, 2001, Accepted Mar. 12, 2001, Published Apr. 2001.

Hofacer R, et al., Omega-3 fatty acid deficiency increases stearoyl-CoA desaturase expression and activity indices in rat liver: Positive association with non-fasting plasma triglyceride levels, Prostaglandins Leukot. Essent. Fatty Acids. Jan./Feb. 2012;86:71-7. (epub Nov. 1, 2011).

Hoffman, "Atherosclerosis: Prevention through the Ages," WebMD, https://www.webmed.com/heart/features/atherosclerosis-prevention-through-ages#1, (Dec. 4, 2007).

Hohenester, "Primary Biliary Cirrhosis," Semin Immunopathol. 31L:283-307, 285 (Sep. 2009)(epub Jul. 15, 2009).

Holmeide, AK, et al., "Oxidative degradation of eicosapentaenoic acid into polyunsaturated aldehydes," Tetrahedron 59:7157-7162 (2003); https://www.sciencedirect.com/science/article/abs/pii/S0040402003010962 Revised Jun. 6, 2003, Accepted Jul. 10, 2003, Available online Aug. 2, 2003.

Holub, B.J., PhD, "Fish Oils and Cardiovascular Disease", Canadian Medical Association Journal, 141(10):1063 (Nov. 15, 1989).

Holvoet P, et al., The metabolic syndrome, circulating oxidized LDL, and risk of myocardial infarction in wellfunctioning elderly people in the health, aging, and body composition cohort. Diabetes. Apr. 2004;53(4):1068-1073; https://diabetes.diabetesjournals.org/content/53/4/1068.short, Accepted Jan. 9, 2004.

Hom et al., "Soft Gelatin Capsules II: Oxygen Permeability Study of Capsule Shells," J Pharm Sci. (May 1975) 64(5):851-857; https://onlinelibrary.wiley.com/doi/abs/10.1002/jps.2600640528, First published May 1975, Manuscript received Jul. 15, 1974. Manuscript accepted Oct. 24, 1974, Version of Record online Sep. 18, 2006.

Hombeck, M, et al., "Biosynthesis of the algal pheromone fucoserratene by the freshwater diatom Asterionella formosa (Bacillariophyceae)." Tetrahedron 54:11033-11042 (1998); https://www.sciencedirect.com/science/article/abs/pii/S0040402098006607, Accepted Jul. 2, 1998, Available online Oct. 21, 1998.

Hong KN, Fuster V, Rosenson RS, Rosendorff C, Bhatt DL. How low to go with glucose, cholesterol, and blood pressure in primary prevention of CVD. J Am Coll Cardiol 70(17):2171-85 (publication date Oct. 24, 2017; epublication date Oct. 16, 2017).

Hoogeveen EK, et al., No effect of n-3 fatty acids supplementation on NT-proBNP after myocardial infarction: the Alpha Omega Trial. Eur J Prev Cardiol. May 2015;22:648-55; https://journals.sagepub.com/doi/abs/10.1177/2047487314536694, Article first published online May 30, 2014, Issue published May 1, 2015.

Horrobin, DF, The Phospholipid Concept of Psychiatric Disorders and its Relationship to the Neurodevelopmental Concept of Schizophrenia. In M. Peet (ed.) Phospholipid Spectrum Disorder in Psychiatry pp. 1-19 (1999).

Hoskins et al., "Combination use of statins and omega-3 fatty acids: an emerging therapy for combined hyperlipidemia," Abstract, 1(5): 579-591(13) (2006); https://www.tandfonline.com/doi/abs/10.2217/17460875.1.5.579, Published online: Jan. 18, 2017.

Howe, PR, et al., "Equal antithrombotic and triglyceride-lowering effectiveness of eicosapentaenoic acid-rich and docosahexaenoic acid-rich fish oil supplements." Lipids 34:S307-S308 (1999); https://search.proquest.com/openview/ee10d66c9b25bf249c00afcdf89e5e60/1?pq-origsite=gscholar&cbl=35263, Jan. 1999.

HPs2-thrive Collaborative Group, "randomized placebo-controlled trial in 25 673 high-risk patients of er niacin/laroprant: Trial design, pre-specified muscle and liver outcomes, and reasons for stopping study treatment." Eur. Heart J. May 2013;34:1279-1291; https://academic.oup.com/eurheartj/article/34/17/1279/444301, Revision received Jan. 18, 2013, Accepted Jan. 30, 2013, Published Feb. 26, 2013.

HPS2-THRIVE Collaborative Group, Landray MJ, Haynes R, et al. Effects of extended-release niacin with laropiprant in high-risk patients. N Engl J Med. Jul. 17, 2014; 371(3):203-12.

Hruska MW, et al., The effect of trimethoprim on CYP2C8 mediated rosiglitazone metabolism in human liver microsomes and healthy subjects. Br. J. Clin. Pharmacol. Jan. 2005;59:70-79; https://bpspubs.onlinelibrary.wiley.com/doi/full/10.1111/j.1365-2125.2005.02263.x, First published:Dec. 16, 2004. Version of Record online: Dec. 16, 2004 Editorial history: Accepted Jul. 20, 2004.

Hughes et al., "Fish oil produces an atherogenic lipid profile in hypertensive men," Atherosclerosis, 84, pp. 229-237 (Oct. 1990); https://www.sciencedirect.com/science/article/abs/pii/002191509090095Z, Revised Apr. 3, 1990, Revised Jun. 18, 1990, Accepted Jun. 26, 1990, Available online Apr. 14, 2005.

Hulthe J, et al., Low adipocyte-derived plasma protein adiponectin CJ concentrations are associated with the metabolic syndrome and small dense low-density lipoprotein particles: atherosclerosis and insulin resistance study. Metab. Clin. Exp. Dec. 2003;52(12):1612-1614; https://www.sciencedirect.com/science/article/abs/pii/S0026049503003135, Accepted Jun. 11, 2003, Available online Nov. 27, 2003.

Huntington's Diesase Drug Works—The DHA Dilemma, http://hddrugworks.org/index2.php?option=com_content&task=view&id=185&pop=1&pa . . . Printed on Aug. 22, 2008.(2 pages).

Ignarro LJ, et al., Endothelium-derived relaxing factor produced and released from artery and vein is nitric oxide. Proc. Natl. Acad. Sci. USA. Dec. 1987;84:9265-9269; https://www.pnas.org/content/84/24/9265.short Dec. 1, 1987.

Illingworth, DR, et al., "Comparative effects of lovastatin and niacin in primary hypercholesterolemia: A prospective trial," Arch. Int. Med., 154:1586-1595, (Jul. 25, 1994).

Inoue, I, et al., "Expression of peroxisome proliferator-activated receptor α (PPARα) in primary cultures of human vascular endothelial cells." Biochem. Biophys. Res. Comm., 246, 370-374 (May 19, 1998).

Inzucchi et al., "Diagnosis of Diabetes," New Engl. Journ of Med., 367(6):541-550 (Aug. 9, 2012).

Ishida, Y, et al., "α-Lipoic Acid and Insulin Autoimmune Syndrome." Diabetes Care, 30(9): 2240-41 (Sep. 2007); https://care.diabetesjournals.org/content/30/9/2240.short, Published in print Aug. 28, 2007, Published online ahead of print Jun. 22, 2007.

Isley, et al., "Pilot study of combined therapy with ω-3 fatty acids and niacin in atherogenic dyslipidemia," Journal of Clinical Lipidology, 1, 211-217 (Jul. 2007); https://www.sciencedirect.com/science/article/abs/pii/S1933287407001389, Revised May 1, 2007, Accepted May 13, 2007, Available online May 18, 2007.

Itoh et al., "Increased adiponectin secretion by highly purified eicosapentaenoic acid in rodent models of obesity and human obses subjects," Arterioscler. Thromb. Vasc. Biol., pp. 1918-1925 (together with online Supplements 1-15) (Sep. 2007)(epub Jun. 14, 2007).

Ivanova et al., "Small Dense Low-Density Lipoprotein as Biomarker for Atherosclerotic Diseases," May 9, 2017, Oxidative Medicine and Cellular Longevity (2017), 10 pp.

Jacob RF, et al., Atorvastatin active metabolite inhibits oxidative modification of small dense low-density lipoprotein. J. Cardiovasc. Pharmacol. Aug. 2013;62(2):160-166; https://journals.lww.com/cardiovascularpharm/Abstract/2013/08000/Atorvastatin_Active_Metabolite_Inhibits_Oxidative.7.aspx.

Jacob RF, Mason RP. Lipid peroxidation induces cholesterol domain formation in model membranes. J. Biol. Chem. Nov. 25, 2005;280(47):39380-39387.(epub Sep. 28, 2005).

Jacobson et al. "Hypertriglyceridemia and Cardiovascular Risk Reduction", Clinical Therapeutics, vol. 29 pp. 763-777 (May 2007); https://www.sciencedirect.com/science/article/abs/pii/S0149291807001208, Available online Aug. 11, 2007.

Jacobson TA, Opening a new lipid "apo-thecary": incorporating apolipoproteins as potential risk factors and treatment targets to reduce cardiovascular risk. Mayo Clin. Proc. Aug. 2011 ;86:762-780; https://www.sciencedirect.com/science/article/abs/pii/S0025619611651781, Available online Dec. 23, 2011.

Jacobson, T. Secondary Prevention of Coronary Artery Disease with Omega-3 Fatty Acids. Am J Cardiol; 98 [suppl]: 61i-70i (Aug. 21, 2006).

Jacobson, T.A., "Role of n-3 fatty acids in the treatment of hypertriglyceridemia and cardiovascular disease." Am J Clin Nutr

(56) References Cited

OTHER PUBLICATIONS

87:1981S-90S (Jun. 2008); https://academic.oup.com/ajcn/article/87/6/1981S/4633487 Published: Jun. 1, 2008.

Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (Jan./Feb. 2012); https://www.sciencedirect.com/science/article/abs/pii/S1933287411007458, Accepted Oct. 23, 2011, Available online Nov. 3, 2011.

Jakus V, et al., Advanced glycation end-products and the progress of diabetic vascular complications. Physiol. Res. 2004;53(2): 131-142; https://www.researchgate.net/profile/Vladimir_Jakus/publication/8653397_Advanced_Glycation_End-Products_and_the_Progress_of_Diabetic_Vascular_Complications/links/0a85e533c07988653b000000.pdf, Accepted Jun. 9, 2003.

Jenner, "Presymptomatic Detection of Parkinson's Disease". J Neural Transm Suppl., 40:23-36. (Abstract only) (1993); https://europepmc.org/article/med/8294898, Dec. 31, 1992.

Jialal I, et al., Antioxidants and atherosclerosis: Don't throw out the baby with the bath water. Circulation. Feb. 25, 2003;107:926-928.

Jialal, I, "Editorial: Remnant lipoproteins: measurement and clinical significance." Clinical Chemistry 48(2):217-219 (Feb. 2002); https://academic.oup.com/clinchem/article/48/2/217/5641526, Feb. 1, 2002.

Jinno Y, Nakakuki M, Kawano H, Notsu T, Mizuguchi K, Imada K. Eicosapentaenoic acid administration attenuates the pro-inflammatory properties of VLDL by decreasing its susceptibility to lipoprotein lipase in macrophages. Atheroscler.Dec. 2011;219:566-572.(epub Oct. 4, 2011).

Jong et al., "Role of ApoCs in Lipoprotein Metabolism: Function Differences Between ApoC1, ApoC2, and ApoC3," Arteriosclerosis, Thrombosis and Vascular Biology. (Mar. 1999) 19(3):472-484; https://www.ahajournals.org/doi/full/10.1161/01.atv.19.3.472, Manuscript received Jun. 3, 1998, Manuscript accepted Jul. 10, 1998, Originally published Mar. 1, 1999.

Jørgensen AB, Frikke-Schmidt R, Nordestgaard BG, Tybjærg-Hansen A. Loss-of-function mutations in APOC3 and risk of ischemic vascular disease. N Engl J Med. Jul. 3, 2014; 371(1):32-41 (epub Jun. 18, 2014).

Journal of Practical Pharmacy, "Hyperlipidemia Drug," 58(4):1303-1324 (2007) (with English abstract); not online.

Journal of the Japan Diabetes Society, "The Relationship Between Postprandial ApoB48 Increase and Insulin Resistance in Type-2 Diabetes," 55(Suppl. 1):S310 (Apr. 2012) (with English Translation), 2 pages.

Journal of the Japanese Diabetes Society, "A Case of Familial Combined Hyperlipidemia Associated with Obesity, Type 2 Diabetes Mellitus and Severe Hypertriglyceridemia," 51(3), pp. 233-237 (Mar. 30, 2008) (with English abstract).

Jun M, et al., Effects of fibrates on cardiovascular outcomes: a systematic review and meta-analysis. Lancet 375 (9729):1875-1884, May 29, 2010 (epub May 10, 2010).

Jung, UJ, et al., "n-3 Fatty acids and cardiovascular disease: mechanisms underlying beneficial effects." Am J Clin Nutr 87: 2003S-9S (Jun. 2008); https://academic.oup.com/ajcn/article/87/6/2003S/4633490, Published: Jun. 1, 2008.

Kamanna et al., "Mechanism of Action of Niacin," *The American Journal of Cardiology* (Apr. 17, 2008), 101(8), S20-S26.

Kamido et al., Lipid Composition of Platelets from Patients with Atherosclerosis:Effect of Purified Eicosapentaenoic Acid Ethyl Ester Administration, Oct. 1988, Lipids, 23, pp. 917-923 [Abstract only], 7 pp.; https://link.springer.com/article/10.1007/BF02536337, Accepted May 10, 1988, Issue Date Oct. 1988.

Kaminski WE, Jendraschak E, Kiefl R, et al. Dietary omega-3 fatty acids lower levels of platelet-derived growth factor mRNA in human mononuclear cells. Blood Apr. 1993, 81(7): 1871-9; not online.

Kanayasu, T, et al., "Eicosapentaenoic acid inhibits tube formation of vascular endothelial cells in vitro." Lipids 26:271-276 (Apr. 1991); https://aocs.onlinelibrary.wiley.com/doi/abs/10.1007/BF02537136 Issue Online: Apr. 1, 1991. Version of Record online: Apr. 1, 1991, Manuscript accepted Jan. 19, 1991, Manuscript received Feb. 19, 1990.

Kastelein et al., Omega-3 Free Fatty Acids for the Treatment of Severe Hypertriglyceridemia: The EpanoVa for Lowering Very High Triglycerides (EVOLVE) Trial, J. Clin. Lipidol. (JACL 597) Jan./Feb. 2014 (epub Oct. 14, 2013).

Katan, MB, et al., "Kinetics of the incorporation of dietary fatty acids into serum cholesteryl esters, erythrocyte membranes, and adipose tissue: an 18-month controlled study." J. Lipid Res. 38: 2012-2022 (Oct. 1997); https://www.jlr.org/content/38/10/2012.short.

Katayama et al., Effect of long-term administration of ethyl eicosapentate (EPA-E) on local cerebral blood flow and glucose utilization in stroke-prone spontaneously hypertensive rats (SHRSP), Brain Research, vol. 761, pp. 300-305 (Dec. 31, 1997).

Katayama et al., "Efficacy and Safety of Ethyl Icosapentate (Epadel) Given for a Long Term Against Hyperlipidemia," Prog. Med., 21:457-467 (2001) (with English translation).

Kato, T, et al., "Palmitate impairs and eicosapentaenoate restores insulin secretion through regulation of SREBP-1c in pancreatic islets." Diabetes, 57(9):2382-2392 (2008) (published online May 5, 2008).

Kawamura et al., "Effects of 4 weeks' intake of polyunsaturated fatty acid ethylester rich in eicosapentaenoic acid (ethylester) on plasma lipids, plasma and platelet phsopholipid fatty acid composition and platelet aggregation; a double blind study," Nihon Naika Gakkai Zasshi, 72(1):18-24 (Jan. 10, 1983).

Kawano, H, et al., "Changes in aspects such as the collagenous fiber density and foam cell size of atherosclerotic lesions composed of foam cells, smooth muscle cells and fibrous components in rabbits caused by all-cis 5, 8, 11, 14, 17-icosapentaenoic acid," J. Atheroscler. Thromb., 9:170-177, (2002); https://www.jstage.jst.go.jp/article/jat/9/4/9_4_170/_article/-char/ja/, 2002-9-4.

Kawashima, H., et al., "Oral Administration of Dihomo-γ-Linolenic Acid Prevents Development of Atopic Dermatitis in NC/Nga Mice." Lipids 43:37-43 (Jan. 2008)(epub Nov. 6, 2007).

Keech A, Simes RJ, Barter P, Best J, Scott R, Taskinen MR, Forder P, Pillai A, Davis T, Glasziou P, Drury P, Kesaniemi Y A, Sullivan D, Hunt D, Colman P, d'Emden M, Whiting M, Ehnholm C, Laakso M. Effects of long-term fenofibrate therapy on cardiovascular events in 9795 people with type 2 diabetes mellitus (the FIELD study): Randomised controlled trial. Lancet. Nov. 26, 2005;366:1849-1861.

Kelley, DS, et al., "Docosahexaenoic Acid Supplementation Decreases Remnant-Like Particle-Cholesterol and Increases the (n-3) Index in Hypertriglyceridemic Men." J. Nutr. 138: 30-35 (Jan. 2008); https://academic.oup.com/jn/article/138/1/30/4665053, Revision received: Sep. 18, 2007, Accepted: Oct. 10, 2007. Published: Jan. 1, 2008.

Kelley, et al., "Docosahexaenoic acid supplementation improves fasting and postprandial lip profiles in hypertriglyceridemic men." The American Journal of Clinical Nutrition, 86: 324-333 (Aug. 2007); https://academic.oup.com/ajcn/article/86/2/324/4754058, Accepted Apr. 5, 2007, Published Aug. 1, 2007.

Kellner-Weibel G, et al., Crystallization of free cholesterol in model macrophage foam cells. Arterioscler. Thromb. Vasc. Biol. Aug. 1999;19(8):1891-1898; https://www.ahajournals.org/doi/full/10.1161/01.ATV.19.8.1891, Manuscript received Oct. 28, 1998, Manuscript accepted Jan. 22, 1999, Originally published Aug. 1, 1999.

Kendall BJ, et al., The risk of Barrett's esophagus associated with abdominal obesity in males and females. Int. J. Cancer May 2013 132 (9): 2192-9; https://onlinelibrary.wiley.com/doi/full/10.1002/ijc.27887 , Issue Online: Feb. 18, 2013. Version of Record online Oct. 30, 2012, Accepted manuscript online Oct. 3, 2012, Manuscript accepted Sep. 7, 2012, Manuscript received Jun. 3, 2012.

Kerr, S, et al., Dominiczak AF, Hamilton CA. Superoxide anion production is increased in a model of genetic hypertension role of the endothelium. Hypertension. Jun. 1999;33:1353-1358; https://www.ahajournals.org/doi/full/10.1161/01.hyp.33.6.1353, Manuscript received Dec. 29, 1998, Manuscript accepted Feb. 15, 1999, Originally published Jun. 1, 1999.

Kew, S, et al., "Effects of oils rich in eicosapentaenoic and docosahexaenoic acids on immune cell composition and function in

(56) References Cited

OTHER PUBLICATIONS healthy humans." Am J Clin Nutr 79:674-81 (Apr. 2004); https://academic.oup.com/ajcn/article/79/4/674/4690168, Accepted Sep. 8, 2003, Published Apr. 1, 2004.
Kholodov et al., "Clinical Pharmacokinetics," M. Medicine. (1985) pp. 89-98, 134-138, 160, 378-380 [with English Summary](27 pages).
Khoueiry G, et al., Do omega-3 polyunsaturated fatty acids reduce risk of sudden cardiac death and ventricular arrhythmias? A meta-analysis of randomized trials, Heart and Lung. Jul./Aug. 2013;42:251-256. (epub May 25, 2013); https://www.sciencedirect.com/science/article/abs/pii/S0147956313000800 Revised Mar. 15, 2013, Accepted Mar. 19, 2013, Available online May 25, 2013.
Kim F, et al., Activation of IKKbeta by glucose is necessary and sufficient to impair insulin signaling and nitric oxide production in endothelial cells. J. Mol. Cell. Cardiol. Aug. 2005;39(2):327-334; https://www.sciencedirect.com/science/article/pii/S0022282805001641, Revised Apr. 13, 2005, Accepted May 16, 2005, Available online Jun. 22, 2005.
Kim KA, et al., Effect of quercetin on the pharmacokinetics of rosiglitazone, a CYP2C8 substrate, in healthy subjects. J. Clin. Pharmacol. Aug. 2005;45:941-946; https://accp1.onlinelibrary.wiley.com/doi/abs/10.1177/0091270005278407, Issue Online: Mar. 19, 2013. Version of Record online: Mar. 19, 2013, Editorial history: Revised version accepted May 5, 2005.
Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (Feb. 2008); https://www.jstage.jst.go.jp/article/bbb/72/2/72_70602/_article/-char/ja/, 2008-72-2.
Kinoshita, "Anti-hyperlipidemic agents," Nihon Rinsho, 60(5):968-74 (May 2002) (w/English Abstract)(11 pages); https://europepmc.org/article/med/12030001, Apr. 30, 2002.
Kinsella, JE, et al., "Dietary n-3 polyunsaturated fatty acids and amelioration of cardiovascular disease: possible mechanisms." Am J Clin Nutr 52:1-28 (Jul. 1990); https://academic.oup.com/ajcn/article-abstract/52/1/1/4695376, Published: Jul. 1, 1990.
Kitada, 9th Diabetes Drug and Drug Related Seminar Diabetes Q&A, Kanazawa Medical University, Diabetes and Endocrine Internal Medicine (http://plaza.umin.ac.jp/iby/etcdata/yakuyaku110410.pdf)(Apr. 10, 2011) (w/English translation)(105 pages).
Klempfner R, et al., Elevated triglyceride level is independently associated with increased all-cause mortality in patients with established coronary heart disease: Twenty-two-year follow-up of the Bezafibrate Infarction Prevention Study and Registry. Circ Cardiovasc Qual Outcomes 9(2):100-8 (publication date Mar. 8, 2016).
Knapp HR, Dietary fatty acids in human thrombosis and hemostasis. Am. J. Clin. Nutr. May 1997 65 (5 Suppl): 1687S-98S; https://academic.oup.com/ajcn/article/65/5/1687S/4655644, Published: May 1, 1997.
Knopp, RH, et al., Contrasting effects of unmodified and time-release forms of niacin on lipoproteins in hyperlipidemic subjects: clues to mechanism of action of niacin, Metabolism, 34:642-650, (Jul. 1985); https://www.sciencedirect.com/science/article/abs/pii/0026049585900927, Available online Apr. 2, 2004.
Koba S, et al., Significance of small dense low-density lipoprotein-cholesterol concentrations in relation to the severity of coronary heart diseases. Atherosclerosis. Nov. 2006;189(1):206-214. (epub Jan. 2006, 18).
Kohno, M, et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (Jul./Aug. 2001); https://www.karger.com/Article/Abstract/51069.
Kojda G, Harrison DG. Interactions between no and reactive oxygen species: Pathophysiological importance in atherosclerosis, hypertension, diabetes and heart failure. Cardiovasc. Res. Aug. 15, 1999;43:562-571.
Kojima, T, et al., "Long-term administration of highly purified eicosapentaenoic acid provides improvement of psoriasis." Dermatologica, 182:225-230 (1991); https://www.karger.com/Article/Abstract/247800.
Koroshetz, WJ, Huntington's Disease, In Samuels, M. (ed.) Office Practice of Neurology, pp. 654-661 (1996); https://books.google.com/books?id=bbZrAAAAMAAJ&source=gbs_book_other_versions.
Kosonen, O., et al., "Inhibition by nitric oxide-releasing compounds of E-selectin expression in and neutrophil adhesion to human endothelial cells." European Journal of Pharmacology 394:149-156 (Apr. 7, 2000).
Koyama et al., Plaque Reduction and Stabilization Observed in Borderline Diabetes Using Coronary CT Angiogram During Administration of Purified Eicosapentaenoic Acid (EPA) Ther. Res. 31(2):219-225 (Feb. 2010) (with English translation)(20 pages).
Krauss RM, Heterogeneity of plasma low-density lipoproteins and atherosclerosis risk. Curr. Opin. Lipidol. Oct. 1994;5(5):339-349; https://europepmc.org/article/med/7858908, Sep. 30, 1994.
Kris-Etherton, et al., "Fish Consumption, Fish Oil, Omega-3 Fatty Acids, and Cardiovascular Disease" Circulation, 106:2747-2757 (Nov. 19, 2002)(epub Jan. 28, 2003).
Kris-Etherton, PM, et al., "Omega-3 Fatty Acids and Cardiovascular Disease—New Recommendations From the American Heart Association." Arterioscler Thromb Vasc Biol. 23:151-152 (Feb. 1, 2003).
Krzynowek et al., "Purification of Omega-3 Fatty Acids from Fish Oils Using HPLC: An Overview," National Marine Fisheries—Proceedings of the first joint conference of the Tropical and Subtropical Fisheries Technological Soceity of the Americas with the Atlantic Fisheries Technological Society, pp. 74-77 (1988).
Ku, K., et al., "Beneficial Effects of to-3 Fatty Acid Treatment on the Recovery of Cardiac Function After Cold Storage of Hyperlipidemic Rats." Metabolism, 48(10):123-1209 (Oct. 1999).
Kunimoto M, et al., Effect of ferrous ion and ascorbate-induced lipid peroxidation on liposomal membranes. Biochem. Biophys. Acta. Aug. 6, 1981;646(1):169-178.
Kurabayashi, T, et al., "Eicosapentaenoic acid effect on hyperlipidemia in menopausal Japanese women. The Niigata Epadel Study Group" Obstet Gynecol 96:521-8 (Oct. 2000); https://www.sciencedirect.com/science/article/abs/pii/S0029784400009881, Revised Apr. 21, 2000, Accepted May 3, 2000, Available online Sep. 20, 2000.
Labor Diagnostik Karlsruhe, "Target Values of Lipid Metabolism [Recommendation for lipid plasma levels in Germany]," (exact publication date unknown; circa 2006) (with English abstract)(4 pages).
Lada et al., "Associations of Low Density Lipoprotein Particle Compositions with Atherogenicity," Curr. Opin. Lipidol. (Feb. 2004) 15(1):19-24; https://journals.lww.com/co-lipidology/Abstract/2004/02000/Associations_of_low_density_lipoprotein_particle.5.aspx.
Lai, E, et al., "Suppression of niacin-induced vasodilation with an antagonist to prostaglandin D2 receptor subtype 1", Clin. Pharm. & Ther., 81:849-857, (Jun. 2007/epub Mar. 28, 2007).
Laidlaw, M, et al., "Effects of supplementation with fish oil-derived n-3 fatty acids and γ-linolenic acid on circulating plasma lipids and fatty acid profiles in women." Am J Clin Nutr 77:37-42 (Jan. 2003); https://academic.oup.com/ajcn/article/77/1/37/4689631, Accepted Feb. 14, 2002, Published Jan. 1, 2003.
Laird et al., "Relationship of early hyperglcemia to mortality in trauma patients," J. Trauma, 56(5):1058-1062 (May 2004); https://journals.lww.com/jtrauma/Fulltext/2004/05000/Association_of_Hyperglycemia_with_Increased.19.aspx.
Lamb RE, Goldstein BJ. Modulating an Oxidative-Inflammatory Cascade: Potential New Treatment Strategy for Improving Glucose Metabolism, Insulin Resistance, and Vascular Function. Int. J. Clin. Pract. Jul. 2008(epub May 16, 2008); 62(7): 1087-1095.
Lamharzi N, et al., Hyperlipidemia in concert with hyperglycemia stimulates the proliferation of macrophages in atherosclerotic lesions: potential role of glucose-oxidized LDL. Diabetes. Dec. 2004;53(12):3217-3225; https://diabetes.diabetesjournals.org/content/53/12/3217.short, History Aug. 20, 2004, Dec. 1, 2003, Published in print Nov. 23, 2004.

(56) References Cited

OTHER PUBLICATIONS

Landmesser U, et al., Oxidation of tetrahydrobiopterin leads to uncoupling of endothelial cell nitric oxide synthase in hypertension. J. Clin. Invest., Apr. 2003;111:1201-1209; https://www.jci.org/articles/view/14172 , First published Apr. 15, 2003—Version history, Accepted: Feb. 18, 2003.

LaRosa JC. Understanding risk in hypercholesterolemia. Clin Cardiol 26(Suppl 1):3-6, Jan. 2003; https://onlinelibrary.wiley.com/doi/abs/10.1002/clc.4960261303, First published: Jul. 5, 2007, Issue Online: Jul. 5, 2007, Version of Record online: Jul. 5, 2007.

Larsen, LN, et al., "Heneicosapentaenoate (21:5n-3): Its incorporation into lipids and its effects on arachidonic acid and eicosanoid Synthesis." Lipids 32:707-714 (Jul. 1997); https://aocs.onlinelibrary.wiley.com/doi/abs/10.1007/s11745-997-0090-4 , Issue Online: Jul. 1, 1997. Version of Record online: Jul. 1, 1997, Manuscript accepted: May 5, 1997, Manuscript revised: May 5, 1997, Manuscript received: Aug. 6, 1996.

Laufs et al., "Upregulation of endothelial nitric oxide synthase by hmg coa reductase inhibitors," Circulation (Mar. 31, 1998) 97:1129-1135.

Law TK, et al., Primary prevention of cardiovascular disease: global cardiovascular risk assessment and management in clinical practice. *Eur Heart J Qual Care Clin Outcomes.* 1(1):31-36 (publication date Jul. 2, 2015; epublication date Jul. 1, 2015).

Law, M.R., et al., "Quantifying effect of statins on low density lipoprotein cholesterol, ischaemic heart disease, and stroke: systematic review and meta-analysis." Br Med J., 326:1423-1427 (Jun. 28, 2003).

Lawson et al., "Human absorption of fish oil fatty acids as triacylglycerols, free acids or ethyl esters," Biochemical and Biophysical Research Communications 152(1):328-335 (Apr. 15, 1988).

Leaf A, et al. for the Fatty Acid Antiarrhythmia Trial Investigators. Prevention of Fatal Arrhythmias in High-Risk Subjects by Fish Oil n-3 Fatty Acid Intake. Circ. Nov. 1, 2005;112:2762-2768.

Leaf A, Kang JX, Prevention of cardiac sudden death by N-3 fatty acids: a review of the evidence. J Intern Med 240:5-12, Jul. 1996; https://onlinelibrary.wiley.com/doi/abs/10.1046/j.1365-2796.1996.449803000.x , First published: Jul. 1996, Issue Online: Oct. 31, 2003. Version of Record online: Oct. 31, 2003.

Leaf, "Hypertriglyceridemia: A Guide to Assessment and Treatment," Hospital Physician 17-23 (Sep. 2008).

Leaf, A., "Historical overview of n3 fatty acids and coronary heart disease." Am J Clin Nutr 87:1978S-80S. (Jun. 2008); https://academic.oup.com/ajcn/article/87/6/1978S/4633486 Published: Jun. 1, 2008.

Lee C, et al., All ApoB-containing lipoproteins induce monocyte chemotaxis and adhesion when minimally modified. Modulation of lipoprotein bioactivity by platelet-activating factor acetylhydrolase. Arterioscler. Thromb. Vase. Biol., Jun. 1999; 19(6): 1437-1446; https://www.ahajournals.org/doi/full/10.1161/01.ATV.19.6.1437 , Manuscript received Jul. 21, 1998. Manuscript accepted Dec. 2, 1998, Originally published Jun. 1, 1999.

Lee et al., "The Role of Omega-3 Fatty Acids in the Secondary Prevention of Cardiovascular Disease", Q J Med, 96:465-480, (Jul. 2003); https://academic.oup.com/qjmed/article/96/7/465/1627745, Published: Jul. 1, 2003.

Lee, JH, et al., "Omega-3 fatty acids for cardioprotection." Mayo Clin Proc., 83(3):324-332 (Mar. 2008); https://www.sciencedirect.com/science/article/abs/pii/S0025619611608665, Available online Oct. 20, 2011.

Leigh-Firbank et al., "Eicosapentaenoic acid and docosahexanoic acid from fish oils: differential associations with lipid responses," Br. J. Nutr. 87:435-445 (May 2002); https://www.cambridge.org/core/journals/british-journal-of-nutrition/article/eicosapentaenoic-acid-and-docosahexaenoic-acid-from-fish-oils-differential-associations-with-lipid-responses/E6EF955A85B6C8BC5F94F76CE9E7087A, Published online by Cambridge University Press: Mar. 9, 2007.

Lemaitre, RN, et al., "n-3 Polyunsaturated fatty acids, fatal ischemic heart disease, and nonfatal myocardial infarction in older adults: the Cardiovascular Health Study." Am J Clin Nutr 77:319-25 (Feb. 2003); https://academic.oup.com/ajcn/article/77/2/319/4689669, Accepted: Aug. 5, 2002. Published: Feb. 1, 2003.

Leonard, Brian E., "Neurological Aspects," Fundamentals of Psychopharmacology,186-187, (1997).

Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials," pp. 51-68, (Jan. 4, 1999).

Levey A, at. al. A New Equation to Estimate Glomerular Filtration Rate. Ann Intern Med. 150:604-612; May 5, 2009.

Li, D, et al., "Effect of dietary a-linolenic acid on thrombotic risk factors in vegetarian men." Am J Clin Nutr 69:872-82 (May 1999); https://academic.oup.com/ajcn/article/69/5/872/4714829, Accepted: Oct. 20, 1998. Published: May 1, 1999.

Li, H, et al., "EPA and DHA reduce LPS-induced inflammation responses in HK-2 cells: Evidence for a PPAR-γ-dependent mechanism." Kidney Int'l. 67:867-74 (Mar. 2005); https://www.sciencedirect.com/science/article/pii/S0085253815505322, Revised Aug. 16, 2004, Accepted Sep. 22, 2004, Available online Dec. 16, 2015.

Li, X, et al., "Protection against fine particle-induced pulmonary and systemic inflammation by omega-3 polyunsaturated fatty acids." vol. 1861, No. 3, pp. 577-584 (Dec. 21, 2016).

Libby P. Triglycerides on the rise: should we swap seats on the seesaw? *Eur Heart J.* 36(13):774-776 (publication date Apr. 1, 2015; epublication date Dec. 29, 2014).

Libby, "Inflammation and atherosclerosis," Nature (Dec. 2002) 420(6917):868-874.

Lichtman et al., "Depression and Coronary Heart Disease, Recommendations for Screening, Referral and Treatment," AHA Science Advisory, Circulation 118:1768-1775 (Sep. 29, 2008).

Lien, EL, "Toxicology and safety of DHA." Prostaglandins Leukot Essent Fatty Acids., 81:125-132 (2009); https://www.sciencedirect.com/science/article/abs/pii/S0952327809000945, Issue date: Aug.-Sep. 2009, Available online Jun. 8, 2009.

Lin, Pao-Yen, et al., "A Meta-Analytic Review of Double-Blind, Placebo-Controlled Trials of Antidepressant Efficacy of Omega-3 Fatty Acids", Psychiatry, 1056-1061 (Jul. 2007); https://brainnutrient.securearea.eu/Files/2/42000/42087/PageHomeDownloadDocs/8867_nl.pdf Journal not online. Accepted Dec. 7, 2006.

Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (Apr. 28, 1995).

Lin, Z., et al., "Cardiovascular Benefits of Fish-Oil Supplementation Against Fine Particulate Air Pollution in China." Apr. 30, 2019; 73(16):2076-2085.

Lindsey, S, et al., "Low density lipoprotein from humans supplemented with n-3 fatty acids depresses both LDL receptor activity and LDLr mRNA abundance in HepG2 cells." J Lipid Res., 33:647-658 (Mar. 1992); https://www.jlr.Org/content/33/5/647.short, May 1992.

Lipitor [package insert]. New York, NY: Parke-Davis (2012). (22 pages).

Lipitor [product information] Dublin, Ireland: Pfizer Inc. (2007).(18 pages).

Liu et al., "Effects of stable fish oil and simvastatin on plasma lipoproteins in patients with hyperlipidemia," Nutrion Res. , vol. 23, pp. 1027-1034 (Aug. 2003); https://www.sciencedirect.com/science/article/pii/S0271531703001027 , Revised Apr. 24, 2003, Accepted Apr. 25, 2003, Available online Jul. 10, 2003.

Liu X, et al., Stearoyl CoA Desaturase 1: Role in Cellular Inflammation and Stress, Adv. Nutr. Jan. 2011 (Jan. 10, 2011); 2:15-22.

Lohmussaar, E., et al., "ALOX5AP Gene and the PDE4D Gene in a Central European Population of Stroke Patients." Stroke, 36:731-736 (Apr. 2005)(epub Feb. 24, 2005).

Lovaza (omega-3-acid ethyl esters) Capsules, Prescribing information, GlaxoSmithKline (Nov. 2008).(9 pages).

Lovaza [package insert]. Research Triangle Park, NC: GlaxoSmithKline (2012). (14 pages).

Lovaza Side Effects, web archived webpage, archived from Drugs.com website on (Jul. 31, 2010), Retrieved from URL <https://web.

(56) References Cited

OTHER PUBLICATIONS archive.org/web/20100731021902/https://www.drugs.com/sfx/lovaza-side-effects.html> (4 pages)(Jul. 2010).
Lovaza TM (omega-3-acid ethyl esters) Capsules, Aug. 2007 (Aug. 1, 2007)m oaget 1-2, XP055589332.
Lovaza United States Prescribing Information, GlaxoSmithKline. Research Triangle Park, USA, May 2014.
Lovaza, (omega-3-acid ethyl esters) Capsules, Prescribing information Smith Kline Beechum (Jul. 2009).(17 pages).
Lovaza, GlaxoSmithKline, Lovaza Prescribing Information, Jun. 2008 [retrieved from Internet Jun. 6, 2012 <https://web.archive.org/web/20090206170311/http://us.gsk.com/products/assets/us_lovaza.pdf>]; Table 3, p. 1, section entitled 'Description;' p. 3, section entitled 'Very High Triglycerides: Monotherapy;' p. 4 section entitled 'Indications and Usage' and 'Information for Patients.' (12 pages).
Lovaza® (omega-3-acid ethyl esters) Capsules, Prescribing information, GlaxoSmithKline, (Dec. 2010)(12 pages).
Lovaza®, Physicians' Desk Reference 2699-2701 (62d ed., 2008). (4 pages).
Lovegrove et al., "Moderate fish-oil supplementation reverses low-platelet, long chain n-3 polyunsaturated fatty acid status and reduced plasma triacylglycerol concentrations in British Indo-Asians," Am. J. Clin. Nutr., 79:974-982 (Jun. 2004); https://academic.oup.com/ajcn/article/79/6/974/4690258, Accepted: Nov. 20, 2003. Published: Jun. 1, 2004.
Lu, G., et al., "Omega-3 fatty acids alter lipoprotein subfraction distributions and the in vitro conversion of very low density lipoproteins to lowdensity lipoproteins." J Nutr Biochem., 10:151-158 (Mar. 1999); https://www.sciencedirect.com/science/article/abs/pii/S0955286398000941, Accepted Nov. 11, 1998, Available online Mar. 4, 1999.
Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (Feb. 2009)(epub Dec. 30, 2008).
Luria, MH, "Effect of low-dose niacin on high-density lipoprotein cholesterol and total cholesterol/high density lipoprotein cholesterol ratio," Arch. Int. Med., 148:2493-2495, (Nov. 1998); https://jamanetwork.com/journals/jamainternalmedicine/article-abstract/610768.
Lvovich V, Scheeline A. Amperometric sensors for simultaneous superoxide and hydrogen peroxide detection. Anal. Chem. Feb. 1, 1997;69:454-462.
Madhavi et al., "Effect of n-6 and n-3 fatty acids on the survival of vincristine sensitive and resistant human cervical carcinoma cells in vitro," Cancer Letters, vol. 84. No. 1, pp. 31-41 (Aug. 29, 1994).
Madsen, L, et al., "Eicosapentaenoic and Docosahexaenoic Acid Affect Mitochondrial and Peroxisomal Fatty Acid Oxidation in Relation to Substrate Preference." Lipids 34:951-963 (Sep. 1999); https://link.springer.com/article/10.1007/s11745-999-0445-x, Revised Jul. 23, 1999. Accepted Aug. 17, 1999, Issue date Sep. 1999.
Mak IT, et al., Antioxidant properties of calcium channel blocking drugs. Methods Enzymol. 1994;234:620-630; https://www.sciencedirect.com/science/article/pii/0076687994341338, Available online Jan. 7, 2004 (book chapter).
Maki et al., "Effects of Adding Prescription Omega-3 Acid Ethyl Esters to Simvastatin (20 mg/day) on Lipids and Lipoprotein Particles in Men and Women with Mixed Dyslipidemia," Am. J. Cardiol., 102:429-433 (Aug. 15, 2008)(Epub May 22, 2008).
Maki, KC, et al., "Baseline lipoprotein lipids and low-density lipoprotein cholesterol response to prescription omega-3 acid ethyl ester added to simvastatin therapy." Am J Cardiol., 105:1409-1412 (May 15, 2010)(epub Mar. 30, 2010).
Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (Jun. 2005); https://www.tandfonline.com/doi/abs/10.1080/07315724.2005.10719465 Accepted Jan. 19, 2005, Published online: Jun. 18, 2013.

Malinowski et al., "Elevation of Low-Density Lipoprotein Cholesterol Concentration with Over-the-Counter Fish Oil Supplementation." Annals of Pharmacotherapy 41:1296-1300 (Jul./Aug. 2007); https://journals.sagepub.com/doi/abs/10.1345/aph.1H695, First Published Jul. 1, 2007.
Malinski T, Taha Z. Nitric oxide release from a single cell measured in situ by a porphyrinic-based microsensor. Nature. Aug. 20, 1992;358:676-678.
Mallat, Z, et al., "Apoptosis in the vasculature: mechanisms and functional importance." British Journal of Pharmacology 130:947-962 (Jul. 2000); https://bpspubs.onlinelibrary.wiley.com/doi/full/10.1038/sj.bjp.0703407 Revised Mar. 30, 2000, Accepted Apr. 3, 2000, First published online: Jan. 29, 2009.
Mallat, Z., et al., "Protective role of interleukin-10 in atherosclerosis." Circ. Res. 85:e17-e24 (Oct. 15, 1999).
Manninen V, et al., Joint effects of serum triglyceride and LDL cholesterol and HDL cholesterol concentrations on coronary heart disease risk in the Helsinki Heart Study. Implications for treatment. Circulation 85:37-45, Jan. 1992; https://www.ahajournals.org/doi/abs/10.1161/01.cir.85.1.37, Originally published Jan. 1, 1992.
Marangell, Lauren B., et al., "A Double-Blind, Placebo-Controlled Stury of the Omega-3 Fatty Acid Docosahexaenoic Acid in the Treatment of Major Depression", Am. J. Psychiatry, 160(5):996-998, (May 2003); https://ajp.psychiatryonline.org/doi/full/10.1176/appi.ajp.160.5.996, Published Online:May 1, 2003.
Marchioli R, et al., GISSI-Prevenzione Investigators. Early protection against sudden death by n-3 polyunsaturated fatty acids after myocardial infarction: time-course analysis of the results of the Gruppo Italiano per lo Studio della Sopravvivenza nell'Infarto Miocardico (GISSI)-Prevenzione. Circulation. 105(16):1897-1903, Apr. 23, 2002.
Marckmann, P, "Fishing for heart protection." Am J Clin Nutr, 78:1-2 (Jul. 2003); https://academic.oup.com/ajcn/article/78/1/1/4689890, Published: Jul. 1, 2003.
Marcoux et al., "Plasma remnant-like particle lipid and apolipoprotein levels in normolipidemic and hyperlipidemic subjects," Atherosclerosis, vol. 139, pp. 161-171 (Jul. 1998); https://www.sciencedirect.com/science/article/abs/pii/S0021915098000422, Revised Jan. 5, 1998, Accepted Jan. 21, 1998, Available online Dec. 21, 1998.
Marder, "An Approach to Treatment Resistance in Schizophrenia," British Journ. Psychiatry, 37:19-22 (1999); https://www.cambridge.org/core/journals/the-british-journal-of-psychiatry/article/an-approach-to-treatment-resistance-in-schizophrenia/A1560127B71799F95FBDE2350B239323, Feb. 1999, Published online by Cambridge University Press: Aug. 6, 2018.
Margolis, Simeon "What is Hyperlipidemia?" (http:www.healthcommunities.com/highcholesterol/whatishyperlipidemia.shtml, accessed Oct. 20, 2015, published Aug. 25, 2011)(4 pages).
Martin SS, Blaha MJ, Elshazly MB, et al. Comparison of a novel method vs the Friedewald equation for estimating low-density lipoprotein cholesterol levels from the standard lipid profile. JAMA. Nov. 20, 2013;310:2061-8.
Martinez et al., "Serum level changes of long chain-polyunsaturated fatty acids in patients undergoing periodontal therapy combined with one year of omega-3 supplementation: a pilot randomized clinical trial;" Journal of Periodontal & Implant Science, Aug. 28, 2014, vol. 44, pp. 169-177.
Martinez-Gonzalez J, et al., 3-hydroxy-3-methylglutaryl coenzyme a reductase inhibition prevents endothelial no synthase downregulation by atherogenic levels of native ldls: Balance between transcriptional and posttranscriptional regulation. Arterioscler. Thromb. Vasc. Biol. May 2001;21:804-809; https://www.ahajournals.org/doi/full/10.1161/01.atv.21.5.804, Manuscript received Nov. 27, 2000. Manuscript accepted Dec. 22, 2000 Originally published May 1, 2001.
Martinez-Gonzalez, Jose, et al., "Estatinas y acidos grasos omega-3. Disminucion de la mortalidad cardiovascular dependiente e independiente de la reduccion de la colesterolemia," (2006) Rev Esp Cardiol Suppl., 6(D):20D-30D [with English abstract]; https://www.sciencedirect.com/science/article/abs/pii/S1131358706748233, Available online Jan. 6, 2009.
Martin-Jadraque, R. et al., Effectiveness of low dose crystalline nicotinic acid in men with low density lipoprotein cholesterol levels. Arch. Int. Med. 156: 1081-1088. (May 27, 1996).

(56) References Cited

OTHER PUBLICATIONS

Martz, "Moving Upstream in Huntington's," Science-Business eXchange, 2 pgs., Oct. 2008; https://link.springer.com/article/10.1038/scibx.2008.841, Issue Date Oct. 2, 2008.
Mason et al., "Comparative lipid antioxidant effects of omega-3 fatty acids in combination with HMG-CoA reductase inhibitors," Journ. Clin. Lipidology (May/Jun. 2011) 5(3):201; https://www.lipidjournal.com/article/S1933-2874(11)00091-2/abstract.
Mason et al., "Direct evidence for cholesterol crystalline domains in biological membranes: role in human pathobiology," Biochimica et Biophysica Acta 198-207 (Mar. 10, 2003).
Mason et al., "Eicosapentaenoic Acid (EPA) inhibits the formation of membrane cholesterol crystalline domains by a potent antioxidant mechanism," Journ. Clin. Lipid., 7(3): 272-273 (May/Jun. 2013) [Abstract only]; https://www.lipidjournal.com/article/S1933-2874(13)00135-9/abstract, May 1, 2013 https://www.sciencedirect.com/science/article/abs/pii/S1933287413001359, Available online May 30, 2013.
Mason et al., "Eicosapentaenoic acid inhibits glucose-induced membrane cholesterol crystalline domain formation through a potent antioxidant mechanism," Biochim. Biophy. Acta., 1848(2):502-9, (Feb. 2015); https://www.sciencedirect.com/science/article/pii/S0005273614003514, Revised Oct. 2, 2014, Accepted Oct. 14, 2014, Available online Oct. 22, 2014.
Mason et al., "Eicosapentaenoic Acid Inhibits Oxidation of ApoB-containing Lipoprotein Particles of Different Size In Vitro When Administered Alone or in Combination With Atorvastatin Active Metabolite Compared With Other Triglyceride-lowering Agents," J. Cardiovasc. Pharmacol., 68(1):33-40 (Jul. 2016); https://www.ncbi.nlm.nih.gov/pmc/articles/PMC4936437/, Published online Mar. 3, 2016.
Mason et al., "Eicosapentaenoic acid reduces membrane fluidity, inhibits cholesterol domain formation, and normalizes bilayer width in atherosclerotic-like model membranes," Biochim. Biophy. Acta., 1858(12):3131-3140 (Dec. 2016); https://www.sciencedirect.com/science/article/pii/S0005273616303297, Revised Sep. 1, 2016, Accepted Oct. 3, 2016, Available online Oct. 5, 2016.
Mason RP, et al., Effect of enhanced glycemic control with saxagliptin on endothelial nitric oxide release and CD40 levels in obese rats. J. Atheroscler. Thromb. Epub Jun. 13, 2011;18:774-783.
Mason RP, et al., Partitioning and location of Bay K 8644, 1,4-dihydropyridine calcium channel agonist, in model and biological membranes. Biophys. J. Apr. 1989;55(4):769-778; https://www.ncbi.nlm.nih.gov/pmc/articles/PMC1330560/.
Mason RP, Jacob RF. Membrane microdomains and vascular biology: Emerging role in atherogenesis. Circulation. May 6, 2003; 107:2270-2273.
Mason RP, Kalinowski L, Jacob RF, Jacoby AM, Malinski T. Nebivolol reduces nitroxidative stress and restores nitric oxide bioavailability in endothelium of black americans. Circulation. Dec. 13, 2005 (epub Dec. 5, 2005); 112:3795-3801.
Mason RP, Kubant R, Heeba G, Jacob RF, Day CA, Medlin YS, Funovics P, Malinski T. Synergistic effect of amlodipine and atorvastatin in reversing ldl-induced endothelial dysfunction. Pharm. Res. Aug. 2008 (epub 2007 Dec. 2018); 25:1798-1806.
Mason RP, Walter MF, Day CA, Jacob RF. Active metabolite of atorvastatin inhibits membrane cholesterol domain formation by an antioxidant mechanism. J. Biol. Chem. Apr. 7, 2006 (epub Feb. 7, 2006) ;281(14):9337-9345.
Mason RP, Walter MF, Day CA, Jacob RF. Intermolecular differences for HMG-CoA reductase inhibitors contribute to distinct pharmacologic and pleiotropic actions. Am. J Cardiol. Sep. 5, 2005;96(5A):11F-23F.
Mason RP, Walter MF, Jacob RF. Effects of hmg-coa reductase inhibitors on endothelial function: Role of microdomains and oxidative stress. Circulation. Jun. 1, 2004;109:II34-II41.
Mason RP, Walter MF, Mason PE. Effect of oxidative stress on membrane structure: Small angle x-ray diffraction analysis. Free Radic. Biol. Med. 1997;23(3):419-425; https://www.ncbi.nlm.nih.gov/pmc/articles/PMC1330560/.

Mason RP. Molecular basis of differences among statins and a comparison with antioxidant vitamins. Am. J. Cardiol. Dec. 4, 2006 (epub Oct. 10, 2006); 98:34P-41P.
Mataki et al., "Effect of Eicosapentaenoic Acid in Combination with HMG-CoA Reductase Inhibitor on Lipid Metabolism," Int. Med. J. 5(1):35-36 (Mar. 1998); https://www.sciencedirect.com/science/article/abs/pii/S0021915097886984, Oct. 1997, Available online May 27, 1999.
Mater, MK, et al., "Arachidonic acid inhibits lipogenic gene expression in 3T3-L1 adipocytes through a prostanoid pathway." J. Lipid Res. 39:1327-1334 (Jul. 1998); https://www.jlr.org/content/39/7/1327.short , Revision received Feb. 2, 1998. Revision received Mar. 9, 1998.
Matsumoto, M, et al., "Orally administered eicosapentaenoic acid reduces and stabilizes atherosclerotic lesions in ApoE-deficient mice." Atherosclerosis, 197(2):524-533 (Apr. 2008/epub Sep. 4, 2007).
Matsuzaki et al., "Incremental Effects of Eicosapentaenoic Acid on Cardiovascular Events in Statin-Treated Patients with Coronary Artery Disease," Circ. J. 73:1283-1290 (Jul. 2009/epub May 8, 2009).
Matsuzawa, Y., et al., "Effect of Long-Term Administration of Ethyl Icosapentate (MND-21) In Hyperlipaemic Patients," J. Clin Therapeutic & Medicines, 7: 1801-16 (1991).
Mattson MP, Modification of ion homeostasis by lipid peroxidation: roles in neuronal degeneration and adaptive plasticity. Trends Neurosci. Feb. 1998;21(2):53-57; https://www.sciencedirect.com/science/article/abs/pii/S0166223697011880, Available online Jul. 6, 1998.
Mayatepek, E., et al., The Lancet, vol. 352, Leukotriene C4-synthesis deficiency: a new inborn error of metabolism linked to a fatal developmental syndrome, pp. 1514-1517 (Nov. 7, 1998).
Mayo Clinic at http://www.mayoclinic.org.diseases-conditions/high-blood-cholesterol/in-depth/cholesterol (2014)(5 pages).
Mayo Clinic, Diabetes Diagnosis and Treatment, 1998, http://www.mayoclinic.org/diseases-conditions/diabetes/diagnosis-treatment/drc-20371451 (1998-2018).
McCabe, John B. "Literature of Resuscitation", Resuscitation, Elsevier, IE, vol. 19, No. 3 (Jun. 1, 1990), vol. 19, pp. 303-319, DOI: 10.1016/0300-9572 (90)90109-R.
McElroy, SL, et al., "Clozapine in the Treatment of Psychotic Mood Disorders, Schizoaffective Disorder, and Schizophrenia", Journal of Clinical Psychiatry, vol. 52, No. 10, pp. 411-414 (Oct. 1991); https://psycnet.apa.org/record/1992-13950-001, Manuscript received Jun. 12, 1997. Manuscript accepted Jun. 16, 1997, Originally published Dec. 1, 1997.
McIntyre M, et al., Sex differences in the abundance of endothelial nitric oxide in a model of genetic hypertension. Hypertension. Dec. 1997;30:1517-1524; https://www.ahajournals.org/doi/full/10.1161/01.hyp.30.6.1517.
McKenney et al., "Prescription omega-3 fatty acids for the treatment of hypertriglyceridemia," Am. J. Health Syst. Pharm., 64(6):595-605 (Mar. 15, 2007).
McKenney et al., CMRO, "Comparison of the efficacy of rosuvastatin versus atorvastatin, simvastatin and pravastatin in achieving lipid goals: results from the STELLAR trial," 689-98 (2003); https://www.tandfonline.com/doi/abs/10.1185/030079903125002405, Accepted Sep. 5, 2003, Published online: Sep. 22, 2008.
McKenney, J., "Niacin for dyslipidemia: considerations in product selection," Am. J. Health Syst. Pharm., 60:995-1005, (May 15, 2003).
McKenney, James et al., "Role of prescription omega-3 fatty acids in the treatment of Hypertriglyceridemia," Pharmacotherapy, LNKD— Pubmed: 17461707, vol. 27, No. 5, pp. 715-728 (May 2007); https://accpjournals.onlinelibrary.wiley.com/doi/abs/10.1592/phco.27.5.715, Issue Online: Jan. 6, 2012, Version of Record online: Jan. 6, 2012.
McKenney, JM, et al. Study of the pharmacokinetic interaction between simvastatin and prescription omega-3-acid ethyl esters. J. Clin. Pharmacol. 46, 785-791 (Jul. 2006); https://accp1.onlinelibrary.wiley.com/doi/abs/10.1177/0091270006289849 , Issue Online: Mar. 8, 2013. Version of Record online: Mar. 8, 2013, Editorial history: Submitted for publication Jan. 13, 2006, revised version accepted Apr. 11, 2006.

(56) References Cited

OTHER PUBLICATIONS

McKeone et al., "Alterations in serum phosphatidylcholine fatty acyl species by eicosapentaenoic and docosahexaenoic ethyl esters in patients with severe hypertriglyceridemia." J. Lipid Res. 38:429-436 (Mar. 1997); https://www.jlr.org/content/38/3/429.short.

McMurchie, E.J., et al., "Incorporation and effects of dietary eicosapentaenoate (20 : 5(n-3)) on plasma and erythrocyte lipids of the marmoset following dietary supplementation with differing levels of linoleic acid." Biochimica et Biophysics Acta, 1045:164-173 (Jul. 16, 1990).

McNamara JR, et al., Remnant-like particle (RLP) Cholesterol is an independent cardiovascular disease risk factor in women: results from the Framingham Heart Study, Atherosclerosis, vol. 154(1), pp. 229-236 (Jan. 2001); https://www.sciencedirect.com/science/article/abs/pii/S0021915000004846 , Revised Mar. 16, 2000, Accepted Mar. 23, 2000, Available online Dec. 21, 2000.

MedlinePlus. "Coronary heart disease," Available at: https://medlineplus.gov/ency/article/007115.htm (review date Jul. 14, 2015)(accessed Sep. 2, 2016)(5 pages).

Menuet, R, et al., "Importance and management of dyslipidemia in the metabolic syndrome," American Journal of the Medical Sciences 200512 US, vol. 33, No. 6, pp. 295-302 (2005); https://www.sciencedirect.com/science/article/abs/pii/S0002962915328809, Dec. 2005, Available online Dec. 16, 2015.

Merched, AJ, et al., "Atherosclerosis: evidence for impairment of resolution of vascular inflammation governed by specific lipid mediators." FASEB J. 22:3595-3606 (Oct. 2008/epub Jun. 17, 2008).

Merkl et al., "Antisense Oligonucleotide Directed to Human Apolipoprotein B-100 Reduces Lipoprotein(a) Levels and Oxidized Phospholipids On Human Apolipoprotein B-100 Particles in Lipoprotein(a) Transgenic Mice," Circulation, vol. 118, pp. 743-753 (epub Jul. 28, 2008).

Mesa, M, "Effects of oils rich in Eicosapentaenoic and docosahexaenoic acids on the oxidizability and thrombogenicity of low-density lipoprotein," Artheroclerosis 175, pp. 333-343 (Aug. 2004); https://www.sciencedirect.com/science/article/abs/pii/S0021915004002151 , Revised Mar. 22, 2004, Accepted Apr. 20, 2004, Available online Jun. 15, 2004.

Metcalf, RG et al., "Effects of fish-oil supplementation on myocardial fatty acids in humans." Am J Clin Nutr 85:1222-28 (May 2007); https://academic.oup.com/ajcn/article/85/5/1222/4633062, Accepted Dec. 11, 2006, Published: May 1, 2007.

Metcalf, RG et al., "Effect of dietary n-3 polyunsaturated fatty acids on the inducibility of ventricular tachycardia in patients with ischemic cardiomyopathy." Am J Cardiol 101:758-761 (Mar. 15, 2008/epub Jan. 14, 2008).

Meyer et al., "Comparison of Seal Oil to Tuna Oil on Plasma Lipid Levels and Blood Pressure in Hypertriglyceridaemic Subjects," Lipids, 44:827-835 (Sep. 2009); https://link.springer.com/article/10.1007/s11745-009-3333-3, Accepted Jul. 20, 2009. Published Aug. 29, 2009, Issue date Sep. 2009.

Meyer et al., "Dose-Dependent Effects of Docosahexaenoic Acid Supplementation on Blood Lipids in Statin-Treated Hyperlipidaemic Subjects." Lipids, 42:109-15 (Mar. 2007/epub Feb. 8, 2007).

Meyers, et al., "Nicotinic acid induces secretion of prostaglandin D2 in human macrophages: An in vitro model of the niacin-flush," Atherosclerosis, 192:253-258, (Jun. 2007/ epub Sep. 1, 2006).

Micheletta F, Natoli S, Misuraca M, Sbarigia E, Diczfalusy U, Iuliano L. Vitamin E supplementation in patients with carotid atherosclerosis: Reversal of altered oxidative stress in plasma but not in plaque. Arterioscler. Thromb. Vasc. Biol. Jan. 2004 (epub Dec. 16, 2006); 24:136-140.

Michos et al., "Niacin and Statin Combination Therapy for Atherosclerosis Regression and Prevention of Cardiovascular Disease Events," Journ. Amer. Coll. Cardiol., vol. 59, No. 23:2058-2064 (Jun. 5, 2012)(epub Apr. 18, 2012).

Mii, S, et al., "Perioperative use of eicosapentaenoic acid and patency of infrainguinal vein bypass: a retrospective chart review." Curr Ther Res Clin Exp. 68:161-174 (May 2007); https://www.sciencedirect.com/science/article/pii/S0011393X07000525, Accepted Apr. 11, 2007, Available online Aug. 22, 2007.

Miles, et al., "Effect of orlistat in overweight and obese patients with type 2 diabetes treated with metformin," Diabetes Care, 25(7):1123-1128 (2002); https://care.diabetesjournals.org/content/25/7/1123.short.

Miller AK, DiCicco RA, Freed MI. The effect of ranitidine on the pharmacokinetics of rosiglitazone in healthy adult male volunteers. Clin. Ther. Jul. 2002;24:1062-1071; https://www.tandfonline.com/doi/abs/10.1185/03007990802205985, Accepted May 16, 2008, Published online: Jun. 25, 2008.

Miller AK, Inglis AM, et al., The effect of acarbose on the pharmacokinetics of rosiglitazone. Eur. J. Clin. Pharmacol. May 2001;57:105-109; https://link.springer.com/article/10.1007/s002280100275 Published Feb. 7, 2014. Issue date May 2001.

Miller M, Cannon CP, et al. Impact of triglyceride levels beyond low-density lipoprotein cholesterol after acute coronary syndrome in the PROVE IT-TIMI 22 trial. J Am Coll Cardiol 51:724-730, Feb. 19, 2008.

Miller M, Stone NJ, et al. Triglycerides and cardiovascular disease: a scientific statement from the American Heart Association. Circulation. May 24, 2011 (epub Apr. 18, 2011); 123:2292-2333.

Miller, M, Current perspectives on the management of hypertriglyceridemia. Am Heart J 140:232-40, 2000; https://www.sciencedirect.com/science/article/abs/pii/S0002870300784870 , Accepted Mar. 27, 2000, Available online May 25, 2002.

Miller, M, et al., "Impact of lowering triglycerides on raising HDL-C in hypertriglyceridemic and non-hypertriglyceridemic subjects." International Journal of Cardiology 119:192-195 (Jul. 10, 2007) (epub Oct. 18, 2006).

Minihane, AM, et al., "ApoE polymorphism and fish oil supplementation in subjects with an atherogenic lipoprotein phenotype." Arterioscler. Thromb. Vasc. Biol. 20:1990-1997 (Aug. 2000); https://www.ahajournals.org/doi/full/10.1161/01.ATV.20.8.1990, Originally published Aug. 1, 2000.

Mishra, A., et al., "Oxidized omega-3 fatty acids inhibit NF-κB activation via a PPARα-Dependent Pathway." Arterioscler Thromb Vasc Biol. 24:1621-1627 (Sep. 2004)(epub Jul. 1, 2004).

Missouri DUReport, Statin Therapy (Oct./Nov. 2003) Drug Use Review Newsletter 8(6):1-9.

Mita, T. et al., Eicosapentaenoic acid reduces the progression of carotid intima-media thickness in patients with type 2 diabetes, Atherosclerosis 191:162-167 (Mar. 2007)(epub Apr. 17, 2006).

Mizota M, et al. "Pharmacological studies of eicosapentaenoic acid ethylester (EPA E) on high cholesterol diet-fed rabbits," Nippon Yakurigaku Zasshi, 91:255-66 (Apr. 1988) (with English abstract); https://europepmc.org/article/med/2839398, Mar. 31, 1988.

Mizota M, et al., "The effects of eicosapentaenoic acid ethylester (EPA E) on arterial thrombosis in rabbits and vascular lesions in rats," Nippon Yakurigaku Zasshi, 91:81-9 (Feb. 1988)(with English abstract); https://europepmc.org/article/med/2836280, Jan. 31, 1988.

Mizuguchi K, Yano T, et al., "Hypolipidemic effect of ethyl all-cis-5,8,11,14,17-eicosapentaenoate (EPA-E) in rats," Jpn J Pharmacol., 59(3):307-12 (Jul. 1992); https://www.jstage.jst.go.jp/article/jphs1951/59/3/59_3_307/_article/-char/ja/.

Mizuguchi, K., et al., "Ethyl all-cis-5,8,11,14,17-icosapentaenoate modifies the biochemical properties of rat very low-density lipoprotein." European Journal of Pharmacology, 231:221-227 (Apr. 28, 1993).

Mizuguchi, K., et al., "Mechanism of the lipid-lowering effect of ethyl all-cis-5,8,11,14,17-icosapentaenoate." European Journal of Pharmacology, 231:121-127 (Jan. 1993); https://www.sciencedirect.com/science/article/abs/pii/001429999390692B , Revised Oct. 12, 1992, Accepted Nov. 3, 1993, Available online Nov. 26, 2002.

Mochida Press Release, Pharmaceutical Col., Ltd.: Conclusion of Distributorship Agreement Concerning Switch-OTC Drug for Hyperlipidemia Treatment, Epadel, (Apr. 30, 2009)(1 page).

Mochida, Announcement, Mochida Announces Completion of "JELIS" Major Clinical Trial for "Epadel," Mar. 22, 2005 (2 pages).

Mochida's Epadel Reduces Risk of Stroke Recurrence—New Results of JELIS Major Clinical Trial, JCNNetwork Newswire Nov. 13, 2006 (2 pages).

(56) References Cited

OTHER PUBLICATIONS

Mora, S, et al., "LDL particle subclasses, LDL particle size, and carotid atherosclerosis in the Multi-Ethnic Study of Atherosclerosis (MESA)." Atherosclerosis. ;192:211-217 (May 2007); https://www.sciencedirect.com/science/article/abs/pii/S0021915006002590, Revised May 2, 2006, Accepted May 4, 2006, Available online Jun. 12, 2006.
Mori et al., "Differential Effects of Eicosapentaenoic Acid and Docosahexaenoic Acid on Vascular Reactivity of the Forearm Microcirculation in Hyperlipidemic, Overweight Men," Circulation, 102:1264-1269 (Sep. 12, 2000).
Mori TA, Woodman RJ. "The independent effects of eicosapentaenoic acid and docosahexaenoic acid on cardiovascular risk factors in humans," Curr Opin Clin Nutr Metab Care 2006; 9:95-104 (Mar. 2006); https://journals.lww.com/co-clinicalnutrition/Abstract/2006/03000/The_independent_effects_of_eicosapentaenoic_acid.6.aspx, Originally published: Mar. 2006.
Mori TA. Omega-3 fatty acids and blood pressure. Cell Mol Biol. Feb. 25, 2010;56(1):83-92; https://europepmc.org/article/med/20196972, Feb. 24, 2010.
Mori, et al., "Purified Eicosapentaenoic and docosahexaenoic acids have differential effects on serum lipids and lipoproteins, LDL particle size, glucose, and insulin in mildly hyperlipidemic men," Am J Clin Nutr 71:1085-1094 (May 2000); https://academic.oup.com/ajcn/article/71/5/1085/4729166, Accepted: Oct. 20, 1999, Published: May 1, 2000.
Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781 (Oct. 1, 2003).
Mori, Trevor, et al., "Docosahexaenoic Acid but Not Eicosapentaenoic Acid Lowers Ambulatory Blood Pressure and Heart Rate in Humans", Hypertension, 34(2):253-60 (Aug. 1999); https://www.ahajournals.org/doi/full/10.1161/01.hyp.34.2.253 Manuscript received Feb. 22, 1999. Manuscript accepted Apr. 6, 1999 Originally published Aug. 1, 1999.
Morin et al., "Anti-proliferative effects of a new docosapentaenoic acid monoacylglyceride in colorectal carcinoma cells;" Prostaglandins, Leukotrienes and Essential Fatty Acids, Aug. 7, 2013, vol. 89, pp. 203-213.
Morita, I, et al., "Effects of purified eicosapentaenoic acid on arachidonic acid metabolism in cultured murine aortic smooth muscle cells, vessel walls and platelets." Lipids 18:42-490 (Jan. 1983); https://aocs.onlinelibrary.wiley.com/doi/abs/10.1007/BF02534689, Manuscript received: Aug. 9, 1982. Issue Online: Jan. 1, 1983, Version of Record online: Jan. 1, 1983.
Morris M, et al., Does fish oil lower blood pressure? A meta-analysis of controlled trials. Circ., Aug. 1993;88:523-533; https://www.ahajournals.org/doi/abs/10.1161/01.cir.88.2.523, Originally published Aug. 1, 1993.
Morrow JD, "Release of markedly increased quantities of prostaglandin D2 in vivo in humans following the administration of nicotinic acid", Prostaglandins, 38:263-274, (Aug. 1989); https://www.sciencedirect.com/science/article/abs/pii/0090698089900889, Accepted Jul. 24, 1989, Available online Dec. 1, 2003.
Morton RE, "Specificity of lipid transfer protein for molecular species of cholesteryl ester." J Lipid Res., 27:523-529 (May 1986); https://www.jlr.org/content/27/5/523.short, May 1, 1986.
Mosher LR, et al., "Nicotinic Acid Side Effects and Toxicity: A review," Am J Psychiat., 126: 1290-1296 (Mar. 1970); https://ajp.psychiatryonline.org/doi/abs/10.1176/ajp.126.9.129, Published Online:Apr. 1, 2006. Published in print Mar. 1, 1970.
Mostad et al., "Effects of Marine N-3 Fatty Acid Supplementation on Lipoprotein Subclasses Measured by Nuclear Magnetic Resonance in Subjects with Type II Diabetes," European Journ. Clin. Nutr., 62(3):419-429 (Mar. 2008/epub Feb. 27, 2007).
Mostad, I.L., et al., "Effects of n-3 fatty acids in subjects with type 2 diabetes: reduction of insulin sensitivity and time-dependent alteration from carbohydrate to fat oxidation." Am J Clin Nutr 84:540-50 (Sep. 2006); https://academic.oup.com/ajcn/article/84/3/540/4648766, Accepted: Apr. 20, 2006. Published: Dec. 1, 2006.

Mozaffarian D, Benjamin EJ, et al., on behalf of the American Heart Association Statistics Committee and Stroke Statistics Subcommittee. Heart disease and stroke statistics—2016 update: a report from the American Heart Association [published online ahead of print Dec. 16, 2015]. Circulation, doi: 10.1161/CIR.0000000000000350.
Mozaffarian D, et al., Effect of Fish Oil on Heart Rate in Humans A Meta-Analysis of Randomized Controlled Trials. Circ.Sep. 27, 2005/ epub Sep. 19, 2005; 112:1945-1952; https://academic.oup.com/ajcn/article/87/6/1991S/4633489, Published: Jun. 1, 2008.
Mozaffarian D, Marchioli R, et al. Fish Oil and Postoperative Atrial Fibrillation The Omega-3 Fatty Acids for Prevention of Post-operative Atrial Fibrillation (OPERA) Randomized Trial. JAMA. Nov. 21, 2012;308(19):2001-11.
Mozaffarian D, Psaty B, et al., Fish Intake and Risk of Incident Atrial Fibrillation. Circ., Jul. 27, 2004/epub Jul. 19, 2004; 110:368-373.
Mozaffarian et al., "Omega-3 fatty acids and cardiovascular disease: effects on risk factors, molecular pathways and clinical events," J. Am. Coll. Cardiol. (Nov. 8, 2011) 58(2):2047-2067.
Mozaffarian, "JELIS, fish oil, and cardiac events," www.thelancet.com vol. 369, pp. 1062-1063 (Mar. 31, 2007).
Mozaffarian, D, "Fish and n-3 fatty acids for the prevention of fatal coronary heart disease and sudden cardiac death." Am J Clin Nutr, 87:1991S-6S (Jun. 2008); https://academic.oup.com/ajcn/article/87/6/1991S/4633489 , Published: Jun. 1, 2008.
Mozaffarian, D, et al., "Dietary fish and ω-3 fatty acid consumption and heart rate variability in US adults." Circulation, 117:1130-1137 (Mar. 4, 2008/ epub Feb. 19, 2008).
Murck et al., "Ethyl-EPA in Huntington disease—Potentially relevant mechanism of action," Brain Research Bulletin, 72:159-164 (2007) (available online Nov. 15, 2006).
Murphy SA, Cannon CP, Blazing MA, et al. Reduction in total cardiovascular events with ezetimibe/simvastatin post-acute coronary syndrome. J Am Coll Cardiol. 67(4):353-361 (publication date Feb. 2, 2016; epublication date Jan. 25, 2016).
Naba, H, et al., "Improving effect of ethyl eicosapentanoate on statin-induced rhabdomyolysis in Eisai hyperbilirubinemic rats." Biochemical and Biophysical Research Communications, 340:215-220 (Feb. 2006/epub Dec. 9, 2005).
Nagakawa et al., Effect of [EPA] on the Platelet Aggregation and Composition of Fatty Acid in Man: A Double Blind Study, Atherosclerosis 47(1):71-75 (Apr. 1983); https://www.sciencedirect.com/science/article/abs/pii/0021915083900734 , Revised Nov. 16, 1982, Accepted Nov. 18, 1982, Available online Apr. 14, 2005.
Naik H, Wu JT, Palmer R, McLean L. The effects of febuxostat on the pharmacokinetic parameters of rosiglitazone, a CYP2C8 substrate. Br. J. Clin. Pharmacol. Jan. 13, 2012;74:327-335.
Nakamura et al., Remnant lipoproteinemia is a risk factor for endothelial vasomotor dysfuction and coronary artery disease in metabolic syndrome, Atherosclerosis, vol. 181(2), pp. 321-327 (Aug. 2005/epub Feb. 16, 2005).
Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (May/Jun. 1998); https://europepmc.org/article/med/9706476 Apr. 30, 1998.
Nakamura, H, et al., "Evaluation of ethyl icosapentate in the treatment of hypercholesterolemia in kidney transplant recipients." Transplantation Proceedings, 30:3047-3048 (Nov. 1998); https://pascal-francis.inist.fr/vibad/index.php?action=getRecordDetail&idt=1650649 , Congress of the Asian Society for Transplantation (5; Manila Dec. 4, 1997).
Nakamura, N, et al., "Joint effects of HMG-CoA reductase inhibitors and eicosapentaenoic acids on serum lipid profile and plasma fatty acid concentrations in patients with hyperlipidemia," International Journal of Clinical and Laboratory Research, Springer, Berlin, DE LNKD-DOI: 10.1007/S005990050057, vol. 29, No. 1, pp. 22-25 (1999); https://link.springer.com/article/10.1007/s005990050057 , Accepted Jan. 12, 1988, Issue Date Mar. 1999.
Nambi V, Bhatt DL. Primary prevention of atherosclerosis: Time to take a selfie? J Am Coll Cardiol 2017;70(24):2992-4 (publication date Dec. 19, 2017; epublication date Dec. 11, 2017).

(56) References Cited

OTHER PUBLICATIONS

Nambi, V., et al., "Combination therapy with statins and omega-3 fatty acids." Am J Cardiol 98:34i-38i (Aug. 21, 2006/epub May 30, 2006).

Nasa et al., "Long-Term Supplementation With Eicosapentaenoic Acid Salvages Cardiomyocytes From Hypoxia/Reoxygenation-Induced Injury in Rats Fed With Fish-Oil-Deprived Diet," Jpn. J. Pharmacol. 77, 137-146 (Jun. 1998); https://www.jstage.jst.go.jp/article/jjp/77/2/77_2_137/_article/-char/ja/.

National Kidney Foundation, "Glomerular Filtration Rate (GFR)," Jan. 30, 2017 (Jan. 30, 2017), retrieved on Jul. 30, 2018 from https://web.archive.org/web/20170130183218/https://www.kidney.org/atoz/content/gfr; entire document, especially p. 1 paragraph 1 and p. 3, paragraph 2.

National Kidney Foundation, "The Heart and Kidney Connection," Apr. 17, 2017 (Apr. 17, 2017), retrieved on Jul. 30, 2018 from https://web.archive.org/web/20170417004l6/https://www.kidney.org/atoz/content/heart-and-kidney-connection; entire document, especially p. 2, paragraph 1.

Natsuno et al., "Clinical Effects of Eicosapentaenoic Acid on Type-2 Diabetes Effects on Serum Lipids, Pulse Wave Speed, and Ankle-Brachial Blood Pressure Index," Diagnosis and Treatment 93(12):133-137 (2005)(16 pages).

Nattel S, et al., "Atrial remodeling and atrial fibrillation: Mechanisms and implications." Circ Arrhythmia Electrophysiol, 1:62-73 (Apr. 2008); https://www.ahajournals.org/doi/full/10.1161/CIRCEP.107.754564 Originally published Apr. 1, 2008.

Needleman P, et al., Triene prostaglandins: prostacyclin and thromboxane biosynthesis and unique biological properties. Proc Natl Acad Sci USA. Feb. 1979;76:944-948; https://www.pnas.org/content/76/2/944.short?__cf_chl_jschl_tk__=ac2fd629e3183e15c541f712df7a9f121128e4bd-1593527565-0-AaVshpn8aqJ6sLwi4-CdjCnbRDi7KbxHebg9ijR1uxqtVRVw6oCucSKnLOREHMPhmpjbNbNiY4sHOc7MjgbNNpaMDfS-qHpGrPmP6oC7-3Xh-Ns5k-wL5RvxdJR6_SaRvSRgvCM6_ud-XzblOjXQKl2oiP9ocNekcqgPcoj-rbPli4vpEUaeTCydRySjvoUCTVsOjDydfU947TSTsloosVEYwFoC0NLpCIWrR0Dp-sDs8iQ6lj_2AteaKUQiNoNIK0QreRzmzX6yHENk7s8lqlZmXSNaX8wyjW-mSiEQ-orR0A-Arv-tEL0nhhdX3Y4-Xw, Feb. 1, 1979.

Negre-Salvayre, A., et al., "Advanced lipid peroxidation end products in oxidative damage to proteins. Potential role in diseases and therapeutic prospects for the inhibitors." British Journal of Pharmacology 153:6-20 (Jan. 2008/epub Jul. 23, 2007).

Nelson et al., "Icosapent Ethyl for Treatment of Elevated Trigylceide Levels," Annals of Pharmacotheraphy, 47(11):1517-1523 (Nov. 2013/epub Nov. 5, 2013).

Nelson JR, et al., Potential benefits of eicosapentaenoic acid on atherosclerotic plaques. Vascul Pharmacol. 91:1-9 (publication date Apr. 2017; epublication date Mar. 2, 2017).

Nelson, G.J., et al., "The Effect of Dietary Docosahexaenoic Acid on Plasma Lipoproteins and Tissue Fatty Acid Composition in Humans", Lipids, 32(11):1137-1146, (Nov. 1997); https://aocs.onlinelibrary.wiley.com/doi/abs/10.1007/s11745-997-0146-5 , First published Nov. 1, 1997. Version of Record online Nov. 1, 1997, Manuscript accepted Oct. 6, 1997. Manuscript revised Sep. 23, 1997, Manuscript received Jul. 14, 1997.

Nemets, Boris, "Addition of Omega-3 Fatty Acid to Maintenance Medication Treatment for Recurrent Unipolar Depressive Disorder", Am. J. Psychiatry, 159(3):477-479, (Mar. 2002); https://ajp.psychiatryonline.org/doi/full/10.1176/appi.ajp.159.3.477, Published Online Mar. 1, 2002.

Nemoto et al., "Ethyl-eicosapentaenoic Acid Reduces Liver Lipids and Lowers Plasma Levels of Lipids in Mice Fed a High-Fat Diet, in vivo," 23:685-690 (Sep./Oct. 2009); http://iv.iiarjournals.org/content/23/5/685.short, Revision received Jun. 4, 2009, Accepted Jun. 26, 2009.

Nenseter, MS et al., "Effect of dietary supplementation with n-3 polyunsaturated fatty acids on physical properties and metabolism of low density lipoprotein in humans," Arterioscler. Thromb. Vasc. Biol., 12;369-379 (Mar. 1992); https://www.ahajournals.org/doi/abs/10.1161/01.atv.12.3.369 Originally publishedMar. 1, 1992.

Nestel et al., "The n-3 fatty acids eicosapentaenoic acid and docosahexaenoic acid increase systemic arterial compliance in humans," Am J Clin Nutr., 76:326-30 (Aug. 2002); https://academic.oup.com/ajcn/article/76/2/326/4689508, Accepted Aug. 2, 2001, Published Aug. 1, 2002.

Nestel, PJ, "Effects of N-3 fatty acids on lipid metabolism." Ann Rev Nutr., 10:149-167 (1990); https://www.annualreviews.org/doi/pdf/10.1146/annurev.nu.10.070590.001053.

Nichols GA, et al., Increased cardiovascular risk in hypertriglyceridemic patients with statin-controlled LDL cholesterol. J Clin Endocrinol Metab 103(8):3019-27 (publication date Aug. 1, 2018; epublication date May 29, 2018).

Nichols GA, et al., Increased residual cardiovascular risk in patients with diabetes and high vs. normal triglycerides despite statin-controlled LDL Cholesterol. Diabetes Obes Metab (publication date Sep. 17, 2018; epublication date Sep. 17, 2018).

Niemi M, Backman JT, Grantors M, et al., Gemfibrozil considerably increases the plasma concentrations of rosiglitazone. Diabetologia. Oct. 2003/ Jul. 29, 2003); 46: 1319-1323; https://ascpt.onlinelibrary.wiley.com/doi/abs/10.1016/j.clpt.2004.05.001, First published Sep. 4, 2004, Version of Record online Sep. 4, 2004, Manuscript accepted May 3, 2004, Manuscript received Feb. 10, 2004.

Niemi M, Backman JT, Neuvonen PJ, Effects of trimethoprim and rifampin on the pharmacokinetics of the cytochrome P450 2C8 substrate rosiglitazone. Clin. Pharmacol. Ther., Sep. 2004;76:239-249.

Nigon F, et al., Discrete subspecies of human low density lipoproteins are heterogeneous in their interaction with the cellular LDL receptor. J. Lipid Res., Nov. 1991;32(11):1741-1753; https://www.jlr.org/content/32/11/1741.short.

Nippon Rinsho, Metabolic Syndrome 2nd Edition—Basics and New Clinical Findings, Jan. 20, 2011, Special Issue 1 (vol. 69), pp. 503-506 (with English translation).

Nishikawa M, et al., "Effects of Eicosapentaenoic acid (EPA) on prostacyclin production in diabetics. GC/MS analysis of PG12 and PG13 levels" Methods Find Exp Clin Pharmacol. 19(6):429-33 (Jul./Aug. 1997); https://europepmc.org/article/med/9385592, Jun. 30, 1997.

Nobukata, H, et al., "Age-related changes in coagulation, fibrinolysis, and platelet aggregation in male WBN/Kob rats." Thrombosis Research 98: 507-516 (Jun. 15, 2000).

Nobukata, H, et al., "Long-term administration of highly purified eicosapentaenoic acid ethyl ester improves the dysfunction of vascular endothelial and smooth muscle cells in male WBN/Kob rats." Metabolism, 49(12): 1588-1591 (Dec. 2000); https://www.sciencedirect.com/science/article/abs/pii/S0026049500435912, Available online May 25, 2002.

Nobukata, H, et al., "Long-term administration of highly purified eicosapentaenoic acid ethyl ester prevents diabetes and abnormalities of blood coagulation in male WBN/Kob rats." Metabolism, 49(12): 912-919 (Jul. 2000); https://www.sciencedirect.com/science/article/abs/pii/S0026049500131701, Available online May 25, 2002.

Noguchi et al., Chemoprevention of DMBA-induced mammary carcinogenesis in rats by low-dose EPA and DHA, Br. J. Cancer 75(3): 348-353 (1997); https://www.nature.com/articles/bjc199757, Feb. 1, 1997.

Nomura et al., "The effects of pitavastatin, eicosapentaenoic acid and combined therapy on platelet-derived microparticles and adiponectin in hyperlipidemic, diabetic patients." Platelets, 20(1):16-22 (Feb. 2009); https://www.tandfonline.com/doi/abs/10.1080/09537100802409921 , Accepted Aug. 14, 2008, Published online: Jul. 7, 2009.

Nomura S, et al., Effects of eicosapentaenoic acid on endothelial cell-derived microparticles, angiopoietins and adiponectin in patients with type 2 diabetes. J Atheroscler Throm., Apr. 2009;16:83-90; https://www.jstage.jst.go.jp/article/jat/advpub/0/advpub_E091/_article/-char/ja/.

Nourooz-Zadeh J, et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (May 13, 2005).

(56) References Cited

OTHER PUBLICATIONS

Nozaki S, et al., "Effects of purified Eicosapentaenoic acid ethyl ester on plasma lipoproteins in primary hypercholesterolemia" Int J Vitam Nutr Res. 62(3):256-260 (1992); https://europepmc.org/article/med/1473909 Dec. 31, 1991.

Obata et al., Eicosapentaenoic acid inhibits prostaglandin D2 generation by inhibiting cyclo-oxygenase in cultured human mast cells, Clin. & Experimental Allergy, 29:1129-1135, (Aug. 1999); https://europepmc.org/article/med/10457118, Jul. 31, 1999.

O'Donnell CJ, et al., "Leukocyte telomere length and carotid artery intimal medial thickness—the Framingham heart study." Arteriosclerosis, Thrombosis, and Vascular Biology.28:1165-1171 ( Jun. 2008/epub Apr. 3, 2008).

Oemar BS, et al., Reduced endothelial nitric oxide synthase expression and production in human atherosclerosis. Circulation., Jun. 30, 1998;97:2494-2498.

Oh, Robert C et al., Management of Hypertriglyceridemia, American Family Physician, LNKD-PUBMED: 17508532, vol. 75, No. 9, pp. 1365-1371 (May 1, 2007).

Ohara Y, et al., Hypercholesterolemia increases endothelial superoxide anion production. J. Clin. Invest. Jun. 1993;91:2546-2551; https://www.jci.org/articles/view/116491, First published Jun. 1, 1993.

Ohashi, Journal of Clinical and Experimental Medicine, Feb. 14, 2009, vol. 228, No. 7, pp. 795-805 (with English translation).

Okuda Y, et al., Eicosapentaenoic acid enhances nitric oxide production by cultured human endothelial cells. Biochem. Biophys. Res. Commun. 232: 487-491 (Mar. 17, 1997).

Okuda Y, et al., Long-term effects of eicosapentaenoic acid on diabetic peripheral neuropathy and serum lipids in patients with type II diabetes mellitus, Journal of Diabetes and Its Complications 10:280-287 (Sep./Oct. 1996); https://www.sciencedirect.com/science/article/abs/pii/105687279500081X, Available online Mar. 19, 1999.

Okumura T, et al., "Eicosapentaenoic acid improves endothelial function in hypertriglyceridemic subjects despite increased lipid oxidizability." Am J Med Sci 324(5):247-253 (Nov. 2002); https://www.sciencedirect.com/science/article/abs/pii/S000296291534369X, Accepted Jun. 17, 2002, Available online Dec. 16, 2015.

Oliw EH, et al., "Biosynthesis of prostaglandins from 17(18)epoxyeicosatetraenoic acid, a cytochrome P-450 metabolite of eicosapentaenoic acid." Biochimica el Biophysica Acta, 1126, 261-268 (Jun. 26, 1992).

Olofsson et al., "Apolipoprotein B: a clinically important apolipoprotein which assembles atherogenic lipoproteins and promotes the development of atherosclerosis" Journal of Internal Medicine, 258: 395-410 (Nov. 2005); https://onlinelibrary.wiley.com/doi/full/10.1111/j.1365-2796.2005.01556.x, First published:Sep. 22, 2005. Version of Record online: Sep. 22, 2005.

Omacor Summary of Product Characteristics, Pronova BioPharma Norge AS. Lysaker, Norway, Mar. 2015.

Omacor® Prescribing Information (Omega-3-acid ethyl esters, capsules) (2004). (9 pages).

Omacor®, Physicians' Desk Reference 2735 (60th ed. 2006)(3 pages).

Ona VO, et al., Nature, vol. 399, Inhibition of caspase-1 slows disease progression in a mouse model of Huntington's disease, pp. 263-267 (May 20, 1999).

Ooi EM, "Apolipoprotein C-III: Understanding an emerging cardiovascular risk factor", Clin.Sci. (London), vol. 114, pp. 611-624 (May 2008); https://portlandpress.com/clinsci/article-abstract/114/10/611/68347 Apr. 14, 2008. Revision Received Nov. 19, 2007, Accepted Dec. 12, 2007.

Opalinska et al., "Increasing Level of Prostate-Specific Antigen and Prostate Cancer Risk Factors Among 193 Men Examined in Screening Procedure," Ann. Univ. Curie Sklowoska Med., 58(2):57-63 (Abstract Only)(2003)(2 pages); https://europepmc.org/article/med/15323167, Dec. 31, 2002.

ORIGIN Trial Investigators (The). n-3 fatty acids and cardiovascular outcomes in patients with dysglycemia. N Engl J Med Jul. 6, 2012/epub Jun. 11, 2012; 367:309-318.

O'Riordan, DHA and EPA have differential effects on LDL-cholsterol, May 24, 2011 [online][Retrieved on Aug. 21, 2015] Retrieved from website: http://www.medscape.com/viewarticle/743305 (2 pages).

Osher et al., Omega-3 Eicosapentaenoic Acid in Bipolar Depression: Report of a Small Open-Label Study, J. Clin. Psych. 66:726-729 (Jun. 2005); https://www.psychiatrist.com/jcp/article/pages/2005/v66n06/v66n0608.aspx.

Otvos et al., "Clinical Implications of Discordance Between LDL Cholesterol and LDL Particle Number," J. Clin. Lipidol, 5(2):105-113 (Mar-Apr. 2011)(available online Mar. 1, 2011).

Ou Z, et al., L-4f, an apolipoprotein a-1 mimetic, restores nitric oxide and superoxide anion balance in low-density lipoprotein-treated endothelial cells. Circulation. Mar. 25, 2003;107:1520-1524.

Ozaki M, et al., Overexpression of endothelial nitric oxide synthase accelerates atherosclerotic lesion formation in apoe-deficient mice. J. Clin. Invest. Aug. 2002; 110:331-340; https://www.jci.org/articles/view/15215 , Accepted Jun. 3, 2002, First published Aug. 1, 2002.

Ozawa et al., Determination of higher fatty acids in various lipid fractions of human plasma, platelets, and erythrocyte membrane using thin layer chromatography and gas chromatography, Bunseki Kagaku, 32:174-8 (1982) (with English abstract).

Padgett et al., Phylogenetic and immunological definition of four lipoylated proteins from *Novosphingobium aromaticivorans*, implications for primary biliary cirrhosis, Journ. Autoimmunity 24:209-219 (May 2005); https://www.sciencedirect.com/science/article/abs/pii/S0896841105000156, Available online Feb. 24, 2005.

Park JH, et al., Metabolic syndrome is associated with erosive esophagitis. World J. Gastroenterol. Sep. 14, 2008 (35): 5442-7; https://www.ncbi.nlm.nih.gov/pmc/articles/PMC2744163/ Published online Sep. 21, 2008.

Park JY, et al., Effect of rifampin on the pharmacokinetics of rosiglitazone in healthy subjects. Clin. Pharmacol. Ther., Mar. 2004;75:157-162; https://ascpt.onlinelibrary.wiley.com/doi/abs/10.1016/j.clpt.2003.10.003 , First published Mar. 9, 2004. Version of Record online Mar. 9, 2004, Manuscript accepted Oct. 8, 2003. Manuscript received Aug. 5, 2003.

Park Y, et al., "Omega-3 fatty acid supplementation accelerates chylomicron triglyceride clearance." J. Lipid Res. 44:455-463 (Mar. 2003); https://www.jlr.org/content/44/3/455.short, First Published on Dec. 1, 2002.

Pase M, et al., Do long-chain n-3 fatty acids reduce arterial stiffness? A meta-analysis of randomized controlled trials.Br J Nutr., Oct. 2011; 106:974-980; https://www.cambridge.org/core/journals/british-journal-of-nutrition/article/do-longchain-n3-fatty-acids-reduce-arterial-stiffness-a-metaanalysis-of-randomised-controlled-trials/3D293E4E535EFAA111C0B0914EE2143F, Oct. 14, 2011. Published online by Cambridge University Press: Jul. 6, 2011.

Patel et al., Rosiglitazone monotherapy improves glycaemic control in patients with type 2 diabetes: a twelve-week, randomized, placebo-controlled study, Diabetes, Obesity and Metabolism, vol. 1, pp. 165-172 (May 1999); https://dom-pubs.onlinelibrary.wiley.com/doi/abs/10.1046/j.1463-1326.1999.00020.x returned for revision Feb. 25, 1999, revised version accepted Mar. 28, 1999, First published Dec. 25, 2001.

Paton, CM, Ntambi, JM., Biochemical and physiological function of stearoyl-CoA desaturase, AM. J. Physiol. Endocrinol. Metab. Jul. 2009/epub Dec. 9, 2008; 297:E28-E37.

PCT/GB00/00164 International Search Report dated Oct. 20, 2000 (8 pages).

PCT/US2011/062247 International Search Report and Written Opinion dated Jun. 14, 2012 (12 pages).

PCT/US2013/020526 International Search Report dated Mar. 29, 2013 (2 pages).

PCT/US2013/048241 International Search Report dated Dec. 13, 2013 (3 pages).

PCT/US2013/048516 International Search Report dated Dec. 20, 2013 (3 pages).

PCT/US2013/048559 International Search Report dated Dec. 13, 2013 (3 pages).

PCT/US2013/068647 International Search Report and Written Opinion dated May 13, 2014 (18 pages).

(56) References Cited

OTHER PUBLICATIONS

PCT/US2014/019454 International Search Report and Written Opinion dated Jun. 3, 2014 (12 pages).
Pedersen RS, Damkier P, Brosen K. The effects of human CYP2C8 genotype and fluvoxamine on the pharmacokinetics of rosiglitazone in healthy subjects. Br. J. Clin. Pharmacol. Dec. 2006/epub Jul. 12, 2006; 62:682-689.
Pedersen, T., et al., "Randomised trial of cholesterol lowering in 4444 patients with coronary heart disease: the Scandinavian Simvastation Survival Study (4S)," The Lancet, No. 19, vol. 344, 8934, p. 1383-1389 (Nov. 19, 1994).
Peet et al., "A Dose-Ranging Study of the Effects of Ethyl-Eicosapentaenoate in Patients with Ongoing Depression Despite Apparently Adequate Treatment with Standard Drugs", Arch. Gen. Psychiatry, 59:913-919, (Oct. 2002); https://jamanetwork.com/journals/jamapsychiatry/article-abstract/206794, Submitted for publication Apr. 27, 2001; final revision received Oct. 19, 2001; accepted Nov. 1, 2001, presented as a poster at the Society of Biological Psychiatry Meeting in New Orleans, La, May 2001, at the Fourth International Conference on Bipolar Disorder in Pittsburgh, Pa, Jun. 2001, and at the British Association of Psychopharmacology Meeting, Harrogate, England, Jul. 2001.
Peet, M., et al., Phospholipid Spectrum Disorder in Psychiatry pp. 1-19, (1999).
Pejic et al., "Hypertriglyceridimia", Journ. Amer. Board Fam. Med., vol. 19(3):310-316 (May/Jun. 2006); https://www.jabfm.org/content/19/3/310.short, May 2006.
Pennathur S, et al., Mechanisms for oxidative stress in diabetic cardiovascular disease. Antioxid. Redox Signal. Jul. 2007;9(7):955-969; https://www.liebertpub.com/doi/abs/10.1089/ars.2007.1595, Published Online:May 17, 2007.
Pepys, MB, et al, C-reactive protein: a critical update, Journal of Clinical Investigation, e-pub Jun. 15, 2003; Jul. 2003, vol. 111(12), pp. 1805-1812; https://www.jci.org/articles/view/18921, First published Jun. 15, 2003.
Piccini M, et al., FACL4, a new gene encoding long-chain acyl-CoA synthetase 4, is deleted in a family with Alport syndrome, elliptocytosis, and mental retardation, Genomics, vol. 47, pp. 350-358 (Feb. 1998); https://www.sciencedirect.com/science/article/pii/S0888754397951041, Accepted Oct. 24, 1997, Available online May 25, 2002.
Piche ME, et al., Relation of High-Sensitivity C-Reactive Protein, Interleukin-6Tumor Necrosis Factor-Alpha, and Fibrinogen to Abdominal Adipose Tissue, Blood Pressure, and Cholesterol and Triglyceride Levels in Healthy Postmenopausal Women, American Journal of Cardiology, 2005, 96(1), 92-97; https://www.sciencedirect.com/science/article/abs/pii/S0002914905005874, Accepted Feb. 28, 2005, Available online May 10, 2005.
Pike NB, Flushing out the role of GPR109A (HM74V) in the clinical efficacy of nicotinic acid, J. Clin. Invest., 115:3400-3403, (Dec. 2005); https://www.jci.org/articles/view/27160, First published Dec. 1, 2005.
PLUSEPA® Product brochure "Super Critically Different from Other Omega-3 Fish Oil Supplements for Depression and ADHD," by Minami Nutrition (Apr. 2009, pp. 1-6).
Poirier, "Obesity and Cardiovascular Disease: Pathophysiology, Evaluation, and Effect of Weight Loss," Circulation, Feb. 14, 2006;113(6):898-918. Epub Dec. 27, 2005.
Pollin TI, Damcott CM, Shen H, et al. A null mutation in human APOC3 confers a favorable plasma lipid profile and apparent cardioprotection. Science. Dec. 12, 2008;322(5908):1702-1705.
Pownall HJ, et al., Correlation of serum triglyceride and its reduction by ω-3 fatty acids with lipid transfer activity and the neutral lipid compositions of high-density and low-density lipoproteins, Atherosclerosis 143:285-297 (Apr. 1999); https://www.sciencedirect.com/science/article/abs/pii/S0021915098003013, Revised Sep. 8, 1998, Accepted Nov. 6, 1998, Available online Mar. 18, 1999.
Press Release: Amarin Corporation Says Huntington's Diease Drug Failed in Trials, http://www.fiercebiotech.com/node/6607/print (Apr. 24, 2007) (Printed on Aug. 22, 2008)(2 pages).

Pritchard KA, Ackerman AW, et al., Native low-density lipoprotein induces endothelial nitric oxide synthase dysfunction: Role of heat shock protein 90 and caveolin-1. Free Radic. Biol. Med. Jul. 2002;33:52-62; https://www.sciencedirect.com/science/article/abs/pii/S0891584902008511, Accepted Mar. 20, 2002, Available online Jun. 19, 2002.
Pritchard KA, Groszek L, et al., Native low-density lipoprotein increases endothelial cell nitric oxide synthase generation of superoxide anion. Circ. Res. Sep. 1995;77:510-518; https://www.ahajournals.org/doi/full/10.1161/01.res.77.3.510, Manuscript received Sep. 26, 1994, Manuscript accepted May 8, 1995, Originally published Sep. 1, 1995.
Puri B, et al., "Sustained remission of positive and negative symptoms of schizophrenia following treatment with eicosapentaenoic acid," Archives of General Psychiatry, No. 55, pp. 188-189, (Feb. 1998); https://jamanetwork.com/journals/jamapsychiatry/article-abstract/190490.
Puri B, et al., "Eicosapentaenoic Acid in Treatment-Resistant Depression Associated with Symptom Remission, Structural Brain Changes and Reduced Neuronal Phospholipid Turnover," Int J Clinical Practice, 55:560-563 (Oct. 2001); https://europepmc.org/article/med/11695079/reload=0 Sep. 30, 2001.
Puri et al., "Reduction in Cerebral Atrophy Associated with Ethyl-eicosapentaenoic Acid Treatment in Patients with Huntington's Disease," Journ. Int'l. Med. Research, 36:896-905 (Oct. 1, 2008).
Puri, BK, et al., "Ethyl-EPA in Huntington Disease: A Double-Blind, Randomized, Placebo-Controlled Trial," Neurology, 65:286-292, (Jul. 26, 2005).
Qi K, et al., Omega-3 fatty acid containing diets decrease plasma triglyceride concentrations in mice by reducing endogenous triglyceride synthesis and enhancing the blood clearance of triglyceride-rich particles, Clinical Nutrition 27(8):424-430 (Jun. 2008/epub Mar. 24, 2008).
Rader, Lipid Disorders, in Eric J. Topol (ed.)Textbook of Cardiovascular Medicine pp. 55-75 (2007) [chapter of book].
Rahimy M, et al., Effect of tolterodine on the anticoagulant actions and pharmacokinetics of single-dose warfarin in healthy volunteers. Arzneimittelforschung 2002 52 (12): 890-5; https://www.thieme-connect.com/products/ejournals/abstract/10.1055/s-0031-1299986, Publication date: Dec. 26, 2011 (online).
Raitt MH, et al., "Fish oil supplementation and risk of ventricular tachycardia and ventricular fibrillation in patients with implantable defibrillators—a randomized controlled trial." JAMA. 293(23):2884-2891 (Jun. 15, 2005).
Rambjor GS, et al., "Elcosapentaenoic Acid is Primarily Responsible for Hypotrigylceridemic Effect of Fish Oil in Humans", Fatty Acids and Lipids from Cell Biology to Human Disease: Proceedings of the 2nd international Congress of the ISSFAL (International Society for the Study of Fatty Acids and Lipids, AOCS Press, 31:S-45-S-49, (Mar. 1, 1996).
Randomised trial of cholesterol lowering in 4444 patients with coronary heart disease, The Scandinavian Simvastatin Survival Study, Lancet. 344: 1383-1389 (1994); https://www.sciencedirect.com/science/article/abs/pii/S0140673694905665, Nov. 19, 1994. Available online Sep. 22, 2003.
Rao MN, et al., Lack of effect of sucralfate on the absorption and pharmacokinetics of rosiglitazone. J. Clin. Pharmacol. Jun. 2002;42:670-675; https://accp1.onlinelibrary.wiley.com/doi/abs/10.1177/00970002042006010, Revised version accepted Feb. 18, 2002. Version of Record online: Mar. 8, 2013 First published:Mar. 8, 2013.
Rauch B, et al., OMEGA, a randomized, placebo-controlled trial to test the effect of highly purified omega-3 fatty acids on top of modern guideline-adjusted therapy after myocardial infarction, Circulation. Nov. 23, 2010 (epub Nov. 8, 2010); 122:2152-2159.
Rees DD, et al., The role of endothelium-derived nitric oxide in the regulation of blood pressure. Proc. Natl. Acad. Sci. USA. May 1989;86:3375-3378; https://www.ahajournals.org/doi/full/10.1161/01.res.87.12.1108, Manuscript received Oct. 3, 2000. Manuscript accepted Oct. 19, 2000, Originally published Dec. 8, 2000.
Reich, "Formulation and physical properties of soft capsules," Pharmaceutical capsules; (2004) Chapter 11:201-212; http://www.

(56) References Cited

OTHER PUBLICATIONS pharmpress.com/files/docs/Chap%2011.pdf, Book chapter from Pharmaceutical Capsules, Pharmaceutical Press, London (2004).
Reiffel JA, et al., "Antiarrhythmic effects of omega-3 fatty acids." Am J Cardiol 98:50i-60i (Aug. 21, 2006/epub May 26, 2006).
Reiner Z, et al., ESC/EAS Guidelines for the management of dyslipidaemias: the Task Force for the management of dyslipidaemias of the European Society of Cardiology (ESC) and the European Atherosclerosis Society (EAS). Eur. Heart J. Jul. 2011 (epub Jun. 28, 2011); 32:1769-1818.
Richter WO, "Hypertriglyceridamie: Ein klinischer·Leitfaden," Wissenschaftliche Verlagsgesellschaft mbH Stuttgart, front page to p. V, pp. 2 to 55, 64 to 85, 90 to 97 (2008) (with English Summary).
Ridker PM, et al., Antiinflammatory Therapy with canakinumab for atherosclerotic disease, N Engl J Med 377(12):1119-31 (publication date Sep. 21, 2017; epublication date Aug. 27, 2017).
Ridker, "C-Reactive Protein : A Simple Test to Help Predict Risk of Heart Attack and Stroke", Circulation: Journal of the American Heart Association, Sep. 23, 2003, 108, e81-e85.
Riediger ND, et al., "A systemic review of the roles of n-3 fatty acids in health and disease." J Am Diet Assoc. 109:668-679. (Apr. 2009); https://www.sciencedirect.com/science/article/abs/pii/S0002822308023353 , Accepted Oct. 3, 2008, Available online Mar. 26, 2009.
Rifai, High-Sensitivity C-Reactive Protein: A Novel and Promising Marker of Coronary Heart Diseas, Clinical Chemistry, Mar. 2001, 47(3), 403-411; https://academic.oup.com/clinchem/article/47/3/403/5639279, Published: Mar. 1, 2001.
Risé P, et al., Effects of simvastatin on the metabolism of polyunsaturated fatty acids and on glycerolipid, cholesterol, and de novo lipid synthesis in THP-1 cells, J. Lipid Res. 38:1299-1307 (Jul. 1997); https://www.jlr.org/content/38/7/1299.short.
Risk and Prevention Study Collaborative Group, Roncaglioni MC, Tombesi M, et al. n-3 fatty acids in patients with multiple cardiovascular risk factors. N Engl J Med., May 9, 2013;368(19):1800-8.
Rissanen et al., "Fish Oil-Derived Fatty Acids, Docosahexaenoic Acid and Docosapentaenoic Acid, and the Risk of Acute Coronary Events The Kuopio Ischaemic Heart Disease Risk Factor Study," Circulation. (Nov. 28, 2000)(102):2677-2679 doi:10.1161/01.CIR.102.22.2677.
Rizzo M, et al., Low-density lipoprotein size and cardiovascular risk assessment. Q. J. Med. Jan. 2006; 99(1): 1-14; https://academic.oup.com/qjmed/article/99/1/1/1523832, Published Jan. 1, 2006.
Roach PD, et al., "The effects of dietary fish oil on hepatic high density and low density lipoprotein receptor activities in the rat." FEBS Lett., 222: 159-162 (Sep. 28, 1987).
Robinson JG, et al., "Meta-analysis of the relationship between non-high-density lipoprotein cholesterol reduction and coronary heart risk." J Am Coll Cardiol., 53: 316-322 (Jan. 27, 2009).
Roche HM, et al., "Effect of long-chain n-3 polyunsaturated fatty acids on fasting and postprandial triacylglycerol metabolism." Am J Clin Nutr 71:232S-7S (Jan. 2000); https://academic.oup.com/ajcn/article/71/1/232s/4729393, Published: Jan. 1, 2000.
Roche HM, et al., "Long-chain n-3 polyunsaturated fatty acids and triacylglycerol metabolism in the postprandial state." Lipids 34: S259-S265 (1999); https://link.springer.com/article/10.1007/BF02562313, Published Jan. 1999.
Rodriguez Y, et al., Long-chain ω6 polyunsaturated fatty acids in erythrocyte phospholipids are associated with insulin resistance in non-obese type 2 diabetics, Clinica Chimica Acta 354:195-199 (Apr. 2005); https://www.sciencedirect.com/science/article/abs/pii/S0009898104005571 , Revised Nov. 12, 2004, Accepted Nov. 12, 2004, Available online Jan. 11, 2005.
Roe MT, et al., Prasugrel versus clopidogrel for acute coronary syndromes without revascularization, TRILOGY ACS Investigators, N Engl J Med. 367(14):1297-1309 (publication date Oct. 4, 2012; epublication Aug. 25, 2012).
Rogers PJ, "No effect of n-3 long-chain polyunsaturated fatty acid (EPA and DHA) supplementation on depressed mood and cognitive function: a randomised controlled trial" British Journal of Nutrition, 99:421-431, (Feb. 2008/epub Oct. 24, 2007).
Rost KL, et al., Nonlinear kinetics after high-dose omeprazole caused by saturation of genetically variable CYP2C19. Hepatology Jun. 23, 1996 (6): 1491-7; https://aasldpubs.onlinelibrary.wiley.com/doi/abs/10.1002/hep.510230628. First published: Jun. 1996.
Rubins HB, et al., "Distribution of lipids in 8,500 men with coronary artery disease: Department of Veterans Affairs HDL Intervention Trial Study Group," Am. J. Cardiol, 75:1196-1201, (Jun. 15, 1995).
Rubins HB, et al., "Gemfibrozil for the secondary prevention of coronary heart disease in men with low levels of high-density lipoprotein cholesterol: Veterans Affairs HDL-C Intervention Trial Study Group," N. Eng. J. Med., 341:410-418, (Aug. 5, 1999).
Ruiz-Narváez EA, et al., Abdominal obesity and hyperglycemia mask the effect of a common APOC3 haplotype on the risk of myocardial infarction, Am J Clin Nutr 87:1932-8 (Jun. 2008); https://academic.oup.com/ajcn/article/87/6/1932/4633423, Accepted: Jan. 20, 2008. Published: Jun. 1, 2008.
Ruocco MJ, et al., Interaction of cholesterol with galactocerebroside and galactocerebroside phosphatidylcholine bilayer membranes. Biophys. J. Dec. 1984; 46:695-707; https://www.ncbi.nlm.nih.gov/pmc/articles/PMC1435096/.
Rupp, "Omega-3-Fettsauren in der Sekundarpravention nach Myokardinfarkt," Clin. Res. Cardiol., vol. 95:Suppl. 6, Vi/12/-V1-16 (2006)(with English summary); https://link.springer.com/article/10.1007/s00392-006-1803-7, Published Sep. 2006.
Rustan AC, et al., Eicosapentaenoic acid inhibits cholesterol esterification in cultured parenchymal cells and isolated microsomes from rat liver, J. Bio. Chem. 263(17):8126-32 (Jun. 15, 1988).
Rustan AC, et al., Eicosapentaenoic acid reduces hepatic synthesis and secretion of triacylglycerol by decreasing the activity of acyl-coenzyme A:1,2-diacylglycerol acyltransferase, J. Lipid Res. 29:1417-1426 (Nov. 1988); https://www.jlr.org/content/29/11/1417.short, Nov. 1988.
Rustan AC, et al., Postprandial decrease in plasma unesterified fatty acids during n-3 fatty acid feeding is not caused by accumulation of fatty acids in adipose tissue, Biochimica et Biophysica Acta 1390. 245-25 (Feb. 23, 1998).
Ryan, AM, et al., "Enteral nutrition enriched with eicosapentaenoic acid (EPA) preserves lean body mass following esophageal cancer surgery: results of a double-blinded randomized controlled trial." Ann Surg 249:355-363 (Mar. 2009); https://journals.lww.com/annalsofsurgery/Abstract/2009/03000/Enteral_Nutrition_Enriched_With_Eicosapentaenoic.1.aspx, Originally published Mar. 2009.
Ryan, AS, et al., "Clinical overview of algal-docosahexaenoic acid: effects on triglyceride levels and other cardiovascular risk factors." Am J Ther., 16:183-192 (Mar./Apr. 2009); https://journals.lww.com/americantherapeutics/Abstract/2009/03000/Clinical_Overview_of_Algal_Docosahexaenoic_Acid_.13.aspx.
Sacks, Frank M, The apolipoprotein story, Atherosclerosis Supplements, 23-27 (Aug. 2006/epub Jul. 5, 2006).
Saito et al., "Effects of Ethyl Eicosapentaenoate (EPA-E), Clopidogrel, and Their Combination on Platelet Aggregation and Bleeding Time;" Japanese Pharmacology & Therapeutics, Feb. 20, 2007 (epub Jan. 2007), vol. 35, No. 2, pp. 179-185 (English abstract only).
Saito et al., "Effects of EPA on coronary artery disease in hypercholesterolemic patients with multiple risk factors: Sub-analysis of primary prevention cases from the Japan EPA Lipid Intervention Study (JELIS)," Atherosclerosis, 200:135-140 (Sep. 2008/epub Jun. 19, 2008).
Saito et al., "Results of Clinical Usage of Improved Formulation (MND-21S) Epadel Capsule 300 with Respect to Hyperlipidemia," 26(12) Jpn. Pharmacol. Ther. 2047-62 (1998) (with English abstract).
Saito, J, et al., "Mechanisms of enhanced production of PGI2 in cultured rat vascular smooth muscle cells enriched with eicosapentaenoic acid." Atherosclerosis 131: 219-228 (Jun. 1997); https://www.sciencedirect.com/science/article/abs/pii/S0021915097000488, Revised Feb. 12, 1997, Accepted Feb. 27, 1997, Available online Sep. 9, 1997.

(56) References Cited

OTHER PUBLICATIONS

Sampath H, et al., Role of stearoyl-CoA desaturase in human metabolic disease, Future Lipidol. 2008;3:2,163-73; https://www.tandfonline.com/doi/abs/10.2217/17460875.3.2.163, Published online Jan. 18, 2017.
Sampath H, et al., The Role of stearoyl-CoA desaturase in obesity, insulin resistance, and inflammation, Ann. NY. Acad. Sci. Dec. 2011; 1243:4 7-53; https://nyaspubs.onlinelibrary.wiley.com/doi/full/10.1111/j.1749-6632.2011,06303.x, First published:Dec. 23, 2011.
Samuels, Martin A, et al., Huntington's Disease, Office Practice of Neurology, (122):654-655, (1996); Published by Churchill Livingstone, Edinburgh.
Sanders T.A., et al., "Influence of an algal triacylglycerol containing docosahexaenoic acid (22:6n-3) and docosapentaenoic acid (22:5n-6) on cardiovascular risk factors in healthy men and women," British Journal of Nutrition, 95, 525-531 (Mar. 2006); https://www.cambridge.org/core/journals/british-journal-of-nutrition/article/influence-of-an-algal-triacylglycerol-containing-docosahexaenoic-acid-226n3-and-docosapentaenoic-acid-225n6-on-cardiovascular-risk-factors-in-healthy-men-and-women/8206943D80EE8C7EA5E61FAFF6C13270, Published online by Cambridge University Press Mar. 8, 2007.
Sanders, A, et al., Influence of n-3 fatty acids on blood lipids in normal subjects, Journal of Internal Medicine. 225:99-104,(1989); https://onlinelibrary.wiley.com/doi/abs/10.1111/j.1365-2796.1989.tb01442.x, First published Dec. 1989, Version of Record online: Feb. 13, 2014.
Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (Sep. 2006).
Sanders, T.A., et al., "Triglyceride-lowering effect of marine polyunsaturates in patients with hypertriglyceridemia." Arterioscler. Thromb. Vasc. Biol. 5:459-465 (Sep./Oct. 1985); https://academic.oup.com/ajcn/article/84/3/513/4648804, Accepted May 11, 2006, Published Dec. 1, 2006.
Sarwar N, et al., Triglycerides and the risk of coronary heart disease: 10,158 incident cases among 262,525 participants in 29 Western prospective studies. Circulation 115:450-458, Jan. 30, 2007/epub Dec. 26, 2006.
Sasaki J, et al., Administration of highly purified eicosapentaenoic acid to stain-treated diabetic patients further improves vascular function. Endocrine J. Jan. 27, 2012; 59(4):297-304.
Sasaki J, et al., Relationship between coronary artery disease and non-HDL-C, and effect of highly purified EPA on the risk of coronary artery disease in hypercholesterolemic patients treated with statins: sub-analysis of the Japan EPA Lipid Intervention Study (JELIS). J. Atheroscler. Thromb. Dec. 17, 2012;19:194-204.
Sasaki YF, et al., Bio-anticlastogenic effects of unsaturated fatty acids included in fish oil—docosahexaenoic acid, docosapentaenoic acid, and eicosapentaenoic acid—in cultured Chinese hamster cells, Mutation Research, 320: 9-22 (Jan. 1994); https://www.sciencedirect.com/science/article/abs/pii/0165121894900558, Revised Jun. 22, 1993, Accepted Jun. 29, 1993, Available online Nov. 18, 2002.
Sato et al., General Pharmacological Studies on 5 8 11 14 17 Eicosapentaenoic Acid Ethyl Ester EPA-E, Folia Pharmacol JPN, 94 (1), 35-47. (Jul. 1989) (with English abstract); https://europepmc.org/article/med/2551801, Jun. 30, 1989.
Sato, Effects of Highly Purified Ethyl All-cis-5,8,11,14,17-icosapentaenoate (EPA-E) on Rabbit Platelets, Biol. Pharm. Bull., 16(4)362-367 (Apr. 1993); https://www.jstage.jst.go.jp/article/bpb1993/16/4/16_4_362/_article/-char/ja/.
Satoh et al., "Highly purified eicosapentaenoic acid reduces cardio-ankle vascular index in association with decreased serum amyloid A-LDL in metabolic syndrome," Hypertension Research (Nov. 2009/epub Sep. 18, 2009) (32):1004-1008.
Satoh, N., et al., "Purified eicosapentaenoic acid reduces small dense LDL, remnant lipoprotein particles, and C-reactive protein in metabolic syndrome." Diabetes Care, 30(1): 144-146 (Jan. 2007); https://care.diabetesjournals.org/content/30/1/144.short.
Satoh-Asahara N, et al., Highly purified eicosapentaenoic acid increases interleukia-10 levels of peripheral blood monocytes in obese patients with dyslipidemia, Diabetes Care. Dec. 2012/epub Aug. 21, 2012; 35(12):2631-2639.
Schaefer EJ, et al., "Effects of eicosapentaenoic acid, docosahexaenoic acid, and olive oil on cardiovascular disease risk factors [abstract 20007]." Circulation, 122:A20007 (2010) (Abstract only); https://www.ahajournals.org/doi/abs/10.1161/circ.122.suppl_21.a20007, Originally publishedMar. 23, 2018.
Schectman G, et al., "Dietary fish oil decreases low-density-lipoprotein clearance in nonhuman primates." Am J Clin Nutr., 64:215-221 (Aug. 1996); https://academic.oup.com/ajcn/article/64/2/215/4650420, Published: Aug. 1, 1996.
Schectman G, et al., "Heterogeneity of Low Density Lipoprotein Responses to Fish-Oil Supplementation in Hypertriglyceridemic Subjects." Arterioscler. Thromb. Vasc. Biol. 9:345-354 (May/Jun. 1989); https://www.ahajournals.org/doi/abs/10.1161/01.ATV.9.3.345, Originally publishedMay 1, 1989.
Schectman G, et al., Drug therapy for hypercholesterolemia in patients with cardiovascular disease: factors limiting achievement of lipid goals, Am. J. Med., 100:197-204, (Feb. 1996); https://www.sciencedirect.com/science/article/abs/pii/S0002934397894594 , Accepted Jul. 21, 1995, Available online Apr. 3, 2001.
Schmidt EB, et al., Lipoprotein-associated phospholipase A2 concentrations in plasma are associated with the extent of coronary artery disease and correlate to adipose tissue levels of marine n-3 fatty acids, Atherosclerosis 196: 420-424 (Jan. 2008); https://www.sciencedirect.com/science/article/abs/pii/S0021915006007015, Revised Nov. 15, 2006, Accepted Nov. 17, 2006, Available online Dec. 8, 2006.
Schmitz PG, et al., Prophylaxis of hemodialysis graft thrombosis with fish oil: double-blind, randomized, prospective trial. J. Am. Soc. Nephrol. Jan. 13, 2002 (1): 184-90; https://jasn.asnjournals.org/content/13/1/184.short.
Schmitz, G, et al., "The opposing effects of n-3 and n-6 fatty acids." Progress in Lipid Research, 47:147-155 (Mar. 2008/epub Dec. 27, 2007).
Schreiner et al., Lipoprotein[a] as a Risk Factor for Preclinical Atherosclerosis, 13 Atherosclerosis, Thrombosis & Vascular Biology 6: 826-833 (1993); https://www.ahajournals.org/doi/abs/10.1161/01.ATV.13.6.826; Originally published Jun. 1, 1993.
Schuirmann, DJ, A comparison of the two one-sided tests procedure and the power approach for assessing the equivalence of average bioavailability, J. Pharmacokinet. Biopharm. 15(6), 657-680 (Dec. 1987); https://link.springer.com/article/10.1007%2FBF01068419, Revised Sep. 22, 1987, Published Dec. 1, 1987.
Schunkert H, König IR, Kathiresan S, et al. Large-scale association analysis identifies 13 new susceptibility loci for coronary artery disease. Nat Genet. Mar. 6, 2011;43(4):333-8.
Schwartz GG, Bessac L, Berdan LG, et al. Effect of alirocumab, a monoclonal antibody to PCSK9, on long-term cardiovascular outcomes following acute coronary syndromes: rationale and design of the ODYSSEY outcomes trial. Am Heart J 168(5):682-9 (publication date Nov. 2014, epublication date Aug. 7, 2017).
Schwarz S., et al., "Lycopene inhibits disease progression in patients with benign prostate hyperplasia." J. Nutr. 138: 49-53 (Jan. 2008); https://academic.oup.com/jn/article/138/1/49/4665062 , Revision received May 19, 2007, Accepted Oct. 22, 2007, Published Jan. 1, 2008.
Schwellenbach et al., The Triglyceride-Lowering Effects of a Modest Dose of Docosahexaenoic Acid Alone Versus in Combination with Low Dose Eicosapentaenoic Acid in Patients with Coronary Artery Disease and Elevated Triglycerides, J. Am. Coll. Nutr. 25(6):480-485 (Dec. 2006); https://www.tandfonline.com/doi/abs/10.1080/07315724.2006.10719562, Accepted Apr. 18, 2006, Published online: Jun. 18, 2013.
Segrest et al., Structure of Apolipoprotein B-100 in Low Density Lipoproteins, J. Lipid Res. 42(9):1346-1367 (Sep. 2001); https://www.jlr.org/content/42/9/1346.short.

(56) References Cited

OTHER PUBLICATIONS

Self-Medlin Y, Byun J, Jacob RF, Mizuno Y, Mason RP. Glucose promotes membrane cholesterol crystalline domain formation by lipid peroxidation. Biochim. Biophys. Acta. Jun. 2009/epub Apr. 17, 2009; 1788(6): 1398-1403.
Serhan C, et al., Resolving inflammation: dual anti-inflammatory and pro-resolution lipid mediators. Nat Rev Immunol. May 2008; 8:3449-361; https://www.nature.com/articles/nri2294/, Published May 2008.
Serhan CN, et al., Resolvins: A family of bioactive products of omega-3 fatty acid transformation circuits initiated by aspirin treatment that counter proinflammation signals, J. Exp. Med. 196:1025-1037 (Oct. 21, 2002).
Sevanian A, et al., Lipid peroxidation in membranes and low-density lipoproteins: similarities and differences. Free Radic. Biol. Med., Aug. 2000;29(3-4):306-311; https://www.sciencedirect.com/science/article/abs/pii/S0891584900003427, Accepted May 18, 2000, Available online Sep. 25, 2000.
Shah S, et al., "Eicosapentaenoic Acid (EPA) as an Adjunct in the Treatment of Schizophrenia", Schizophrenia Research, vol. 29, No. 1/02 (1998); https://www.infona.pl/resource/bwmeta1.element.elsevier-554c669f-0994-3a2f-b34d-0a00044944be.
Shan Z, et al., "A combination study of spin-trapping, LC/ESR and LC/MS on carbon-centred radicals formed from lipoxygenase-catalysed peroxidation of eicosapentaenoic acid." Free Radical Research, 43(1):13-27 (Jan. 2009); https://www.tandfonline.com/doi/abs/10.1080/10715760802567606, Published online Aug. 6, 2009.
Shearer et al., "Red Blood Cell Fatty Acid Patters and Acute Coronary Syndrome," PLoS ONE 4(5): e5444, publ. May 6, 2009 (doi:10.1371/journal/pone.0005444).
Shen, W., et al., "Influence of Omega-3 Fatty Acids Intake on Human Responsiveness to Ambient Air Pollution Exposure", Apr. 1, 2017, The FASEB Journal; retrieved from Internet: URL://https://www.fasebj.org/doi/abs/10.1096/fasebj.31,1_supplement.971.2; [retrieved on Jan. 7, 2020].
Sherratt SCR, Mason RP. Eicosapentaenoic acid and docosahexaenoic acid have distinct membrane locations and lipid interactions as determined by X-ray diffraction. Chem Phys Lipids 212:73-9 (publication date May 2018, epublication date Jan. 31, 2018).
Shimizu et al., "Effects of Highly Purified Eicosapentaenoic Acid on Erythrocyte Fatty Acid Composition and Leukocyte and Colonic Mucosa Leukotriene B4 Production in Children with Ulcerative Colitis," J. Pediatr. Gastroenterol. Nutr., vol. 37, No. 5, pp. 581-585 (Nov. 2003); https://journals.lww.com/jpgn/fulltext/2003/11000/effects_of_highly_purified_eicosapentaenoic_acid.15.aspx.
Shimizu H, et al., "Long-term effect of eicosapentaenoic acid ethyl (EPA-E) on albuminuria of non-insulin dependent diabetic patients." Diabetes Research and Clinical Practice 28: 35-40 (Apr. 1995); https://www.sciencedirect.com/science/article/abs/pii/016882279501056J, Revised Mar. 6, 1995, Accepted Apr. 5, 1995, Available online Feb. 4, 2000.
Shimokawa H, et al., Loss of endothelial pertussis toxin-sensitive g protein function in atherosclerotic porcine coronary arteries. Circulation. Feb. 1991;83:652-660; https://www.ahajournals.org/doi/abs/10.1161/01.CIR.83.2.652, Originally publishedFeb. 1, 1991.
Shinozaki K, et al., The long-term effect of Eicosapentaenoic acid on serum levels of lipoprotein (a) and lipids in patients with vascular disease, J Atheroscler Thromb. 2(2):207-9 (1996); https://www.jstage.jst.go.jp/article/jat1994/2/2/2_2_107/_article/-char/ja/.
Shishehbor MH, et al., Statins promote potent systemic antioxidant effects through specific inflammatory pathways. Circulation. Jul. 29, 2003;108(4):426-431.
Sicherer et al., "Prevalence of seafood allergy in the United States determined by a random telephone survey," J. Allergy Clin. Immunol., 114(1):159-165 (Jul. 2004); https://www.sciencedirect.com/science/article/abs/pii/S0091674904013296, Revised Apr. 2, 2004, Accepted Apr. 2, 2004, Available online Jul. 2, 2004.
Sierra S, et al., "Dietary eicosapentaenoic acid and docosahexaenoic acid equally incorporate as decosahexaenoic acid but differ in inflammatory effects." Nutrition 24: 245-254 (Mar. 2008); https://www.sciencedirect.com/science/article/abs/pii/S0899900707003504, Accepted Nov. 27, 2007, Available online Feb. 5, 2008.
Signori S, et al., "Administration of omega-3 fatty acids and Raloxifene to women at high risk of breast cancer: interim feasibility and biomarkers analysis from a clinical trial," European Journ of Clin. Nutr., 66, 878-884 (published online Jun. 6, 2012).
Silvers Karen M, et al., "Randomised double-blind placebo-controlled trial of fish oil in the treatment of depression", Prostagandins, Leukotrienes and Essential Fatty Acids, 72:211-218, (Mar. 2005); https://www.sciencedirect.com/science/article/abs/pii/S0952327804001905, Accepted Nov. 21, 2004, Available online Jan. 1, 2005.
Simoens CM, et al., Inclusion of 10% fish oil in mixed medium-chain triacylglycerol-long chain triacylglycerol emulsions increases plasma triacylglycerol clearance and induces rapid eicosapentaenoic acid (20:5n-3) incorporation into blood cell phospholipids, Am J Clin Nutr 88: 282-8 (Aug. 2008); https://academic.oup.com/ajcn/article/88/2/282/4649896, Accepted Apr. 30, 2008, Published Aug. 1, 2008.
Simon Joel A, et al., "Serum Fatty Acids and the Risk of Coronary Heart Disease", American Journal of Epidemiology, 142(5):469-476, (Sep. 1, 1995).
Simopolous, The Importance of the Omega-6/Omega-3 Fatty Acid Ratio in Cardiovascular Disease and Other Chronic Diseases, Exp. Biol. Med., 233:674-688 (Jun. 1, 2008)(available online Jun. 1, 2008); https://academic.oup.com/ajcn/article-abstract/54/3/438/4694393, Accepted Mar. 20, 1991, Published Sep. 1, 1991.
Simopoulos, Omega-3 fatty acids in health and disease and in growth and development, Am. J. Clin. Nutr. 54:438-63 (Sep. 1991); https://academic.oup.com/ajcn/article-abstract/54/3/438/4694393, Accepted Mar. 20, 1991, Published: Sep. 1, 1991.
Singer Peter, "Fluvastatin plus fish oil are more effective on cardiovascular risk factors than fluvastatin alone," Letter to the Editor, Prostaglandinis, Leukotrienes and Essential Fatty Acids, vol. 72, pp. 379-380 (May 2005).
Singh RB, et al., Randomized, double-blind, placebo-controlled trial of fish oil and mustard oil in patients with suspected acute myocardial infarction: the Indian experiment of infarct survival—4, Cardiovascular Drugs and Therapy 11:485-491 (Jul. 1997); https://link.springer.com/article/10.1023/A:1007757724505, Published Jul. 1997.
Sirtori CR, et al., One-year treatment with ethyl esters of n-3 fatty acids in patients with hypertriglyceridemia and glucose intolerance—Reduced triglyceridemia, total cholesterol and increased HDL-C, Atherosclerosis 137: 419-427 (Apr. 1998); https://www.sciencedirect.com/science/article/abs/pii/S0021915097002980, Revised Nov. 21, 1997, Accepted Nov. 27, 1997, Available online Jun. 15, 1998.
Siscovick et al., "Dietary Intake and Cell Membrane levels of Long-chain N-3 Polyunsaturated Fatty Acids and the Risk of Primary Cardiac Arrest", JAMA, vol. 274, No. 17, Nov. 1, 1995, pp. 1363-1367, XP008041164.
Skinner JS, et al., on behalf of the Guideline Development Group, Secondary prevention for patients following a myocardial infarction; summary of NICE guidance, Heart, 93:862-864 (Jul. 2007); https://heart.bmj.eom/content/93/7/862.short, Published Online First: Jun. 14, 2007.
Slides for the Oct. 16, 2013 Meeting of the Endocrinologic and Metabolic Drugs Advisory Committee, (158 pages).
Smith et al., Pharmacokinetics and Pharmacodynamics of Epoetin Delta in Two Studies in Health Volunteers and Two Studies in Patients with Chronic Kidney Disease, Clinical Therapeutics/vol. 29, pp. 1368-1380 (Jul. 2007); https://www.sciencedirect.com/science/article/abs/pii/S0149291807002068, Available online Sep. 4, 2007.
Sniderman A, et al., Update on the detection and treatment of atherogenic low-density lipoproteins. Curr. Opin. Endocrinol. Diabetes Obes. Apr. 20, 2013;20:140-147.
Sohma R, et al., Protective effect of n-3 polyunsaturated fatty acid on primary culture of rat hepatocytes without glycemic alterations, Journal of Gastroenterology and Hepatology 22: 1965-1970 (Nov. 2007); https://onlinelibrary.wiley.com/doi/abs/10.1111/j.1440-1746.2006.04684.x, First published: Oct. 2, 2007.

(56) References Cited

OTHER PUBLICATIONS

Spector AA, Arachidonic acid cytochrome P450 epoxygenase pathway, Journal of Lipid Research, 50: S52-S56 (2009) (published online on Oct. 23, 2008).

Spector AA, et al., Epoxyeicosatrienoic acids (EETs): metabolism and biochemical function, Progress in Lipid Research 43: 55-90 (Jan. 2004); https://www.sciencedirect.com/science/article/abs/pii/S0163782703000493, Available online Aug. 27, 2003.

Springer TA, Traffic signals for lymphocyte recirculation and leukocyte emigration: The multistep paradigm, Cell, 76: 301-314 (Jan. 28, 1994).

Squires RW, et al., "Low-dose, time release nicotinic acid: effects in selected patients with low concentrations of high density lipoprotein cholesterol", Mayo Clinic Proc., 67:855-860, (Sep. 1992); https://www.sciencedirect.com/science/article/abs/pii/S0025619612608246, Available online Dec. 13, 2012.

Srinivas et al., Controlled release of lysozyme from succinylated gelatin microspheres, J. Biomater. Sci., Polymer Ed., vol. 12(2):137-148 (2001); https://www.tandfonline.com/doi/abs/10.1163/156856201750180870, Published online: Apr. 2, 2012.

Stalenhoef AF, et al., "The effect of concentrated n-3 fatty acids versus gemfibrozil on plasma lipoproteins, low density lipoprotein heterogeneity and oxidizability in patients with hypertriglyceridemia." Atherosclerosis 153: 129-138 (Nov. 2000); https://www.sciencedirect.com/science/article/abs/pii/S0021915000003816, Revised Dec. 6, 1999, Accepted Jan. 7, 2000, Available online Oct. 27, 2000.

Stampfer MJ, et al., A prospective study of triglyceride level, lowdensity lipoprotein particle diameter, and risk of myocardial infarction. JAMA. Sep. 1996;276:882-888; https://jamanetwork.com/journals/jama/article-abstract/407965, Sep. 18, 1996.

Stancu et al., Statins: Mechanism of Action and Effects, *Journal of Cellular and Molecular Medicine* (Oct.-Dec. 2001), 5(4), 378-387; https://onlinelibrary.wiley.com/doi/abs/10.1111/j.1582-4934.2001.tb00172.x, Accepted Dec. 5, 2001, Issue online May 1, 2007, First published: May 1, 2007.

Stark KD, "The percentage of n-3 highly unsaturated fatty acids in total HUFA as a biomarker for omega-3 fatty acid status in tissues." Lipids 43:45-53 (Jan. 2008/epub Nov. 6, 2007).

Stark KD, et al., "Effect of a fish-oil concentrate on serum lipids in postmenopausal women receiving and not receiving hormone replacement therapy in a placebo-controlled, double-blind trial." Am J Clin Nutr 72:389-94 (Aug. 2000); https://academic.oup.com/ajcn/article/72/2/389/4729436, Accepted Jan. 31, 2000, Published Aug. 1, 2000.

Stark KD, Holub, B.J., Differential eicosapentaenoic acid elevations and altered cardiovascular disease risk factor responses after supplementation with docosahexaenoic acid in postmenopausal women receiving and not receiving hormone replacement therapy, Am. J. Clin. Nutr., vol. 79, pp. 765-773 (May 2004); https://academic.oup.com/ajcn/article/79/5/765/4690185, Accepted Oct. 8, 2003, Published May 1, 2004.

Steg PG, et al; REACH Registry Investigators. One-year cardiovascular event rates in outpatients with atherothrombosis. JAMA. 297(11):1197-1206 (publication date May 21, 2007).

Stein et al., "Effect of Statin Therapy on Remnant Lipoprotein Cholesterol Levels in Patients with Combined Hyperlipidemia," Arteriosclerosis, Thrombosis and Vascular Biology, vol. 21, pp. 2026-2031 (Dec. 1, 2001).

Steinberg D, Lewis A, Conner Memorial Lecture: Oxidative modification of LDL and atherogenesis. Circulation. Feb. 18, 1997;95(4):1062-1071.

Steinberg D, Witztum JL. Is the oxidative modification hypothesis relevant to human atherosclerosis? Do the antioxidant trials conducted to date refute the hypothesis? Circulation. Apr. 30, 2002;105:2107-2111.

Stepp DW, et al., Native ldl and minimally oxidized ldl differentially regulate superoxide anion in vascular endothelium in situ. Am. J. Physiol. Aug. 2002;283:H750-H759; https://journals.physiology.org/doi/full/10.1152/ajpheart.00029.2002, Accepted Mar. 18, 2002, Published online Aug. 1, 2002, Published in print Aug. 1, 2002.

Sternbach, "The Glasgow Coma Scale." The Journal of Emergency Medicine, 19(1):67-71 (Feb. 8, 2000).

Stielow et al., "Novel Nox Inhibitor of oxLDL-Induced Reactive Oxygen Species Formation in Human Endothelial Cells," Biochem. Biophys. Res. Comm., 344:200-205 (May 26, 2006/epub Mar. 26, 2006).

Stiles, FDA approves EPA-only omega-3 PUFA capsule for high TG, Jul. 26, 2012, http://www.medscape.com/viewarticle/791268, accessed Dec. 17, 2014 (1 page).

Stitziel N, Stirrups K, Masca N, et al. Supplement to: Coding variation in ANGPTL4, LPL, and SVEP1 and the risk of coronary disease. N Engl J Med. DOI: 10.1056/NEJMoa1507652; Mar. 24, 2016/epub Mar. 2, 2016.

Stojancevic et al., "The impact of farnesoid X receptor activation on intestinal permeability in inflammatory bowel disease," Can. J Gastroenterol. 26(9):631-637 (Sep. 2012); https://www.hindawi.com/journals/cjgh/2012/538452/, Accepted Dec. 30, 2011.

Stoll Andrew L, et al., "Omega 3 Fatty Acids in Bipolar Disorder", Arch. Gen. Psychiatry, 56:407-412, (May 1999); https://jamanetwork.com/journals/jamapsychiatry/article-abstract/204999, Accepted for publication Oct. 2, 1998. Presented in part at the 36th Annual Meeting of the American College of Neuropsychopharmacology, Waikoloa, Hawaii, Dec. 10, 1997.

Stone NJ, et al. ACC/AHA Prevention Guideline: 2013 ACC/AHA Guideline on the Treatment of Blood Cholesterol to Reduce Atherosclerotic Cardiovascular Risk in Adults: A Report of the American College of Cardiology/American Heart Association Task Force on Practice Guidelines. erratum in Circulation. Jun. 24, 2014;129:S46-S48.

Su KP, et al., "Omega-3 Fatty Acids in Major Depressive Disorder A Preliminary Double-Blind, Placebo-Controlled Trial", European Neuropsychopharmacology, 13:267-271, (Aug. 2003); https://www.sciencedirect.com/science/article/abs/pii/S0924977X03000324, Revised Jan. 28, 2003, Accepted Jan. 28, 2003, Available online Apr. 18, 2003.

Sugiyama et al., A Comparison of the Hypotensive Effects of Eicosapentaenoic Acid Ethyl (EPA) on Three Diseases (Occluded Arteriosclerosis, Hyperlipidemia, and These Two Diseases Combined) P2-504 Abstract, Annual Meeting of the Japanese Society of Pharmaceutical Health Care and Sciences 20:473 (Nov. 2010) (with English translation)(3 pages).

Sugiyama, E., et al., "Eicosapentaenoic acid lowers plasma and liver cholesterol levels in the presence of peroxisome proliferators-activated receptor alpha," Life Sciences, 83:19-28 (Jul. 4, 2008/epub May 1, 2008).

Superko et al., "Lipid Management to Reduce Cardiovascular Risk: A New Strategy is Required," Circulation, 117:560-568 (Jan. 29, 2008).

Surette ME, et al., "Dependence on dietary cholesterol for n-3 polyunsaturated fatty acid induced changes in plasma cholesterol in the Syrian hamster," J Lipid Res., 33:263-271 (Feb. 1992); https://www.jlr.org/content/33/2/263.short.

Surette ME, et al., "Evidence for mechanisms of the hypotriglyceridemic effect of n-3 polyunsaturated fatty, acids." Biochimica et Biophysic Acta, 1126: 199-205 (Jun. 22, 1992).

Tagawa H, et al., Long-term treatment with eicosapentaenoic acid augments both nitric oxide-mediated and non-nitric oxide-mediated endothelium-dependent forearm vasodilatation in patients with coronary artery disease. J Cardiovasc Pharmacol 33(4):633-40, Apr. 1999; https://journals.lww.com/cardiovascularpharm/Fulltext/1999/04000/Short_Term_Estrogen_Augments_Both_Nitric.17.aspx.

Takaki A, et al., Add-on therapy of epa reduces oxidative stress and inhibits the progression of aortic stiffness in patients with coronary artery disease and statin therapy: A randomized controlled study. J. Atheroscler. Thromb. Jun. 23, 2011;18:857-866.

Takaku et al., Study on the Efficacy and Safety of Ethyl Icosapentate (MND-21) in Treatment of Hyperlipidemia Based on a Long-Term Administration Test, 7 J. Clin. Ther. Med. 191 (1991) (w/English Translation)(27 pages).

Talayero BG, et al., The role of triglycerides in atherosclerosis, Curr. Cardiol. Rep. 2011;13:544-552; https://link.springer.com/article/10.1007%2Fs11886-011-0220-3, Published Oct. 4, 2011.

(56) References Cited

OTHER PUBLICATIONS

Tamura et al., Study of the Clinical Usefulness of Ethyl Icosapentate (MND-21) in Long-Term Treatment of Hyperlipaemic Patients, J Clin Thera & Medicines, 7:1817-1834 (1991).

Tanaka et al., "Administration of high dose eicosapentaenoic acid enhances anti-inflammatory properties of high-density lipoprotein in Japanese patients with dyslipidemia," Atherosclerosis, 237(2):577-83 (Dec. 2014); https://www.sciencedirect.com/science/article/abs/pii/S0021915014014440 , Revised Sep. 22, 2014, Accepted Oct. 14, 2014, Available online Oct. 18, 2014.

Tanaka et al., "Eicosapentaenoic Acid-Enriched High-Density Lipoproteins Exhibit Anti-Atherogenic Properties," Circ. J., doi: 10.1253/circj.CJ-17-0294. [Epub ahead of print] (Jun. 23, 2017)(6 pages).

Tanaka et al., Genome-Wide Association Study of Plasma Polyunsaturated Fatty Acids in the InCHIANTI Study, PLoS Genetics 5(1):1-8 (Jan. 2009); https://journals.plos.org/plosgenetics/article?id=10.1371/journal.pgen.1000338 , Published: Jan. 16, 2009.

Tanaka et al., Suppression of prostaglandin synthesis by arachidonic acid or eicosapentaenoic acid in a macrophage-like cell line, RAW 264.7, treated with LPS, Biol. Pharm. Bull., 22(10):1052-7 (Oct. 1999); https://www.jstage.jst.go.jp/article/bpb1993/22/10/22_10_1052/_article/-char/ja/.

Tanaka, KT, et al., "Reduction in the recurrence of stroke by eicosapentaenoic acid for hypercholesterolemic patients—Subanalysis of the JELIS trial." Stroke, 39(7):2052-8 (Jul. 2008/epub May 1, 2008).

Tatarczyk et al., "Analysis of long-chain ω-3 fatty acid content in fish-oil supplements," Wien Klin Wochenschr, 119/13-14: 417-422 (2007); https://link.springer.com/article/10.1007/s00508-007-0820-5 Accepted Apr. 16, 2007, Issue Date Jul. 2007.

Tatsuno et al., Efficacy and safety of TAK-085 compared with eicosapentaenoic acid in Japanese subjects with hypertriglyceridemia undergoing lifestyle modification: The omega-3 fatty acids randomized double-blind (ORL) study, J. Clin. Lipid; vol. 7(6), pp. 615-625 (Sep. 12, 2013).

Taylor et al., "Fish allergy: fish and products thereof," Journal Food Science (2004) 69.8 R175-R180; https://onlinelibrary.wiley.com/doi/abs/10.1111/j.1750-3841.2004.tb18022.x#:~:text=All%20species%20of%20fish%20are,occurring%20muscle%20protein%20called%20parvalbumin , Accepted May 31, 2004, Version of Record Online May 9, 2011.

Taylor, AJ, et al., Arterial Biology for the Investigation of the Treatment Effects of Reducing Cholesterol (ARBITER) 2: a double-blind, placebo-controlled study of extended-release niacin on atherosclerosis progression in secondary prevention patients treated with statins, Circulation, 110:3512-3517, (Dec. 7, 2004/epub Nov. 10, 2004).

Tedgui A, et al., "Anti-inflammatory mechanisms in the vascular wall." Circ. Res. 88:877-887 (May 11, 2001).

Teissier E, et al., Peroxisome proliferator-activated receptor alpha induces NADPH oxidase activity in macrophages, leading to the generation of LDL with PPAR-alpha activation properties. Circ. Res. Dec. 10, 2004/epub Nov. 11, 2004;95(12):1174-1182.

Teramoto T, et al., Diagnosis of atherosclerosis. Executive Summary of the Japan Atherosclerosis Society (JAS) Guidelines for the Diagnosis and Prevention of Atherosclerotic Cardiovascular Diseases in Japan—2012 Version. J Atheroscler Thromb. 2014;21(4):296-8. Electronic publication Dec. 10, 2013.

Terano et al., "Effect of Oral Administration of Highly Purified Eicosapentaenoic Acid on Platelet Function, Blood Viscosity and Red Cell Deformability in Healthy Human Subjects," Atherosclerosis, 46, 321-331 (Mar. 1983); https://www.sciencedirect.com/science/article/abs/pii/0021915083901818, Revised Oct. 15, 1982, Accepted Oct. 25, 1982, Available online Apr. 14, 2005.

The TG and HDL Working Group of the Exome Sequencing Project, National Heart, Lung, and Blood Institute. Loss-of-function mutations in APOC3, triglycerides, and coronary disease. N Engl J Med. Jul. 3, 2014/epub Jun. 18, 2014; 371(1):22-31.

Theilla M, et al., "A diet enriched in eicosapentaenoic acid, gamma-linolenic acid and antioxidants in the prevention of new pressure ulcer formation in critically ill patients with acute lung injury: A randomized, prospective, controlled study." Clinical Nutrition 26: 752-757 (Dec. 2007/epub Oct. 22, 2007).

Theobald et al., LDL Cholesterol-Raising Effect of Low-Dose Docosahexaenoic Acid in Middle-Aged Men and Women, Am. J. Clin. Nutr. 79:558-63 (Apr. 2004); https://academic.oup.com/ajcn/article/79/4/558/4690135, Accepted Sep. 22, 2003, Published Apr. 1, 2004.

Thies F, et al., "Association of n-3 polyunsaturated fatty acids with stability of atherosclerotic plaques: a randomised controlled trial." Lancet 361: 477-85 (Feb. 8, 2003).

Thies F, et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (Mar. 2001); https://academic.oup.com/ajcn/article/73/3/539/4737356, Accepted: Jul. 28, 2000. Published: Mar. 1, 2001.

Third Report of the National Cholesterol Education Program (NCEPP) Expert Panel on Detection, Evaluation, and Treatment of High blood Cholesterol in Adults (Adult Treatment Panel III) May 2001, National Institutes of Health, Publication No. 01-3670.

Third Report of the NCEP Expert Panel on Detection, Evaluation, and Treatment of High Blood Cholesterol in Adults (Adult Treatment Panel III) Final Report, NIH Publication No. 02-5215 Sep. 2002 (220 pages in three parts).

Thomas et al., "Renal Failure—Measuring the Glomerular Filtration Rate," Dtsch Arztebl Int., Dec. 18, 2009, 106(51-52); 849-54.

Thomas II et al., "Prostate Cancer Risk in Men with Baseline History of Coronary Artery Disease: Results from the REDUCE Study," Cancer Epidemiology, Biomarkers and Prevention, 21(4) published online Feb. 7, 2012.

Thorwest M, et al., Dietary fish oil reduces microvascular thrombosis in a porcine experimental model. Thromb. Res. Jul. 2000, 99(2): 203-8; https://www.sciencedirect.com/science/article/abs/pii/S0049384800002334, Revised Mar. 9, 2000, Accepted Mar. 9, 2000, Available online Aug. 15, 2000.

Thygesen K, et al., Third Universal Definition of Myocardial Infarction. J Am Coll Cardiol.,Oct. 16, 2012/epub Sep. 5, 2012; 60(16):1581-1598.

Tilg H, et al., Inflammatory Mechanisms in the Regulation of Insulin Resistance. Mol. Med., Mar./Apr. 2008;14(3-4):222-231; https://link.springer.com/article/10.2119/2007-00119.Tilg, Accepted Jan. 18, 2008. Published Mar. 1, 2008.

Tirosh et al., "Changes in Triglyceride Levels and Risk for Coronary Heart Disease in Young Men," American College of Physicians, pp. 377-385 (Sep. 18, 2007).

Tong H, et al., "Omega-3 fatty acid supplementation appears to attenuate particulate air pollution-induced cardiac effects and lipid changes in healthy middle-aged adults." Eniron. Health Perspect, Jul. 2012, epub Apr. 19, 2012; 120(7):952-7.

Torrejon C, et al., "n-3 Fatty acids and cardiovascular disease: Actions and molecular mechanisms," Prostaglandins Leukotrienes & Essent. Fatty Acids, 77(5-6):319-26 Nov./Dec. 2007/epub Dec. 3, 2007. doi:10.1016/j.plefa.2007.10.014 (2007).

Toth PP, et al., High Triglycerides are associated with increased cardiovascular events, medical costs, and resource use: A real-world administrative claims analysis of statin-treated patients with high residual cardiovascular risk. Journal of the American Heart Association, 7(15):e008740 (publication date Jul. 25, 2018; epublication Aug. 7, 2018).

Transcript from Oct. 16, 2013 Meeting of the Endocrinologic and Metabolic Drugs Advisory Committee, 76 pages.

TREND-HD Investigators, Randomized controlled trial of ethyl-eicosapentaenoic acid in Huntington disease: the TREND-HD study, Arch Neurol., vol. 65(12): 1582-9 (Dec. 2008); https://jamanetwork.com/journals/jamaneurology/fullarticle/1107464, Accepted for Publication: May 9, 2008.

Tribble DL, et al., Enhanced oxidative susceptibility and reduced antioxidant content of metabolic precursors of small, dense low-density lipoproteins. Am. J. Med. Feb. 1, 2001;110(2):103-110.

Tribble DL, et al., Variations in oxidative susceptibility among six low density lipoprotein subfractions of differing density and particle size. Atherosclerosis. Apr. 1992;93(3):189-199; https://www.

(56) References Cited

OTHER PUBLICATIONS sciencedirect.com/science/article/abs/pii/002191509290255F, Accepted Jan. 9, 1992, Available online Apr. 14, 2005.
Trilipix Package Insert (Sep. 2010)(10 pages).
Tsimikas S, et al., High-dose atorvastatin reduces total plasma levels of oxidized phospholipids and immune complexes present on apolipoprotein B-1 00 in patients with acute coronary syndromes in the MIRACL trial. Circulation., Sep. 14, 2004/epub Sep. 7, 2004; 110(11):1406-1412.
Tsuruta K, et al., Effects of purified eicosapentaenoate ethyl ester on fibriolytic capacity in patients with stable coronary artery disease and lower extremity ischaemia, Coron Artery Dis. 7(11):837-42 (Nov. 1996); https://europepmc.org/article/med/8993942, Oct. 31, 1996.
Tulenko TN, et al., Physical effects of cholesterol on arterial smooth muscle membranes: Evidence of immiscible cholesterol domains and alterations in bilayer width C during atherogenesis. J. Lipid Res. May 1998;39:947-956; https://www.jlr.org/content/39/5/947.short.
Tungsiripat et al., "Dyslipidemia in HIV patients," Cleveland Clinic Journal of Medicine, v. 72, No. 12 (Dec. 2005); https://mdedge-files-live.s3.us-east-2.amazonaws.com/files/s3fs-public/issues/articles/content_72_1113.pdf.
Turini et al., Short-term fish oil supplementation improved innate immunity, but increased ex vivo oxidation of LDL in man—a pilot study, Eur. J. Nutr. 40:56-65 (Apr. 2001); https://link.springer.com/article/10.1007%2Fs003940170016, Published Apr. 2001.
U.S. Appl. No. 14/245,499, filed Apr. 4, 2014 (now abandoned) (43 pages).
U.S. District Court of Nevada, judgment dated Mar. 30, 2020 in *Amarin Pharma, Inc. et al.* v. *Hikma Pharmaceuticals USA Inc. et al.*, Case 2:16-cv-02525-MMC-NJK Document 381 Filed Mar. 30, 2020 (70 pages).
U.S. Food and Drug Administration and Dept of Health and Human Services. Substances affirmed as generally recognized as safe: Menhaden Oil. Fed Register, 62:30751-30757 (Jun. 5, 1997).
Ullian ME, "Fatty acid inhibition of angiotensin II-stimulated inositol phosphates in smooth muscle cells." Am J Physiol Heart Circ Physiol., 264 (2 Pt 2):H595-603 (Feb. 1993); https://journals.physiology.org/doi/abs/10.1152/ajpheart.1993.264.2.H595, Published online Feb. 1, 1993. Published in print Feb. 1, 1993.
Urakaze M, et al., "Infusion of emulsified trieicosapentaenoylglycerol into rabbits—The effects on platelet aggregation, polymorphonuclear leukocyte adhesion, and fatty acid composition in plasma and platelet phospholipids", Thromb. Res., 44(5):673-682 (Dec. 1986); https://www.sciencedirect.com/science/article/abs/pii/0049384886901684, Accepted Aug. 11, 1986, Available online Apr. 2, 2004.
Urquhart et al., Profile of eicosanoids produced by human saphenous vein endothelial cells and the effect of dietary fatty acids, Prostaglandins Leukot. Essent. Fatty Acid, 65(1):15-22 (Jul. 2001); https://www.sciencedirect.com/science/article/abs/pii/S0952327801902820, Accepted Jun. 1, 2001, Available online May 25, 2002.
Vaagenes et al., "The Hypolipidaemic Effect of EPA is Potentiated by 2- and 3-Methylation." In P. Quant & S. Eaton (eds.) Current Views of Fatty Acid Oxidation and Ketogenesis from Organelles to Point Mutations; Advances in Experimental Medicine and Biology, vol. 466, pp. 221-226 (1999); book chapter.
Vaddadi KS, et al., "A Randomised, Placebo-Controlled, Double-Blind Study of Treatment of Huntington's Disease with Unsaturated Fatty Acids", Clinical Neuroscience and Neuropathology, 13(1):29-33, (Jan. 2002); https://journals.lww.com/neuroreport/Abstract/2002/01210/A_randomised,_placebo_controlled,_double_blind.11.aspx, Jan. 21, 2002.
Vaduganathan M, et al., Moving toward global primordial prevention in cardiovascular disease: The heart of the matter. J Am Coll Cardiol Oct. 6, 2015;66(14):1535-7.
Van der Steeg WA, et al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (Feb. 12, 2008).
Van Do et al., "Allergy to fish parvalbumins: Studies on the cross-reactivity of allergens from 9 commonly consumed fish," Journ. Allergy & Clin. Immunol., 16(6):1314-1320 (Dec. 1, 2005).
Van Wijk et al., Rosiglitazone improves postprandial triglyceride and free fatty acid metabolism in type 2 diabetes. Diabetes Care, vol. 28, No. 4, (Apr. 2005) pp. 844-849; https://care.diabetesjournals.org/content/28/4/844.short, Accepted Dec. 21, 2004.
Varbo A, et al., Reply to letters regarding article, "Elevated remnant cholesterol causes both low-grade inflammation and ischemic heart disease, whereas elevated low-density lipoprotein cholesterol causes ischemic heart disease without inflammation." Circulation. Jun. 17, 2014; 129(24):e656.
Varbo et al., Remnant Cholesterol as a Causal Risk Factor for Ischemic Heart Disease, J. Am. Coll. Cardiol., vol. 61(4), pp. 427-436 (Jan. 29, 2013/epub Dec. 19, 2012).
Varbo et al., Remnant cholesterol as a cause of ischemic heart disease: Evidence, definition, measurement, atherogenicity, high risk patients, and present and future treatment, Pharmacol. Ther., vol. 141(3), pp. 358-367 (Mar. 2014/epub Nov. 26, 2013).
Vascepa [package insert], Bedminster, NJ: Amarin Pharma Inc.; Jul. 2012. (12 pages).
Vascepa [package insert]. Bedminster, NJ: Amarin Pharma Inc.; Nov. 2013. (11 pages).
Vasudevan et al., "Effective Use of Combination Lipid Therapy", Curr. Atheroscl. Rep., vol. 8, pp. 76-84 (Jan. 2006); https://link.springer.com/article/10.1007%2Fs11883-006-0068-y, Published Jan. 2006.
Vedin I, et al., Effects of docosahexaenoic acid-rich n-3 fatty acid supplementation on cytokine release from blood mononuclear leukocytes: the OmegAD study, Am J Clin Nutr 87:1616-22 (Jun. 2008); https://academic.oup.com/ajcn/article/87/6/1616/4633436, Accepted Jan. 18, 2008, Published Jun. 1, 2008.
Velliquette et al., "Regulation of human stearoyl-CoA desaturase by omega-3 and omega-6 fatty acids: Implications for the dietary management of elevated serum triglycerides," Journal of Clinical Lipdology, (Aug. 2009/epub Jun. 21, 2009) 3:281-288.
Vergnani L, et al., Effect of native and oxidized low-density lipoprotein on endothelial nitric oxide and superoxide production: Key role of 1-arginine availability, Circulation, Mar. 21, 2000; 101:1261-1266.
Verma S, et al., CANTOS ushers in a new calculus of inflammasome targeting for vascular protection—and maybe more. Cell Metab 26(5):703-5 (publication date Nov. 7, 2017; epublication date Oct. 19, 2017).
Vidal F, et al., Atherogenic concentrations of native low density lipoproteins down-regulate nitric-oxide-synthase mma and protein levels in endothelial cells. Eur. J. Biochem. Mar. 15, 1998; 252:378-384.
Vidgren HM, et al., Incorporation of n-3 fatty acids into plasma lipid fractions, and erythrocyte membranes and platelets during dietary supplementation with fish, fish oil, and docosahexaenoic acid-rich oil among healthy young men, Lipids 32: 697-705 (Jul. 1997); https://link.springer.com/article/10.1007/s11745-997-0089-x, Revised Apr. 29, 1996, Accepted Apr. 30, 1997, Published Jul. 1997.
Virani et al., "The Role of Lipoprotein-associated Phospholipase A2 as a marker for atherosclerosis", Curr. Atheroscler. Rep. 9[2]: 97-103 (Aug. 2007); https://link.springer.com/article/10.1007%2Fs11883-007-0004-9, Published Apr. 26, 2007.
Volcik KA, et al., "Peroxisome proliferator-activated receptor αgenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (Jun. 2008); https://academic.oup.com/ajcn/article/87/6/1926/4633499, Accepted Jan. 16, 2008, Published Jun. 1, 2008.
Von Schacky C, "A review of omega-3 ethyl esters for cardiovascular prevention and treatment of increased blood triglyceride levels." Vascular Health and Risk Management 2(3): 251-262 (Sep. 2006); https://www.ncbi.nlm.nih.gov/pmc/articles/PMC1993981/, Published online Sep. 2006.
Von Schacky C, et al., The effect of n-3 fatty acids on coronary atherosclerosis: results from SCIMO, an angiographic study, back-

(56) References Cited

OTHER PUBLICATIONS ground and implications. Lipids 2001 36 Suppl: S99-102; https://link.springer.com/article/10.1007/s11745-001-0689-5, Accepted Nov. 17, 2001, Issue Date Jan. 2001.

Von Schacky, C, et al., "The Effect of Dietary ω-3 Fatty Acids on Cornoray Atherosclerosis: A Randomized, Double-Blind, Placebo-Controlled Trial," American College of Physicians—American Society of Internal Medicine, 130(7):554-562, (Apr. 6, 1999).

Wada M, et al., "Enzymes and receptors of prostaglandin pathways with arachidonic acid-derived versus eicosapentaenoic acid-derived substrates and products." J. Biol. Chem. 282(31): 22254-22266 (Aug. 3, 2007/epub May 22, 2007).

Wagner AH, et al., Improvement of nitric oxide-dependent vasodilation by hmg-coa reductase inhibitors through attenuation of endothelial superoxide anion formation. Arterioscler. Thromb. Vasc. Biol., Jan. 2000;20:61-69; https://www.ahajournals.org/doi/full/10.1161/01.ATV.20.1.61, Originally published Jan. 1, 2000.

Walker G, Mandagere A, Dufton C, et al. The pharmacokinetics and pharmacodynamics of warfarin in combination with ambrisentan in healthy volunteers. Br. J. Clin. Pharmacol. May 2009/epub Feb. 4, 2009; 67 (5): 527-34.

Wall R, et al., Fatty acids from fish: the anti-inflammatory potential of long-chain omega-3 fatty acids. Nutr Rev. May 2010; 68:280-289; https://academic.oup.com/nutritionreviews/article/68/5/280/1829259, Published: May 1, 2010.

Walldius G, et al., "Editorial: Rationale for using apolipoprotein B and apolipoprotein A-I as indicators of cardiac risk and as targets for lipid-lowering therapy." European Heart Journal 26, 210-212 (Feb. 2005/epub Dec. 15, 2004).

Walter MF, et al., Circulating lipid hydroperoxides predict cardiovascular events in patients with stable coronary artery disease: the PREVENT study. J. Am. Coll. Cardiol., Mar. 25, 2008;51(12):1196-1202.

Walter MF, et al., Serum levels of thiobarbituric acid reactive substances predict cardiovascular events in patients with stable coronary artery disease: A longitudinal analysis of the PREVENT study. J. Am. Coll. Cardiol. Nov. 16, 2004; 44(10):1996-2002.

Wander RC, et al., "Influence of long.chain polyunsaturated fatty acids on oxidation of low density lipoprotein." Prostaglandins, Leukotrienes and Essential Fatty Acids 59(2):143-151 (Aug. 1998); https://www.sciencedirect.com/science/article/abs/pii/S095232789890093X, Accepted Jul. 2, 1998, Available online Jun. 18, 2004.

Wang C, et al., "n-3 Fatty acids from fish or fish-oil supplements, but not α-linolenic acid, benefit cardiovascular disease outcomes in primary- and secondary-prevention studies: a systematic review." Am J Clin Nutr 84:5-17 (Jan. 2006); https://academic.oup.com/ajcn/article/84/1/5/4633070, Accepted Jan. 22, 2006, Published Jun. 1, 2006.

Wang L, et al., "Triglyceride-rich lipoprotein lipolysis releases neutral and oxidized FFAs that induce endothelial cell inflammation." J. Lipid Res. 50:204-213 (Feb. 2009/epub Sep. 23, 2008).

Wang Q, Liang X, Wang L, Lu X, Huang J, Cao J, Li H, Gu D. Effect of omega-3 fatty acids supplementation on endothelial function: A meta-analysis of randomized controlled trials. Atherosc. Apr. 2012/epub Jan. 20, 2012; 221:563-543.

Warren, Stephen T, "The Expanding World of Trinucleotide Repeats," Science, 271:1374-1375, (Mar. 8, 1996).

Wassmann S, et al., Cellular antioxidant effects of atorvastatin in vitro and in vivo. Arterioscler. Thromb. Vasc. Biol. Feb. 1, 2002; 22:300-305.

Watanabe et al., "Bile acids lower triglyceride levels via a pathway involving FXR, SHP, and SREBP-1c," J Clin Invest. 113(10):1408-1418 (May 2004); https://www.jci.org/articles/view/21025 Accepted Mar. 23, 2004. First published May 15, 2004.

Watanabe T, et al., A randomized controlled trial of eicosapentaenoic acid in patients with coronary heart disease on statins. J Cardiol 70(6):537-44 (publication date Dec. 2017; epublication date Aug. 31, 2017).

Watanabe, Ikuyoshi, et al., "Usefulness of EPA-E (eicosapentaenoic acid ethyl ester) in preventing neointimal formation after vascular injury," Kokyu to Junkan, 42(7):673-677 (1994) (with English summary).

Weaver, KL, et al., "Effect of Dietary Fatty Acids on Inflammatory Gene Expression in Healthy Humans." J. Biol. Chem., 284(23): 15400-15407 (2009) (published online Apr. 9, 2009).

Webcast Information for the Oct. 16, 2013 Meeting of the Endocrinologic and Metabolic Drugs Advisory Committee, (1 page).

Weber P, Triglyceride-lowering effect of n-3 long chain polyunsaturated fatty acid: eicosapentaenoic acid vs. docosahexaenoic acid, Lipids 34: S269 (1999); https://search.proquest.com/openview/c450f60b01bd53d0c43c78e8a12e39e8/1?pq-origsite=gscholar&cbl=35263, (ProQuest db) Jan. 1999.

Wei et al., Effects of [EPA] Versus [DHA] on Serum Lipids: A Systematic Review and Meta-Analysis, 13 Current Atherosclerosis Rep. 13(6):474-483 (Dec. 2011); https://www.researchgate.net/profile/Melissa_Wei/publication/278649556_EPA_DHA_meta/links/558192c708ae1b14a0a0fc1a/EPA-DHA-meta.pdf, Published online Oct. 6, 2011.

Wei LJ, et al., Regression analysis of multivariate incomplete failure time data by modeling marginal distributions. J Am Stat Assoc. 84(408):1065-1073 (publication date Dec. 1989); https://amstat.tandfonline.com/doi/abs/10.1080/01621459.1989.10478873, Published online: Mar. 12, 2012.

Westerveld HT, et al., "Effects of low-dose EPA-Eon glycemic control, lipid profile, lipoprotein(a), platelet aggretation, viscosity, and platelet and vessel wall interaction in NIDDM" Diabetes Care 16(5):683-8 (May 1993); https://care.diabetesjournals.org/content/16/5/683.short.

Westphal S, et al., "Postprandial chylomicrons and VLDLs in severe hypertriacylglycerolemia are lowered more effectively than are chylomicron remnants after treatment with n23 fatty acids." Am J Clin Nutr 71:914-20 (Apr. 2000); https://academic.oup.com/ajcn/article/71/4/914/4729124, Accepted Sep. 14, 1999, Published Apr. 1, 2000.

Whelan J, et al., "Evidence that dietary arachidonic acid increases circulating triglycerides." Lipids 30, 425-429 (May 1995); https://link.springer.com/article/10.1007/BF02536300, Revised Mar. 15, 1995, Accepted Mar. 15, 1995, Issue Date May 1995.

Wierzbicki, AS, "Editorial: Newer, lower, better? Lipid drugs and cardiovascular disease—the continuing story." Int J Clin Pract, 61(7):1064-1067 (Jul. 2007); https://onlinelibrary.wiley.com/doi/abs/10.1111/j.1742-1241.2007.01375.x, First published:Jun. 15, 2007.

Wierzbicki, AS, "Editorial: Raising HDL-C: back to the future?" Int J Clin Pract, 61(7): 1069-1071 (Jul. 2007); https://onlinelibrary.wiley.com/doi/abs/10.1111/j.1742-1241.2007.01412.x, First published:Jun. 15, 2007.

Wikipedia, "Diabetes mellitus," Dec. 12, 2016 (Dec. 12, 2016), retrieved on Jul. 30, 2018 from https://en.wikipedia.org/w/index.php?title=Diabetes_mellitus&oldid=754431573; entire document, especially p. 1, paragraph 1.

Wikipedia, "Ethyl eicosapentaenoic acid," Apr. 1, 2016 (Apr. 1, 2016); retrieved on Jul. 27, 2018 from https://en.wikipedia.org/w/index.php?title=Ehtyl_eicosapentaenoic_acid&oldid=713086755; entire document, especially p. 1, col. 2 and p. 3, paragraph 2.

Williams et al., "NADPH Oxidase Inhibitors New Antihypertensive Agents?" J. Cardiovasc Pharmacol 50(1):9-16 (Jul. 1, 2007).

Willumsen N, et al., "On the effect of 2-deuterium- and 2-methyl-eicosapentaenoic acid derivatives on triglycerides, peroxisomal beta-oxidation and platelet aggregation in rats," Biochimica et Biophysica Acta, vol. 1369,pp. 193-203, (Mar. 2, 1998); https://aocs.onlinelibrary.wiley.com/doi/abs/10.1007/BF02523828, First published: Jun. 1, 1996.

Willumsen, N., et al., "Eicosapentaenoic acid, but not docosahexaenoic acid, increased, mitochondrial fatty acid oxidation and upregulates 2,3-dienoyl-CoA reductase gene expression in rats." Lipids, 31:579-592 (Jun. 1996).

Wilson Omega 3 fish oil: EPA versus DHA (Dietivity.com, 1-16) (2006).

(56) References Cited

OTHER PUBLICATIONS

Wilt VM, Gumm, JG, "Isolated low high-density lipoprotein cholesterol", Ann. Pharmacol., 31:89-97, (Jan. 1997); https://journals.sagepub.com/doi/abs/10.1177/106002809703100115, First Published Jan. 1, 1997.
Wink J, et al., Effect of very-low-dose niacin on high-density lipoprotein in patients undergoing long-term statin therapy, Am. Heart J., 143:514-518, (Mar. 2002); https://www.sciencedirect.com/science/article/abs/pii/S0002870302935040, Accepted Sep. 7, 2001, Available online May 25, 2002.
Wittrup HH, et al., Lipoprotein lipase mutations, plasma lipids and lipoproteins, and risk of ischemic heart disease: a meta-analysis. Circulation, Jun. 8, 1999; 99:2901-2907.
Witztum JL, The oxidation hypothesis of atherosclerosis. Lancet, Sep. 17, 1994;344(8925):793-795.
Wojczynski et al., "High-fat meal effect on LDL, HDL and VLDL particle size and number in the Genetics of Lipid-Lowering Drugs and Diet Network (GOLDN): an interventional study," Lipids in Health and Disease 10:181, pp. 1-11 (Oct. 18, 2011).
Wojenski CM, et al., "Eicosapentaenoic acid ethyl ester as an antithrombotic agent: comparison to an extract of fish oil." Biochimica et Biophysica Acta. 1081:33-38 (Jan. 4, 1991).
Wong SH, et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (Nov./Dec. 1989); https://www.ahajournals.org/doi/abs/10.1161/01.ATV.9.6.836, Originally publishedNov. 1, 1989.
Wood et al., "Carbohydrate Restriction Alters Lipoprotein Metabolism by Modifying VLDL, LDL and HDL Subraction Distribution and Size in Overweight Men," Journ. of Nutrition, 136(2):384-9 (Feb. 2006); https://academic.oup.com/jn/article/136/2/384/4664306, Revision received: Oct. 26, 2005, Accepted: Nov. 1, 2005. Published: Feb. 1, 2006.
Woodman et al., Effects of Purified Eicosapentaenoic and Docosahexaenoic Acids on Glycemic Control, Blood Pressure, and Serum Lipids in Type 2 Diabetic Patients with Treated Hypertension, The American Journal of Clinical Nutrition: Official Journal of the American Society for Clinical Nutrition, Inc., 76(5):1007-1015 (Nov. 1, 2002).
Woodman, RJ, et al., "Effects of purified eicosapentaenoic acid and docosahexaenoic acid on platelet, fibrinolytic and vascular function in hypertensive type 2 diabetic patients." Atherosclerosis 166: 85-93 (Jan. 2003); https://www.sciencedirect.com/science/article/abs/pii/S0021915002003076, Revised Jul. 8, 2002, Accepted Jul. 17, 2002, Available online Oct. 4, 2002.
Wu et al., "Diabetic dyslipidemia," Metabolism Clinical and Experimental, 63:1469-1479 (Dec. 2014)(available online Aug. 29, 2014); https://www.nature.com/articles/1602328, Revised Aug. 16, 2005, Accepted Sep. 14, 2005, Published Nov. 9, 2005, Issue Date Mar. 1, 2006.
Wu WH, et al., "Effects of docosahexaenoic acid supplementation on blood lipids, estrogen metabolism, and in vivo oxidative stress in postmenopausal vegetarian women." Eur J Clin Nutr., 60:386-392 (Mar. 2006).
Xiao, YF, et al., "Blocking effects of polyunsaturated fatty acids on Na+ channels of neonatal rat ventricular myocytes." Proc. Natl. Acad. Sci. 92: 11000-11004 (Nov. 21, 1995).
Xiao, YF, et al., "Fatty acids suppress voltage-gated Na+ currents in HEK293t cells transfected with the a-subunit of the human cardiac Na+ channel." Proc. Natl. Acad. Sci. 95: 2680-2685 (Mar. 3, 1998).
Xiao, YF, et al., "Inhibitory effect of n-3 fish oil fatty acids on cardiac Na+/Ca2+ exchange currents in HEK293t cells." Biochemical and Biophysical Research Communications 321: 116-123 (Aug. 13, 2004).
Xydakis AM, et al., "Combination therapy for combined dyslipidemia," American Journal of Cardiology, 20021120 US, vol. 90, No. 10 Suppl. 2, p. 21 K-29K (Nov. 20, 2002).
Yacyshyn BR, Thomson AB. The clinical importance of proton pump inhibitor pharmacokinetics. Digestion 2002 66 (2): 67-78; https://www.karger.com/Article/Abstract/65588.
Yadav D, et al., Issues in Hyperlipidemic Pancreatitis. J Clin Gastroenterol 236(1):54-62, Jan. 2003; https://journals.lww.com/jcge/Fulltext/2003/01000/Issues_in_Hyperlipidemic_Pancreatitis.16.aspx.
Yagi K, Assay for blood plasma or serum, Methods Enzymol 1984;105:328-331; https://www.sciencedirect.com/science/article/pii/S0076687984050424, Available online Jan. 7, 2004.
Yamagishi K, et al., Plasma fatty acid composition and incident heart failure in middle-aged adults: The Atherosclerosis Risk in Communities (ARIC) Study. Am Heart J., Nov. 2008/epub Aug. 29, 2008; 156:965-974.
Yamakawa K, et al., Eicosapentaenoic Acid Supplementation Changes Fatty Acid Composition and Corrects Endothelial Dysfunction in Hyperlipidemic Patients. Cardiol Res Practice. Dec. 26, 2012; epub Article ID 754181.
Yamamoto H, et al., Improvement of coronary vasomotion with Eicosapentaenoic acid does not inhibit acetylcholine-induced coronary vasospasm in patients with variant angina: Jpn Cir J. 59(9):608-16 (Sep. 1995); https://www.jstage.jst.go.jp/article/circj1960/59/9/59_9_608/_article/-char/ja/.
Yamamoto K, et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (Mar. 14, 2008/epub Jan. 10, 2008).
Yamano T, et al. Impact of eicosapentaenoic acid treatment on the fibrous cap thickness in patients with coronary atherosclerotic plaque: an optical coherence tomography study. J Atheroscler Thromb. 2015/epub Aug. 15, 2014;22:52-61.
Yamashita et al., J. Biochem., vol. 122, No. 1, "Acyl-transferases and Transaclyases Involved in Fatty Acid Remodeling of Phospholipids and Metabolism of Bioactive Lipids in Mammalian Cells," pp. 1-16 (Jul. 1997); https://academic.oup.com/jb/article/122/1/1/764052, Received Apr. 1, 1997, Published Jul. 1, 1997.
Yamashita N, et al., "Inhibition of natural killer cell activity of human lymphocytes by eicosapentaenoic acid." Biochem. Biophys. Res. Comm. 138(3): 1058-1067 (Aug. 25, 1986).
Yamazaki et al., "Changes in fatty acid composition in rat blood and organs after infusion of eicosapentaenoic acid ethyl ester," Biochim. Biophys. ACTA, 1128(1):35-43, (Sep. 22, 1992).
Yamazaki et al., "Dissolution tests by RDC method for soft gelatin capsules containing ethyl icosapentate," Pharm. Tech. Japan, vol. 15, No. 4, pp. 595-603 Abstract (Apr. 1999) (with English abstract).
Yang SP, et al., "Eicosapentaenoic acid attenuates vascular endothelial growth factor-induced proliferation via inhibiting Flk-1 receptor expression in bovine carotid artery endothelial cells." J. Cell. Physio. 176:342-349 (Aug. 1998); https://onlinelibrary.wiley.com/doi/abs/10.1002/(SICI)1097-4652(199808)176:2%3C342::AID-JCP12%3E3.0.CO;2-5, First published Dec. 6, 1998.
Yano T, et al., "Effects of ethyl-all-cis-5,8,11,14,17-icosapentaenoate (EPA-E), pravastatin and their combination on serum lipids and intimal thickening of cuff-sheathed carotid artery in rabbits", Life Sciences, 61(20):2007-2015 (Oct. 10, 1997); https://www.sciencedirect.com/science/article/abs/pii/S002432059700859X, Revised Aug. 11, 1997, Available online Jan. 21, 1998.
Yano T, et al., Effects of ethyl all-cis-5,8,11,14,17-icosapentaenoate on low density lipoprotein in rabbits, Yakugaku Zasshi, 115:843-51 (Oct. 1995); https://europepmc.org/article/med/8531063, Sep. 30, 1995.
Yao et al., "Oxidized high density lipoprotein induces macrophage apoptosis via toll-like receptor 4-dependent CHOIP pathway," Journ. Lipid Res., 58:164-177 (Jan. 2017) (First published Nov. 28, 2016).
Yates RA, et al., The effect of anastrozole on the single-dose pharmacokinetics and anticoagulant activity of warfarin in healthy volunteers. Br. J. Clin. Pharmacol. May 2001 51(5): 429-35; https://bpspubs.onlinelibrary.wiley.com/doi/full/10.1046/j.1365-2125.2001.01358.x, accepted Dec. 18, 2000, Issue Online:Jan. 12, 2002.
Yerram NR, et al., "Eicosapentaenoic acid metabolism in brain microvessel endothelium: effect on prostaglandin formation." J. Lipid Res.30:1747-1757 (Nov. 1989); https://www.jlr.org/content/30/11/1747.short.
Yokoyama et al., "Effects of eicosapentaenoic acid on cardiovascular events in Japanese patients with hypercholeterolemia: Ratio-

(56) References Cited

OTHER PUBLICATIONS nale, design, and baseline characteristics of the Japan EPA Lipid Intervention Study (JELIS)," Amer. Heart Journal 146(4):613-620 (Oct. 2003); https://www.sciencedirect.com/science/article/abs/pii/S0002870303003673, Accepted Mar. 11, 2003, Available online Oct. 8, 2003.

Yokoyama et al., "Effects of eicosapentaenoic acid on major coronary events in hypercholesterolaemic patients (JELIS): a randomized open-label, blinded endpoint analysis," Lancet, vol. 369, pp. 1090-1098 (Mar. 31, 2007).

Yorioka N, "Lipid-lowering therapy and coagulation/fibrinolysis parameters in patients on peritoneal dialysis," The International Journal of Artificial Organs, vol. 23(1):27-32 (Jan. 2000); https://journals.sagepub.com/doi/abs/10.1177/039139880002300105, Issue published Jan. 1, 2000.

Yoshimura et al., "Effects of highly purified eicosapentaenoic acid on plasma beta thromboglobulin level and vascular reactivity to angiotensin II," Artery, 14(5):295-303 (1987); https://pubmed.ncbi.nlm.nih.gov/2821970/.

Zaima N., et al., "Trans geometric isomers of EPA decrease LXRα-induced cellular triacylglycerol via suppression of SREBP-1c and PGC-1β," J. Lipid Res. 47: 2712-2717 (Dec. 2006); https://www.jlr.org/content/47/12/2712.short, First Published on Sep. 27, 2006.

Zalewski et al., Role of Lipoprotein-Associated Phospholipase A2 in Atherosclerosis: Biology, Epidemiology, and Possible Therapeutic Target, Arteriosclerosis, Thrombosis, & Vascular Biology 25(5):923-931 (May 2005/epub Feb. 24, 2005).

Zanarini et al., "Omega-3 Fatty Acid Treatment of Women with Borderline Personality Disorder: A Double-Blind, Placebo-Controlled Pilot Study," Am J Psychiatry, 160:167-169 (Jan. 2003); https://ajp.psychiatryonline.org/doi/full/10.1176/appi.ajp.160.1.167, Published Online Jan. 1, 2003.

Zhan S, et al. "Meta-analysis of the effects of soy protein containing isoflavones on the lipid profile," Am. J. Clin. Nutr. (Feb. 2005), 81, p. 397-408; https://academic.oup.com/ajcn/article/81/2/397/4607461 Accepted: Oct. 4, 2004. Published: Feb. 1, 2005.

Zhang M, et al., "Effects of eicosapentaenoic acid on the early stage of type 2 diabetic nephropathy in KKAy/Ta mice: involvement of anti-inflammation and antioxidative stress." Metabolism Clinical and Experimental 55:1590-1598 (Dec. 2006); https://www.sciencedirect.com/science/article/abs/pii/S002604950600268X, Accepted Jul. 20, 2006, Available online Dec. 2, 2006.

Zhang YW, et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential FattyAcids 67(4):253-261 (Oct. 2002); https://www.sciencedirect.com/science/article/abs/pii/S0952327802904278, Accepted Jun. 11, 2002, Available online Oct. 20, 2002.

Zhang YW, et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (Jul. 1999); https://www.sciencedirect.com/science/article/abs/pii/S0952327899900704, Accepted Apr. 13, 1999, Available online May 25, 2002.

Zhao et al., "Polyunsaturated Fatty Acids are FXR Ligands and Differentially Regulate Expression of FXR Targets," DNA and Cell Biology, 23(8):519-526 (Aug. 25, 2004).

Zhao G, et al., "Dietary α-linolenic acid inhibits proinflammatory cytokine production by peripheral blood mononuclear cells in hypercholesterolemic subjects." Am J Clin Nutr 85:385-91 (Feb. 2007); https://academic.oup.com/ajcn/article/85/2/385/4649479, Accepted Sep. 11, 2006, Published Feb. 1, 2007.

Zhao G, et al., "Dietary α-linolenic acid reduces inflammatory and lipid cardiovascular risk factors in hypercholesterolemic men and women." J. Nutr. 134: 2991-2997 (Nov. 2004); https://academic.oup.com/jn/article/134/11/2991/4688439, Revision received Jun. 28, 2004, Accepted Aug. 9, 2004, Published Nov. 1, 2004.

Zheng et al., "Function of ω-3 long chain unsaturated fatty acid in metabolic syndrome," Chinese Journal of Endocrinology and Metabolism, vol. 27, No. 9, pp. 787-790 (Sep. 30, 2011)(with English translation).

Ziegler D, et al., "Treatment of symptomatic diabetic polyneuropathy with the antioxidant α-lipoic acid: A 7-month multicenter randomized controlled trial (ALADIN III Study)." Diabetes Care 22:1296-1301 (Aug. 1999); https://care.diabetesjournals.org/content/22/8/1296.short.

Zimmer et al., "Danger signaling in Atherosclerosis," Circulation Research, Jan. 16, 2015, vol. 116, pp. 323-340.

Zimmerman JJ, et al., Evaluation of a potential tigecycline-warfarin drug interaction. Pharmacotherapy Jul. 28, 2008 (7): 895-905; https://accpjournals.onlinelibrary.wiley.com/doi/abs/10.1592/phco.28.7.895, Manuscript received Aug. 2, 2007. Accepted for publication in final form Jan. 23, 2008, Issue online: Jan. 6, 2012.

Zuijdgeest-van Leeuwen et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, pp. 89-100 (2000).

Zuijdgeest-van Leeuwen, SD, et al., "Eicosapentaenoic acid inhibits lipolysis in weight-losing cancer patients as well as in healthy volunteers," Eur J Gastroenterol & Hepatol., 10(12):A67 (1998); https://journals.lww.com/eurojgh/Citation/1998/12000/Eicosapentaenoic_acid_inhibits_lipolysis_in.217.aspx, Dec. 1998.

Zuijdgeest-van Leeuwen, SD, et al., Incorporation and washout of orally administered n-3 fatty acid ethyl esters in different plasma lipid fractions, British Journal of Nutrition 82:481-488 (1999); https://www.cambridge.org/core/journals/british-journal-of-nutrition/article/incorporation-and-washout-of-orally-administered-n3-fatty-acid-ethyl-esters-in-different-plasma-lipid-fractions/0385A1191F944083C729D7F158CDFA6D, Dec. 1999, Published online by Cambridge University Press Mar. 9, 2007.

Zvyaga T, et al., Evaluation of six proton pump inhibitors as inhibitors of various human cytochromes P450: focus on cytochrome P450 2C19. Drug Metab. Dispos. Sep. 2012 40(9): 1698-711; http://dmd.aspetjournals.org/content/40/9/1698.short, Sep. 2012.

Akil et al., Relationships between obesity and cardiovascular diseases in four souther states and colorado, J Health Care Poor Underserved, 2011, 22(4 Suppl): 61-72.

At-a-Glance: Coronary Heart Disease; National Heart, Lung and Blood Institute, NIH Publication, Aug. 2009.

Ballantyne et al., Icosapent ethyl (eicosapentaenoic acid ethyl ester): effects on remnant-like particle cholesterol from the marine and anchor studies; Atherosclerosis, Aug. 20, 2016, pp. 81-87.

Brinton et al., Prescription omega-3 fatty acid products containing highly purified eicosapentaenoic acid (epa); Lipids in Health and Disease, 2017, 16:23, DOI 10.1186/x12944-017-0415-8.

Calo et al., N-3 fatty acids for the prevention of atrial fibrillation after coronary artery bypass surgery, J. Amer. Coll. Cardiology, May 17, 2005, vol. 45, No. 10; pp. 1723-1728.

Claudel et al., The Farnesoid x receptor, a molecular link between bile acid and lipid and glucose metabolism; Arterioscler Thromb Vasc Biol; Oct. 1, 2005; 25:2020-2031.

Colihan, Statins lower blood pressure; WebMD, Apr. 11, 2008.

Deuster et al., Dietary Supplements and Military Divers, A synopsis for Undersea Medical Officers, Jan. 2004.

Förstermann et al., "Roles of Vascular Oxidative Stress and Nitric Oxide in the Pathogenesis of Atherosclerosis," Circ. Res. Feb. 17, 2017; 120(4):713-735 (Accepted Dec. 26, 2016).

Guise, Bone loss and fracture risk associated with cancer therapy, The Oncologist, 2006; 11:1121-1131, available online at www.theoncologist.com.

Lawrence MJ, Polyoxyethylene Sorbitan Fatty Acid Esters, Handbook of Pharmaceutical Excipients Fifth Edition by Rowe et al., 2006, Pharmaceutical Press, London/Chicago, XP002765740, ISBN: 0853696187, pp. 580-584 (table VIII).

Li et al., Lipid profile and incidence of atrial fibrillaiton: a prospective cohort study in China; Wiley Clinical Cardiology, Mar. 2018, vol. 41, No. 3, pp. 314-320.

Li, Q, et al., Eicosapentaenoic acid modifies lipid composition in caveolae and induces translocation of endothelial nitric oxide synthase, Biochimie 89 (2007) pp. 169-177 (publ online Nov. 7, 2006).

(56) References Cited

OTHER PUBLICATIONS

Lins et al., "Pharmacokinetics of Atorvastatin and its Metabolites After Single and Multiple Dosing in Hypercholesterolaemic Haemodialysis Patients," Nephrol. Dial. Transplant., May 2003; 18(5):967-76 (Received for publication Apr. 2, 2002; Accepted in Revised Form May 12, 2002).

Luo et al., The emerging role of apolipoprotein C-III: beyond effects on triglyceride metabolism; Lipids in Health and Disease, 2016, 15:184, 7 pages.

National Kidney Foundation, Clinical Practice Guidelines for Chronic Kidney Disease: Evaluation, Classification and Stratification; Copyright 2002, 356 pages.

NCBI, Table 6-1 "Factors for Converting International Units of Vitamin $E^a$ to α-Tocopherol$^b$ (mg) to Meet Recommended Intake," taken from Dietary Reference Intakes for Vitamin C, Vitamin E, Selenium and Carotenoids, Institute of Medicine (US) Panel on Dietary Antioxidants and Related Compounds, Washington DC, National Academies Press (US) 2000.

Toyoda, Pharmacotherapy for the Secondary Prevention of Stroke, Drugs, 69(6) pp. 633-647 (2009).

Vega et al., Hypercholesterolemia with Cholesterol-Enriched LDL and Normal Levels of LDL-Apolipoprotein B; Arteriosclerosis, Thrombosis and Vascular Biology, Apr. 1996; 16(4):517-22 (Accepted Jan. 3, 1996).

Bays H.E. et al., Comparison of once-daily, niacin extended-release/lovastatin with standard dosdes of atorvastatin and simvastatin (the advisor versus other cholesterol-modulating agents trial evaluation [Advocate], Am J. Cardiol, Mar. 15, 2003, vol. 91, pp. 667-672.

Fontela et al., Estimated glomerular filtration rate in patients with type 2 diabetes mellitus; Rev Assoc Med Bras 2014; 60(6):531-537.

Hong, Coronary artery calcification and risk factors for atherosclerosis in patients with venous thromboembolism, Atherosclerosis, 2005, vol. 183, pp. 169-174.

Pocock et al., A Score for predicting risk of death from cardiovascular disease in adults with raised blood pressure, based on individual patent data from randomised controlled trials, British Medical Journal, Jul. 14, 2001, vol. 3223, pp. 75-81.

The Lipid, 2003, vol. 14, No. 1, pp. 68-75, in Japanese.

Triglyceride vs. Ethyl Ester Forms of Fish Oil Omega-3s, ScienceBased Health, Apr. 18, 2012; URL:https://web.archive.org/web/20120420022941/https://www.sciencebasedhealth.com/Fish-Oil-EE-vs-TGomega-3s-which-is-better-W119.aspx.

* cited by examiner

COMPOSITIONS AND METHODS FOR LOWERING TRIGLYCERIDES

CROSS-REFERENCE TO RELATED APPLICATIONS

This application is a continuation of U.S. patent application Ser. No. 16/795,761 filed Feb. 20, 2020, which is a continuation of U.S. patent application Ser. No. 16/364,720 filed Mar. 26, 2019 (now U.S. Pat. No. 10,842,768), which is a continuation of U.S. patent application Ser. No. 16/273,875 filed on Feb. 12, 2019, which is a continuation of U.S. patent application Ser. No. 15/182,695 filed on Jun. 15, 2016, which is a continuation of U.S. patent application Ser. No. 15/095,860 filed on Apr. 11, 2016, which is a continuation of U.S. patent application Ser. No. 13/404,686 filed on Feb. 24, 2012, which is a continuation of U.S. patent application Ser. No. 12/815,569 filed on Jun. 15, 2010 (now U.S. Pat. No. 8,455,472), which claims priority from U.S. Provisional Patent Application No. 61/187,132, filed Jun. 15, 2009, the entirety of each which is incorporated herein by reference.

BACKGROUND

Cardiovascular disease is one of the leading causes of death in the United States and most European countries. It is estimated that over 70 million people in the United States alone suffer from a cardiovascular disease or disorder including but not limited to high blood pressure, coronary heart disease, dislipidemia, congestive heart failure and stroke.

SUMMARY

In various embodiments, the present invention provides pharmaceutical compositions and methods of using such compositions to treat and/or prevent cardiovascular-related diseases. In one embodiment, the subject is on concomitant statin therapy. In another embodiment, the subject on statin therapy has a baseline fasting serum triglyceride level of about 200 mg/dL to about 500 mg/dL.

In one embodiment, the invention provides a method of lowering triglycerides in a subject on stable statin therapy having baseline fasting triglycerides of about 200 mg/dl to about 500 mg/dl, the method comprising administering to the subject a pharmaceutical composition comprising polyunsaturated fatty acids, for example about 1 g to about 4 g of EPA per day, wherein upon administering the composition to the subject daily for a period of 12 weeks the subject exhibits at least 5% lower fasting triglycerides than a control subject maintained on stable statin therapy (optionally with placebo matching the EPA) without concomitant EPA for a period of 12 weeks wherein the control subject also has baseline fasting triglycerides of about 200 mg/dl to about 500 mg/dl. In another embodiment, upon administering the composition to the subject daily for a period of 12 weeks the subject exhibits no serum LDL-C increase, no statistically significant serum LDL-C increase, a serum LDL-C decrease, or the subject is statistically non-inferior to the control subjects (statin plus optional placebo) in regard to serum LDL-C elevation).

These and other embodiments of the present invention will be disclosed in further detail herein below.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

In one embodiment, the invention provides a method for treatment and/or prevention of cardiovascular-related diseases. The term "cardiovascular-related disease" herein refers to any disease or disorder of the heart or blood vessels (i.e. arteries and veins) or any symptom thereof. Non-limiting examples of cardiovascular-related disease and disorders include hypertriglyceridemia, hypercholesterolemia, mixed dyslipidemia, coronary heart disease, vascular disease, stroke, atherosclerosis, arrhythmia, hypertension, myocardial infarction, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, the present invention provides a method of blood lipid therapy comprising administering to a subject or subject group in need thereof a pharmaceutical composition as described herein. In another embodiment, the subject or subject group has hypertriglyceridemia, hypercholesterolemia, mixed dyslipidemia and/or very high triglycerides.

In another embodiment, the subject or subject group being treated has a baseline triglyceride level (or mean or median baseline triglyceride level in the case of a subject group), fed or fasting, of about 200 mg/dl to about 500 mg/dl. In another embodiment, the subject or subject group has a baseline LDL-C level (or mean or median baseline LDL-C level), despite stable statin therapy, of about 40 mg/dl to about 115 or about 40 to about 100 mg/dl.

In one embodiment, the subject or subject group being treated in accordance with methods of the invention is on concomitant statin therapy, for example atorvastatin, rosuvastatin or simvastatin therapy (with or without ezetimibe). In another embodiment, the subject is on concomitant stable statin therapy at time of initiation of ultra-pure EPA therapy.

In another embodiment, the subject or subject group being treated in accordance with methods of the invention has a body mass index (BMI or mean BMI) of not more than about 45 kg/m$^2$.

In one embodiment, the invention provides a method of lowering triglycerides in a subject on stable statin therapy having baseline fasting triglycerides of about 200 mg/dl to about 500 mg/dl, the method comprising administering to the subject a pharmaceutical composition comprising about 1 g to about 4 g of EPA (e.g. ultra-pure EPA), wherein upon administering the composition to the subject daily for a period of about 12 weeks the subject exhibits at least 10%, at least 15%, at least 20%, at least 25%, at least 30%, at least 35%, at least 40%, at least 45%, at least 50%, at least 55%, at least 60%, at least 65%, at least 70%, or at least 75% lower fasting triglycerides than a control subject maintained on stable statin therapy (and optionally placebo matching the ultra-pure EPA) without concomitant ultra-pure EPA for a period of about 12 weeks, wherein the control subject also has baseline fasting triglycerides of about 200 mg/dl to about 500 mg/dl. The term "stable statin therapy" herein means that the subject, subject group, control subject or control subject group in question has been taking a stable daily dose of a statin (e.g. atorvastatin, rosuvastatin or simvastatin) for at least 4 weeks prior to the baseline fasting triglyceride measurement (the "qualifying period"). For example, a subject or control subject on stable statin therapy would receive a constant daily (i.e. the same dose each day) statin dose for at least 4 weeks immediately prior to baseline fasting triglyceride measurement. In one embodiment, the subject's and control subject's LDL-C is maintained between about 40 mg/dl and about 115 mg/dl or about 40 mg/dl to about 100 mg/dl during the qualifying period. The subject and control subject are then continued on their stable statin dose for the 12 week period post baseline.

In one embodiment, the statin is administered to the subject and the control subject in an amount of about 1 mg to about 500 mg, about 5 mg to about 200 mg, or about 10 mg to about 100 mg, for example about 1 mg, about 2 mg, about 3 mg, about 4 mg, about 5 mg, about 6 mg, about 7 mg, about 8 mg, about 9 mg, or about 10 mg; about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In another embodiment, the subject (and optionally the control subject) has a baseline LDL-C level, despite stable statin therapy, of about 40 mg/dl to about 115 mg/dl or about 40 mg/dl to about 100 mg/dl. In another embodiment, the subject and/or control subject has a body mass index (BMI; or mean BMI) of not more than about 45 kg/m$^2$.

In another embodiment, the invention provides a method of lowering triglycerides in a subject group on stable statin therapy having mean baseline fasting triglycerides of about 200 mg/dl to about 500 mg/dl, the method comprising administering to members of the subject group a pharmaceutical composition comprising about 1 g to about 4 g of ultra-pure EPA per day, wherein upon administering the composition to the members of the subject group daily for a period of about 12 weeks the subject group exhibits at least 10%, at least 15%, at least 20%, at least 25%, at least 30%, at least 35%, at least 40%, at least 45%, at least 50%, at least 55%, at least 60%, at least 65%, at least 70%, at least 75% lower mean fasting triglycerides than a control subject group maintained on stable statin therapy without concomitant ultra-pure EPA (optionally with matching placebo) for a period of about 12 weeks, wherein the control subject group also has mean baseline fasting triglycerides of about 200 mg/dl to about 500 mg/dl. In a related embodiment, the stable statin therapy will be sufficient such that the subject group has a mean LDL-C level about at least about 40 mg/dl and not more than about 100 mg/dl or about 40 mg/dl to about 100 mg/dl for the 4 weeks immediately prior to the baseline fasting triglyceride measurement.

In another embodiment, the invention provides a method of lowering triglycerides in subject group on stable statin therapy and having a mean baseline fasting triglyceride level of about 200 mg/dl to about 500 mg/dl, the method comprising administering to members of the subject group a pharmaceutical composition comprising about 1 g to about 4 g of ultra-pure EPA, wherein upon administering the composition to members of the subject group daily for a period of about 12 weeks the subject group exhibits: (a) at least 10%, at least 15%, at least 20%, at least 25%, at least 30%, at least 35%, at least 40%, at least 45%, at least 50%, at least 55%, at least 60%, at least 65%, at least 70%, at least 75% lower mean fasting triglycerides by comparison with a control subject group maintained on stable statin therapy without concomitant ultra-pure EPA (optionally with matching placebo) for a period of about 12 weeks, and (b) no serum LDL-C increase, no statistically significant serum LDL-C increase, a serum LDL-C decrease, or the subject is statistically non-inferior to the control subjects (statin plus optional placebo) in regard to serum LDL-C elevation) no increase in mean serum LDL-C levels compared to baseline, wherein the control subject also has mean baseline fasting triglycerides of about 200 mg/dl to about 500 mg/dl.

In another embodiment, the invention provides a method of lowering triglycerides in subject on stable statin therapy and having mean baseline fasting triglyceride level of about 200 mg/dl to about 500 mg/dl, the method comprising administering to the subject a pharmaceutical composition comprising about 1 g to about 4 g of ultra-pure EPA, wherein upon administering the composition to the subject daily for a period of about 12 weeks the subject exhibits (a) at least 10%, at least 15%, at least 20%, at least 25%, at least 30%, at least 35%, at least 40%, at least 45%, at least 50%, at least 55%, at least 60%, at least 65%, at least 70%, or at least 75% lower fasting triglycerides by comparison with a control subject maintained on stable statin therapy without concomitant ultra-pure EPA for a period of about 12 weeks and (b) no increase in serum LDL-C levels compared to baseline, wherein the control subject also has baseline fasting triglycerides of about 200 mg/dl to about 500 mg/dl.

In another embodiment, the invention provides a method of lowering triglycerides in subject group on stable statin therapy and having mean baseline fasting triglyceride level of about 200 mg/dl to about 500 mg/dl, the method comprising administering to members of the subject group a pharmaceutical composition comprising about 1 g to about 4 g of ultra-pure EPA, wherein upon administering the composition to the members of the subject group daily for a period of about 12 weeks the subject group exhibits: (a) at least 10%, at least 15%, at least 20%, at least 25%, at least 30%, at least 35%, at least 40%, at least 45%, at least 50%, at least 55%, at least 60%, at least 65%, at least 70%, at least 75% lower mean fasting triglycerides and (b) at least 5%, at least 10%, at least 15%, at least 20%, at least 25%, at least 30%, at least 35%, at least 40%, at least 45% or at least 50% lower mean serum LDL-C levels by comparison with a control subject group maintained on stable statin therapy without concomitant ultra-pure EPA (optionally with matching placebo) for a period of about 12 weeks, no serum LDL-C increase, no statistically significant serum LDL-C increase, no statistically significant serum LDL-C increase, a serum LDL-C decrease, or the subject group is statistically non-inferior to the control subject group (statin plus optional placebo) in regard to serum LDL-C elevation), wherein the control subject group also has mean baseline fasting triglycerides of about 200 mg/dl to about 500 mg/dl.

In another embodiment, the invention provides a method of lowering triglycerides in subject group on stable statin therapy and having mean baseline fasting triglyceride level of about 200 mg/dl to about 500 mg/dl, the method comprising administering to members of the subject group a pharmaceutical composition comprising about 1 g to about 4 g of ultra-pure EPA, wherein upon administering the composition to the members of the subject group daily for a period of about 12 weeks the subject group exhibits (a) at least 10%, at least 15%, at least 20%, at least 25%, at least 30%, at least 35%, at least 40%, at least 45%, at least 50%, at least 55%, at least 60%, at least 65%, at least 70%, at least 75% lower mean fasting triglycerides and (b) at least 5%, at least 10%, at least 15%, at least 20%, at least 25%, at least 30%, at least 35%, at least 40%, at least 45% or at least 50% lower mean serum LDL-C levels by comparison with a control subject group maintained on stable statin therapy without concomitant ultra-pure EPA (optionally with matching placebo) for a period of about 12 weeks, no serum LDL-C increase, no statistically significant serum LDL-C increase, no statistically significant serum LDL-C increase, a serum LDL-C decrease, or the subject group is statistically non-inferior to the control subject group (statin plus optional placebo) in regard to serum LDL-C elevation), wherein the control subject group also has mean baseline fasting triglycerides of about 200 mg/dl to about 500 mg/dl.

In another embodiment, the subject or subject group being treated in accordance with methods of the invention exhibits a fasting baseline absolute plasma level of free total fatty acid (or mean thereof) not greater than about 300 nmol/ml, not greater than about 250 nmol/ml, not greater than about 200 nmol/ml, not greater than about 150 nmol/ml, not greater than about 100 nmol/ml, or not greater than about 50 nmol/ml.

In another embodiment, the subject or subject group being treated in accordance with methods of the invention exhibits a fasting baseline absolute plasma level of free EPA (or mean thereof in the case of a subject group) not greater than about 0.70 nmol/ml, not greater than about 0.65 nmol/ml, not greater than about 0.60 nmol/ml, not greater than about 0.55 nmol/ml, not greater than about 0.50 nmol/ml, not greater than about 0.45 nmol/ml, or not greater than about 0.40 nmol/ml. In another embodiment, the subject or subject group being treated in accordance with methods of the invention exhibits a baseline fasting plasma level (or mean thereof) of free EPA, expressed as a percentage of total free fatty acid, of not more than about 3%, not more than about 2.5%, not more than about 2%, not more than about 1.5%, not more than about 1%, not more than about 0.75%, not more than about 0.5%, not more than about 0.25%, not more than about 0.2% or not more than about 0.15%. In one such embodiment, free plasma EPA and/or total fatty acid levels are determined prior to initiating therapy.

In another embodiment, the subject or subject group being treated in accordance with methods of the invention exhibits a fasting baseline absolute plasma level of free EPA (or mean thereof) not greater than about 1 nmol/ml, not greater than about 0.75 nmol/ml, not greater than about 0.50 nmol/ml, not greater than about 0.4 nmol/ml, not greater than about 0.35 nmol/ml, or not greater than about 0.30 nmol/ml.

In another embodiment, the subject or subject group being treated in accordance with methods of the invention exhibits a fasting baseline plasma, serum or red blood cell membrane EPA level not greater than about 150 µg/ml, not greater than about 125 µg/ml, not greater than about 100 µg/ml, not greater than about 95 µg/ml, not greater than about 75 µg/ml, not greater than about 60 µg/ml, not greater than about 50 µg/ml, not greater than about 40 µg/ml, not greater than about 30 µg/ml, or not greater than about 25 µg/ml.

In another embodiment, methods of the present invention comprise a step of measuring the subject's (or subject group's mean) baseline lipid profile prior to initiating therapy. In another embodiment, methods of the invention comprise the step of identifying a subject or subject group having one or more of the following: baseline non-HDL-C value (or mean) of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value (or mean) of about 250 mg/dl to about 400 mg/dl, for example at least about 260 mg/dl, at least about 270 mg/dl, at least about 280 mg/dl or at least about 290 mg/dl; baseline vLDL-C value (or mean) of about 140 mg/dl to about 200 mg/dl, for example at least about 150 mg/dl, at least about 160 mg/dl, at least about 170 mg/dl, at least about 180 mg/dl or at least about 190 mg/dl; baseline HDL-C value (or mean) of about 10 to about 100 mg/dl, for example not more than about 90 mg/dl not, not more than about 80 mg/dl, not more than about 70 mg/dl, not more than about 60 mg/dl, not more than about 60 mg/dl, not more than about 50 mg/dl, not more than about 40 mg/dl, not more than about 35 mg/dl, not more than about 30 mg/dl, not more than about 25 mg/dl, not more than about 20 mg/dl, or not more than about 15 mg/dl; and/or baseline LDL-C value (or mean) of about 30 to about 300 mg/dl, for example not less than about 40 mg/dl, not less than about 50 mg/dl, not less than about 60 mg/dl, not less than about 70 mg/dl, not less than about 90 mg/dl or not less than about 90 mg/dl.

In a related embodiment, upon treatment in accordance with the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits one or more of the following outcomes:

(a) reduced triglyceride levels compared to baseline or placebo control (e.g. a subject on stable statin plus placebo matching the EPA treatment group);

(b) reduced Apo B levels compared to baseline or placebo control;

(c) increased HDL-C levels compared to baseline or placebo control;

(d) no increase in LDL-C levels compared to baseline or placebo control;

(e) a reduction in LDL-C levels compared to baseline or placebo control;

(f) a reduction in non-HDL-C levels compared to baseline or placebo control;

(g) a reduction in vLDL levels compared to baseline or placebo control;

(h) an increase in apo A-I levels compared to baseline or placebo control;

(i) an increase in apo A-I/apo B ratio compared to baseline or placebo control;

(j) a reduction in lipoprotein A levels compared to baseline or placebo control;

(k) a reduction in LDL particle number compared to baseline or placebo control;

(l) an increase in LDL size compared to baseline or placebo control;

(m) a reduction in remnant-like particle cholesterol compared to baseline or placebo control;

(n) a reduction in oxidized LDL compared to baseline or placebo control;

(o) no change or a reduction in fasting plasma glucose (FPG) compared to baseline or placebo control;

(p) a reduction in hemoglobin $A_{1c}$ ($HbA_{1c}$) compared to baseline or placebo control;

(q) a reduction in homeostasis model insulin resistance compared to baseline or placebo control;

(r) a reduction in lipoprotein associated phospholipase A2 compared to baseline or placebo control;

(s) a reduction in intracellular adhesion molecule-1 compared to baseline or placebo control;

(t) a reduction in interleukin-6 compared to baseline or placebo control;

(u) a reduction in plasminogen activator inhibitor-1 compared to baseline or placebo control;

(v) a reduction in high sensitivity C-reactive protein (hsCRP) compared to baseline or placebo control;

(w) an increase in serum or plasma EPA compared to baseline or placebo control;

(x) an increase in red blood cell membrane EPA compared to baseline or placebo control; and/or (y) a reduction or increase in one or more of serum and/or red blood cell content of docosahexaenoic acid (DHA), docosapentaenoic acid (DPA), arachidonic acid (AA), palmitic acid (PA), stearidonic acid (SA) or oleic acid (OA) compared to baseline or placebo control.

In one embodiment, methods of the present invention comprise measuring baseline levels of one or more markers set forth in (a)-(y) above prior to dosing the subject or subject group. In another embodiment, the methods comprise administering a composition as disclosed herein to the subject after baseline levels of one or more markers set forth in (a)-(y) are determined, and subsequently taking an additional measurement of said one or more markers.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more, any 24 or more, or all 25 of outcomes (a)-(y) described immediately above.

In another embodiment, upon treatment with a composition of the present invention, the subject or subject group exhibits one or more of the following outcomes:

(a) a reduction in triglyceride level of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control (e.g. a subject on statin and placebo matching the EPA treatment group);

(b) a less than 30% increase, less than 20% increase, less than 10% increase, less than 5% increase or no increase in non-HDL-C levels or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(c) substantially no change in HDL-C levels, no change in HDL-C levels, or an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(d) a less than 60% increase, less than 50% increase, less than 40% increase, less than 30% increase, less than 20% increase, less than 10% increase, less than 5% increase or no increase in LDL-C levels, or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 55% or at least about 75% (actual % change or median % change) as compared to baseline or placebo control;

(e) a decrease in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(f) a reduction in vLDL levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(g) an increase in apo A-I levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(h) an increase in apo A-I/apo B ratio of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(i) a reduction in lipoprotein (a) levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(j) a reduction in mean LDL particle number of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(k) an increase in mean LDL particle size of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(l) a reduction in remnant-like particle cholesterol of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(m) a reduction in oxidized LDL of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(n) substantially no change, no statistically significant change, or a reduction in fasting plasma glucose (FPG) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(o) substantially no change, no statistically significant change, a reduction in hemoglobin $A_{1c}$ ($HbA_{1c}$) of at least about 5%, at least about 10%, at least about 15%, at least about 20%, at least about 25%, at least about 30%, at least about 35%, at least about 40%, at least about 45%, or at least about 50% (actual % change or median % change) compared to baseline or placebo control;

(p) a reduction in homeostasis model index insulin resistance of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(q) a reduction in lipoprotein associated phospholipase A2 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(r) a reduction in intracellular adhesion molecule-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(s) a reduction in interleukin-6 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(t) a reduction in plasminogen activator inhibitor-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(u) a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(v) an increase in serum, plasma and/or RBC EPA of at least about 5%, at least about 10%, at least about 15%, at least about 20%, at least about 25%, at least about 30%, at least about 35%, at least about 40%, at least about 45%, at least about 50%, at least about 100%, at least about 200% or at least about 400% (actual % change or median % change) compared to baseline or placebo control;

(w) an increase in serum phospholipid and/or red blood cell membrane EPA of at least about 5%, at least about 10%, at least about 15%, at least about 20%, at least about 25%, at least about 30%, at least about 35%, at least about 40%, at least about 45%, r at least about 50%, at least about 100%, at least about 200%, or at least about 400% (actual % change or median % change) compared to baseline or placebo control;

(x) a reduction or increase in one or more of serum phospholipid and/or red blood cell DHA, DPA, AA, PA and/or OA of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or placebo control; and/or (y) a reduction in total cholesterol of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or placebo control.

In one embodiment, methods of the present invention comprise measuring baseline levels of one or more markers set forth in (a)-(y) prior to dosing the subject or subject group. In another embodiment, the methods comprise administering a composition as disclosed herein to the subject after baseline levels of one or more markers set forth in (a)-(y) are determined, and subsequently taking a second measurement of the one or more markers as measured at baseline for comparison thereto.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, or all 26 or more of outcomes (a)-(y) described immediately above.

Parameters (a)-(y) can be measured in accordance with any clinically acceptable methodology. For example, triglycerides, total cholesterol, HDL-C and fasting blood sugar can be sample from serum and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo Al, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants lipoproteins and LDL-phospholipase A2 can be determined from EDTA plasma or serum and serum, respectively, using enzymatic immunoseparation techniques. Oxidized LDL, intercellular adhesion molecule-1 and interleukin-2 levels can be determined from serum using standard enzyme immunoassay techniques. These techniques are described in detail in standard textbooks, for example Tietz Fundamentals of Clinical Chemistry, $6^{th}$ Ed. (Burtis, Ashwood and Borter Eds.), WB Saunders Company.

In one embodiment, subjects fast for up to 12 hours prior to blood sample collection, for example about 10 hours.

In another embodiment, the subject being treated is in the highest risk category of Adult Treatment Panel (ATP) III Classification of LDL, Total, and HDL Cholesterol (mg/dL) (e.g. CHD or CHD Risk Equivalents (10-year risk >20%)). In another embodiment, the subject is in the ATP III Multiple (2+) risk factor category.

In one embodiment, the invention provides a method of lowering triglycerides in a subject in the highest risk category of Adult Treatment Panel (ATP) III Classification of LDL, Total, and HDL Cholesterol (mg/dL) (e.g. CHD or CHD Risk Equivalents (10-year risk >20%)). In another embodiment, the subject is in the ATP III Multiple (2+) risk factor category. In another embodiment, the method includes a step of identifying a subject in the ATP III Multiple (2+) risk factor category prior to administering ultra-pure E-EPA to the subject.

In another embodiment, the present invention provides a method of treating or preventing primary hypercholesterolemia and/or mixed dyslipidemia (Fredrickson Types IIa and IIb) in a patient in need thereof, comprising administering to the patient one or more compositions as disclosed herein. In a related embodiment, the present invention provides a method of reducing triglyceride levels in a subject or subjects when treatment with a statin or niacin extended-release monotherapy is considered inadequate (Frederickson type IV hyperlipidemia).

In another embodiment, the present invention provides a method of treating or preventing risk of recurrent nonfatal myocardial infarction in a patient with a history of myocardial infarction, comprising administering to the patient one or more compositions as disclosed herein.

In another embodiment, the present invention provides a method of slowing progression of or promoting regression of atherosclerotic disease in a patient in need thereof, comprising administering to a subject in need thereof one or more compositions as disclosed herein.

In another embodiment, the present invention provides a method of treating or preventing very high serum triglyceride levels (e.g. Types IV and V hyperlipidemia) in a patient in need thereof, comprising administering to the patient one or more compositions as disclosed herein.

In one embodiment, a composition of the invention is administered to a subject in an amount sufficient to provide a daily dose of EPA of about 1 mg to about 10,000 mg, 25 about 5000 mg, about 50 to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg or about 2500 mg.

In another embodiment, any of the methods disclosed herein are used in treatment of a subject or subjects that consume a traditional Western diet. In one embodiment, the methods of the invention include a step of identifying a subject as a Western diet consumer or prudent diet consumer and then treating the subject if the subject is deemed a Western diet consumer. The term "Western diet" herein refers generally to a typical diet consisting of, by percentage of total calories, about 45% to about 50% carbohydrate, about 35% to about 40% fat, and about 10% to about 15% protein. A Western diet may alternately or additionally be characterized by relatively high intakes of red and processed meats, sweets, refined grains, and desserts, for example more than 50%, more than 60% or more or 70% of total calories come from these sources.

In another embodiment, any of the methods disclosed herein are used in treatment of a subject or subjects that consume less than (actual or average) about 150 g, less than about 125 g, less than about 100 g, less than about 75 g, less than about 50 g, less than about 45 g, less than about 40 g, less than about 35 g, less than about 30 g, less than about 25 g, less than about 20 g or less than about 15 g of fish per day.

In another embodiment, any of the methods disclosed herein are used in treatment of a subject or subjects that consume less than (actual or average) about 10 g, less than about 9 g, less than about 8 g, less than about 7 g, less than about 6 g, less than about 5 g, less than about 4 g, less than about 3 g, less than about 2 g per day of omega-3 fatty acids from dietary sources.

In another embodiment, any of the methods disclosed herein are used in treatment of a subject or subjects that consume less than (actual or average) about 2.5 g, less than about 2 g, less than about 1.5 g, less than about 1 g, less than about 0.5 g, less than about 0.25 g, or less than about 0.2 g per day of EPA and DHA (combined) from dietary sources.

In one embodiment, compositions useful in various embodiments of the invention comprise a polyunsaturated fatty acid as an active ingredient. In another embodiment, such compositions comprise EPA as an active ingredient. The term "EPA" as used herein refers to eicosapentaenoic acid (e.g. eicosa-5,8,11,14,17-pentaenoic acid) and/or a pharmaceutically acceptable ester, derivative, conjugate or salt thereof, or mixtures of any of the foregoing.

In one embodiment, the EPA comprises all-cis eicosa-5,8,11,14,17-pentaenoic acid. In another embodiment, the EPA is in the form of an eicosapentaenoic acid ester. In another embodiment, the EPA comprises a $C_1C_5$ alkyl ester of EPA. In another embodiment, the EPA comprises eicosapentaenoic acid ethyl ester, eicosapentaenoic acid methyl ester, eicosapentaenoic acid propyl ester, or eicosapentaenoic acid butyl ester. In still another embodiment, the EPA comprises all-cis eicosa-5,8,11,14,17-pentaenoic acid ethyl ester.

In still other embodiments, the EPA comprises ethyl-EPA, lithium EPA, mono, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree.

The term "pharmaceutically acceptable" in the present context means that the substance in question does not produce unacceptable toxicity to the subject or interaction with other components of the composition.

In one embodiment, EPA present in a composition suitable for use according to the invention comprises ultra-pure EPA. The term "ultra-pure" as used herein with respect to EPA refers to a composition comprising at least 96% by weight EPA (as the term "EPA" is defined and exemplified herein). Ultra-pure EPA can comprise even higher purity EPA, for example at least 97% by weight EPA, at least 98% by weight EPA or at least 99% by weight EPA, wherein the EPA is any form of EPA as set forth herein. Ultra-pure EPA can further be defined (e.g. impurity profile) by any of the description of EPA provided herein.

In some embodiments, EPA is present in a composition in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

In various embodiments, one or more antioxidants can be present in the EPA (e.g. E-EPA or ultra pure E-EPA). Non-limiting examples of suitable antioxidants include tocopherol, lecithin, citric acid and/or ascorbic acid. One or more antioxidants, if desired, are typically present in the EPA in an amount of about 0.01% to about 0.1%, by weight, or about 0.025% to about 0.05%, by weight.

In one embodiment, a composition of the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of total fatty acids, docosahexaenoic acid or derivative thereof such as E-DHA, if any. In another embodiment, a composition of the invention contains substantially no docosahexaenoic acid or derivative thereof such as E-DHA. In still another embodiment, a composition of the invention contains no docosahexaenoic acid or E-DHA.

In another embodiment, EPA represents at least about 60%, at least about 70%, at least about 80%, at least about 90%, at least about 95%, at least about 97%, at least about 98%, at least about 99%, or 100%, by weight, of all fatty acids present in a composition useful in accordance with the invention.

In another embodiment, a composition of the invention contains less than 30%, less than 20%, less than 10%, less than 9%, less than 8%, less than 7%, less than 6%, less than 5%, less than 4%, less than 3%, less than 2%, less than 1%, less than 0.5% or less than 0.25%, by weight of the total composition or by weight of the total fatty acid content, of any fatty acid other than EPA, or derivative thereof. Illustrative examples of a "fatty acid other than EPA" include linolenic acid (LA) or derivative thereof such as ethyl-linolenic acid, arachidonic acid (AA) or derivative thereof such as ethyl-AA, docosahexaenoic acid (DHA) or derivative thereof such as ethyl-DHA, alpha-linolenic acid (ALA) or derivative thereof such as ethyl-ALA, stearadonic acid (STA) or derivative thereof such as ethyl-SA, eicosatrienoic acid (ETA) or derivative thereof such as ethyl-ETA and/or docosapentaenoic acid (DPA) or derivative thereof such as ethyl-DPA.\

In another embodiment, a composition of the invention has one or more of the following features: (a) eicosapentaenoic acid ethyl ester represents at least 96%, at least 97%, or at least 98%, by weight, of all fatty acids present in the composition; (b) the composition contains not more than 4%, not more than 3%, or not more than 2%, by weight, of total fatty acids other than eicosapentaenoic acid ethyl ester; (c) the composition contains not more than 0.6%, 0.5%, 0.4% or 0.3% of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (f) the composition contains not more than 20 ppm, 15 ppm or 10 ppm heavy metals, (g) the composition contains not more than 5 ppm, 4 ppm, 3 ppm, or 2 ppm arsenic, and/or (h) the composition has a peroxide value not more than 5, 4, 3, or 2 Meq/kg.

In another embodiment, a composition useful in accordance with the invention comprises, consists essentially of or consists of at least 95% by weight ethyl eicosapentaenoate (EPA-E), about 0.2% to about 0.5% by weight ethyl octadecatetraenoate (ODTA-E), about 0.05% to about 0.25% by weight ethyl nonaecapentaenoate (NDPA-E), about 0.2% to about 0.45% by weight ethyl arachidonate (AA-E), about 0.3% to about 0.5% by weight ethyl eicosatetraenoate (ETA-E), and about 0.05% to about 0.32% ethyl heneicosapentaenoate (HPA-E). In another embodiment, the composition is present in a capsule shell. In still another embodiment, the capsule shell contains no chemically modified gelatin.

In another embodiment, compositions useful in accordance with the invention comprise, consist essentially of, or consist of at least 95%, 96% or 97%, by weight, ethyl eicosapentaenoate, about 0.2% to about 0.5% by weight ethyl octadecatetraenoate, about 0.05% to about 0.25% by weight ethyl nonaecapentaenoate, about 0.2% to about 0.45% by weight ethyl arachidonate, about 0.3% to about 0.5% by weight ethyl eicosatetraenoate, and about 0.05% to about 0.32% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, about 500 mg to about 1 g of the composition is provided in a capsule shell. In another embodiment, the capsule shell contains no chemically modified gelatin.

In another embodiment, compositions useful in accordance with the invention comprise, consist essentially of, or consist of at least 96% by weight ethyl eicosapentaenoate, about 0.22% to about 0.4% by weight ethyl octadecatetraenoate, about 0.075% to about 0.20% by weight ethyl nonaecapentaenoate, about 0.25% to about 0.40% by weight ethyl arachidonate, about 0.3% to about 0.4% by weight ethyl eicosatetraenoate and about 0.075% to about 0.25% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In one embodiment, the dosage form is a gel- or liquid-containing capsule and is packaged in blister packages of about 1 to about 20 capsules per sheet.

In another embodiment, compositions useful in accordance with the invention comprise, consist essentially of or consist of at least 96%, 97% or 98%, by weight, ethyl eicosapentaenoate, about 0.25% to about 0.38% by weight ethyl octadecatetraenoate, about 0.10% to about 0.15% by weight ethyl nonaecapentaenoate, about 0.25% to about 0.35% by weight ethyl arachidonate, about 0.31% to about 0.38% by weight ethyl eicosatetraenoate, and about 0.08% to about 0.20% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In another embodiment, the capsule shell contains no chemically modified gelatin.

In another embodiment, a composition as described herein is administered to a subject once or twice per day. In another embodiment, 1, 2, 3 or 4 capsules, each containing about 1 g of a composition as described herein, are administered to a subject daily. In another embodiment, 1 or 2 capsules, each containing about 1 g of a composition as described herein, are administered to the subject in the morning, for example between about 5 am and about 11 am, and 1 or 2 capsules, each containing about 1 g of a composition as described herein, are administered to the subject in the evening, for example between about 5 pm and about 11 pm.

In one embodiment, a subject being treated in accordance with methods of the invention is not on fibrate or nitrate therapy.

In another embodiment, compositions useful in accordance with methods of the invention are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. In one embodiment, the composition is present in a capsule, for example a soft gelatin capsule.

A composition for use in accordance with the invention can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In another embodiment, the invention provides use of any composition described herein for treating moderate to severe hypertriglyceridemia in a subject in need thereof, comprising: providing a subject having a fasting baseline triglyceride level of about 500 mg/dl to about 1500 mg/dl and administering to the subject a pharmaceutical composition as described herein. In one embodiment, the composition comprises about 1 g to about 4 g of eicosapentaenoic acid ethyl ester, wherein the composition contains substantially no docosahexaenoic acid.

EXAMPLES

Example 1. Safety and Efficacy of Ultra-Pure EPA

A multi-center, placebo-controlled, randomized, double-blind, 12-week study is performed to evaluate the efficacy and safety of >96% E-EPA in patients with fasting triglyceride levels ≥200 mg/dl and <500 mg/dl despite statin therapy (the mean of two qualifying entry values needs to be ≥185 mg/dl and at least one of the values needs to be ≥200 mg/dl). The primary objective of the study is to determine the efficacy of >96% E-EPA 2 g daily and 4 g daily, compared to placebo, in lowering fasting TG levels in patients with high risk for cardiovascular disease and with fasting TG levels ≥200 mg/dL and <500 mg/dL, despite treatment to LDL-C goal on statin therapy.

The secondary objectives of this study are the following:
1. To determine the safety and tolerability of >96% E-EPA 2 g daily and 4 g daily;
2. To determine the effect of >96% E-EPA on lipid and apolipoprotein profiles including total cholesterol (TC), non-high-density lipoprotein cholesterol (non-HDL-C), low density lipoprotein cholesterol (LDL-C), high density lipoprotein cholesterol (HDL-C), and very high density lipoprotein cholesterol (VHDL-C);
3. To determine the effect of >96% E-EPA (on lipoprotein associated phospholipase $A_2$ (Lp-$PLA_2$) from baseline to week 12;
4. To determine the effect of >96% E-EPA on low-density lipoprotein (LDL) particle number and size;
5. To determine the effect of >96% E-EPA on oxidized LDL;
6. To determine the effect of >96% E-EPA on fasting plasma glucose (FPG) and hemoglobin $A_{1c}$ ($HbA_{1c}$);
7. To determine the effect of >96% E-EPA on insulin resistance;
8. To determine the effect of >96% E-EPA on high-sensitivity C-reactive protein (hsCRP);
9. To determine the effects of >96% E-EPA 2 g daily and 4 g daily on the incorporation of fatty acids into red blood cell membranes and into plasma phospholipids;
10. To explore the relationship between baseline fasting TG levels and the reduction in fasting TG levels; and
11. To explore the relationship between changes of fatty acid concentrations in plasma and red blood cell membranes, and the reduction in fasting TG levels.

The population for this study is men and women >18 years of age with a body mass index ≤45 $kg/m^2$ with fasting TG levels greater than or equal to 200 mg/dl and less than 500 mg/dl and on a stable does of statin therapy (with or without ezetimibe). The statin must be atorvostatin, rosuvastatin or simvastatin. The dose of statin must be stable for ≥4 weeks prior to the LDL-C/TG baseline qualifying measurement for randomization. The statin dose will be optimal such that the patients are at their LDL-C goal at the LDL-C/TG baseline qualifying measurements. The same statin at the same dose will be continued until the study ends.

Patients taking any additional non-statin, lipid-altering medications (niacin >200 mg/day, fibrates, fish oil, other products containing omega-3 fatty acids, or other herbal products or dietary supplements with potential lipid-altering effects), either alone or in combination with statin therapy (with or without ezetimibe), must be able to safely discontinue non-statin, lipid-altering therapy at screening.

Patients at high risk for CVD, i.e., patients with clinical coronary heart disease (CHD) or clinical CHD risk equivalents (10-year risk >20%) as defined in the National Cholesterol Education Program (NCEP) Adult Treatment Panel III (ATP III) Guidelines will be eligible to participate in this study. Those include patients with any of the following criteria: (1) Known CVD, either clinical coronary heart disease (CHD), symptomatic carotid artery disease (CAD), peripheral artery disease (PAD) or abdominal aortic aneurism; or (2) Diabetes Mellitus (Type 1 or 2).

Approximately 648 patients will be randomized at approximately 80 centers in the U.S. The study will be a 18- to 20-week, Phase 3, multi-center study consisting of 2 study periods: (1) A 6- to 8-week screening period that includes a diet and lifestyle stabilization, a non-statin lipid-altering treatment washout, and an LDL-C and TG qualifying period and (2) A 12-week, double-blind, randomized, placebo-controlled treatment period.

During the screening period and double-blind treatment period, all visits are to be within ±3 days of the scheduled time. All patients will continue to take the statin product (with or without ezetimibe) at the same dose they were taking at screening throughout their participation in the study.

The 6- to 8-week screening period includes a diet and lifestyle stabilization, a non-statin lipid-altering treatment washout, and an LDL-C and TG qualifying period. The screening visit (Visit 1) will occur for all patients at either 6 weeks (for patients on stable statin therapy [(with or without ezetimibe] at screening) or 8 weeks (for patients who will require washout of their current non-statin lipid-altering therapy at screening) before randomization, as follows:

Patients who do not require a washout: The screening visit will occur at Visit 1 (Week −6). Eligible patients will enter a 4-week diet and lifestyle stabilization period. At the screening visit, all patients will receive counseling regarding the importance of the National Cholesterol Education Program (NCEP) Therapeutic Lifestyle Changes (TLC) diet and will receive basic instructions on how to follow this diet.

Patients who will require a washout: The screening visit will occur at Visit 1 (Week −8). Eligible patients will begin a 6-week washout period at the screening visit (i.e. 6 weeks washout before the first LDL-C/TG qualifying visit). Patients will receive counseling regarding the NCEP TLC diet and will receive basic instructions on how to follow this diet. Site personnel will contact patients who do not qualify for participation based on screening laboratory test results to instruct them to resume their prior lipid-altering medications.

At the end of the 4-week diet and lifestyle stabilization period or the 6-week diet and stabilization and washout period, eligible patients will enter the 2-week LDL-C and TG qualifying period and will have their fasting LDL-C and TG levels measured at Visit 2 (Week −2) and Visit 3 (Week −1). Eligible patients must have an average fasting LDL-C level ≥40 mg/dL and <100 mg/dL and an average fasting TG level ≥200 mg/dL and <500 mg/dL to enter the 12-week double-blind treatment period. The LDL-C and TG levels for qualification will be based on the average (arithmetic mean) of the Visit 2 (Week −2) and Visit 3 (Week −1) values. If a patient's average LDL-C and/or TG levels from Visit 2 and Visit 3 fall outside the required range for entry into the study, an additional fasting lipid profile can be collected 1 week later at Visit 3.1. If a third sample is collected at Visit 3.1, entry into the study will be based on the average (arithmetic mean) of the values from Visit 3 and Visit 3.1.

After confirmation of qualifying fasting LDL-C and TG values, eligible patients will enter a 12-week, randomized, double-blind treatment period. At Visit 4 (Week 0), patients will be randomly assigned to 1 of the following treatment groups:
>96% E-EPA 2 g daily,
>96% E-EPA 4 g daily, or
Placebo.

Approximately 216 patients per treatment group will be randomized in this study. Stratification will be by type of statin (atorvastatin, rosuvastatin or simvastatin), the presence of diabetes, and gender.

During the double-blind treatment period, patients will return to the site at Visit 5 (Week 4), Visit 6 (Week 11), and Visit 7 (Week 12) for efficacy and safety evaluations.

Eligible patients will be randomly assigned at Visit 4 (Week 0) to receive orally >96% E-EPA 2 g daily, >96% E-EPA 4 g daily, or placebo.

>96% E-EPA is provided in 1 g liquid-filled, oblong, gelatin capsules. The matching placebo capsule is filled with light liquid paraffin and contains 0 g of >96% E-EPA. >96% E-EPA capsules are to be taken with food (i.e. with or at the end of a meal).

During the double-blind treatment period, patients will take 2 capsules (>96% E-EPA or matching placebo) in the morning and 2 capsules in the evening for a total of 4 capsules per day.

Patients in the >96% E-EPA 2 g/day treatment group will receive 1 >96% E-EPA 1 g capsule and 1 matching placebo capsule in the morning and in the evening.

Patients in the >96% E-EPA 4 g/day treatment group will receive 2 >96% E-EPA 1 g capsules in the morning and evening.

Patients in the placebo group will receive 2 matching placebo capsules in the morning and evening.

The primary efficacy variable for the double-blind treatment period is percent change in TG from baseline to Week 12 endpoint. The secondary efficacy variables for the double-blind treatment period include the following:

Percent changes in total cholesterol (TC), high-density lipoprotein cholesterol (HDL-C), LDL-C, calculated non-HDL-C, and very low-density lipoprotein cholesterol (VLDL-C) from baseline to Week 12 endpoint;

Percent change in very low-density lipoprotein TG from baseline to Week 12;

Percent changes in apolipoprotein A-I (apo A-I), apolipoprotein B (apo B), and apo A-I/apo B ratio from baseline to Week 12;

Percent changes in lipoprotein(a) from baseline to Week 12;

Percent changes in LDL particle number and size, measured by nuclear magnetic resonance, from baseline to Week 12;

Percent change in remnant-like particle cholesterol from baseline to Week 12;

Percent change in oxidized LDL from baseline to Week 12;

Changes in FPG and $HbA_{1c}$ from baseline to Week 12;

Change in insulin resistance, as assessed by the homeostasis model index insulin resistance, from baseline to Week 12;

Percent change in lipoprotein associated phospholipase $A_2$ (Lp-$PLA_2$) from baseline to Week 12;

Change in intracellular adhesion molecule-1 from baseline to Week 12;

Change in interleukin-2 from baseline to Week 12;

Change in plasminogen activator inhibitor-1 from baseline to Week 12. Note: this parameter will only be collected at sites with proper storage conditions;

Change in hsCRP from baseline to Week 12; and

Change in plasma concentration and red blood cell membrane content of fatty acid from baseline to Week 12 including EPA, docosapentaenoic acid (DPA), docosahexaenoic acid (DHA), arachidonic acid (AA), dihomo-γ-linolenic acid (DGLA), the ratio of EPA/AA, ratio of oleic acid/stearic acid (OA/SA), and the ratio of total omega-3 acids over total omega-6 acids.

Safety assessments will include adverse events, clinical laboratory measurements (chemistry, hematology, and urinalysis), 12-lead electrocardiograms (ECGs), vital signs, and physical examinations.

For TG, TC, HDL-C, LDL-C, calculated non-HDL-C, and VLDL-C, baseline will be defined as the average of Visit 4 (Week 0) and the preceding lipid qualifying visit (either Visit 3 [Week −1] or if it occurs, Visit 3.1) measurements. Baseline for all other efficacy parameters will be the Visit 4 (Week 0) measurement.

For TG, TC, HDL-C, LDL-C, calculated non-HDL-C, and VLDL-C, Week 12 endpoint will be defined as the average of Visit 6 (Week 11) and Visit 7 (Week 12) measurements.

Week 12 endpoint for all other efficacy parameters will be the Visit 7 (Week 12) measurement.

The primary efficacy analysis will be performed using a 2-way analysis of covariance (ANCOVA) model with treatment as a factor and baseline TG value as a covariate. The least-squares mean, standard error, and 2-tailed 95% confidence interval for each treatment group and for each comparison will be estimated. The same 2-way ANCOVA model will be used for the analysis of secondary efficacy variables.

The primary analysis will be repeated for the per-protocol population to confirm the robustness of the results for the intent-to-treat population.

Non-inferiority tests for percent change from baseline in LDL-C will be performed between >96% E-EPA doses and placebo using a non-inferiority margin of 6% and a significant level at 0.05.

For the following key secondary efficacy parameters, treatment groups will be compared using Dunnett's test to control the Type 1 error rate: TC, LDL-C, HDL-C, non-HDL-C, VLDL-C, Lp-$PLA_2$, and apo B. For the remaining secondary efficacy parameters, Dunnett's test will not be used and the ANCOVA output will be considered descriptive.

The evaluation of safety will be based primarily on the frequency of adverse events, clinical laboratory assessments, vital signs, and 12-lead ECGs. The primary efficacy variable is the percent change in fasting TG levels from baseline to Week 12. A sample size of 194 completed patients per treatment group will provide 90.6% power to detect a difference of 15% between >96% E-EPA and placebo in percent change from baseline in fasting TG levels, assuming a standard deviation of 45% in TG measurements and a significance level of $p<0.05$.

Previous data on fasting LDL-C show a difference in percent change from baseline of 2.2%, with a standard deviation of 15%, between study drug and placebo. A sample size of 194 completed patients per treatment group will provide 80% power to demonstrate non-inferiority ($p<0.05$, one-sided) of the LDL-C response between >96% E-EPA 4 g daily and placebo, within a 6% margin. To accommodate a 10% drop-out rate from randomization to completion of the double-blind treatment period, a total of 648 randomized patients is planned (216 patients per treatment group).

Example 2. Improvement of Cognitive Performance in Subjects with Age-Associated Memory Impairment A single-center, 6-week, double-blind, randomizes, parallel-group, placebo-controlled, dose-ranging pilot study was performed to evaluate the efficacy, tolerability, and safety of >96% ethyl-EPA in subjects with subjective and objective memory impairment according to generally accepted criteria for Age-Associated Memory Impairment ("AAMI"). The primary objective of the study was to determine the effect of >96% ethyl-EPA 1 g, 2 g, and 4 g daily, compared to placebo, on cognitive performance in subjects with AAMI.

The secondary objectives of this study were the following:
1. To determine the effect of >96% E-EPA on the following tests in the computerized cognitive battery:
   Continuity of attention tasks;
   Quality of working memory tasks;
   Quality of episodic memory tasks; and
   Speed of attention tasks;
2. To determine the safety and tolerability of >96% E-EPA from routine clinical laboratory tests, adverse events ("AE") monitoring, and vital signs; and
3. To determine the potential dose-effect relationship of >96% E-EPA on the cognitive endpoints by measurement of essential fatty acids in plasma and red blood cell membranes.

The population for this study was men and women between ages 50 and 70 with self-reported complaints of memory loss, subjective and objective cognitive impairment with a score of at least one standard deviation below that of the mean for age-matched elderly population as determined by the total score of between 13 and 20 from the Paired Associated Learning ("PAL") subset of the Wechsler Memory Scale, evidence of adequate intellectual function as determined by a scaled score of at least 9 (raw score of at least 32) on the Vocabulary subtest of the Wechsler Adult Intelligence Scale and absence of dementia as determined by a score of 24 or higher on the Mini-Mental State Examination ("MMSE").

Potential subjects were excluded based on the following exclusion criteria:
  Unlikely or unable to comply with investigational medication dosing requirements;
  Diagnosis of major depressive disorder, Alzheimer's or vascular dementia as defined according to the Mini International Neuropsychiatric Interview ("MINI")/Diagnostic and Statistical Manual of Mental Disorders (4th edition) Text Revision ("TR") criteria;
  Past or current history of:
    a neurological or psychiatric disorder that could have affected cognitive function;
    inflammatory gastrointestinal disease such as Crohn's Disease or ulcerative colitis;
    cancer other than basal cell carcinoma;
    clinically significant cardiac abnormality as measured by 12-lead ECG;
  Any other medical condition or intercurrent illness not adequately controlled, which, in the opinion of the study investigator, may have put the subject at risk when participating in the study or may have influenced the results of the study or affected the subject's ability to take part in the study;
  Clinically significant abnormal screening results (e.g., haematology, biochemistry) on screening or vital signs that fell outside the normal range for this population, which in the opinion of the study investigator affected the subject's suitability for the study;
  Changes to prescribed medication for a medical condition within 4 weeks of the baseline visit;
  Omega-3 supplementation within 4 weeks of the baseline visit or during the study treatment period;
  Currently taking anticoagulants or daily dose of aspirin greater than 325 mg.
  Cough or flu remedies containing opiates or antihistamines within 2 weeks of the baseline visit or during the 6-week treatment period; and
  Known allergy to any ingredients of the study drug or placebo.

Ninety-four subjects were randomized into one of six groups: 1 g E-EPA daily (n=23), 2 g E-EPA daily (n=24), 4 g E-EPA daily (n=24), 1 g placebo daily (n=7), 2 g placebo daily (n=8), and 4 g placebo daily (n=8). E-EPA was provided as 500 mg soft gel capsules containing >96% E-EPA and 0.2% dl-$\alpha$-tocopherol as an antioxidant. Placebo capsules contained 467 mg of liquid paraffin and 0.2% dl-a-tocopherol. Ninety-one subjects completed the study. Two subjects in the 2 g E-EPA group and one subject in the 2 g placebo group discontinued the study.

The study consisted of a screening visit, a training visit, and four study visits. At the screening visit, subjects' eligibility was determined through cognitive tests (verbal paired associated learning [PAL] subscale, vocabulary subtest, Memory Assessment Clinics Questionnaire [MAC-Q], mini mental state evaluation [MMSE] and MINI [mini international neuropsychiatric interview; sections 1 and 2 of Diagnostic and Statistical Manual of Mental Disorders, 4th Edition (DSM-IV) plus dysthymia]), haematology, clinical chemistry and 12-lead electrocardiogram (ECG). At the training visit, subjects were shown how to use the CDR computerized system. Subjects took study drug for 6 weeks and on Days 0, 14, 28 and 42, subjects underwent the CDR cognitive test battery.

At screening cognitive testing and suitability for the study were assessed using the Verbal Paired Associates 1 (Wechsler Memory Scale), Vocabulary Subtest of the WAIS, MAC-Q, MMSE and MINI (DSM-IV Sections 1 and 2 plus Dysthymia).

A selection of tasks from the CDR computerized cognitive assessment system were administered at Visit 2 (training visit), Visit 3 (baseline), Visit 4 (Day 14), Visit 5 (Day 28) and Visit 6 (Day 42). Parallel forms of the tests were presented at each testing session. All tasks were computer-controlled, the information presented on high resolution monitors, and the responses recorded via a response model containing two buttons: one marked 'no' and the other 'yes'. Five CDR composite scores were used as the primary/secondary outcome variables. The task titles were:
  Word Presentation
  Immediate Word Recall
  Picture Presentation
  Simple Reaction Time
  Digit Vigilance
  Choice Reaction Time
  Spatial Working Memory
  Numeric Working Memory
  Delayed Word Recall
  Word Recognition
  Picture Recognition
  Bond-Lader Visual Analogue Scales of Mood and Alertness
  Screen, Using the Computer Mouse To ensure consistency of approach, full training on the cognitive tests and CDR test battery was provided to study site staff and study subjects. The results of each variable were automatically recorded using the machine interface developed by CDR.

Blood samples (10 mL) were collected at Visit 1 (screening) and at Visits 4, 5 and 6. Analysis was performed by MSR Lipid Analysis, Scottish Crop Research Institute, Dundee, UK. The screening sample acted as baseline for the EFA measurements. Lipid was extracted from plasma, serum and RBC suspensions and converted into fatty acid methyl esters which were analyzed by gas chromatography to give fatty acid profiles as micrograms fatty acid per gram of sample (µgFA/g) and normalized area percent.

All randomized subjects with at least 1 visit post-baseline were included in the Intent to Treat ("ITT") population, regardless of treatment actually received.

All randomized subjects that completed the study, excluding significant protocol deviators, were defined as the Safety Per Protocol population. An Efficacy Per Protocol population was based on the Efficacy completers. The intercept of the Safety and Efficacy Per Protocol populations defined the Study Per Protocol Population.

All randomized subjects that received at least 1 dose of study medication were included in the Safety Population.

Summary statistics were provided for the ITT and Study Per Protocol Populations separately for all composite scores, major and supportive variables. Summary statistics were performed for both the unadjusted and difference from baseline data (i.e. the difference from the time matched predose assessments on Day 0). Summary statistics were calculated by treatment, day and time-point. The summary statistics comprised n, mean, median, SD, standard error of mean ("SEM"), minimum and maximum values.

Difference from baseline data for each major variable was evaluated by an Analysis of Covariance ("ANCOVA") using SAS® PROC MIXED Version 8.2. Fixed effects for treatment, day, time point, treatment by day, treatment by time point, treatment by day by time-point were fitted. Subject within treatment was fitted as a repeated effect using the repeated statement. The compound symmetry covariance structure was used. Subjects' time-matched predose assessments on Day 0 were used as a covariate in the analysis.

Least squares means (LS means) were calculated for treatment by day, treatment by time-point and treatment by day by time-point interaction. This formal analysis was conducted for the ITT and Study PP Populations separately.

Safety evaluations were based on the safety population. Safety and tolerability were assessed in terms of AEs, vital signs, 12-lead ECG, clinical laboratory data, medical history, and study drug compliance. Safety and tolerability data were presented by treatment group.

RBC and plasma EFA data were collected at baseline, Day 14, 28 and 42 and summarized by visit for each treatment group. Change from baseline and percent change from baseline were also summarized. ANCOVA comparison of ethyl-EPA dose groups and ethyl-EPA versus placebo was performed.

Efficacy Results

All CDR cognitive test battery analyses were completed for the ITT and Study PP analysis populations.

For the Intent-to-Treat Analysis for Power of Attention, there was no statistically significant effect of treatment, nor any treatment by day, treatment by time-point or treatment by day by time-point interactions. There was no LS mean difference between active treatment and placebo at any time-point.

For the contributing subtasks Simple Reaction Time and Digit Vigilance Speed, there were no statistically significant effects of treatment, nor any treatment by day, treatment by time-point or treatment by day by time-point interactions. For the subtask measure Choice Reaction Time, there was a statistically significant treatment by day interaction (p=0.011).

For the Study Per-Protocol Power of Attention, there was no statistically significant effect of treatment, nor any treatment by day, treatment by time-point or treatment by day by time-point interactions. There was no difference between active treatment and placebo at any time-point.

For the subtasks Simple Reaction Time and Digit Vigilance Speed, there were no statistically significant effects of treatment, nor any treatment by day, treatment by time-point or treatment by day by time-point interactions. For the subtask measure, Choice Reaction Time, there was a statistically significant treatment by day interaction (p=0.013).

The Intent-to-Treat Continuity of Attention and the contributing subtask Digit Vigilance Targets Detected tests showed no statistically significant effect of treatment, nor any treatment by day, treatment by time-point or treatment by day by time-point interactions.

For the Study Per Protocol Continuity of Attention test, there was no statistically significant effect of treatment, nor any treatment by day, treatment by time-point or treatment by day by time-point interactions.

For the subtask Digit Vigilance Targets Detected, there was a statistically significant treatment by time-point interaction (p=0.040).

For the Intent-to-Treat Quality of Working Memory test, there was a statistically significant treatment by day interaction (p=0.019).

For the contributing subtask Spatial Working Memory Sensitivity Index, there was a statistically significant treatment by day interaction (p=0.015).

For Numeric Working Memory Sensitivity Index, there was a statistical trend for a treatment by day interaction (p=0.089).

For the Study Per-Protocol Quality of Working Memory test, there was a statistically significant treatment by day interaction (p=0.021).

For the contributing subtask Spatial Working Memory Sensitivity Index, there was a statistically significant treatment by day interaction (p=0.014).

For the Intent-to-Treat Quality of Episodic Secondary Memory test, there was no statistically significant effect of treatment, nor any treatment by day, treatment by time-point or treatment by day by time-point interactions. The LS mean differences showed overall statistically significant decreases versus placebo for ethyl-EPA 1 g and 2 g (p=0.040 and p=0.035, respectively).

For the contributing subtasks Immediate and Delayed Word Recall Accuracies and for Word and Picture Recognition Sensitivity Indices, there were no statistically significant effects of treatment or treatment by day, treatment by time-point or treatment by day by time-point interactions. For Immediate Word Recall Accuracy, the LS mean differences showed statistically significant decreases for 1 g on Day 14 (p=0.028) and for 2 g on Day 28 (p=0.017). There were statistically significant decreases versus placebo for 1 g and 2 g at AM 1 (p=0.040 and p=0.028, respectively). There were statistically significant decreases for ethyl-EPA 1 g versus placebo on Day 14 at PM 2 (p=0.020) and for 2 g on Day 28 at AM 1 (p=0.006). For Word Recognition Sensitivity Index, the LS mean differences showed statistically significant decreases for ethyl-EPA 1 g on Day 28 (p=0.024) and for 4 g on Day 42 (p=0.038) versus placebo. There was a statistically significant decrease for 4 g at PM 2 (p=0.045) and a statistically significant decrease for 4 g versus placebo on Day 28 at PM 2 (p=0.030). For Picture Recognition Sensitivity Index, the LS mean differences showed statistically significant decrease for 1 g versus placebo on Day 28 at AM 2 (p=0.017) and at PM 2 (p=0.040). For the Study Per-Protocol Quality of Episodic Secondary Memory test, there were no statistically significant effects of treatment, nor treatment by day, treatment by time-point or treatment by day by time-point interactions. The LS mean differences showed overall statistically significant decreases versus placebo for 1 g and 2 g (p=0.043 and p=0.036, respectively).

For the contributing subtasks Immediate and Delayed Word Recall Accuracies and for Word and Picture Recognition Sensitivity Indices, there were no statistically significant effects of treatment or treatment by day, treatment by time-point or treatment by day by time-point interactions. For Immediate Word Recall Accuracy, the LS mean differences to placebo showed statistically significant decreases for ethyl-EPA 1 g on Day 14 (p=0.024) and for 2 g on Day 28 (p=0.017). There were statistically significant decreases for 1 g and 2 g at AM 1 (p=0.038 and p=0.029, respectively) and for 1 g at AM 2 (p=0.048). There were statistically significant decreases for 1 g versus placebo on Day 14 at PM 2 (p=0.019) and for 2 g on Day 28 at AM 1 (p=0.006).

For Word Recognition Sensitivity Index, the LS mean differences to placebo showed statistically significant decreases for 4 g on Day 42 (p=0.038) and for 1 g on Day 28 (p=0.027).

For Picture Recognition Sensitivity Index, the LS mean differences showed statistically significant decreases versus placebo for 1 g on Day 28 at AM 2 (p=0.020) and PM 2 (p=0.026).

For Intent-to-Treat Speed of Memory and the contributing subtasks Spatial and Numeric Working Memory Speeds and Word, and Picture Recognition Speeds, there were no statistically significant effects of treatment, nor treatment by day, treatment by time-point or treatment by day by time-point interactions. For Spatial Working Memory Speed, the LS mean differences showed a statistically significant benefit versus placebo for ethyl-EPA 4 g on Day 14 at PM 1 (p=0.048) and a trend for a benefit for 4 g on Day 42 at AM 1 (p=0.061). For Picture Recognition Speed, there were trends for benefits versus placebo for 1 g on Day 14 at AM 2 (p=0.084) and on Day 28 at AM 1 (p=0.085).

For Study Per-Protocol Speed of Memory and the contributing subtasks Spatial and Numeric Working Memory Speed and Word, and Picture Recognition Speed, there were no statistical significant effects of treatment, nor any treatment by day, treatment by time-point or treatment by day by time-point interactions.

For Intent-to-Treat Self-Rated Alertness, there was no statistically significant effect of treatment, nor any treatment by day, treatment by time-point or treatment by day by time-point interactions. The LS mean differences showed a statistically significant decrease in ratings for ethyl-EPA 2 g on Day 28 (p=0.047) versus placebo. There was a statistically significant decrease in ratings versus placebo for 2 g on Day 28 at AM 2 (p=0.041). For Study Per-Protocol Self-Rated Alertness, there was no statistically significant effect of treatment, nor any treatment by day, treatment by time-point or treatment by day by time-point interactions. The LS mean differences showed a statistically significant decrease in ratings for ethyl-EPA 2 g on Day 28 (p=0.035) versus placebo. There was a statistically significant decrease in ratings versus placebo for 2 g on Day 28 at AM 2 (p=0.033).

For Intent-to-Treat Self-Rated Contentment, there was a statistically significant treatment by day interaction (p<0.001). The LS mean difference to placebo showed no statistically significant effects. For Study Per-Protocol Self-Rated Contentment, there was a statistically significant treatment by day interaction (p<0.001). The LS mean difference to placebo showed no statistically significant effects.

For Intent-to-Treat Self-Rated Calmness, there was no statistically significant effect of treatment, nor any treatment by day, treatment by time-point or treatment by day by time-point interactions. For Study Per-Protocol Self-Rated Calmness, there was no statistically significant effect of treatment, nor any treatment by day, treatment by time-point or treatment by day by time-point interactions. The LS mean differences showed a statistical trend for an increase in ratings versus placebo for ethyl-EPA 4 g on Day 42 at PM 1 (p=0.071).

A post-hoc analysis compared the individual placebo groups (1 g, 2 g and 4 g paraffin oil) with the corresponding ethyl-EPA doses.

The pattern of data provided evidence that ethyl-EPA 4 g might improve speed in the attention based measures. For Power of Attention, there was an overall benefit versus the corresponding placebo for 4 g on Day 42. The subtask Simple Reaction Time showed improvements in performance for 4 g at PM 2 collapsed across days and at several time-points on Days 14 and 42. The improvements for 4 g were most pronounced in the Choice Reaction Time task, where there was an overall benefit versus corresponding placebo for 4 g, reflecting a benefit for 4 g over placebo on all study days. The pattern of improvement in performance throughout the assessment days was quite convincing as the improvements began on Day 14 with improvements seen at 2 time points, whereas on Day 42 ethyl-EPA 4 g was superior to placebo at every time point.

For Continuity of Attention, there were isolated declines or improvements in performance, but there was no general pattern of effects and it was considered unlikely these differences were due to the study compound. For Quality of Working Memory and in the subtask measure Numeric Working Memory Sensitivity Index, there were, as in the original analyses, only isolated improvements and declines in performance that were most likely not treatment-related. However, for Spatial Working Memory Sensitivity Index, there was an overall benefit for ethyl-EPA 4 g over placebo on Day 42 in the Study PP Population, which corresponds to the improvements seen for the attention based measures.

For Quality of Episodic Secondary Memory and contributing subtasks, there were a number of decreases for ethyl-EPA that could be explained by the pre-existing differences in performance between the placebo and active treatment groups which was seen in the original analyses. In contrast to the original analysis, the subtask measures of Speed of Memory showed some signs of improvement in performance for active treatment, mostly for 1 g versus placebo. For Self-rated Alertness and Self-rated Contentment, the 1 g dose showed decreases in ratings on Days 14 and 28. However, these decreases were not correlated with a decline in performance in the CDR attention tasks. As with the original planned analysis, there were no differences between active treatment and placebo in Self-Rated Calmness.

Safety Results

Subjects who used less than 80% of the prescribed dose were to be considered non-compliant; other than those subjects who withdrew for other reasons only 1 subject fell into this category and was withdrawn.

Overall, 139 treatment emergent AEs ("TEAEs") were reported by 62 (66.0%) of subjects during the study. Most TEAEs were considered mild in severity and unrelated to study drug. More TEAEs were reported for the ethyl-EPA treatment groups (105 events) compared to the placebo treatment groups (34 events). One SAE was reported for the ethyl EPA 2 g treatment group and 3 subjects discontinued due to TEAEs: 2 subjects from the ethyl-EPA 2 g treatment group (the primary reason for discontinuation for 1 of these subjects was non-compliance), and 1 subject from the placebo 2 g treatment group.

There were no deaths during the study. No TEAEs were Definitely Related to the study drug. One subject receiving 1 g ethyl-EPA experienced nausea that was Probably Related to the study drug. Another subject receiving 4 g ethyl-EPA experienced diarrhea that was Probably Related to the study drug; another subject receiving 2 g placebo also experienced diarrhea that was Probably Related to the study drug. Five subjects experienced nausea that was Possibly Related to the study drug; two were in the 1 g ethyl-EPA cohort; one was in the 2 g ethyl-EPA cohort; two were in the 4 g ethyl-EPA cohort. One subject receiving 2 g placebo experienced headache that was Possibly Related to the study drug. All other TEAEs were Not Related or Unlikely Related to the study drug, and included nasopharyngitis (n=3), cystitis (n=2), cough (n=7), toothache (n=2), pharyngolaryngeal pain (n=2), back pain (n=2), pollakiuria (n=2), influenza-like illness (n=2), headache (n=15), diarrhea (n=2), and nausea (n=1).

One subject with a history of transient ischaemic attack, hypertension and osteoarthritis of the hand and osteopaenia receiving 2 g ethyl-EPA experienced worsening epigastric chest pain 17 days after the start of the study and 9 days after the last dose of the study drug. A planned endoscopy revealed oesophagitis and a small hiatus hernia. The subject was treated with omeprazole, which settled her symptoms. The subject had taken felodipine, rosuvastatin, aspirin, glucosamine, and quinine within 14 days of the onset of her symptoms. The study investigator determined that her symptoms were unrelated to the study drug and withdrew the subject from the study. No other Serious Adverse Events occurred during the study.

Essential fatty acid parameters in plasma and RBCs was measured at baseline and on Day 14, 28 and 48 (shown in Tables 1-6). Notable changes for these parameters occurred in the ethyl-EPA treatment groups at Days 14, 28 and 42 compared to placebo. EPA, DPAn-3 and EPA/AA ratio values increased substantially from baseline, in plasma and RBC, to Day 42 for the ethyl-EPA 1, 2 and 4 g treatment groups, but remained similar to baseline in the placebo treatment groups. AA, DHA and DGLA values decreased substantially from baseline, in plasma and RBC, to day 42 for the ethyl EPA 1, 2 and 4 g treatment groups, but remained similar to baseline in the placebo treatment groups. The difference in EPA, AA (RBC only), DPAn-3, DGLA (1 g only for plasma) and EPA/AA ratio levels in the plasma and RBC were significantly (LS means, $p \leq 0.05$) different for the ethyl-EPA 4 g treatment group compared to the ethyl-EPA 1 g and 2 g treatment groups.

TABLE 1

EFA Parameter EPA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 48.3 (31.03) | 4.49 (25.01) | 49.1 (17.23) | 47.5 (26.41) | 42.1 (16.18) | 42.5 (11.86) |
| Day 14: n | 23 | 22 | 24 | 7 | 7 | 8 |
| Mean (SD) | 61.2 (26.61) | 124.6 (42.25) | 207.7 (57.05) | 1.6 (24.69) | −1.2 (19.82) | 21.9 (32.91) |
| Day 28: n | 22 | 22 | 24 | 7 | 7 | 8 |
| Mean (SD) | 60.3 (36.03) | 142.2 (46.23) | 215.2 (58.68) | 6.5 (15.46) | 1.6 (13.64) | 1.3 (14.03) |
| Day 42: n | 23 | 22 | 24 | 7 | 7 | 8 |
| Mean (SD) | 62.0 (39.43) | 133.4 (43.34) | 204.6 (80.69) | 11.9 (26.34) | 0.4 (21.18) | 4.4 (23.32) |
| 1 or 2 g versus 4 g | | | | | | |
| LS Mean | −111.8 | −60.9 | — | — | — | — |
| CI | −123.6, −100 | −72.7, −49.0 | — | — | — | — |
| p-value | <0.001 | <0.001 | — | — | — | — |
| RBC | | | | | | |
| Baseline: n | 23 | 24 | 24 | 7 | 7 | 8 |
| Mean (SD) | 19.8 (10.85) | 18.9 (8.91) | 19.8 (5.28) | 20.4 (5.77) | 19.3 (6.58) | 17.2 (4.94) |
| Day 14: n | 23 | 22 | 24 | 7 | 7 | 8 |
| Mean (SD) | 12.3 (7.39) | 26.9 (9.15) | 39.5 (13.16) | −0.5 (6.32) | 0.0 (7.17) | 2.6 (6.73) |
| Day 28: n | 22 | 22 | 24 | 7 | 7 | 8 |
| Mean (SD) | 14.5 (10.47) | 32.9 (10.11) | 50.2 (15.82) | 1.5 (4.16) | 0.0 (7.06) | 0.6 (4.42) |
| Day 42: n | 23 | 22 | 24 | 7 | 7 | 8 |
| Mean (SD) | 17.6 (11.89) | 38.3 (12.46) | 52.5 (20.56) | −0.2 (5.90) | 1.0 (8.01) | −0.2 (6.97) |
| 1 or 2 g versus 4 g | | | | | | |
| LS Mean | −24.4 | −11.8 | — | — | — | — |
| CI | −27.6, −21.2 | −15.0, −8.6 | — | — | — | — |
| p-value | <0.001 | <0.001 | — | — | — | — |

TABLE 2

EFA Parameter AA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 202.5 (44.40) | 227.3 (42.26) | 220.9 (42.80) | 210.7 (35.68) | 191.6 (28.24) | 248.0 (53.52) |
| Day 14: n | 23 | 22 | 24 | 7 | 7 | 8 |
| Mean (SD) | −9.7 (22.20) | −13.9 (22.13) | −27.2 (28.89) | 0.8 (40.00) | −14.4 (19.45) | −5.9 (25.00) |
| Day 28: n | 22 | 22 | 24 | 7 | 7 | 8 |
| Mean (SD) | −11.3 (28.13) | 21.6 (28.32) | −43.7 (32.24) | 3.8 (28.11) | −7.4 (23.72) | −16.4 (31.42) |
| Day 42: n | 23 | 22 | 24 | 7 | 7 | 8 |
| Mean (SD) | −8.7 (31.35) | −27.3 (26.76) | −48.3 (22.20) | 8.2 (20.30) | −11.5 (20.88) | −11.0 (25.82) |
| 1 or 2 g versus 4 g | | | | | | |
| LS Mean | 4.2 | 15.6 | — | — | — | — |
| CI | −8.0, 16.4 | 3.4, 27.8 | — | — | — | — |
| p-value | 0.496 | 0.013 | — | — | — | — |
| RBC | | | | | | |
| Baseline: n | 23 | 24 | 24 | 7 | 8 | 8 |
| Mean (SD) | 171.2 (19.79) | 172.8 (22.79) | 171.0 (25.17) | 176.4 (17.65) | 152.8 (17.36) | 180.4 (23.68) |
| Day 14: n | 23 | 22 | 24 | 7 | 7 | 8 |
| Mean (SD) | −8.1 (21.95) | −3.1 (25.84) | −15.7 (26.76) | −8.5 (22.75) | 3.0 (18.20) | −8.1 (27.53) |
| Day 28: n | 22 | 22 | 24 | 7 | 7 | 8 |
| Mean (SD) | −17.0 (20.69) | −14.1 (26.89) | −22.8 (29.56) | 5.2 (22.95) | −2.6 (17.78) | −8.2 (26.89) |
| Day 42: n | 23 | 22 | 24 | 7 | 7 | 8 |
| Mean (SD) | −14.2 (27.69) | −18.8 (25.62) | −34.4 (31.44) | −9.8 (21.59) | 9.7 (16.58) | −10.6 (33.49) |
| 1 or 2 g versus 4 g | | | | | | |
| LS Mean | 8.4 | 9.8 | — | — | — | — |
| CI | 2.0, 14.9 | 3.3, 16.2 | — | — | — | — |
| p-value | 0.010 | 0.003 | — | — | — | — |

TABLE 3

EFA Parameter DHA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 73.1 (30.43) | 75.1 (24.02) | 78.8 (19.00) | 73.7 (14.21) | 73.3 (27.74) | 76.7 (15.68) |
| Day 14: n | 23 | 22 | 24 | 7 | 7 | 8 |
| Mean (SD) | −6.4 (13.30) | −5.4 (14.29) | −10.3 (13.35) | 0.4 (18.86) | −0.8 (14.28) | 13.8 (21.05) |
| Day 28: n | 22 | 22 | 24 | 7 | 7 | 8 |
| Mean (SD) | −6.6 (15.53) | −8.1 (15.82) | −13.5 (14.10) | 4.7 (16.31) | −0.6 (8.29) | 6.0 (17.36) |
| Day 42: n | 23 | 22 | 24 | 7 | 7 | 8 |
| Mean (SD) | −5.4 (18.17) | −6.0 (16.69) | −13.8 (15.31) | 11.8 (21.27) | 0.8 (17.57) | 6.2 (13.40) |
| 1 or 2 g versus 4 g | | | | | | |
| LS Mean | −0.8 | 1.5 | — | — | — | — |
| CI | −7.3, 5.7 | −5.0, 8.1 | — | — | — | — |
| p-value | 0.810 | 0.644 | — | — | — | — |
| RBC | | | | | | |
| Baseline: n | 23 | 24 | 24 | 7 | 8 | 8 |
| Mean (SD) | 66.5 (18.65) | 64.8 (17.65) | 68.3 (14.24) | 71.1 (7.48) | 66.0 (15.90) | 66.2 (15.83) |
| Day 14: n | 23 | 22 | 24 | 7 | 7 | 8 |
| Mean (SD) | −4.6 (9.76) | −2.0 (9.46) | −6.9 (9.13) | −5.5 (11.93) | −0.2 (12.39) | −0.4 (12.50) |
| Day 28: n | 22 | 22 | 24 | 7 | 7 | 8 |
| Mean (SD) | −6.4 (11.57) | −6.2 (9.34) | −8.7 (11.63) | 0.6 (12.86) | −0.3 (11.29) | 1.1 (12.54) |
| Day 42: n | 23 | 22 | 24 | 7 | 7 | 8 |
| Mean (SD) | −7.0 (12.20) | −6.3 (9.42) | −13.8 (13.76) | −4.1 (12.02) | 4.6 (12.94) | −0.1 (17.63) |
| 1 or 2 g versus 4 g | | | | | | |
| LS Mean | 1.0 | 1.0 | — | — | — | — |
| CI | −3.5, 5.4 | −3.5, 5.5 | — | — | — | — |
| p-value | 0.674 | 0.664 | — | — | — | — |

TABLE 4

EFA Parameter DPAn-3 (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 21.1 (6.62) | 19.7 (4.50) | 21.7 (4.69) | 17.9 (5.18) | 18.0 (4.39) | 19.0 (2.67) |
| Day 14: n | 23 | 22 | 24 | 7 | 7 | 8 |
| Mean (SD) | 7.5 (5.11) | 17.4 (7.49) | 24.5 (11.28) | −0.2 (3.13) | −1.0 (3.59) | 2.2 (4.98) |
| Day 28: n | 22 | 22 | 24 | 7 | 7 | 8 |
| Mean (SD) | 8.9 (5.62) | 19.4 (8.48) | 29.7 (13.23) | 1.2 (2.06) | 0.6 (3.44) | 1.3 (3.40) |
| Day 42: n | 23 | 22 | 24 | 7 | 7 | 8 |
| Mean (SD) | 11.3 (6.61) | 19.3 (8.63) | 32.0 (16.01) | 2.2 (3.29) | 0.1 (3.61) | 0.8 (6.70) |
| 1 or 2 g versus 4 g | | | | | | |
| LS Mean | −15.1 | −9.5 | — | — | — | — |
| CI | −17.6, −12.7 | −12.0, −7.1 | — | — | — | — |
| p-value | <0.001 | <0.001 | — | — | — | — |
| RBC | | | | | | |
| Baseline: n | 23 | 24 | 24 | 7 | 8 | 8 |
| Mean (SD) | 34.1 (5.43) | 33.2 (4.51) | 34.5 (4.34) | 34.0 (4.27) | 33.0 (1.20) | 32.4 (2.41) |
| Day 14: n | 23 | 22 | 24 | 7 | 7 | 8 |
| Mean (SD) | 0.9 (5.03) | 5.6 (6.28) | 5.4 (5.38) | −2.8 (4.86) | −0.3 (4.96) | −0.9 (4.74) |
| Day 28: n | 22 | 22 | 24 | 7 | 7 | 8 |
| Mean (SD) | 3.3 (5.42) | 9.4 (6.74) | 12.4 (6.98) | 0.1 (4.51) | −0.8 (4.03) | −0.6 (5.19) |
| Day 42: n | 23 | 22 | 24 | 7 | 7 | 8 |
| Mean (SD) | 6.5 (6.19) | 13.2 (7.23) | 16.2 (10.07) | −1.8 (4.64) | 2.2 (4.44) | −0.9 (6.03) |
| 1 or 2 g versus 4 g | | | | | | |
| LS Mean | −6.2 | −2.5 | — | — | — | — |
| CI | −7.8, −4.7 | −4.1, −1.0 | — | — | — | — |
| p-value | <0.001 | 0.002 | — | — | — | — |

TABLE 5

EFA Parameter DGLA (Plasma and RBC) Mean change from Baseline to Days 14, 28 and 42.

| EFA Parameter (µg/g) | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 7 |
| Mean (SD) | 51.2 (15.01) | 53.5 (14.12) | 57.1 (14.73) | 51.6 (9.20) | 41.6 (10.30) | 52.6 (7.74) |
| Day 14: n | 23 | 22 | 24 | 7 | 7 | 8 |
| Mean (SD) | −10.4 (10.90) | −14.1 (6.88) | −22.9 (9.00) | −4.1 (8.07) | −0.0 (8.63) | −1.0 (11.58) |
| Day 28: n | 22 | 22 | 24 | 7 | 7 | 8 |
| Mean (SD) | −10.6 (10.23) | −16.2 (9.88) | −24.2 (10.73) | −4.6 (7.43) | −0.6 (5.91) | 1.5 (11.78) |
| Day 42: n | 23 | 22 | 24 | 7 | 7 | 8 |
| Mean (SD) | −9.4 (9.41) | −17.3 (9.92) | −22.5 (10.87) | −3.9 (12.90) | 0.9 (9.34) | 0.8 (11.04) |
| 1 or 2 g versus 4 g | | | | | | |
| LS Mean | 3.7 | 2.5 | — | — | — | — |
| CI | 0.4, 7.0 | −0.9, 5.8 | — | — | — | — |
| p-value | 0.028 | 0.143 | — | — | — | — |
| RBC | | | | | | |
| Baseline: n | 23 | 24 | 24 | 7 | 8 | 7 |
| Mean (SD) | 23.0 (5.19) | 23.0 (5.76) | 24.0 (5.77) | 22.4 (5.06) | 19.7 (5.87) | 22.4 (4.91) |
| Day 14: n | 23 | 22 | 24 | 7 | 7 | 8 |
| Mean (SD) | −2.7 (3.82) | −2.6 (3.54) | −5.3 (4.10) | −1.5 (2.08) | 0.2 (1.76) | −1.8 (4.00) |
| Day 28: n | 22 | 22 | 24 | 7 | 7 | 8 |
| Mean (SD) | −3.8 (3.31) | −4.5 (3.58) | −7.1 (4.63) | 0.2 (3.63) | −0.7 (4.06) | −0.7 (3.81) |
| Day 42: n | 23 | 22 | 24 | 7 | 7 | 8 |
| Mean (SD) | −3.5 (4.51) | −5.3 (3.65) | −8.0 (4.98) | −1.6 (4.93) | 1.9 (3.61) | −1.1 (5.31) |
| 1 or 2 g versus 4 g | | | | | | |
| LS Mean | 1.5 | 1.5 | — | — | — | — |
| CI | 0.2, 2.9 | 0.1, 2.9 | — | — | — | — |
| p-value | 0.027 | 0.032 | — | — | — | — |

TABLE 6

EFA Parameter EPA/AA (Plasma and RBC) Mean change from Baseline to Days 14, 28 and 42.

| EFA Parameter | Ethyl-EPA | | | Placebo | | |
|---|---|---|---|---|---|---|
| | 1 g (N = 23) | 2 g (N = 24) | 4 g (N = 24) | 1 g (N = 7) | 2 g (N = 8) | 4 g (N = 8) |
| Plasma | | | | | | |
| Baseline: n | 23 | 24 | 24 | 7 | 8 | 8 |
| Mean (SD) | 0.2 (0.14) | 0.2 (0.12) | 0.2 (0.07) | 0.2 (0.11) | 0.2 (0.10) | 0.2 (0.07) |
| Day 14: n | 23 | 22 | 24 | 7 | 7 | 8 |
| Mean (SD) | 0.3 (0.4) | 0.6 (0.23) | 1.1 (0.28) | 0.0 (0.09) | 0.0 (0.12) | 0.1 (0.12) |
| Day 28: n | 22 | 22 | 24 | 7 | 7 | 8 |
| Mean (SD) | 0.3 (0.20) | 0.8 (0.35) | 1.3 (0.42) | 0.0 (0.08) | 0.0 (0.09) | 0.0 (0.06) |
| Day 42: n | 23 | 22 | 24 | 7 | 7 | 8 |
| Mean (SD) | 0.3 (0.24) | 0.7 (0.29) | 1.3 (0.45) | 0.0 (0.10) | 0.0 (0.12) | 0.0 (0.08) |
| 1 or 2 g versus 4 g | | | | | | |
| LS Mean | −0.66 | −0.41 | — | — | — | — |
| CI | −1.731, −0597 | −0.475, −0.341 | — | — | — | — |
| p-value | <0.001 | <0.001 | — | — | — | — |
| RBC | | | | | | |
| Baseline: n | 23 | 24 | 24 | 7 | 8 | 8 |
| Mean (SD) | 0.1 (0.07) | 0.1 (0.06) | 0.1 (0.04) | 0.1 (0.04) | 0.1 (0.06) | 0.1 (0.03) |
| Day 14: n | 23 | 22 | 24 | 7 | 7 | 8 |
| Mean (SD) | 0.1 (0.04) | 0.2 (0.04) | 0.3 (0.07) | 0.0 (0.03) | −0.0 (0.05) | 0.0 (0.03) |
| Day 28: n | 22 | 22 | 24 | 7 | 7 | 8 |
| Mean (SD) | 0.1 (0.05) | 0.02 (0.06) | 0.4 (0.11) | 0.0 (0.01) | −0.0 (0.04) | 0.0 (0.02) |
| Day 42: n | 23 | 22 | 24 | 7 | 7 | 8 |
| Mean (SD) | 0.1 (0.06) | 0.3 (0.06) | 0.4 (0.14) | 0.0 (0.03) | −0.0 (0.05) | 0.0 (0.03) |
| 1 or 2 g versus 4 g | | | | | | |
| LS Mean | −0.18 | −0.11 | — | — | — | — |
| CI | −0.204, −0.162 | −0.126, −0.085 | — | — | — | — |
| p-value | <0.001 | <0.001 | — | — | — | — |

What is claimed is:

1. A method of lowering triglycerides in a subject on stable statin therapy having type 2 diabetes mellitus and fasting triglycerides of about 200 mg/dl to about 500 mg/dl, the method comprising administering to the subject a composition comprising about 4 g of ethyl eicosapentaenoate per day for a period of time effective to reduce the fasting triglycerides in the subject wherein the composition comprises at least 96% by weight ethyl eicosapentanoate.

2. The method of claim 1, wherein the subject has serum LDL-C levels of about 40 mg/dl to about 115 mg/dl.

3. The method of claim 1, wherein the composition is administered to the subject 1 to 4 times per day.

4. The method of claim 3, wherein the composition is present in one or more capsules.

5. The method of claim 1, wherein the composition contains not more than about 10% by weight of docosahexaenoic acid or derivatives thereof.

6. The method of claim 1, wherein the period is about 1 week to about 12 weeks.

7. The method of claim 1, wherein the period is about 12 weeks.

* * * * *